United States Patent
Zelder et al.

(10) Patent No.: US 7,323,559 B2
(45) Date of Patent: Jan. 29, 2008

(54) GENES ENCODING GENETIC STABILITY, GENE EXPRESSION AND FOLDING PROTEINS

(75) Inventors: Oskar Zelder, Speyer (DE); Markus Pompejus, Freinsheim (DE); Hartwig Schröder, Nußloch (DE); Burkhard Kröger, Limburgerhof (DE); Corinna Klopprogge, Mannheim (DE); Gregor Haberhauer, Limburgerhof (DE)

(73) Assignee: BASF AG, Ludwigshafen (DE)

( * ) Notice: Subject to any disclaimer, the term of this patent is extended or adjusted under 35 U.S.C. 154(b) by 0 days.

(21) Appl. No.: 11/591,868

(22) Filed: Nov. 2, 2006

(65) Prior Publication Data

US 2007/0072273 A1 Mar. 29, 2007

Related U.S. Application Data

(62) Division of application No. 10/494,541, filed as application No. PCT/EP02/12138 on Oct. 31, 2002, now Pat. No. 7,138,513.

(30) Foreign Application Priority Data

Nov. 5, 2001 (DE) ................ 101 54 180

(51) Int. Cl.
*C07H 21/04* (2006.01)
*C12N 1/20* (2006.01)
*C12N 15/00* (2006.01)
*C12P 21/06* (2006.01)

(52) U.S. Cl. ............. 536/23.7; 435/69.1; 435/252.1; 435/320.1

(58) Field of Classification Search ........... 536/23.7; 435/69.1, 252.1, 320.1
See application file for complete search history.

(56) References Cited

U.S. PATENT DOCUMENTS

2002/0197605 A1 12/2002 Nakagawa et al.

FOREIGN PATENT DOCUMENTS

| DE | 19929365 A1 | 12/2000 |
|---|---|---|
| EP | 1108790 A2 | 6/2001 |
| WO | WO-01/00804 A2 | 1/2001 |
| WO | WO-01/04322 A1 | 1/2001 |

OTHER PUBLICATIONS

Bathe, Brigitte et al., "A physical and genetic map of the *Corynebacterium glutamicum* ATCC 13032 chromosome," *Mol. Gen. Genet.*, vol. 252:255-265 (1996).
GenBank Accession No. AP005279, Nakagawa, S., "Complete genomic sequence of *Corynebacterium glutamicum* ATCC 13032," (2002).
European Search Report for Application No. 06110205.9-2401, dated Nov. 23, 2006.

*Primary Examiner*—Mark Navarro
(74) *Attorney, Agent, or Firm*—Lahive & Cockfield, LLP; Elizabeth A. Hanley; Maria Laccotripe Zacharakis

(57) ABSTRACT

The invention relates to novel nucleic acid molecules, to the use thereof for constructing genetically improved microorganisms and to methods for preparing fine chemicals, in particular amino acids, with the aid of said genetically improved microorganisms.

19 Claims, No Drawings

GENES ENCODING GENETIC STABILITY, GENE EXPRESSION AND FOLDING PROTEINS

RELATED APPLICATIONS

The present application is a divisional of U.S. application Ser. No. 10/494,541, filed May 3, 2004, now U.S. Pat. No. 7,138,513, which is a 35 U.S.C. 371 national stage filing of International Application No. PCT/EP02/12138, filed Oct. 31, 2002, which claims priority to German Application No. 101 54 180.5, filed Nov. 5, 2001. The entire contents of each of these applications are hereby incorporated by reference herein.

Incorporation of Material Submitted on Compact Discs

This application incorporates herein by reference the material contained on the compact discs submitted herewith as part of this application. Specifically, the file "Seqlist" (545 KB) contained on each of Copy 1 and Copy 2 of the Sequence Listing is hereby incorporated herein by reference. This file was created on October 31, 2006.

BACKGROUND OF THE INVENTION

Particular products and byproducts of naturally occurring metabolic processes in cells are used in many branches of industry, including the food industry, the animal feed industry, the cosmetics industry and the pharmaceutical industry. These molecules which are collectively referred to as "fine chemicals" comprise organic acids, both proteinogenic and nonproteinogenic amino acids, nucleotides and nucleosides, lipids and fatty acids, diols, carbohydrates, aromatic compounds, vitamins, cofactors and enzymes. They are best produced by means of cultivating, on a large scale, bacteria which have been developed to produce and secrete large amounts of the molecule desired in each particular case. An organism which is particularly suitable for this purpose is *Corynebacterium glutamicum*, a Gram-positive nonpathogenic bacterium. Using strain selection, a number of mutant strains have been developed which produce various desirable compounds. The selection of strains which are improved with respect to the production of a particular molecule is, however, a time-consuming and difficult process.

BRIEF DESCRIPTION OF THE INVENTION

The present invention provides novel nucleic acid molecules which can be used for identifying or classifying *Corynebacterium glutamicum* or related bacterial species. *C. glutamicum* is a Gram-positive, aerobic bacterium which is normally widely used in industry for the large-scale production of a number of fine chemicals and also for the degradation of hydrocarbons (for example in the case of crude oil spills) and for the oxidation of terpenoids. The nucleic acid molecules may therefore be used for identifying microorganisms which can be used for producing fine chemicals, for example by fermentation processes. Although *C. glutamicum* itself is nonpathogenic, it is, however, related to other *Corynebacterium* species such as *Corynebacterium diphteriae* (the diphtheria pathogen), which are major pathogens in humans. The ability to identify the presence of *Corynebacterium* species may therefore also be of significant clinical importance, for example in diagnostic applications. Moreover, said nucleic acid molecules may serve as reference points for mapping the *C. glutamicum* genome or genomes of related organisms.

These novel nucleic acid molecules encode proteins which are referred to herein as proteins for gene stability, gene expression or protein secretion/protein folding (SES proteins). These SES proteins may, for example, exert a function which is involved in repair or recombination of DNA, transposition of genetic material, expression of genes (i.e. which are involved in transcription or translation), protein folding or protein secretion in *C. glutamicum*. Owing to the availability of cloning vectors which can be used in *Corynebacterium glutamicum* as disclosed, for example in Sinskey et al., U.S. Pat. No. 4,649,119, and of techniques for the genetic manipulation of *C. glutamicum* and the related *Brevibacterium* species (e.g. lactofermentum) (Yoshihama et al., J. Bacteriol. 162: 591-597 (1985); Katsumata et al., J. Bacteriol. 159: 306-311 (1984); and Santamaria et al. J. Gen. Microbiol. 130: 2237-2246 (1984)), the nucleic acid molecules of the invention can be used for genetic manipulation of said organism in order to make it a more efficient producer of one or more fine chemicals. This improved production or efficiency of production of a fine chemical may be caused directly by manipulation of a gene of the invention or indirectly by such a manipulation.

There is a number of mechanisms by which modification of an SES protein of the invention can directly influence the yield, production and/or efficiency of production of a fine chemical from a *C. glutamicum* strain containing this modified protein. For example, modulation of proteins directly involved in transcription or translation (e.g. polymerases or ribosomes) so as to increase their number or activity should overall increase cellular transcription or translation (or the rate of these processes). This increased cellular gene expression should include those proteins which are involved in the biosynthesis of fine chemicals so that the yield, production or efficiency of production of one or more compounds of interest can be increased. Modifications of the transcriptional/translational protein machinery of *C. glutamicum* so as to modify regulation of these proteins may also enable the increased expression of genes involved in the production of fine chemicals. Modulation of the activity of a number of proteins involved in peptide folding may increase the overall production of correctly folded molecules in the cell, thereby increasing the possibility of proteins of interest (e.g. proteins of the biosynthesis of fine chemicals) functioning correctly. Furthermore, it may be possible, by mutating proteins involved in the secretion from *C. glutamicum* so as to increase their number or activity, to increase secretion of a fine chemical (e.g. an enzyme) from cells in a fermentative culture from which said fine chemical can be readily obtained.

Genetic modification of the SES molecules of the invention may also modulate indirectly the production of one or more fine chemicals. For example, it is possible, by increasing the number or activity of a DNA-repair or DNA-recombination protein of the invention, to increase the ability of the cell to detect and repair DNA damage. This should effectively increase the ability of the cell to keep a mutated gene in its genome and thereby increase the probability of a transgene genetically introduced into *C. glutamicum* (which encodes, for example, a protein which increases the biosynthesis of a fine chemical) not being lost during cultivation of the microorganism. In contrast, it may be possible, by reducing the number or activity of one or more DNA-repair or DNA-recombination proteins, to increase the genetic instability of the organism. These manipulations should improve the ability of said organism to be modified by mutagenesis, without correcting the introduced mutation. The same is true for proteins which are involved in the transposition or rearrangement of genetic elements in *C. glutamicum* (e.g. transposons). Mutagenesis of these proteins so as to either increase or reduce their number or activity makes it possible to increase or reduce at the same time the genetic stability of the microorganism. This crucially affects the possibility of introducing another mutation into *C. glutamicum* and of retaining the introduced mutation. Transposons likewise provide a suitable mechanism which makes possible the mutagenesis of *C. glutamicum*; duplication of genes of interest (e.g. genes of the biosynthesis of fine chemicals) as well as disruption of unwanted genes (e.g. genes involved in the degradation of fine chemicals of interest) can be readily carried out by means of transposon mutagenesis.

It may be possible, by modulating one or more proteins (e.g. sigma factors) which are involved in the regulation of transcription or translation in reaction to particular environmental conditions, to prevent the cell from slowing down or stopping protein synthesis under unfavorable environmental conditions as found in a large-scale fermentative culture. This should increase gene expression, and this in turn may enable the increased biosynthesis of fine chemicals of interest under said conditions. Mutagenesis of proteins involved in secretion systems may result in modulated secretion rates. Many of these secreted proteins have functions which are important for cell viability (e.g. cell surface proteases or cell surface receptors). A change in the secretion pathway so that these proteins are transported more readily to their extracellular location may increase the overall viability of the cell and thus result in higher numbers of *C. glutamicum* cells able to produce fine chemicals during large-scale cultivation. It is furthermore known that the secretion apparatus (e.g. the sec system) is also involved in the insertion of integral membrane proteins (e.g. pores, channels or transporters) into the membrane. Thus, modulation of the activity of proteins involved in protein secretion from *C. glutamicum* may influence the ability of the cell to secrete waste products or to import necessary metabolites. If the activity of these secretory proteins is increased, the ability of the cell to produce fine chemicals may likewise be increased. If the activity of said secretory proteins is reduced, there may not be enough nutrients to support overproduction of compounds of interest or waste products may interfere with this biosynthesis.

The invention provides novel nucleic acid molecules encoding proteins which are referred to herein as SES proteins and which may be involved, for example, in the repair or recombination of DNA, transposition of genetic material, expression of genes (i.e. in transcriptional or translational processes), protein folding or protein secretion in *Corynebacterium glutamicum*. Nucleic acid molecules encoding an SES protein are referred to herein as SES nucleic acid molecules. In a preferred embodiment, an SES protein is involved in improving or reducing the genetic stability in *C. glutamicum*, in the expression of genes (e.g. in transcription or translation) or in protein folding in this organism or in protein secretion from *C. glutamicum*. Examples of such proteins are those encoded by the genes listed in Table 1.

Consequently, one aspect of the invention relates to isolated nucleic acid molecules (e.g. cDNAs) comprising a nucleotide sequence which encodes an SES protein or biologically active sections thereof and also nucleic acid fragments which are suitable as primers or hybridization probes for detecting or amplifying SES-encoding nucleic acid (e.g. DNA or mRNA). In particularly preferred embodiments, the isolated nucleic acid molecule comprises any of the nucleotide sequences listed in Appendix A or the coding region or a complement thereof of any of these nucleotide sequences. In other preferred embodiments, the isolated nucleic acid molecule encodes any of the amino acid sequences listed in Appendix B. The preferred SES proteins of the invention likewise have preferably at least one of the SES activities described herein.

Appendix A defines hereinbelow the nucleic acid sequences of the sequence listing together with the sequence modifications at the relevant position, described in Table 1.

Appendix B defines hereinbelow the polypeptide sequences of the sequence listing together with the sequence modifications at the relevant position, described in Table 1.

In a further embodiment, the isolated nucleic acid molecule is at least 15 nucleotides in length and hybridizes under stringent conditions to a nucleic acid molecule which comprises a nucleotide sequence of Appendix A. Such stringent conditions, for example, hybridization in 6× sodium chloride/sodium citrate (SSC) at about 45° C., followed by one or more washes in 0.2×SSC, 0.1% SDS at 50-65° C., are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, NY (1989), chapters 7, 9, and 11. The isolated nucleic acid molecule preferably corresponds to a naturally occuffing nucleic acid molecule. The isolated nucleic acid more preferably encodes a naturally occurring *C. glutamicum* SES protein or a biologically active section thereof.

A further aspect of the invention relates to vectors, for example recombinant expression vectors, which contain the nucleic acid molecules of the invention and to host cells into which said vectors have been introduced. In one embodiment, an SES protein is prepared by using said host cell which is cultivated in a suitable medium. The SES protein may then be isolated from the medium or the host cell.

A further aspect of the invention relates to a genetically modified microorganism into which an SES gene has been introduced or in which an HA gene has been modified. In one embodiment, the genome of said microorganism has been modified by introducing at least one inventive nucleic acid molecule which encodes the mutated SES sequence as transgene. In another embodiment, an endogenous SES gene in the genome of said microorganism has been modified, for example, functionally disrupted, by homologous recombination with a modified SES gene. In a preferred embodiment, the microorganism belongs to the genus *Corynebacterium* or *Brevibacterium*, with *Corynebacterium glutamicum* being particularly preferred. In a preferred embodiment, the microorganism is also used for preparing a compound of interest, such as an amino acid, lysine being particularly preferred.

A further aspect of the invention relates to an isolated SES protein or a section therof, for example a biologically active section. In a preferred embodiment, the isolated SES protein or its section may take part in the repair or recombination of DNA, transposition of genetic material, gene expression (i.e. transcriptional or translational processes), protein folding or protein secretion in *Corynebacterium glutamicum*. In another preferred embodiment, the isolated SES protein or a section thereof is sufficiently homologous to an amino acid sequence of Appendix B for the protein or its section to retain the ability, for example, to take part in the repair or recombination of DNA, transposition of genetic material, gene expression (i.e. transcriptional or translational processes), protein folding or protein secretion in *Corynebacterium glutamicum*.

Another preferred embodiment are host cells having more than one of the nucleic acid molecules described in Appendix A. Such host cells can be prepared in various ways known to the skilled worker. They may be transfected, for example, by vectors carrying several of the nucleic acid molecules of the invention. However, it is also possible to use a vector for introducing in each case one nucleic acid molecule of the invention into the host cell and therefore to use a plurality of vectors either simultaneously or sequentially. Thus it is possible to construct host cells which carry numerous, up to several hundred, nucleic acid sequences of the invention. Such an accumulation can often produce superadditive effects on the host cell with respect to fine-chemical productivity.

Moreover, the invention provides an isolated SES protein preparation. In preferred embodiments, the. SES protein comprises an amino acid sequence of Appendix B. In a further preferred embodiment, the invention relates to an isolated full-length protein which is essentially homologous to a complete amino acid sequence of Appendix B (which is encoded by an open reading frame in Appendix A).

The SES polypeptide or a biologically active section thereof may be functionally linked to a non-SES polypeptide in order to produce a fusion protein. In preferred embodiments, this fusion protein has a different activity from that of the SES protein alone. In other preferred embodiments, said fusion protein takes part in the repair or recombination of DNA, transposition of genetic material, gene expression (i.e. transcriptional or translational processes), protein folding or protein secretion in *Corynebacterium glutamicum*. In particularly preferred embodiments, integration of said fusion protein into a host cell modulates the production of a compound of interest by the cell.

A further aspect of the invention relates to a method for preparing a fine chemical. The method provides for the cultivation of a cell containing a vector which causes expression of an SES nucleic acid molecule of the invention so that a fine chemical is produced. In a preferred embodiment, this method moreover comprises the step of obtaining a cell containing such a vector, said cell being transfected with a vector which causes expression of an SES nucleic acid. In a further preferred embodiment, said method moreover comprises the step in which the fine chemical is obtained from the culture. In a particularly preferred embodiment, the cell belongs to the genus *Corynebacterium* or *Brevibacterium*.

A further aspect of the invention relates to methods for modulating the production of a molecule from a microorganism. These methods comprise contacting the cell with a substance which modulates SES-protein activity or SES nucleic-acid expression such that a cell-associated activity is modified in comparison with the same activity in the absence of said substance. In a preferred embodiment, the cell is modulated with regard to one or more *C. glutamicum* processes which are involved in genetic stability, gene expression, protein folding or protein secretion, so as to improve the yield, production or efficiency of production of a fine chemical of interest by this microorganism. The substance which modulates SES protein activity may be a substance which stimulates SES-protein activity or SES nucleic-acid expression. Examples of substances stimulating SES protein activity or SES nucleic-acid expression include small molecules, active SES proteins and nucleic acids which encode SES proteins and have been introduced into the cell. Examples of substances which inhibit SES activity or SES expression include small molecules and SES antisense nucleic acid molecules.

A further aspect of the invention relates to methods for modulating the yields of a compound of interest from a cell, comprising introducing an SES wild-type gene or HA-mutant gene into a cell, which gene either remains on a separate plasmid or is integrated into the genome of the host cell. Integration into the genome may take place randomly or via homologous recombination so that the native gene is replaced by the introduced copy, leading to the production of the compound of interest from the cell to be modulated. In a preferred embodiment, said yields are increased. In a further preferred embodiment, the chemical is a fine chemical which, in a particularly preferred embodiment, is an amino acid. In a particularly preferred embodiment, this amino acid is L-lysine.

DETAILED DESCRIPTION OF THE INVENTION

The present invention provides SES nucleic acid and SES-protein molecules which are involved in the repair or recombination of DNA, transposition of genetic material, gene expression (i.e. transcriptional or translational processes), protein folding or protein secretion in *Corynebacterium glutamicum*. The molecules of the invention can be used for modulating the production of fine chemicals from microorganisms such as *C. glutamicum* either directly (for example, if overexpression or optimization of the activity of a protein involved in the secretion of a fine chemical (e.g. an enzyme) has a direct effect on the yield, production and/or efficiency of production of a fine chemical from the modified *C. glutamicum* cells) or via an indirect effect which nevertheless causes an increase in the yield, production and/or efficiency of the compound of interest (for example, if modulating the activity or copy number of a *C. glutamicum* DNA-repair protein to changes in the ability of the microorganism to maintain the introduced mutation, and this in turn may influence the production of one or more fine chemicals from said strain). The aspects of the invention are further illustrated below.

I. Fine Chemicals

The term "fine chemicals" is known in the art and includes molecules which are produced by an organism and are used in various branches of industry such as, for example, but not restricted to, the pharmaceutical industry, the agricultural industry and the cosmetics industry. These compounds comprise organic acids such as tartaric acid, itaconic acid and diaminopimelic acid, both proteinogenic and nonproteinogenic amino acids, purine and pyrimidine bases, nucleosides and nucleotides (as described, for example, in Kuninaka, A. (1996) Nucleotides and related compounds, pp. 561-612, in Biotechnology Vol. 6, Rehm et al., Editors VCH: Weinheim and the references therein), lipids, saturated and unsaturated fatty acids (e.g. arachidonic acid), diols (e.g. propanediol and butanediol), carbohydrates (e.g. hyaluronic acid and trehalose), aromatic compounds (e.g. aromatic amines, vanilline and indigo), vitamins and cofactors (as described in Ullmann's Encyclopedia of Industrial Chemistry, Vol. A27, "Vitamins", pp. 443-613 (1996) VCH: Weinheim and the references therein; and Ong, A. S., Niki, E. and Packer, L. (1995) "Nutrition, Lipids, Health and Disease" Proceedings of the UNESCO/Confederation of Scientific and Technological Associations in Malaysia and the Society for Free Radical Research—Asia, held Sep. 1-3, 1994 in Penang, Malaysia, AOCS Press (1995)), enzymes and all other chemicals described by Gutcho (1983) in Chemicals by Fermentation, Noyes Data Corporation, ISBN: 0818805086 and the references indicated therein. The metabolism and the uses of particular fine chemicals are further illustrated below.

A. Metabolism and Uses of Amino Acids

Amino acids comprise the fundamental structural units of all proteins and are thus essential for normal functions of the cell in all organisms. The term "amino acid" is known in the art. Proteinogenic amino acids, of which there are 20 types, serve as structural units for proteins, in which they are linked together by peptide bonds, whereas the nonproteinogenic amino acids (hundreds of which are known) usually do not occur in proteins (see Ullmann's Encyclopedia of Industrial Chemistry, vol. A2, pp. 57-97 VCH: Weinheim (1985)). Amino acids can exist in the optical D or L configuration, although L-amino acids are usually the only type found in naturally occurring proteins. Biosynthetic and degradation pathways of each of the 20 proteinogenic amino acids are well characterized both in prokaryotic and eukaryotic cells (see, for example, Stryer, L. Biochemistry, $3^{rd}$ edition, pp. 578-590 (1988)). The "essential" amino acids (histidine, isoleucine, leucine, lysine, methionine, phenylalanine, threonine, tryptophan and valine), so called because, owing to the complexity of their biosyntheses, they must usually be taken in with the diet, are converted by simple biosynthetic pathways into the other 11 "nonessential" amino acids (alanine, arginine, asparagine, aspartate, cysteine, glutamate, glutamine, glycine, proline, serine and tyrosine). Higher animals are able to synthesize some of these amino acids but the essential amino acids must be taken in with the food in order that normal protein synthesis takes place.

Apart from their function in protein biosynthesis, these amino acids are interesting chemicals as such, and it has been found that many have various applications in the human food, animal feed, chemicals, cosmetics, agricultural and pharmaceutical industries. Lysine is an important amino acid not only for human nutrition but also for monogastric livestock such as poultry and pigs. Glutamate is most frequently used as flavor additive (monosodium glutamate, MSG) and elsewhere in the food industry, as are aspartate, phenylalanine, glycine and cysteine. Glycine, L-methionine and. tryptophan are all used in the pharmaceutical industry. Glutamine, valine, leucine, isoleucine, histidine, arginine, proline, serine and alanine are used in the pharmaceutical industry and the cosmetics industry. Threonine, tryptophan and D/L-methionine are widely used animal feed additives (Leuchtenberger, W. (1996) Amino acids—technical production and use, pp. 466-502 in Rehm et al., (editors) Biotechnology Vol. 6, Chapter 14a, VCH: Weinheim). It has been found that these amino acids are additionally suitable as recursors for synthesizing synthetic amino acids and proteins, such as N-acetylcysteine, S-carboxymethyl-L-cysteine, (S)-5-hydroxytryptophan and other substances described in Ullmann's Encyclopedia of Industrial Chemistry, Vol. A2, pp. 57-97, VCH, Weinheim, 1985.

The biosynthesis of these natural amino acids in organisms able to produce them, for example bacteria, has been well characterized (for a review of bacterial amino acid biosynthesis and its regulation, see Umbarger, H. E. (1978) Ann. Rev. Biochem. 47: 533-606). Glutamate is synthesized by reductive amination of α-ketoglutarate, an intermediate product in the citric acid cycle. Glutamine, proline and arginine are each generated successively from glutamate. The biosynthesis of serine takes place in a three-step process, starts with 3-phosphoglycerate (an intermediate product of glycolysis), and affords this amino acid after oxidation, transamination and hydrolysis steps. Cysteine and glycine are each produced from serine, specifically the former by condensation of homocysteine with serine, and the latter by transfer of the side-chain β-carbon atom to tetrahydrofolate in a reaction catalyzed by serine transhydroxy-methylase. Phenylalanine and tyrosine are synthesized from the precursors of the glycolysis and pentose phosphate pathway, and erythrose 4-phosphate and phosphoenolpyruvate in a 9-step biosynthetic pathway which diverges only in the last two steps after the synthesis of prephenate. Tryptophan is likewise produced from these two starting molecules but it is synthesized by an 11-step pathway. Tyrosine can also be prepared from phenylalanine in a reaction catalyzed by phenylalanine hydroxylase. Alanine, valine and leucine are each biosynthetic products derived from pyruvate, the final product of glycolysis. Aspartate is formed from oxalacetate, an intermediate product of the citrate cycle. Asparagine, methionine, threonine and lysine are each produced by the conversion of aspartate. Isoleucine is formed from threonine. Histidine is formed from 5-phosphoribosyl 1-pyrophosphate, an activated sugar, in a complex 9-step pathway.

Amounts of amino acids exceeding those required for protein biosynthesis cannot be stored and are instead broken down so that intermediate products are provided for the principal metabolic pathways in the cell (for a review, see Stryer, L., Biochemistry, $3^{rd}$ edition, Chapter 21 "Amino Acid Degradation and the Urea Cycle"; pp. 495-516 (1988)). Although the cell is able to convert unwanted amino acids into the useful intermediate products of metabolism, production of amino acids is costly in terms of energy, the precursor molecules and the enzymes necessary for their synthesis. It is therefore not surprising that amino acid biosynthesis is regulated by feedback inhibition, whereby the presence of a particular amino acid slows down or completely stops its own production (for a review of feedback mechanism in amino acid biosynthetic pathways, see Stryer, L., Biochemistry, $3^{rd}$ edition, Chapter 24, "Biosynthesis of Amino Acids and Heme", pp. 575-600 (1988)). The output of a particular amino acid is therefore restricted by the amount of this amino acid in the cell.

B. Metabolism and Uses of Vitamins, Cofactors and Neutracenticals

Vitamins, cofactors and nutraceuticals comprise another group of molecules. Higher animals have lost the ability to synthesize them and therefore have to take them in, although they are easily synthesized by other organisms such as bacteria. These molecules are either bioactive molecules per se or precursors of bioactive substances which serve as electron carriers or intermediate products in a number of metabolic pathways. Besides their nutritional value, these compounds also have a significant industrial value as colorants, antioxidants and catalysts or other processing auxiliaries. (For a review of the structure, activity and industrial applications of these compounds, see, for example, Ullmann's Encyclopedia of Industrial Chemistry, "vitamins", Vol. A27, pp. 443-613, VCH: Weinheim, 1996). The term "vitamin" is known in the art and comprises nutrients which are required for normal functional of an organism but cannot be synthesized by this organism itself. The group of vitamins may include cofactors and nutraceutical compounds. The term "cofactor" comprises nonproteinaceous compounds necessary for the appearance of a normal enzymic activity. These compounds may be organic or inorganic; the cofactor molecules of the invention are preferably organic. The term "nutraceutical" comprises food additives which are health-promoting in plants and animals, especially humans. Examples of such molecules are vitamins, antioxidants and likewise certain lipids (e.g. polyunsaturated fatty acids).

The biosynthesis of these molecules in organisms able to produce them, such as bacteria, has been comprehensively characterized (Ullmann's Encyclopedia of Industrial Chemistry, "Vitamins", Vol. A27, pp. 443-613, VCH: Weinheim, 1996, Michal, G. (1999) Biochemical Pathways: An Atlas of Biochemistry and Molecular Biology, John Wiley & Sons; Ong, A. S., Niki, E. and Packer, L. (1995) "Nutrition, Lipids, Health and Disease" Proceedings of the UNESCO/Confederation of Scientific and Technological Associations in Malaysia and the Society for free Radical Research—Asia, held on Sep. 1-3, 1994, in Penang, Malaysia, AOCS Press, Champaign, Ill. X, 374 S).

Thiamine (vitamin $B_1$) is formed by chemical coupling of pyrimidine and thiazole units. Riboflavin (vitamin $B_2$) is synthesized from guanosine 5'-triphosphate (GTP) and ribose 5'-phosphate. Riboflavin in turn is employed for the synthesis of flavin mononucleotide (FMN) and flavin adenine dinucleotide (FAD). The family of compounds together referred to as "vitamin B6" (for example pyridoxine, pyridoxamine, pyridoxal 5'-phosphate and the commercially used pyridoxine hydrochloride), are all derivatives of the common structural unit 5-hydroxy-6-methylpyridine. Panthothenate (pantothenic acid, R-(+)-N-(2,4-dihydroxy-3,3-dimethyl-1-oxobutyl)-β-alanine) can be prepared either by chemical synthesis or by fermentation. The last steps in pantothenate biosynthesis consist of ATP-driven condensation of β-alanine and pantoic acid. The enzymes responsible for the biosynthetic steps for the conversion into pantoic acid and into β-alanine and for the condensation to pantothenic acid are known. The metabolically active form of pantothenate is coenzyme A whose biosynthesis takes place by 5 enzymatic steps. Pantothenate, pyridoxal 5'-phosphate, cysteine and ATP are the precursors of coenzyme A. These enzymes catalyze not only the formation of pantothenate but also the production of (R)-pantoic acid, (R)-pantolactone, (R)-panthenol (provitamin $B_5$), pantetheine (and its derivatives) and coenzyme A.

The biosynthesis of biotin from the precursor molecule pimeloyl-CoA in microorganisms has been investigated in detail, and several of the genes involved have been identified. It has emerged that many of the corresponding proteins are involved in the Fe cluster synthesis and belong to the class of nifS proteins. Liponic acid is derived from octanonoic acid and serves as coenzyme in energy metabolism where it is a constituent of the pyruvate dehydrogenase complex and of the α-ketoglutarate dehydrogenase complex. Folates are a group of substances all derived from folic acid which in turn is derived from L-glutamic acid, p-aminobenzoic acid and 6-methylpterin. The biosynthesis of folic acid and its derivatives starting from the intermediate products of the biotransformation of guanosine 5'-triphosphate (GTP), L-glutamic acid and p-aminobenzoic acid has been investigated in detail in certain microorganisms.

Corrinoids (such as the cobalamines and, in particular, vitamin $B_{12}$) and the porphyrins belong to a group of chemicals distinguished by a tetrapyrrole ring system. The biosynthesis of vitamin $B_{12}$ is so complex that it has not yet been completely characterized, but many of the enzymes and substrates involved are now known. Nicotinic acid (nicotinate) and nicotinamide are pyridine derivatives which are also referred to as "niacin". Niacin is the precursor of the important coenzymes AND (nicotinamide adenine dinucleotide) and NADP (nicotinamide adenine dinucleotide phosphate) and their reduced forms.

Production of these compounds on the industrial scale is mostly based on cell-free chemical syntheses, although some of these chemicals, such as riboflavin, vitamin $B_6$, pantothenate and biotin, have also been produced by large-scale cultivation of microorganisms. Only vitamin $B_{12}$ is, because of the complexity of its synthesis, produced only by fermentation. In vitro processes require a considerable expenditure of materials and time and frequently high costs.

C. Purine, Pyrimidine, Nucleoside and Nucleotide Metabolism and Uses

Genes for purine and pyrimidine metabolism and their corresponding proteins are important aims for the therapy of oncoses and viral infections. The term "purine" or "pyrimidine" comprises nitrogen-containing bases which form part of nucleic acids, coenzymes and nucleotides. The term "nucleotide" encompasses the fundamental structural units of nucleic acid molecules, which comprise a nitrogen-containing base, a pentose sugar (the sugar is ribose in the case of RNA and the sugar is D-deoxyribose in the case of DNA) and phosphoric acid. The term "nucleoside" comprises molecules which serve as precursors of nucleotides but have, in contrast to the nucleotides, no phosphoric acid unit. It is possible to inhibit RNA and DNA synthesis by inhibiting the biosynthesis of these molecules or their mobilization to form nucleic acid molecules; targeted inhibition of this activity in cancer cells allows the ability of tumor cells to divide and replicate to be inhibited. There are also nucleotides which do not form nucleic acid molecules but serve as energy stores (i.e. AMP) or as coenzymes (i.e. FAD and AND).

Several publications have described the use of these chemicals for these medical indications, the purine and/or pyrimidine metabolism being influenced (for example Christopherson, R. I. and Lyons, S. D. (1990) "Potent inhibitors of de novo pyrimidine and purine biosynthesis as chemotherapeutic agents", Med. Res. Reviews 10: 505-548). Investigations of enzymes involved in purine and pyrimidine metabolism have concentrated on the development of novel medicaments which can be used, for example, as immunosuppressants or antiproliferative agents (Smith, J. L. (1995) "Enzymes in Nucleotide Synthesis" Curr. Opin. Struct. Biol. 5: 752-757; (1995) Biochem. Soc. Transact. 23: 877-902). However, purine and pyrimidine bases, nucleosides and nucleotides also have other possible uses: as intermediate products in the biosynthesis of various fine chemicals (e.g. thiamine, S-adenosylmethionine, folates or riboflavin), as energy carriers for the cell (for example ATP or GTP) and for chemicals themselves, which are ordinarily used as flavor enhancers (for example IMP or GMP) or for many medical applications (see, for example, Kuninaka, A., (1996) "Nucleotides and Related Compounds in Biotechnology" Vol. 6, Rehm et al., editors VCH: Weinheim, pp. 561-612). Enzymes involved in purine, pyrimidine, nucleoside or nucleotide metabolism are also increasingly serving as targets against which chemicals are being developed for crop protection, including fungicides, herbicides and insecticides.

The metabolism of these compounds in bacteria has been characterized (for reviews, see, for example, Zalkin, H. and Dixon, J. E. (1992) "De novo purine nucleotide biosynthesis" in Progress in Nucleic Acids Research and Molecular biology, Vol. 42, Academic Press, pp. 259-287; and Michal, G. (1999) "Nucleotides and Nucleosides"; Chapter 8 in : Biochemical Pathways: An Atlas of Biochemistry and Molecular Biology, Wiley, New York). Purine metabolism, the object of intensive research, is essential for normal functioning of the cell. Disordered purine metabolism in higher animals may cause severe illnesses, for example gout. Purine nucleotides are synthesized from ribose 5-phosphate by a number of steps via the intermediate compound inosine 5'-phosphate (IMP), leading to the production of guanosine 5'-monophosphate (GMP) or adenosine 5'-monophosphate (AMP), from which the triphosphate forms used as nucleotides can easily be prepared. These compounds are also used as energy stores, so that breakdown thereof provides energy for many different biochemical processes in the cell. Pyrimidine biosynthesis takes place via formation of uridine 5'-mono-phosphate (UMP) from ribose 5-phosphate. UMP in turn is converted into cytidine 5'-triphosphate (CTP). The deoxy forms of all nucleotides are prepared in a one-step reduction reaction from the diphosphate ribose form of the nucleotide to give the diphosphate deoxyribose form of the nucleotide. After phosphorylation, these molecules can take part in DNA synthesis.

D. Trehalose Metabolism and Uses

Trehalose consists of two glucose molecules linked together by an α,α-1,1 linkage. It is ordinarily used in the food industry as sweetener, as additive for dried or frozen foods and in beverages. However, it is also used in the pharmaceutical industry or in the cosmetics industry and biotechnology industry (see, for example, Nishimoto et al., (1998) U.S. Pat. No. 5,759,610; Singer, M. A. and Lindquist, S. (1998) Trends Biotech. 16: 460-467; Paiva, C. L. A. and Panek, A. D. (1996) Biotech Ann. Rev. 2: 293-314; and Shiosaka, M. (1997) J. Japan 172: 97-102). Trehalose is produced by enzymes of many microorganisms and is naturally released into the surrounding medium from which it can be isolated by methods known in the art.

II. Genetic Stability, Protein Synthesis and Protein Secretion in *C. glutamicum*

The production of a compound of interest from a cell such as *C. glutamicum* is the culmination of a large number of separate processes which are nevertheless linked to one another and each of which is crucial for the overall production and release of said compound from the cell. When modifying a cell for it to overproduce one or more chemicals, each of these processes must be taken into account in order to ensure that the biochemical machinery of the cell is compatible with this genetic manipulation. Particularly important cellular mechanisms include the stability of the modified gene(s) when introduced into the cell, the ability of the mutated gene to be transcribed and translated correctly (including codon usage) and the ability of the mutated protein product to be folded and/or secreted correctly.

A. Bacterial Repair and Recombination Systems

Cells are constantly exposed to nucleic-acid damaging agents such as UV irradiation, oxygen-free radicals and alkylation. Furthermore, even the action of DNA polymerases is not free of errors. The cells must maintain an equilibrium between genetic stability (which ensures that genes required for cellular functions are not damaged during normal growth and metabolism) and genetic variability (which makes it possible for the cells to adapt to a changing environment). Therefore, most cells contain separate pathways for DNA repair and DNA recombination, which are, however, connected to one another. The former serves to strictly correct errors in DNA molecules either by directly reverting the damage or by excising the damaged region and replacing it with the correct sequence. The latter recombination system also repairs nucleic acid molecules, but only the damage which causes damage in both DNA strands so that it is not possible to use any strand as a template for correcting the other one. Recombination repair and SOS reaction may readily lead to inversions, deletions or other genetic rearrangements within or around the damaged region, and this in turn promotes a certain degree of genomic instability which may contribute to the ability of the cell to adapt to changing environments or to stress.

High-fidelity repair mechanisms include the direct reversal of the DNA damage and excision of said damage and resynthesis using the information encoded in the complementary strand. The direct reversal of said damage requires an enzyme having an activity which causes the opposite of what originally damaged the DNA. For example, the action of DNA-repair methyltransferases can correct incorrect DNA methylation and the activity of deoxyribodipyrimidine photolyase can repair nucleotide dimers generated by UV irradiation by cleaving said dimer again into the corresponding nucleotides in the presence of light (see Michal, G. (1999) Biochemical Pathways: An Atlas of Biochemistry and Molecular Biology, Wiley: New York, and the references therein).

Accurate repairing of large damage requires specialized repair mechanisms. These include the mismatch repair and excision repair systems. The damage to an individual base can be corrected by a number of cleavage reactions, with the sugar bond being cleaved first, followed by cleavage of the DNA backbone at the damaged site and removal of the damaged base itself. Finally, DNA polymerase and DNA ligase fill in and close the gap by using the second DNA strand as template. A more substantial DNA damage which leads to a modified conformation of the double helix is corrected by the ABC system in which helicase II, DNA polymerase I, the UvrA, UvrB and UvrC proteins together cleave a single strand of the double helix at the damaged site, unwind the damaged region in an ATP-dependent manner, excise the damaged region and fill in the missing region using the other strand as template. Finally, DNA ligase closes the single-strand break. There are also specific repair systems for G-T mismatches (in which systems the Vsr protein is involved) and for minor deletion/insertion errors owing to erroneous repair of the two strands (in which systems the methylation-controlled pathway is involved).

There are also low-fidelity repair systems which are usually used for correcting very extended DNA damage in bacteria. Double-strand repair and recombination are carried out in the case of damage which affects both DNA strands. It is impossible in this situation to repair the damage by using the other strand as template. Thus, the repair system includes a double-crossover event between the damaged region and another copy of the region on a homologous DNA molecule. This is possible, since bacteria divide so rapidly that a second copy of the genomic DNA is usually available, before cell division actually takes place. Said crossover event may readily lead to inversions, duplications, deletions, insertions and other genetic rearrangements and thus overall increases the genetic instability of the organism.

The SOS reaction is activated if the damage in the DNA is sufficient for DNA polymerase III to stop and not be able to continue replication. Under these circumstances, single-stranded DNA is present. RecA protein is activated by binding to single-stranded DNA, and this activated form leads to activation of the LexA repressor, thereby removing the transcriptional block of more than 20 genes, including UvrA, UvrB, UvrC, helicase II, DNA pol III, UmuC and UmuD. The combined activities of these enzymes fill in the gap region sufficiently for DNA pol III to continue replication. However, these gaps are filled with bases which should not be present; thus, this type of repair leads to error-prone repair and this overall contributes to genetic instability in the cell.

B. Transposons

The abovementioned high- or low-fidelity systems ought to repair DNA damage. Under certain circumstances, this repair may include additional gene rearrangements. Moreover, many bacterial cells have mechanisms which ought to specifically cause such gene rearrangements. Particularly well known examples of such mechanisms are the transposons.

Transposons are genetic elements which can migrate from one site to another, either within a chromosome or between a piece of extrachromosomal DNA (e.g. a plasmid) and a chromosome. The transposition may be carried out in several ways; for example, the transposable element may be excised from the donor site and integrated into the target site (nonreplicative transposition) or, as an alternative, the transposable element may be copied from the donor site to the target site, resulting in two copies of said element (replicative transposition). The sequences of the donor site and the target site are usually not related.

Said transposition event has a multiplicity of possible results. Integration of a transposable element into a gene disrupts said gene, and this normally completely eliminates the function of said gene. An integration event which takes place in the DNA surrounding said gene cannot interfere with the coding sequence itself but may have a fundamental effect on the regulation of said gene and thus on its expression. Recombination events between two copies of a transposable element which is located in different sections of the genome may lead to deletions, duplications, inversions, transpositions or amplifications of segments of the genome. It is also possible for various replicons to fuse.

The simplest transposon-like genetic elements are referred to as insertion (IS) elements. IS elements contain a nucleotide region of variable length (but usually less than 1500 bases) which contains no coding regions and is on each end surrounded by inverted repeats. Since the IS element does not encode any proteins whose activity can be detected, the presence of an IS element is usually observed only due to the loss of function of one or more genes into which the IS element has been inserted.

Transposons are mobile genetic elements which, in contrast to IS elements, contain nucleic acid sequences which are bordered by repeats and may encode one or more proteins. It is not unusual for these repeat regions to comprise IS elements. The transposon-encoded proteins are usually transposases (proteins which catalyze migration of the transposon from one site to another) and antibiotic resistance genes. The mechanisms and regulation of the transposable elements are known in the art and have been described, at least by way of example, in: Lengeler et al. (1999) Biology of Prokaryotes, Thieme Verlag: Stuttgart, pp. 375-361; Neidhardt et al. (1996) *Escherichia coli* and *Salmonella*, ASM Press: Washington, D.C.; Sonenshein, Al.L., et al., Editors, (1993) *Bacillus subtilis*, ASM Press, Washington, D.C.; Voet, D., and Voet, J. G. (1992) Biochemie, VCH: Weinheim, pp. 985-990; Brock, T. D., and Madigan, M. T. (1991) Biology of Mocroorganisms, 6th edition, Prentice Hall: New York, pp. 267-269; and Kleckner, N. (1990) "Regulation of transposition in bacteria", Annu. Rev. Biochem. 61:297-327.

C. Transcription

The expression of genes in bacteria is regulated mainly at the level of transcription. The transcriptional apparatus comprises a number of proteins which can be divided into two groups: RNA polymerase (the operating DNA-transcribing enzyme) and sigma factors (which regulate gene transcription by directing RNA polymerase to specific promoter DNA sequences which recognize said factors). The combination of RNA polymerase and sigma factors generates the RNA-polymerase holoenzyme, an activated complex. Gram-positive bacteria such as *Corynebacteria* contain only one type of RNA polymerase but a number of different sigma factors which are specific for various promoters, growth phases, environmental conditions, substrates, oxygen levels, transport processes and the like, and, as a result, the organism can adapt to various environmental and metabolic conditions.

Promoters are specific DNA sequences which serve as docking sites for the RNA-polymerase holoenzyme. Many promoter elements-have conserved sequence elements which can be detected by homology searching; as an alternative, promoter regions for a particular gene may be identified using standard techniques such as primer extension. Many promoter regions of Gram-positive bacteria are known (see, for example, Sonenshein, A. L., Hoch, J. A., and Losick, R., Editors, (1993) *Bacillus subtilis*, ASM Press: Washington, D.C.).

A plurality of repressing or activating mechanisms influence the transcriptional control of the promoter. Specific regulatory proteins which bind to promoters are capable of blocking (repressors) or supporting (activators) binding of the RNA holoenzyme and thus regulating transcription. Binding of these repressor and activator molecules is in turn regulated by their interactions with other molecules such as proteins or other metabolic compounds. As an alternative, transcription may be regulated by factors which influence processes such as elongation or termination (see, for example, Sonenshein, A. L., Hoch, J. A., and Losick, R., Editors, (1993) *Bacillus subtilis*, ASM Press: Washington, D.C.). The ability to regulate the transcription of genes as a reaction to a multiplicity of environmental or metabolic signals enables the cells to control exactly when a gene can be expressed and how much gene product can be present in the cell at a point in time. This in turn prevents unnecessary wasting of energy or the unnecessary use of possibly rare intermediates or cofactors.

D. Translation and Aminoacyl-tRNA Synthetases

Translation is the process which synthesizes a polypeptide from amino acids according to the information contained in an RNA molecule. The major components of this process are ribosomes and specific initiation or elongation factors, such as IF1-3, INVENTIVE-G and EFTu (see, for example, Sonenshein, A. L., Hoch, J. A., and Losick, R., Editors, (1993) *Bacillus subtilis*, ASM Press: Washington, D.C.).

Each codon of the mRNA molecule encodes a particular amino acid. mRNA is converted into amino acid via transfer-RNA (tRNA) molecules. These molecules consist of an RNA single strand (between 60 and 100 bases) which is present in a L-shaped three-dimensional structure with extending regions or "arms". One of these arms forms base pairs with a particular codon sequence on the mRNA molecule. A second arm interacts specifically with a particular amino acid (which is encoded by the codon). Other tRNA arms include the variable arm, the TψC arm (which carries thymidylate and pseudouridylate modifications) and the D arm (which carries a dihydrouridine modification). The function of said latter structures is still unknown, but their conservation among the tRNA molecules suggests a role in protein synthesis.

A family of enzymes which are referred to as aminoacyl-tRNA synthetases must act in order for the nucleic acid-based tRNA molecule to pair with the correct amino acid. There is a large variety of these enzymes and each of them is specific for a particular tRNA and a particular amino acid. Said enzymes bind the 3'-hydroxyl of the terminal tRNA-adenosin-ribose unit to the amino acid in a two-step reaction. Firstly, the enzyme is activated via reaction with ATP and the amino acid, resulting in an aminoacyl-tRNA-synthetase-aminoacyl-adenylate complex. Secondly, the aminoacyl group is transferred from the enzyme to the target tRNA on which it remains in a high-energy state. Binding of the tRNA molecule to its recognition codon on the mRNA molecule then contacts the tRNA-bound high energy amino acid with the ribosome. Within the ribosome, the amino acid-loaded tRNA (aminoacyl tRNA) occupies a binding site (the A site) beside a second site (the P site) which carries a tRNA molecule whose amino acid is bound to the nascent polypeptide chain (peptidyl tNRA). The activated amino acid on the aminoacyl tRNA is sufficiently reactive for a peptide bond to form spontaneously between this amino acid and the next amino acid on the nascent polypeptide chain. GTP hydrolysis provides the energy for transferring the tRNA which is now loaded with the polypeptide chain from the A site to the P site of the ribosome, and this process is repeated until it reaches a stop codon.

There is a number of different steps at which translation can be regulated. These steps include binding of the ribosome to mRNA, the presence of mRNA secondary structure, the codon usage or the frequency of particular tRNAs. Specific regulatory mechanisms such as attenuation, too, may act at the translational level. An in-depth overview over many of these mechanisms can be found, for example, in Vellanoweth, R. L. (1993) "Translation and its Regulation", in: *Bacillus subtilis* and other Gram Positive Bacteria, Sonenshein, A. L., et al., Editors, ASM Press: Washington, D.C., pp. 699-711 and the references cited therein.

E. Protein Folding and Protein Secretion

Ribosomal synthesis of proteins leads to polypeptide chains which must adopt a three-dimensional form before the protein can function normally. The three-dimensional structure is achieved by a folding process. Polypeptide chains are flexible and (in principle) move readily and freely in solution until they adopt a conformation which leads to a more stable three-dimensional structure. Sometimes, however, it is difficult for proteins to fold correctly, either due to the environmental conditions (e.g. high temperature at which the kinetic energy present in the system makes it more difficult for the protein to reach the energy minimum of a stable structure) or due to the type of the protein itself (for example, hydrophobic regions in proteins closely located to one another tend to aggregate, thereby precipitating themselves from aqueous solutions).

Protein-like factors have been identified which can catalyze, accompany or otherwise support the folding of proteins and which are synthesized co- or posttranslationally. These protein-folding molecules include the prolyl-peptidyl isomerases (e.g. trigger factor, cyclophilin and FKBP homologs) and also proteins of the group of heat shock proteins (e.g. DnaK, DnaJ, GroEL, small heat shock proteins, HtpG and members of the Clp family (e.g. ClpA, ClpB, ClpW, ClpP and ClpX). Many of these proteins are important for the viability of cells: in addition to their function in protein folding, protein translocation and protein processing, they frequently serve as targets for the overall regulation of protein synthesis (see, for example, Bukau, B. (1993) Molecular Microbiology 9(4):671-680; Bukau, B., and Horwich, A. L. (1998) Cell 92(3):351-366; Hesterkamp, T., Bukau, C. (1996) FEBS Lett. 389(1):32-34; Yaron, A., Naider, F. (1993) Critical Reviews in Biochemistry and Molecular Biology 28(1):31-81; Scheibel, R., Buchner, J. (1998) Biochemical Pharmacology 56(6):675-682; Ellis, R. J., Hartl, F. U. (1996) FASEB Journal 10(1):20-26; Wawrzynow, A., et al. (1996) Molecular Microbiology 21(5):895-899; Ewalt, K. L., et al. (1997) Cell 90(3):491-500).

The chaperones identified previously act in two ways: they either bind to and stabilize polypeptides or provide an environment in which folding can take place without disruption. The former group, including, for example, DnaK, DnaJ and the heat shock proteins, binds directly to the nascent or wrongly folded polypeptide, frequently accompanied by ATP hydrolysis. Binding of the chaperone prevents the polypeptide from aggregating with other polypeptides and can force dissolution of these aggregates if they have already formed. After interaction with a second chaperone GrpE (which makes it possible for an ADP-ATP exchange to take place), the polypeptide is released in the molten-globule state and is able to fold. If the folding is wrong, the chaperones rebind to the wrongly folded protein and force its return to an unfolded state. This cycle can be repeated until the protein is correctly folded. In contrast to the first group of chaperones which simply bind to the polypeptide, the second group (e.g. GroEL/ES) not only binds to the polypeptide but encloses it completely so that it is protected from the environment. The GroEL/ES complex consists of two stacked 14-membered rings with a hydrophobic inner surface and a "lid" made of a 7-membered ring. In an ATP-dependent reaction, the polypeptide is drawn into the channel in the center of this complex, where it can fold without disruption by other polypeptides. Wrongly folded proteins are not released from the complex.

An important step in protein folding is the formation of disulfide bonds. These bonds, either within a subunit or between subunits of proteins, are important for protein stability. Disulfide bonds form readily in aqueous solution, and it is difficult to reverse a wrong disulfide bridge formation without the aid of a reducing environment. In order to support this process of correct disulfide bridge formation, the cytosol of most cells contains thiol-containing molecules such as glutathion or thioredoxin and their corresponding oxidation/reduction systems (Loferer, H., Hennecke, H. (1994) Trends in Biochemical Sciences 19(4):169-171).

At certain times, however, the folding of nascent polypeptide chain is not desirable, for example if these proteins are to be secreted. The folding process usually results in the hydrophobic regions of the protein being located in the center of said protein, removed from the aqueous solution, and the hydrophilic regions being presented on the outer surfaces of said protein. Although this conformation arrangement generates higher stability for the protein, it makes translocation of the protein via membranes more difficult, since the hydrophobic core of the membrane is per se incompatible with the hydrophilic exterior of the protein. Thus, the proteins synthesized by the cell, which have to be secreted to the exterior of the cell (e.g. cell surface enzymes and membrane receptors) or which have to be inserted into the membrane itself (e.g. transporter proteins and channel proteins) are usually secreted or inserted prior to folding. The same chaperones which prevent the aggregation of nascent polypeptide chains also prevent folding of polypeptides, until they are no longer needed. Thus, these proteins can "escort" nascent polypeptide chains to a suitable location in the cell, where they either are removed so as to enable folding or transfer the protein to a transport system which either secretes the polypeptide or supports its insertion into a membrane.

During the course of evolution, a specialized protein machinery has formed, which recognizes, binds, transports and processes proteins with specific prosequences (which are later removed from the protein by cleavage). Said machinery comprises a number of proteins which are collectively referred to as sec (type II secretion) system.(for an overview, see Gilbert, M., et al. (1995) Critical Reviews in Biotechnology 15(l):13-39 and references therein; Freudl, R. (1992) Journal of Biotechnology 23(3):231-240 and references therein; Neidhardt, F. C., et al. (1996) *E. coli* and *Salmonella*, ASM Press: Washington, D.C., pp. 967-978; Binet, R., et al. (1997) Gene 192(1):7-11 und Rapoport, T. A. (1986) Critical Reviews in Biochemistry 20(1):73-137 and references therein). The sec system comprises chaperones (e.g. SecA and SecB), integral membrane proteins which are also referred to as translocases (e.g. SecY, SecE and SecG) and signal peptidases (e.g. LepB). The nascent polypeptide with a prosequence leading to secretion is bound by SecB which transfers it to SecA on the inner surface of the cell membrane. SecA binds to the prosequence and, after ATP hydrolysis, inserts into the membrane and also forces part of the polypeptide through the membrane. The rest of the polypeptide is led through the membrane via a complex of translocases such as SecY, SecE and SecG. Finally, the signal peptidase removes the prosequence by cleavage and the polypeptide is located freely on the extracellular side of the membrane, where it folds spontaneously.

Sec-independent secretory mechanisms are also known. For example, the signal recognition particle-dependent pathway comprises. binding of a signal recognition particle (SRP) protein to the nascent polypeptide during its synthesis, thereby stopping the ribosome. A receptor for SRP on the inner surface of the membrane then binds the ribosome-polypeptide-SRP complex. GTP hydrolysis provides the energy required for transferring the complex to the sec-translocase complex on which the polypeptide is led across the membrane during its synthesis by the ribosome. It is known that other secretory mechanisms exist, which are specific for only a few proteins.

III. Elements and Methods of the Invention

The present invention is based, at least partially, on the detection of new molecules which are referred to herein as SES nucleic-acid and SES-protein molecules and which take part in the repair or recombination of DNA in *C. glutamicum*, transposition or other rearrangement of *C. glutamicum* DNA, gene expression in *C. glutamicum* (i.e. transcriptional or translational processes), protein folding or protein secretion of this microorganism. In one embodiment, the SES molecules take part in the repair or recombination of DNA, transposition of genetic material, gene expression (i.e. transcriptional or translational processes), protein folding or protein secretion in *Corynebacterium glutamicum*. In a preferred embodiment, the activity of the SES molecules of the invention affects the production of a fine chemical of interest by said microorganism with regard to the repair or recombination of DNA, transposition of DNA, gene expression, protein folding or protein secretion. In a particularly preferred embodiment, the activity of the SES molecules of the invention is modulated such that the activity of the cellular processes of *C. glutamicum*, in which the SES proteins of the invention are involved, (e.g. repair or recombination of DNA, transposition of DNA, gene expression, protein folding or protein secretion), is also modified, and this results directly or indirectly in a modulation of the yield, production and/or efficiency of production of a fine chemical of interest by *C. glutamicum*.

The term "SES protein" or "SES polypeptide" comprises proteins which are involved in a number of cellular processes which are related to genetic stability, gene expression, protein folding or protein secretion of *C. glutamicum*. For example, an SES protein may be involved in the DNA repair or in recombination mechanisms in *C. glutamicum*, in rearrangements of the genetic material of *C. glutamicum* (such as those mediated by transposons), in the transcription or translation of genes in this microorganism, in mediating protein folding in *C. glutamicum* (such as the activity of chaperones) or in the secretion of proteins from *C. glutamicum* cells (e.g. on the sec system). Examples of SES proteins comprise those which are encoded by the SES genes listed in Table 1 and Appendix A. The terms "SES gene" or "SES nucleic acid sequence" comprise nucleic acid sequences encoding an SES protein which comprises a coding region and corresponding untranslated 5' and 3' sequence regions. Examples of SES genes are those listed in Table 1. The terms "production" or "productivity" are known in the art and include the concentration of the fermentation products (for example of the fine chemical of interest, which is produced within a predetermined time interval and a predetermined fermentation volume (e.g. kg of product per h per 1)). The term "efficiency of production" comprises the time required by the cell for reaching a particular production quantity (for example, the time required by the cell for reaching a particular output rate of a fine chemical). The term "yield" or "product/carbon yield" is known in the art and comprises the efficiency of converting the carbon source into the product (i.e. the fine chemical). This is, for example, usually expressed as kg of product per kg of carbon source. Increasing the yield or production of the compound increases the amount of the molecules obtained or of the suitable obtained molecules of this compound in a particular culture volume over a predetermined period. The terms "biosynthesis" or "biosynthetic pathway" are known in the art and comprise the synthesis of a compound, preferably an organic compound, from intermediates by a cell, for example in a multistep process or highly regulated process. The terms "degradation" and "degradation pathway" are known in the art and comprise cleavage of a compound, preferably an organic compound, into degradation products (in more general terms: smaller or less complex molecules) by a cell, for example in a multistep process or highly regulated process. The term "metabolism" is known in the art and comprises the entirety of biochemical reactions which take place in an organism. The metabolism of a particular compound (e.g. the metabolism of an amino acid such as glycine) then comprises all biosynthetic, modification and degradation pathways in the cell, which relate to said compound. The term "DNA repair" is known in the art and includes cellular mechanisms by which the errors in the DNA (either due to damage such as, but not limited to, ultraviolet radiation, methylases, low-fidelity replication or mutagens) are excised and corrected. The term "recombination" or "DNA recombination" is known in the art and comprises cellular mechanisms which correct extended DNA damage which affects both strands of a DNA molecule via homologous recombination with another undamaged copy of the DNA molecule within the same cell. These repairs are usually of low fidelity and may result in gene rearrangements. The term "transposon" is known in the art and comprises a DNA element which can insert randomly into the genome of an organism and may result in the disruption of genes or their regulatory regions or in duplications, inversions, deletions and other gene arrangements. The term "protein folding" is known in the art and comprises the migration of a polypeptide chain through several three-dimensional configurations until the stable active three-dimensional configuration is attained. The formation of disulfide bonds and sequestering of hydrophobic region from the surrounding aqueous solution provides some of the driving forces for this protein folding process and correct folding can be enhanced by the activity of chaperones. The terms "secretion" or "protein secretion" are known in the art and comprise the movement of proteins from the cell interior to the cell exterior in a mechanism in which a system of secretory proteins enables their passage via the cell membrane to the cell exterior.

In another embodiment, the SES molecules of the invention are able to modulate the production of a molecule of interest, such as a fine chemical, in a microorganism such as *C. glutamicum*. There is a number of mechanisms by which modification of an SES protein of the invention can directly influence the yield, production and/or efficiency of production of a fine chemical from a *C. glutamicum* strain containing this modified protein. For example, modulation of proteins directly involved in transcription or translation (e.g. polymerases or ribosomes) so as to increase their number or activity should overall increase cellular transcription or translation (or the rate of these processes). This increased cellular gene expression should include those proteins which are involved in the biosynthesis of fine chemicals so that the yield, production or efficiency of production of one or more compounds of interest can be increased. Modifications of the transcriptional/translational protein machinery of *C. glutamicum* so as to modify regulation of these proteins may also enable the increased expression of genes involved in the production of fine chemicals. Modulation of the activity of a number of proteins involved in peptide folding may increase the overall production of correctly folded molecules in the cell, thereby increasing the possibility of proteins of interest (e.g. proteins of the biosynthesis of fine chemicals) functioning correctly. Furthermore, it may be possible, by mutating proteins involved in the secretion from *C. glutamicum* so as to increase their number or activity, to increase secretion of a fine chemical (e.g. an enzyme) from cells in a fermentative culture from which said fine chemical can be readily obtained.

Genetic modification of the SES molecules of the invention may also modulate indirectly the production of one or more fine chemicals. For example, it is possible, by increasing the number or activity of a DNA-repair or DNA-recombination protein of the invention, to increase the ability of the cell to detect and repair DNA damage. This should effectively increase the ability of the cell to keep a mutated gene in its genome and thereby increase the probability of a transgene genetically introduced into *C. glutamicum* (which encodes, for example, a protein which increases the biosynthesis of a fine chemical) not being lost during cultivation of the microorganism. In contrast, it may be possible, by reducing the number or activity of one or more DNA-repair or DNA-recombination proteins, to increase the genetic instability of the organism. These manipulations should improve the ability of said organism to be modified by mutagenesis, without correcting the introduced mutation. The same is true for proteins which are involved in the transposition or rearrangement of genetic elements in *C. glutamicum* (e.g. transposons). Mutagenesis of these proteins so as to either increase or reduce their number or activity makes it possible to increase or reduce at the same time the genetic stability of the microorganism. This crucially affects the possibility of introducing another mutation into *C. glutamicum* and of retaining the introduced mutation. Transposons likewise provide a suitable mechanism which makes possible the mutagenesis of *C. glutamicum*; duplication of genes of interest (e.g. genes of the biosynthesis of fine chemicals) as well as disruption of unwanted genes (e.g. genes involved in the degradation of fine chemicals of interest) can be readily carried out by means of transposon mutagenesis.

It may be possible, by modulating one or more proteins (e.g. sigma factors) which are involved in the regulation of transcription or translation in reaction to particular environmental conditions, to prevent the cell from slowing down or stopping protein synthesis under unfavorable environmental conditions as found in a large-scale fermentative culture. This should increase gene expression, and this in turn may enable the increased biosynthesis of fine chemicals of interest under said conditions. Many of these secreted proteins have functions which are important for cell viability (e.g. cell surface proteases or cell surface receptors). Changing the secretion pathway so that said proteins are transported more easily to their extracellular location may increase the overall viability of the cell and thus result in higher numbers of *C. glutamicum* cells which are able to produce fine chemicals during a large-scale cultivation. Since it is furthermore known that particular bacterial protein secretion pathways (e.g. the sec system) are also involved in the insertion of integral membrane proteins (e.g. receptors, channels, pores, or transporters) into the membrane, modulating the activity of proteins involved in protein secretion from *C. glutamicum* may affect the ability of the cell to eliminate waste products or to import necessary metabolites. If the activity of these secretory proteins is increased, the ability of the cell to produce fine chemicals (due to an increased presence of transporters/channels in the membrane, which can import nutrients or eliminate waste products) may likewise be increased. If the activity of said secretory proteins is reduced, it may be possible that there are not enough nutrients for supporting the overproduction of compounds of interest or that waste products interfere with this biosynthesis.

A suitable starting point for preparing the nucleic acid sequences of the invention is the genome of a *Corynebacterium glutamicum* strain which can be obtained from the American Type Culture Collection under the name ATCC 13032.

The nucleic acid sequences of the invention can be prepared from these nucleic acid sequences via the modifications denoted in Table 1, using conventional methods.

The SES protein of the invention or a biologically active section or fragment thereof may take part in the repair or recombination of DNA, transposition of genetic material, gene expression (i.e. transcriptional or translational processes), protein folding or protein secretion in *Corynebacterium glutamicum* or have one or more of the activities described in table 1.

The following subsections describe various aspects of the invention in more detail:

A. Isolated Nucleic Acid Molecules

One aspect of the invention relates to isolated nucleic acid molecules which encode SES polypeptides or biologically active sections thereof and to nucleic acid fragments which are sufficient for the use as hybridization probes or primers for identifying or amplifying SES-encoding nucleic acids (e.g. SES DNA). The term "nucleic acid molecule", as used herein, is intended to comprise DNA molecules (e.g. cDNA or genomic DNA) and RNA molecules (e.g. mRNA) and also DNA or RNA analogs generated by means of nucleotide analogs. Moreover, this term comprises the untranslated sequence located at the 3' and 5' ends of the coding gene region: at least about 100 nucleotides of the sequence upstream of the 5' end of the coding region and at least about 20 nucleotides of the sequence downstream of the 3' end of the coding region of the gene. The nucleic acid molecule may be single-stranded or double-stranded but is preferably a double-stranded DNA. An "isolated" nucleic acid molecule is removed from other nucleic acid molecules which are present in the natural source of the nucleic acid. An "isolated" nucleic acid preferably does not have any sequences which flank the nucleic acid naturally in the genomic DNA of the organism from which the nucleic acid originates (for example sequences located at the 5' or 3' end of the nucleic acid). In various embodiments, the isolated SES nucleic acid molecule may have, for example, less than about 5 kb, 4 kb, 3 kb, 2 kb, 1 kb, 0.5 kb or 0.1 kb of the nucleotide sequences which naturally flank the nucleic acid molecule in the genomic DNA of the cell from which the nucleic acid originates (e.g. a *C. glutamicum* cell). In addition to this, an "isolated" nucleic acid molecule such as a cDNA molecule may be essentially free of another cellular material or culture medium, if prepared by recombinant techniques, or free of chemical precursors or other chemicals, if synthesized chemically.

A nucleic acid molecule of the invention, for example a nucleic acid molecule having a nucleotide sequence of Appendix A or a section thereof, may be prepared by means of molecular biological standard techniques and the sequence information provided here. For example, a *C. glutamicum* SES CDNA may be isolated from a *C. glutamicum* bank by using a complete sequence from Appendix A or a section thereof as hybridization probe and by using standard hybridization techniques (as described, for example, in Sambrook, J., Fritsch, E. F. and Maniatis, T. Molecular Cloning: A Laboratory Manual. 2nd Ed., Cold Spring Harbor Laboratory, Cold Spring Harbor Laboratory Press, Cold Spring Harbor, N.Y., 1989). Moreover, a nucleic acid molecule comprising a complete sequence from Appendix A or a section thereof can be isolated via polymerase chain reaction, using the oligonucleotide primers produced on the basis of said sequence (for example, it is possible to isolate a nucleic acid molecule comprising a complete sequence from Appendix A or a section thereof via polymerase chain reaction by using oligonucleotide primers which have been produced on the basis of this same sequence of Appendix A). For example, mRNA can be isolated from normal endothelial cells (for example via the guanidinium thiocyanate extraction method of Chirgwin et al. (1979) Biochemistry 18: 5294-5299), and the cDNA can be prepared by means of reverse transcriptase (e.g. Moloney-MLV reverse transcriptase, available from Gibco/BRL, Bethesda, MD, or AMV reverse transcriptase, available from Seikagaku America, Inc., St. Petersburg, Fla.). Synthetic oligonucleotide primers for amplification via polymerase chain reaction can be produced on the basis of any of the nucleotide sequences shown in Appendix A. A nucleic acid of the invention may be amplified by means of cDNA or, alternatively, genomic DNA as template and of suitable oligonucleotide primers according to PCR standard amplification techniques. The nucleic acid amplified in this way may be cloned into a suitable vector and characterized by DNA sequence analysis. Oligonucleotides corresponding to an SES nucleotide sequence may furthermore be prepared by standard syntheses using, for example, an automatic DNA synthesizer.

In a preferred embodiment, an isolated nucleic acid molecule of the invention comprises one of the nucleotide sequences listed in Appendix A.

In a further preferred embodiment, an isolated nucleic acid molecule of the invention comprises a nucleic acid molecule complementary to any of the nucleotide sequences shown in Appendix A or a section thereof, said nucleic acid molecule being sufficiently complementary to any of the nucleotide sequences shown in Appendix A for it to hybridize with any of the sequences indicated in Appendix A, resulting in a stable duplex.

In one embodiment, the nucleic acid molecule of the invention encodes a protein or a section thereof comprising an amino acid sequence which is sufficiently homologous to an amino acid sequence of Appendix B for the protein or a section thereof to retain the ability to take part in the repair or recombination of DNA, transposition of genetic material, gene expression (i.e. transcriptional or translational processes), protein folding or protein secretion in *Corynebacterium glutamicum*. The term "sufficiently homologous", as used herein, relates to proteins or sections thereof whose amino acid sequences have a minimum number of identical or equivalent amino acid residues (for example an amino acid residue having a side chain similar to that of an amino acid residue in any of the sequences of Appendix B) compared to an amino acid sequence of Appendix B so that the protein or a section thereof is able to take part in the repair or recombination of DNA, transposition of genetic material, gene expression (i.e. transcriptional or translational processes), protein folding or protein secretion in *Corynebacterium glutamicum*. Proteins involved in genetic stability, gene expression, protein folding or protein secretion of *C. glutamicum*, as described herein, may play a part in the production and secretion of one or more fine chemicals. Examples of these activities are likewise described herein. Thus the "function of an SES protein" contributes directly or indirectly to the yield, production and/or efficiency of production of one or more fine chemicals. Table 1 shows examples of SES proteins.

Sections of proteins encoded by the SES nucleic acid molecules of the invention are preferably biologically active sections of any of the SES proteins. The term "biologically active section of an SES protein", as used herein, is intended to comprise a section, for example a domain/a motif, of an SES protein, which takes part in the repair or recombination of DNA, transposition of genetic material, gene expression (i.e. transcriptional or translational processes), protein folding or protein secretion in *Corynebacterium glutamicum*, or has any of the activities depicted in table 1. In order to determine whether an SES protein or a biologically active section thereof is able to take part in the repair or recombination of DNA, transposition of genetic material, gene expression (i.e. transcriptional or translational processes), protein folding or protein secretion in *Corynebacterium glutamicum* an enzyme activity assay may be carried out.

These assay methods, as described in detail in example 8 of the examples, are familiar to the skilled worker.

In addition to naturally occurring variants of the SES sequence, which may exist in the population, the skilled worker is likewise aware of the fact that changes may be introduced into a nucleotide sequence of Appendix A by mutation, resulting in a change in the amino acid sequence of the encoded SES protein without impairing the functionality of said SES protein. It is possible, for example, to produce in a sequence of Appendix A nucleotide substitutions which result in amino acid substitutions at "nonessential" amino acid residues. A "nonessential" amino acid residue is a residue which can be modified in the wild-type sequence of any of the SES proteins (Appendix B) without modifying the activity of said SES protein, whereas an "essential" amino acid residue is required for SES-protein activity. However, other amino acid residues (e.g. nonconserved or merely semiconserved amino acid residues in the domain with SES activity) may not be essential for activity and thus can probably be modified without modifying SES activity.

An isolated nucleic acid molecule encoding an SES protein which is homologous to a protein sequence of Appendix B may be generated by introducing one or more nucleotide substitutions, additions or deletions into a nucleotide sequence of Appendix A so that one or more amino acid substitutions, additions or deletions are introduced into the encoded protein. The mutations may be introduced into any of the sequences of Appendix A by standard techniques such as site-directed mutagenesis and PCR-mediated mutagenesis. Preference is given to introducing conservative amino acid substitutions at one or more of the predicted nonessential amino acid residues. A "conservative amino acid substitution" replaces the amino acid residue by an amino acid residue with a similar side chain. Families of amino acid residues with similar side chains have been defined in the art. These families comprise amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine), nonpolar side chains (e.g. alanine, valine, leucine, isoleucine, proline, phenylalanine, methionine, tryptophan), beta-branched side chains (e.g. threonine, valine, isoleucine) and aromatic side chains (e.g. tyrosine, phenylalanine, tryptophan, histidine). A predicted nonessential amino acid residue in an SES protein is thus preferably replaced by another amino acid residue of the same side-chain family. In a further embodiment, the mutations may alternatively be introduced randomly over the entire or over part of the SES-encoding sequence, for example by saturation mutagenesis, and the resulting mutants may be tested for an SES activity described herein in order to identify mutants maintaining SES activity. After mutagenesis of any of the sequences of Appendix A, the encoded protein may be expressed recombinantly, and the activity of said protein may be determined, for example, using the assays described herein (see example 8 of the examples).

B. Recombinant Expression Vectors and Host Cells

A further aspect of the invention relates to vectors, preferably expression vectors, containing a nucleic acid which encodes an SES protein (or a section thereof). The term "vector" as used herein, relates to a nucleic acid molecule capable of transporting another nucleic acid to which it is bound. One type of vector is a "plasmid" which term means a circular double-stranded DNA loop into which additional DNA segments can be ligated. Another type of vector is a viral vector, and here additional DNA segments can be ligated into the viral genome. Certain vectors are capable of replicating autonomously in a host cell into which they have been introduced (for example bacterial vectors with bacterial origin of replication and episomal mammalian vectors). Other vectors (e.g. nonepisomal mammalian vectors) are integrated into the genome of a host cell when introduced into said host cell and thereby replicated together with the host genome. Moreover, particular vectors are capable of controlling the expression of genes to which they are functionally linked. These vectors are referred to as "expression vectors". Normally, expression vectors which may be used in DNA recombination techniques are in the form of plasmids. In the present description, "plasmid" and "vector" may be used interchangeably, since the plasmid is the most commonly used type of vector. However, the present invention is intended to comprise other types of expression vectors such as viral vectors (for example replication-deficient retroviruses, adenoviruses and adenovirus-related viruses), which exert similar functions.

The recombinant expression vectors of the invention comprise a nucleic acid of the invention in a form which is suitable for expressing said nucleic acid in a host cell, meaning that the recombinant expression vectors comprise one or more regulatory sequences which are selected on the basis of the host cells to be used for expression and which are functionally linked to the nucleic acid sequence to be expressed. In a recombinant expression vector, the term "functionally linked" means that the nucleotide sequence of interest is bound to the regulatory sequence(s) such that expression of said nucleotide sequence is possible (for example in an in vitro transcription/translation system or in a host cell, if the vector has been introduced into said host cell). The term "regulatory sequence" is intended to comprise promoters, enhancers and other expression control elements (e.g. polyadenylation signals). These regulatory sequences are described, for example, in Goeddel: Gene Expression Technology: Methods in Enzymology 185, Academic Press, San Diego, Calif. (1990). Regulatory sequences comprise those which control constitutive expression of a nucleotide sequence in many types of host cells and those which control expression of the nucleotide sequence only in particular host cells. The skilled worker understands that designing an expression vector may depend on factors such as the choice of host cell to be transformed, the desired extent of protein expression, etc. The expression vectors of the invention may be introduced into the host cells so as to prepare proteins or peptides, including fusion proteins or fusion peptides, which are encoded by the nucleic acids as described herein (e.g. SES proteins, mutated forms of SES proteins, fusion proteins, etc.).

The recombinant expression vectors of the invention may be designed for expressing SES proteins in prokaryotic or eukaryotic cells. For example, SES genes may be expressed in bacterial cells such as *C. glutamicum*, insect cells (using baculovirus expression vectors), yeast cells and other fungal cells (see Romanos, M. A. et al. (1992) "Foreign gene expression in yeast: a review", Yeast 8: 423-488; van den Hondel, C. A. M. J. J. et al. (1991) "Heterologous gene expression in filamentous fungi" in: More Gene Manipulations in Fungi, J. W. Bennet & L. L. Lasure, Editors, pp. 396-428: Academic Press: San Diego; and van den Hondel, C. A. M. J. J. & Punt, P. J. (1991) "Gene transfer systems and vector development for filamentous fungi in: Applied Molecular Genetics of Fungi, Peberdy, J. F. et al., Editors, pp. 1-28, Cambridge University Press: Cambridge), algal cells and cells of multicellular plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.: 583-586) or mammalian cells. Suitable host cells are further discussed in Goeddel, Gene Expression Technology: Methods in Enzymology 185, Academic Press, San Diego, Calif. (1990). As an alternative, the recombinant expression vector may be transcribed and translated in vitro, for example by using regulatory sequences of the T7 promoter and T7 polymerase.

Proteins are expressed in prokaryotes mainly by using vectors containing constitutive or inducible promoters which control expression of fusion or nonfusion proteins. Fusion vectors control a number of amino acids to a protein encoded therein, usually at the amino terminus of the recombinant protein. These fusion vectors usually have three tasks: 1) enhancing the expression of recombinant protein; 2) increasing the solubility of the recombinant protein; and 3) supporting the purification of the recombinant protein by acting as a ligand in affinity purification. Often a proteolytic cleavage site is introduced into fusion expression vectors at the junction of fusion unit and recombinant protein so that the recombinant protein can be separated from the fusion unit after purifying the fusion. protein. These enzymes and their corresponding recognition sequences comprise factor Xa, thrombin and enterokinase.

Common fusion expression vectors comprise pGEX (Pharmacia Biotech Inc; Smith, D. B. and Johnson, K. S. (1988) Gene 67: 31-40), pMAL (New England Biolabs, Beverly, Mass.) und pRIT 5 (Pharmacia, Piscataway, N.J.), in which glutathione S-transferase (GST), maltose E-binding protein and protein A, respectively, are fused to the recombinant target protein. In one embodiment, the coding sequence of the SES protein is cloned into a pGEX expression vector such that a vector is generated, which encodes a fusion protein comprising, from N terminus to C terminus, GST—thrombin cleavage site—protein X. The fusion protein may be purified via affinity chromatography by means of a glutathione-agarose resin. The recombinant SES protein which is not fused to GST may be obtained by cleaving the fusion protein with thrombin.

Examples of suitable inducible nonfusion *E. coli* expression vectors include pTrc (Amann et al., (1988) Gene 69: 301-315) and pET 11d (Studier et al. Gene Expression Technology: Methods in Enzymology 185, Academic Press, San Diego, Calif. (1990) 60-89). The target gene expression from the pTrc vector is based on transcription from a hybrid trp-lac fusion promoter by host RNA polymerase. The target gene expression from the pET11d vector is based on transcription from a T7-gn10-lac fusion promoter, which is mediated by a coexpressed viral RNA polymerase (T7 gn1). This viral polymerase is provided by the BL21 (DE3) or EMS174 (DE3) host strain by a resident λ prophage which harbors a T7 gn1 gene under the transcriptional control of the lacUV 5 promoter.

One strategy for maximizing expression of the recombinant protein is to express said protein in a host bacterium whose ability to proteolytically cleave said recombinant protein is disrupted (Gottesman, S. Gene Expression Technology: Methods in Enzymology 185, Academic Press, San Diego, Calif. (1990) 119-128). Another strategy is to modify the nucleic acid sequence of the nucleic acid to be inserted into an expression vector such that the individual codons for each amino acid are those which are preferably used in a bacterium selected for expression, such as *C. glutamicum* (Wada et al. (1992) Nucleic Acids Res. 20: 2111-2118). This modification of the nucleic acid sequences of the invention may be carried out by standard techniques of DNA synthesis.

In a further embodiment, the SES-protein expression vector is a yeast expression vector. Examples of vectors for expression in the yeast *S. cerevisiae* include pYepSec1 (Baldari et al., (1987). Embo J. 6: 229-234), pMFa (Kurjan and Herskowitz (1982) Cell 30: 933-943), pJRY88 (Schultz et al. (1987) Gene 54: 113-123) and pYES2 (Invitrogen Corporation, San Diego, Calif). Vectors and methods for constructing vectors which are suitable for use in other fungi such as filamentous fungi include those which are described in detail in: van den Hondel, C. A. M. J. J. & Punt, P. J. (1991) "Gene transfer systems and vector development for filamentous fungi, in: Applied Molecular Genetics of fungi, J. F. Peberdy et al., Editors, pp. 1-28, Cambridge University Press: Cambridge.

As another alternative, it is possible to express the SES proteins of the invention in insect cells using baculovirus expression vectors. Baculovirus vectors available for expression of proteins in cultured insect cells (e.g. Sf9 cells) include the pAc series (Smith et al., (1983) Mol. Cell Biol. 3: 2156-2165) and the pVL series (Lucklow and Summers (1989) Virology 170: 31-39).

In a further embodiment, the SES proteins of the invention may be expressed in cells of unicellular plants (such as algae) or in cells of the higher plants (e.g. spermatophytes such as crops). Examples of expression vectors of plants include those which are described in detail in: Bekker, D., Kemper, E., Schell, J. and Masterson, R. (1992) "New plant binary vectors with selectable markers located proximal to the left border", Plant Mol. Biol. 20: 1195-1197; and Bevan, M. W. (1984) "Binary *Agrobacterium* vectors for plant transformation", Nucl. Acids Res. 12: 8711-8721.

A further embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6: 187-195). When used in mammalian cells, the control functions of the expression vector are often provided by viral regulatory elements. Commonly used promoters are derived, for example, from polyoma, adenovirus 2, cytomegalovirus and simian virus 40. Other suitable expression systems for prokaryotic and eukaryotic cells can be found in chapters 16 and 17 of Sambrook, J., Fritsch, E. F. and Maniatis, T., Molecular cloning: A Laboratory Manual, 2nd Edition, Cold Spring Harbor Laboratory, Cold Spring Harbor Laboratory Press, Cold Spring Harbor, N.Y., 1989.

In a further embodiment, the recombinant mammalian expression vector may preferably cause expression of the nucleic acid in a particular cell type (for example, tissue-specific regulatory elements are used for expressing the nucleic acid). Tissue-specific regulatory elements are known in the art. Non-limiting examples of suitable tissue-specific promoters include the albumin promoter (liver-specific; Pinkert et al. (1987) Genes Dev. 1: 268-277), lymphoid-specific promoters (Calame und Eaton (1988) Adv. Immunol. 43: 235-275), in particular promoters of T-cell receptors (Winoto and Baltimore (1989) EMBO J. 8: 729-733) and immunoglobulins (Banerji et al. (1983) Cell 33: 729-740; Queen and Baltimore (1983) Cell 33: 741-748), neuron-specific promoters (e.g. the neurofilament promoter; Byrne and Ruddle (1989) PNAS 86: 5473-5477), pancreas-specific promoters (Edlund et al., (1985) Science 230: 912-916) and mamma-specific promoters (e.g. milk serum promoter; U.S. Pat. No. 4,873,316 and European Patent Application document-No. 264 166). Development-regulated promoters for example the murine hox promoters (Kessel and Gruss (1990) Science 249: 374-379) and the α-fetoprotein promoter (Campes and Tilghman (1989) Genes Dev. 3: 537-546), are likewise included.

Moreover, the invention provides a recombinant expression vector comprising an inventive DNA molecule which has been cloned into the expression vector in antisense direction. This means that the DNA molecule is functionally linked to a regulator sequence such that an RNA molecule which is antisense to SES mRNA can be expressed (via transcription of the DNA molecule). It is possible to select regulatory sequences which are functionally bound to a nucleic acid cloned in antisense direction and which control continuous expression of the antisense RNA molecule in a multiplicity of cell types; for example, it is possible to select viral promoters and/or enhancers or regulatory sequences which control the constitutive tissue-specific or cell type-specific expression of antisense RNA. The antisense expression vector may be in the form of a recombinant plasmid, phagemid or attenuated virus and produces antisense nucleic acids under the control of a highly effective regulatory region whose activity is determined by the cell type into which the vector is introduced. The regulation of gene expression by means of antisense genes is discussed in Weintraub, H. et al., Antisense-RNA as a molecular tool for genetic analysis, Reviews—Trends in Genetics, Vol. 1(1) 1986.

A further aspect of the invention relates to host cells into which a recombinant expression vector of the invention has been introduced. The terms "host cell" and "recombinant host cell" are used interchangeably herein. Naturally, these terms relate not only to a particular target cell but also to the progeny or potential progeny of this cell. Since particular modifications may appear in successive generations, due to mutation or environmental factors, this progeny is not necessarily identical to the parental cell but is still included within the scope of the term as used herein.

A host cell may be a prokaryotic or eukaryotic cell. For example, an SES protein may be expressed in bacterial cells such as *C. glutamicum*, insect cells, yeast cells or mammalian cells (such as Chinese hamster ovary (CHO) cells or COS cells). Other suitable host cells are familiar to the skilled worker. Microorganisms which are related to *Corynebacterium glutamicum* and can be used in a suitable manner as host cells for the nucleic acid and protein molecules of the invention are listed in Table 3.

Conventional transformation or transfection methods can be used to introduce vector DNA into prokaryotic or eukaryotic cells. The terms "transformation" and "transfection", "conjugation" and "transduction", as used herein, are intended to comprise a multiplicity of methods known in the art for introducing foreign nucleic acid (e.g. DNA) into a host cell, including calcium phosphate or calcium chloride coprecipitation, DEAE dextran-mediated transfection, lipofection, natural competence, chemically mediated transfer or electroporation. Suitable methods for transformation or transfection of host cells can be found in Sambrook et al. (Molecular Cloning: A Laboratory Manual. 2nd Edition, Cold Spring Harbor Laboratory, Cold Spring Harbor Laboratory Press, Cold Spring Harbor, N.Y., 1989) and other laboratory manuals.

In the case of stable transfection of mammalian cells, it is known that, depending on the expression vector used and transfection technique used, only a small proportion of the cells can integrate the foreign DNA into their genome. These integrants are usually identified and selected by introducing a gene which encodes a selectable marker (e.g. resistant to antibiotics) together with the gene of interest into the host cells. Preferred selectable markers include those which impart resistance to drugs such as G418, hygromycin and methotrexate. A nucleic acid which encodes a selectable marker may be introduced into a host cell on the same vector that encodes an SES protein or may be introduced in a separate vector. Cells which have been stably transfected with the introduced nucleic acid may, for example, be identified by drug selection (for example, cells which have integrated the selectable marker survive, whereas the other cells die).

A homologous recombined microorganism is generated by preparing a vector which contains at least one SES-gene section into which a deletion, addition or substitution has been introduced in order to modify, for example functionally disrupt, the SES gene. Said SES gene is preferably a *Corynebacterium glutamicum* SES gene, but it is also possible to use a homolog from a related bacterium or even from a mammalian, yeast or insect source. In a preferred embodiment, the vector is designed such that homologous recombination functionally disrupts the endogenous SES gene (i.e., the gene no longer encodes a functional protein; also referred to as "knockout" vector). As an alternative, the vector may be designed such that homologous recombination mutates or otherwise modifies the endogenous SES gene which, however, still encodes the functional protein (for example, the regulatory region located upstream may be modified such that thereby expression of the endogenous SES protein is modified.). The modified SES-gene fraction in the homologous recombination vector is flanked at its 5' and 3' ends by additional nucleic acids of the SES gene, which makes possible a homologous recombination between the exogenous SES gene carried by the vector and an endogenous SES gene in a microorganism. The length of the additional flanking SES nucleic acid is sufficient for a successful homologous recombination with the endogenous gene. Usually, the vector contains several kilobases of flanking DNA (both at the 5' and the 3' ends) (see, for example, Thomas, K. R. and Capecchi, M. R. (1987) Cell 51: 503, for a description of homologous recombination vectors). The vector is introduced into a microorganism (e.g. by electroporation) and cells in which the introduced SES gene has homologously recombined with the endogenous SES gene are selected using methods known in the art.

In another embodiment, it is possible to produce recombinant microorganisms which contain selected systems which make possible a regulated expression of the introduced gene. The insertion of an SES gene into a vector, as a result of which it is brought under the control of the lac operon, enables, for example, SES-gene expression only in the presence of IPTG. These regulatory systems are known in the art.

A host cell of the invention, such as a prokaryotic or eukaryotic host cell in culture, may be used for producing (i.e. expressing) an SES protein. Moreover, the invention provides methods for producing SES proteins by using the host cells of the invention. In one embodiment, the method comprises the cultivation of the host cell of the invention (into which a recombinant expression vector encoding an SES protein has been introduced or in whose genome a gene encoding a wild-type or modified SES protein has been introduced) in a suitable medium until the SES protein has been produced. In a further embodiment, the method comprises isolating the SES proteins from the medium or the host cell.

C. Uses and Methods of the Invention

The nucleic acid molecules, proteins, protein homologs, fusion proteins, primers, vectors and host cells described herein may be used in one or more of the following methods: identification of *C. glutamicum* and related organisms, mapping of genomes of organisms related to *C. glutamicum*, identification and localization of *C. glutamicum* sequences of interest, evolutionary studies, determination of SES-protein regions required for function, modulation of the activity of an SES protein; modulation of the metabolism of one or more cell membrane components; modulation of transmembrane transport of one or more compounds and modulation of the cellular production of a compound of interest, such as a fine chemical. The SES nucleic acid molecules of the invention have a multiplicity of uses. First, they may be used for identifying an organism as *Corynebacterium glutamicum* or close relatives thereof. They may also be used for identifying the presence of *C. glutamicum* or a relative thereof in a mixed population of microorganisms. The invention provides the nucleic acid sequences of a number of *C. glutamicum* genes. Probing the extracted genomic DNA of a culture of a uniform or mixed population of microorganisms under stringent conditions with a probe which covers a region of a *C. glutamidum* gene which is unique for this organism makes it possible to determine whether said organism is present. Although *Corynebacterium glutamicum* itself is nonpathogenic, it is related to pathogenic species such as *Corynebacterium diphtheriae*. The detection of such an organism is of substantial clinical importance.

The nucleic acid and protein molecules of the invention may furthermore serve as markers for particular regions of the genome. This is suitable not only for mapping the genome but also for functional studies of *C. glutamicum* proteins. The genomic region to which a particular *C. glutamicum* DNA-binding protein binds may be identified, for example, by cleaving the *C. glutamicum* genome and incubating the fragments with the DNA-binding protein. Those fragments which bind the protein may additionally be probed with the nucleic acid molecules of the invention, preferably by using ready detectable labels; binding of such a nucleic acid molecule to the genomic fragment makes it possible to locate the fragment on the map of the *C. glutamicum* genome, and, when carrying out the process several times using different enzymes, facilitates rapid determination of the nucleic acid sequence to which the protein binds. Moreover, the nucleic acid molecules of the invention may be sufficiently homologous to the sequences of related species for these nucleic acid molecules to serve as markers for constructing a genomic map in related bacteria (e.g. *Brevibacterium lactofermentum*).

The SES nucleic acid molecules of the invention are likewise suitable for evolutionary studies and protein structure studies. The metabolic and transport processes in which the molecules of the invention are involved are utilized by a multiplicity of prokaryotic and eukaryotic cells; comparison, of the sequences of the nucleic acid molecules of the invention with those encoding similar enzymes of other organisms makes it possible to determine the degree of evolutionary relationship of said organisms. Correspondingly, such a comparison makes it possible to determine which sequence regions are conserved and which are not, and this can be helpful in determining those regions of the protein, which are essential for enzyme function. This type of determination is valuable for protein engineering studies and may give an indication as to how much mutagenesis the protein can tolerate without losing its function.

Manipulation of the SES nucleic acid molecules of the invention may cause the production of SES proteins with functional differences to wild-type SES proteins. These proteins may be improved with respect to their efficiency or activity, may be present in the cell in larger amounts than normal or may be weakened with respect to their efficiency or activity.

This modulation of the activity of proteins involved in DNA repair, recombination or transposition in *C. glutamicum* should influence the genetic stability of the cell. It is possible, for example, to reduce the ability of the cell to correct genetic errors by reducing the number or activity of proteins involved in DNA-repair mechanisms, and this should enable mutations of interest to be introduced more easily into the genome (such as those encoding proteins involved in the production of fine chemicals). The increase in the activity or number of transposons should likewise result in an increased rate of mutations in the genome and may make possible simple doubling of genes of interest (for example those encoding proteins involved in the production of fine chemicals) or disruption of undesirable genes (for example those encoding proteins for degrading fine chemicals). In contrast, reducing the number or activity of transposons or increasing the number or activity of DNA-repair proteins can possibly increase the genetic stability of *C. glutamicun*, and this in turn should result in better maintenance of introduced mutations in these microorganisms over several generations in culture. Ideally, the activity of one or more DNA repair systems is reduced and the activity of one or more transposons is increased during mutagenesis and strain construction, but the opposite happens, if the mutation of interest has been attained in the strain. This manipulation is possible by putting one or more DNA-repair genes or transposons under the control of an inducible repressor.

The modulation of proteins involved in transcription and translation in *C. glutamicum* may have direct and indirect effects on the production of a fine chemicals from these microorganisms. For example, manipulation of a protein which translates a gene directly (e.g. a polymerase) or regulates transcription directly (a repressor or activator protein) makes it possible to influence directly the expression of the target gene. In the case of genes which encode a protein involved in the biosynthesis or degradation of a fine chemical, this type of genetic manipulation should have a direct effect on the production of said fine chemical. Mutagenesis of a repressor protein so that it is no longer able to repress its target gene or mutagenesis of an activator protein so as to optimize its activity should result in increased transcription of the target gene. If the target gene is, for example, a gene of fine-chemical biosynthesis, the result may be an increased production of this chemical due to the overall larger number of for available transcripts of this gene, and this likewise should increase the amount of the protein. The increase in the amount or activity of a repressor protein for a target sequence or the reduction in the amount or activity of an activator protein for a target sequence should, if said sequence is, for example, a protein for the degradation of fine chemicals, result in a similar increase in the production of said fine chemical.

The manipulation of proteins involved in transcription and translation may also affect the production of fine chemicals indirectly. Modulation of the activity or number of transcription factors (e.g. the sigma factors) or of translational repressors/activators which regulate globally transcription in *C. glutamicum* in reaction to environmental or metabolic factors should make it possible to uncouple cellular transcription from environmental or metabolic regulation. This in turn could enable a continuous transcription under conditions which usually ought to slow down or stop gene expression, such as unfavorable conditions (e.g. high temperature, low oxygen content, high level of waste products) which are present in a large-scale fermentative culture. Increasing the rate of expression of the gene (e.g. gene of fine-chemical biosynthesis) in these situations may also increase the overall rate of the production of fine product, at least due to the comparatively larger number of proteins of fine-chemical biosynthesis in the cell. Principles and examples of modification of transcriptional and translational regulation are described, for example, in Lewin, B. (1990) Genes IV, Part. 3: "Controlling procaryotic genes by transcription", Oxford Univ. Press: Oxford, pp. 213-301.

The modulation of the activity or number of proteins involved in polypeptide folding (e.g. chaperones) may make it possible overall to increase the production of correctly folded molecules in the cell. This has two effects: firstly, an overall increase in the number of proteins in the cell, due to the fact that fewer proteins are wrongly folded and degraded, and, secondly, an increase in the amount of a given protein which is correctly folded and thus active (see, for example, Thomas, J. G., Baneyx, F. (1997) Protein Expression and Purification 11(3): 289-296; Luo, Z. H., and Hua, Z. C. (1998) Biochemistry and Molecular Biology International 46(3):471-477; Dale, G. E., et al. (1994) Protein Engineering 7(7):925-931; Amrein, K. E. et al. (1995) Proc. Natl. Acad. Sci. U.S.A. 92(4):1048-1052 and Caspers, P., et al. (1994) Cell. Mol. Biol. 40(5):635-644). Although such mutations increase the number of active proteins of any kind, they may produce an additive effect on the amount of correctly folded active protein of interest, when they are coupled with additional mutations which increase the activity or amount of, for example, a protein of fine-chemical biosynthesis.

The manipulation of proteins involved in the secretion of polypeptides from *C. glutamicum*, so that their activity or number is improved, can directly improve secretion of a proteinaceous fine chemical (e.g. an enzyme) from this microorganism. It is considerably easier to harvest and purify fine chemicals if they are secreted into the medium of a large-scale culture than if they are retained in the cell, so that the yield and production of a fine chemical should increase due to this modification of the secretion system. The genetic manipulations of these secretion proteins may also lead to direct improvements of the production of one or more fine chemicals. Firstly, the increased or reduced activity of one or more *C. glutamicum* secretion systems (as it is produced by mutagenesis of one or more SES proteins involved in these pathways) may result in overall increased or reduced secretion rates from the cell. Many of these secreted proteins have functions which are important for cell viability (e.g. cell surface proteases or cell surface receptors). A change in the secretion pathway so that these proteins are transported more easily to their extracellular location may increase the overall viability of the cell and thus result in higher numbers of *C. glutamicum* cells which are able to produce fine chemicals during a large-scale cultivation. Secondly, particular bacterial secretion systems (e.g. the sec system) are known to play also a substantial part in the process by which the integral membrane proteins (e.g. channels, pores or transporters) insert into the cell membrane. If the activity of one or more secretion pathway proteins is increased, the ability of the cell to produce fine chemicals may likewise be increased, due to the presence of increased intracellular amounts of nutrients or reduced amounts of intracellular waste substances. If the activity of one or more of these secretion pathway proteins is reduced, it is possible that not enough nutrients are available for supporting the overproduction of compounds of interest or that waste products may interfere with this biosynthesis.

These abovementioned strategies for the mutagenesis of SES proteins, which ought to increase the yields of a fine chemical in *C. glutamicum*, are not intended to be limiting; variations of these mutagenesis strategies are quite obvious to the skilled worker. Using these strategies and including the mechanisms disclosed herein make it possible to use the nucleic acid and protein molecules of the invention in order to generate *C. glutamicum* or related bacterial strains expressing mutated SES nucleic acids and protein molecules so as to improve the yield, production and/or efficiency of production of a compound of interest. The compound of interest may be any product prepared by *C. glutamicum* including the end products of biosynthetic pathways and intermediates of naturally occurring metabolic pathways and also molecules which do not naturally occur in the *C. glutamicum* metabolism but are produced by a *C. glutamicum* strain of the invention.

The following examples which are not to be understood as being limiting further illustrate the present invention. The contents of all references, patent applications, patents and published patent applications cited in this patent application are hereby incorporated by way of reference.

EXAMPLES

Example 1

Preparation of Total Genomic DNA from *Corynebacterium glutamicum* ATCC13032

A *Corynebacterium glutamicum* (ATCC 13032) culture was cultivated with vigorous shaking in BHI medium (Difco) at 30° C. overnight. The cells were harvested by centrifugation, the supernatant was discarded and the cells were resuspended in 5 ml of buffer I (5% of the original culture volume—all volumes stated have been calculated for a culture volume of 100 ml). Composition of buffer I: 140.34 g/l sucrose, 2.46 g/l $MgSO_4.7\ H_2O$, 10 ml/l $KH_2PO_4$ solution (100 g/l, adjusted to pH 6.7 with KOH), 50 ml/l M12 concentrate (10 g/l $(NH_4)_2SO_4$, 1 g/l NaCl, 2 g/l $MgSO_4.7H_2O$, 0.2 g/l $CaCl_2$, 0.5 g/l yeast extract (Difco), 10 ml/l trace element mixture (200 mg/l $FeSO_4.H_2O$, 10 mg/l $ZnSO_4 7H_2O$, 3 mg/l $MnCl_2.4\ H_2O$, 30 mg/l $H_3BO_3$, 20 mg/l $CoCl_2.6H_2O$, 1 mg/l $NiCl_2.6\ H_2O$, 3 mg/l $Na_2MoO_4.2H_2O$, 500 mg/l complexing agents (EDTA or citric acid), 100 ml/l vitamin mixture (0.2 ml/l biotin, 0.2 mg/l folic acid, 20 mg/l p-aminobenzoic acid, 20 mg/l riboflavin, 40 mg/l Ca panthothenate, 140 mg/l nicotinic acid, 40 mg/l pyridoxol hydrochloride, 200 mg/l myoinositol). Lysozyme was added to the suspension at a final concentration of 2.5 mg/ml. After incubation at 37° C. for approx. 4 h, the cell wall was degraded and the protoplasts obtained were harvested by centrifugation. The pellet was washed once with 5 ml of buffer I and once with 5 ml of TE buffer (10 mM Tris-HCl, 1 mM EDTA, pH 8). The pellet was resuspended in 4 ml of TE buffer and 0.5 ml of SDS solution (10%) and 0.5 ml of NaCl solution (5 M) were added. After addition of proteinase K at a final concentration of 200 µg/ml, the suspension was incubated at 37° C. for approx. 18 h. The DNA was purified via extraction with phenol, phenol/chloroform/isoamyl, alcohol and chloroform/isoamyl alcohol by means of standard methods. The DNA was then precipitated by addition of 1/50 volume of 3 M sodium acetate and 2 volumes of ethanol, subsequent incubation at −20° C. for 30 min and centrifugation at 12 000 rpm in a high-speed centrifuge using an SS34 rotor (Sorvall) for 30 min. The DNA was dissolved in 1 ml of TE buffer containing 20 μ/g/ml RNase A and dialyzed against 1000 ml of TE buffer at 4° C. for at least 3 h. The buffer was exchanged 3 times during this period. 0.4 ml of 2 M LiCl and 0.8 ml of ethanol were added to 0.4 ml aliquots of the dialyzed DNA solution. After incubation at −20° C. for 30 min, the DNA was collected by centrifugation (13 000 rpm, Biofuge Fresco, Heraeus, Hanau, Germany). The DNA pellet was dissolved in TE buffer. It was possible to use DNA prepared by this method for all purposes, including Southern blotting and constructing genomic libraries.

Example 2

Construction of Genomic *Corynebacterium glutamicum* (ATCC13032) Banks in *Escherichia coli*

Starting from DNA prepared as described in Example 1, cosmid and plasmid banks were prepared according to known and well-established methods (see, for example, Sambrook, J. et al. (1989) "Molecular Cloning: A Laboratory Manual". Cold Spring Harbor Laboratory Press or Ausubel, F. M. et al. (1994) "Current Protocols in Molecular Biology", John Wiley & Sons).

It was possible to use any plasmid or cosmid. Particular preference was given to using the plasmids pBR322 (Sutcliffe, J. G. (1979) Proc. Natl Acad. Sci. USA, 75: 3737-3741); pACYC177 (Change & Cohen (1978) J. Bacteriol. 134: 1141-1156); pBS series plasmids (pBSSK+, PBSSK− and others; Stratagene, LaJolla, USA) or cosmids such as SuperCos1 (Stratagene, LaJolla, USA) or Lorist6 (Gibson, T. J. Rosenthal, A., and Waterson, R. H. (1987) Gene 53: 283-286.

Example 3

DNA Sequencing and Functional Computer Analysis

Genomic banks, as described in Example 2, were used for DNA sequencing according to standard methods, in particular the chain termination method using ABI377 sequencers (see, for example, Fleischman, R. D. et al. (1995) "Whole-genome Random Sequencing and Assembly of Haemophilus Influenzae Rd., Science 269; 496-512). Sequencing primers having the following nucleotide sequences were used: 5'-GGAAACAGTATGACCATG-3' oder 5'-GTAAAAC-GACGGCCAGT-3'.

Example 4

In Vivo Mutagenesis

In vivo mutagenesis of *Corynebacterium glutamicum* may be carried out by passing a plasmid (or other vector) DNA through *E. coli* or other microorganisms (e.g. *Bacillus* spp. or yeasts such as *Saccharomyces cerevisiae*) which cannot maintain the integrity of their genetic information. Common mutator strains contain mutations in the genes for the DNA repair system (e.g., mutHLS, mutD, mutT, etc., for comparison see Rupp, W. D. (1996) DNA repair mechanisms in *Escherichia coli* and *Salmonella*, pp. 2277-2294, ASM: Washington). These strains are known to the skilled worker. The use of these strains is illustrated, for example, in Greener, A. and Callahan, M. (1994) Strategies 7; 32-34.

Example 5

DNA Transfer between *Escherichia coli* and *Corynebacterium glutamicum*

A plurality of *Corynebacterium* and *Brevibacterium* species contain endogenous plasmids (such as, for example, pHM1519 or pBL1) which replicate autonomously (for a review see, for example, Martin, J. F. et al. (1987) Biotechnology 5: 137-146). Shuttle vectors for *Escherichia coli* and *Corynebacterium glutamicum* can be constructed readily by means of standard vectors for *E. coli* (Sambrook, J. et al., (1989), =Molecular Cloning: A Laboratory Manual", Cold Spring Harbor Laboratory Press or Ausubel, F. M. et al. (1994) "Current Protocols in Molecular Biology", John Wiley & Sons), to which an origin of replication for and a suitable marker from *Corynebacterium glutamicum* is added. Such origins of replication are preferably taken from endogenous plasmids which have been isolated from *Corynebacterium* and *Brevibacterium* species. Particular use as transformation markers for these species are genes for kanamycin resistance (such as those derived from the Tn5 or the Tn903 transposon) or for chloramphenicol (Winnacker, E. L. (1987) "From Genes to Clones—Introduction to Gene Technology, VCH, Weinheim). There are numerous examples in the literature for preparing a large multiplicity of shuttle vectors which replicate in *E. coli* and *C. glutamicum* and which can be used for various purposes, including the overexpression of genes (see, for example, Yoshihama, M. et al. (1985) J. Bacteriol. 162: 591-597, Martin, J. F. et al., (1987) Biotechnology, 5: 137-146 and Eikmanns, B. J. et al. (1992) Gene 102: 93-98).

Standard methods make it possible to clone a gene of interest into one of the above-described shuttle vectors and to introduce such hybrid vectors into *Corynebacterium glutamicum* strains. *C. glutamicum* can be transformed via protoplast transformation (Kastsumata, R. et al., (1984) J. Bacteriol. 159, 306-311), electroporation (Liebl, E. et al., (1989) FEMS Microbiol. Letters, 53: 399-303) and, in cases in which specific vectors are used, also via conjugation (as described, for example, in Schäfer, A., et al. (1990) J. Bacteriol. 172: 1663-1666). Likewise, it is possible to transfer the shuttle vectors for *C. glutamicum* to *E. coli* by preparing plasmid DNA from *C. glutamicum* (by means of standard methods known in the art) and transforming it into *E. coli*. This transformation step can be carried out using standard methods but advantageously an Mcr-deficient *E. coli* strain such as NM522 (Gough & Murray (1983) J. Mol. Biol. 166: 1-19) is used.

Example 6

Determination of the Expression of the Mutant Protein

The observations of the activity of a mutated protein in a transformed host cell are based on the fact that the mutant protein is expressed in a similar manner and in similar quantity to the wild-type protein. A suitable method for determining the amount of transcription of the mutant gene (an indication of the amount of MRNA available for translation of the gene product) is to carry out a Northern blot (see, for example, Ausubel et al., (1988) Current Protocols in Molecular Biology, Wiley: New York), with a primer which is designed such that it binds to the gene of interest being provided with a detectable (usually radioactive or chemiluminescent) label such that—when the total RNA of a culture of the organism is extracted, fractionated on a gel, transferred to a stable matrix and incubated with this probe—binding and binding quantity of the probe indicate the presence and also the amount of mRNA for said gene. This information is an indication of the extent to which the mutant gene has been transcribed. Total cell RNA can be isolated from *Corynebacterium glutamicum* by various methods known in the art, as described in Bormann, E. R. et al., (1992) Mol. Microbiol. 6: 317-326.

The presence or the relative amount of protein translated from said mRNA can be determined by using standard techniques such as Western blot (see, for example, Ausubel et al. (1988) "Current Protocols in Molecular Biology", Wiley, New York). In this method, total cell proteins are extracted, fractionated by gel electrophoresis, transferred to a matrix such as nitrocellulose and incubated with a probe, for example an antibody, which binds specifically to the protein of interest. This probe is usually provided with a chemiluminescent or colorimetric label which can be readily detected. The presence and the observed amount of label indicate the presence and the amount of the desired mutant protein in the cell.

Example 7

Growth of Genetically Modified *Corynebacterium glutamicum*—Media and Cultivation Conditions Genetically modified corynebacteria are cultivated in synthetic or natural growth media. A number of different growth media for corynebacteria are known and readily available (Lieb et al. 20 (1989) Appl. Microbiol. Biotechnol. 32: 205-210; von der Osten et al. (1998) Biotechnology Letters 11: 11-16; Patent DE 4 120 867; Liebl (1992) "The Genus Corynebacterium", in: The Procaryotes, Vol. II, Balows, A., et al., editors Springer-Verlag). These media are composed of one or more carbon sources, nitrogen sources, inorganic salts, vitamins and trace elements. Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch and cellulose. Sugars may also be added to the media via complex compounds such as molasses or other byproducts from sugar refining. It may also be advantageous to add mixtures of various carbon sources. Other possible carbon sources are alcohols and organic acids, such as methanol, ethanol, acetic acid or lactic acid. Nitrogen sources are usually organic or inorganic nitrogen compounds or materials containing these compounds. Examples of nitrogen sources include ammonia gas and ammonium salts such as $NH_4Cl$ or $(NH_4)_2SO_4$, $NH_4OH$, nitrates, urea, amino acids and complex nitrogen sources such as cornsteep liquor, soya meal, soya protein, yeast extracts, meat extract and others.

Inorganic salt compounds which may be present in the media include the chloride, phosphorus or sulfate salts of calcium, magnesium, sodium, cobalt, molybdenum, potassium, manganese, zinc, copper and iron. Chelating agents may be added to the medium in order to keep the metal ions in solution. Particularly suitable chelating agents include dihydroxyphenols such as catechol or protocatechuate and organic acids such as citric acid. The media usually also contain other growth factors such as vitamins or growth promoters, examples of which include biotin, riboflavin, thiamine, folic acid, nicotinic acid, panthothenate and pyridoxine. Growth factors and salts are frequently derived from complex media components such as yeast extract, molasses, cornsteep liquor and the like. The exact composition of the media heavily depends on the particular experiment and is decided upon individually for each specific case. Information on the optimization of media can be found in the textbook "Applied Microbiol. Physiology, A Practical Approach" (editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) or others.

All media components are sterilized, either by heat (20 min at 1.5 bar and 121° C.) or by sterile filtration. The components may be sterilized either together or, if required, separately. All media components may be present at the start of the cultivation or added continuously or batchwise, as desired.

The cultivation conditions are defined separately for each experiment. The temperature should be between 15° C. and 45° C. and may be kept constant or may be altered during the experiment. The pH of the medium should be in the range from 5 to 8.5, preferably around 7.0 and may be maintained by adding buffers to the media. An example of a buffer for this purpose is a potassium phosphate buffer. Synthetic buffers such as MOPS, HEPES; ACES, etc. may be used alternatively or simultaneously. Addition of NaOH or $NH_4OH$ can also keep the pH constant during cultivation. If complex media components such as yeast extract are used, the demand for additional buffers decreases, since many complex compounds have a high buffer capacity. In the case of using a fermenter for cultivating microorganisms, the pH may also be regulated using gaseous ammonia.

The incubation period is usually in a range from several hours to several days. This time is selected such that the maximum amount of product accumulates in the broth. The growth experiments disclosed may be carried out in a multiplicity of containers such as microtiter plates, glass tubes, glass flasks or glass or metal fermenters of different sizes. For the screening of a large number of clones, the microorganisms should be grown in microtiter plates, glass tubes or shaker flasks either with or without baffles. Preference is given to using 100 ml shaker flasks which are filled with 10% (based on volume) of the required growth medium. The flasks should be shaken on an orbital shaker (amplitude 25 mm) at a speed in the range of 100-300 rpm. Losses due to evaporation can be reduced by maintaining a humid atmosphere; alternatively, the losses due to evaporation should be corrected mathematically.

If genetically modified clones are investigated, an unmodified control clone or a control clone containing the basic plasmid without insert should also be assayed. The medium is inoculated to an $OD_{600}$ of 0.5-1.5, with cells being used which have been grown on agar plates such as CM plates (10 g/l glucose, 2.5 g/l NaCl, 2 g/l urea, 10 g/l polypeptone, 5 g/l yeast extract, 5 g/l meat extract, 22 g/l agar pH 6.8 with 2 M NaOH) which have been incubated at 30° C. The media are inoculated either by introducing a saline solution of *C. glutamicum* cells from CM plates or by adding a liquid preculture of said bacterium.

Example 8

In Vitro Analysis of the Function of Mutant Proteins

The determination of the activities and kinetic parameters of enzymes is well known in the art. Experiments for determining the activity of a particular modified enzyme must be adapted to the specific activity of the wild-type enzyme, and this is within the capabilities of the skilled worker. Overviews regarding enzymes in general and also specific details concerning the structure, kinetics, principles, methods, applications and examples of the determination of many enzyme activities can be found, for example, in the following references: Dixon, M., and Webb, E. C: (1979) Enzymes, Longmans, London; Fersht (1985) Enzyme Structure and Mechanism, Freeman, New York; Walsh (1979) Enzymatic Reaction Mechanisms. Freeman, San Francisco; Price, N. C., Stevens, L. (1982) Fundamentals of Enzymology. Oxford Univ. Press: Oxford; Boyer, P. D: editors (1983) The Enzymes, 3rd edition, Academic Press, New York; Bisswanger, H. (1994) Enzymkinetik, 2nd edition VCH, Weinheim (ISBN 3527300325); Bergmeyer, H. U., Bergmeyer, J., Graβl, M. editors (1983-1986) Methods of Enzymatic Analysis, 3rd edition, Vol. I-XII, Verlag Chemie: Weinheim; and Ullmann's Encyclopedia of Industrial Chemistry (1987) Vol. A9, "Enzymes", VCH, Weinheim, pp. 352-363.

The activity of proteins binding to DNA can be measured by many well-established methods such as DNA bandshift assays (which are also referred to as gel retardation assays). The action of these proteins on the expression of other molecules can be measured using reporter gene assays (as described in Kolmar, H. et al., (1995) EMBO J. 14: 3895-3904 and in references therein). Reporter gene assay systems are well known and established for applications in prokaryotic and eukaryotic cells, with enzymes such as beta-galactosidase, green fluorescent protein and several other enzymes being used.

The activity of membrane transport proteins can be determined according to techniques described in Gennis, R. B. (1989) "Pores, Channels and Transporters", in Biomembranes, Molecular Structure and Function, Springer: Heidelberg, pp. 85-137; 199-234; and 270-322.

Example 9

Analysis of the Influence of Mutated Protein on the Production of the Product of Interest The effect of the genetic modification in *C. glutamicum* on the production of a compound of interest (such as an amino acid) can be determined by growing the modified microorganisms under suitable conditions (such as those described above) and testing the medium and/or the cellular components with regard to increased production of the product of interest (i.e. an amino acid). Such analytical techniques are well known to the skilled worker and include spectroscopy, thin-layer chromatography, various types of coloring methods, enzymic and microbiological methods and analytical chromatography such as high performance liquid chromatography (see, for example, Ullman, Encyclopedia of Industrial Chemistry, Vol. A2, pp. 89-90 and pp. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", pp. 469-714, VCH: Weinheim; Belter, P. A. et al. (1988) Bioseparations: downstream processing for Biotechnology, John Wiley and Sons; Kennedy, J. F. and Cabral, J. M. S. (1992) Recovery processes for biological Materials, John Wiley and Sons; Shaeiwitz, J. A. and Henry, J. D. (1988) Biochemical Separations, in Ullmann's Encyclopedia of Industrial Chemistry, Vol. B3; Chapter 11, pp. 1-27, VCH: Weinheim; and Dechow, F. J. (1989) Separation and purification techniques in biotechnology, Noyes Publications).

In addition to measuring the end product of the fermentation, it is likewise possible to analyze other components of the metabolic pathways, which are used for producing the compound of interest, such as intermediates and byproducts, in order to determine the overall efficiency of production of the compound. The analytical methods include measuring the amounts of nutrients in the medium (for example sugars, hydrocarbons, nitrogen sources, phosphate and other ions), measuring biomass composition and growth, analyzing the production of common metabolites from biosynthetic pathways and measuring gases generated during fermentation. Standard methods for these measurements are described in Applied Microbial Physiology; A Practical Approach, P. M. Rhodes and P. F. Stanbury, editors IRL Press, pp. 103-129; 131-163 and 165-192 (ISBN: 0199635773) and the references therein.

Example 10

Purification of the Product of Interest from a *C. glutamicum* Culture

The product of interest may be obtained from *C. glutamicum* cells or from the supernatant of the above-described culture by various methods known in the art. If the product of interest is not secreted by the cells, the cells may be harvested from the culture by slow centrifugation, and the cells may be lysed by standard techniques such as mechanial force or sonication. The cell debris is removed by centrifugation and the supernatant fraction which contains the soluble proteins is obtained for further purification of the compound of interest. If the product is secreted by the *C. glutamicum* cells, the cells are removed from the culture by slow centrifugation and the supernatant fraction is retained for further purification.

The supernatant fraction from both purification methods is subjected to chromatography using a suitable resin, and either the molecule of interest is retained on the chromatography resin while many contaminants in the sample are not, or the contaminants remain on the resin while the sample does not. If necessary, these chromatography steps can be repeated using the same or different chromatography resins. The skilled worker is familiar with the selection of suitable chromatography resins and the most effective application for a particular molecule to be purified. The purified product may be concentrated by filtration or ultrafiltration and stored at a temperature at which product stability is highest.

In the art, many purification methods are known and the above purification method is not intended to be limiting. These purification techniques are described, for example, in Bailey, J. E. & Ollis, D. F. Biochemical Engineering Fundamentals, McGraw-Hill: New York (1986).

The identity and purity of the isolated compounds can be determined by techniques of the prior art. These techniques comprise high performance liquid chromatography (HPLC), spectroscopic methods, coloring methods, thin-layer chromatography, NIRS, enzyme assays or microbiological assays. These analytical methods are compiled in: Patek et al. (1994) Appl. Environ. Microbiol. 60: 133-140; Malakhova et al. (1996) Biotekhnologiya 11: 27-32; and Schmidt et al. (1998) Bioprocess Engineer. 19: 67-70. Ulmann's Encyclopedia of Industrial Chemistry (1996) Vol. A27, VCH: Weinheim, pp. 89-90, pp. 521-540, pp. 540-547, pp. 559-566, 575-581 and pp. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Vol. 17.

Equivalents

The skilled worker knows, or can identify by using simply routine methods, a large number of equivalents of the specific embodiments of the invention. These equivalents are intended to be included in the patent claims below.

The information in Table 1 is to be understood as follows:

In column 1, "DNA ID", the relevant number refers in each case to the SEQ ID NO of the enclosed sequence listing. Consequently, "5" in column "DNA ID" is a reference to SEQ ID NO:5.

In column 2, "AA ID", the relevant number refers in each case to the SEQ ID NO of the enclosed sequence listing. Consequently, "6" in column "AA ID" is a reference to SEQ ID NO:6.

In column 3, "Identification", an unambiguous internal name for each sequence is listed.

In column 4, "AA pos", the relevant number refers in each case to the amino acid position of the polypeptide sequence "AA ID," in the same row. Consequently, "26" in column "AA pos" is amino acid position 26 of the polypeptide sequence indicated accordingly. Position counting starts at the N terminus with +1.

In column 5, "AA wild type", the relevant letter refers in each case to the amino acid, displayed in the one-letter code, at the position in the corresponding wild-type strain, which is indicated in column 4.

In column 6, "AA mutant", the relevant letter refers in each case to the amino acid, displayed in the one-letter code, at the position in the corresponding mutant strain, which is indicated in column 4.

In column 7, "Function", the physiological function of the corresponding polypeptide sequence is listed.

One-Letter Code of the Proteinogenic Amino Acids:
A Alanine
C Cysteine
D Aspartic acid
E Glutamic acid
F Phenylalanine
G Glycine
H His
I Isoleucine
K Lysine
L Leucine
M Methionine
N As paragine
P Proline
Q Glutamine
R Arginine
S Serine
T Threonine
V Valine
w Tryptophan
Y Tyrosine

TABLE 1

Genes coding for proteins for genetic stability, gene expression and folding

| DNA ID: | AA ID: | Identification: | AA pos: | AA wild type | AA mutant | Function: |
|---|---|---|---|---|---|---|
| 1 | 2 | RXA00019 | 337 | P | S | SINGLE-STRANDED-DNA-SPECIFIC EXONUCLEASE RECJ (EC 3.1.—.—) |
|  |  |  | 405 | T | I | SINGLE-STRANDED-DNA-SPECIFIC EXONUCLEASE RECJ (EC 3.1.—.—) |
|  |  |  | 504 | P | S | SINGLE-STRANDED-DNA-SPECIFIC EXONUCLEASE RECJ (EC 3.1.—.—) |
| 3 | 4 | RXA00061 | 754 | S | N | DNA POLYMERASE I (EC 2.7.7.7) |
| 5 | 6 | RXA00209 | 414 | V | A | GLUTAMYL-TRNA(GLN) AMIDOTRANSFERASE SUBUNIT A (EC 6.3.5.—) |
|  |  |  | 454 | L | F | GLUTAMYL-TRNA(GLN) AMIDOTRANSFERASE SUBUNIT A (EC 6.3.5.—) |
| 7 | 8 | RXA00211 | 44 | V | I | GLUTAMYL-TRNA(GLN) AMIDOTRANSFERASE SUBUNIT B (EC 6.3.5.—) |
| 9 | 10 | RXA00314 | 319 | E | K | CYSTEINYL-TRNA SYNTHETASE (EC 6.1.1.16) |
| 11 | 12 | RXA00458 | 170 | L | F | GLUTAMYL-TRNA SYNTHETASE (EC 6.1.1.17) |
| 13 | 14 | RXA00493 | 363 | A | T | 60 KD CHAPERONIN GROEL |
| 15 | 16 | RXA00588 | 23 | A | V | TRANSCRIPTION ELONGATION FACTOR GREA |
| 17 | 18 | RXA00669 | 68 | A | T | TRNA PSEUDOURIDINE SYNTHASE (EC 4.2.1.70) |
| 19 | 20 | RXA01061 | 686 | P | S | LEUCYL-TRNA SYNTHETASE (EC 6.1.1.4) |
| 21 | 22 | RXA01277 | 704 | G | S | PROLYL ENDOPEPTIDASE (EC 3.4.21.26) |
| 23 | 24 | RXA01278 | 543 | T | I | Protein Translation Elongation Factor G (EF-G) |
| 25 | 26 | RXA01284 | 164 | D | N | Bacterial Protein Translation Elongation Factor Tu (EF-TU) |
|  |  |  | 362 | S | F | Bacterial Protein Translation Elongation Factor Tu (EF-TU) |
| 27 | 28 | RXA01344 | 5 | P | L | DNA-DIRECTED RNA POLYMERASE BETA CHAIN (EC 2.7.7.6) |
|  |  |  | 429 | D | V | DNA-DIRECTED RNA POLYMERASE BETA CHAIN (EC 2.7.7.6) |
| 29 | 30 | RXA01345 | 308 | A | V | DNAK PROTEIN |
| 31 | 32 | RXA01404 | 108 | T | I | TRANSCRIPTIONAL REPRESSOR |
| 33 | 34 | RXA01431 | 46 | A | T | THIOREDOXIN |
| 35 | 36 | RXA01438 | 182 | A | T | FERREDOXIN—NADP REDUCTASE (EC 1.18.1.2) |
| 37 | 38 | RXA01490 | 277 | A | V | TRNA PSEUDOURIDINE SYNTHASE B (EC 4.2.1.70) |
| 39 | 40 | RXA01493 | 32 | A | V | Na+ DRIVEN MULTIDRUG EFFLUX PUMP |
| 41 | 42 | RXA01559 | 400 | T | A | PROTEIN TRANSLOCASE SUBUNIT SECD |
| 43 | 44 | RXA01596 | 334 | R | C | DNA REPAIR PROTEIN RECN |
|  |  |  | 493 | G | D | DNA REPAIR PROTEIN RECN |
| 45 | 46 | RXA01651 | 7 | S | F | TRANSPOSASE |
|  |  |  | 33 | L | F | TRANSPOSASE |

TABLE 1-continued

Genes coding for proteins for genetic stability, gene expression and folding

| DNA ID: | AA ID: | Identification: | AA pos: | AA wild type | AA mutant | Function: |
|---|---|---|---|---|---|---|
| 47 | 48 | RXA01710 | 69 | P | S | TRANSCRIPTIONAL REGULATOR |
| 49 | 50 | RXA01852 | 120 | P | S | HISTIDYL-TRNA SYNTHETASE (EC 6.1.1.21) |
| 51 | 52 | RXA01913 | 61 | L | F | Protein Translation Elongation Factor Ts (EF-Ts) |
| 53 | 54 | RXA02145 | 321 | P | L | MENAQUINOL-CYTOCHROME C REDUCTASE CYTOCHROME B SUBUNIT |
| 55 | 56 | RXA02236 | 87 | L | F | Integration host factor |
| 57 | 58 | RXA02267 | 65 | A | T | DNA (CYTOSINE-5)-METHYLTRANSFERASE (EC 2.1.1.37) |
| 59 | 60 | RXA02280 | 502 | A | V | HEAT SHOCK PROTEIN HTPG |
| 61 | 62 | RXA02388 | 401 | E | K | COME OPERON PROTEIN 3 |
|  |  |  | 451 | V | M | COME OPERON PROTEIN 3 |
| 63 | 64 | RXA02416 | 484 | G | D | EXCINUCLEASE ABC SUBUNIT A |
| 65 | 66 | RXA02418 | 45 | V | I | Bacterial Protein Translation Initiation Factor 3 (IF-3) |
| 67 | 68 | RXA02429 | 670 | M | I | PROTEIN TRANSLOCASE SUBUNIT SECA |
| 69 | 70 | RXA02431 | 73 | A | V | DNA POLYMERASE IV |
| 71 | 72 | RXA02445 | 17 | G | E | ATP-DEPENDENT DNA HELICASE RECG |
| 73 | 74 | RXA02476 | 167 | S | F | A/G-SPECIFIC ADENINE GLYCOSYLASE (EC 3.2.2.—) |
| 75 | 76 | RXA02726 | 286 | A | V | ISOLEUCYL-TRNA SYNTHETASE (EC 6.1.1.5) |
| 77 | 78 | RXA02731 | 374 | E | K | EXCINUCLEASE ABC SUBUNIT B |
|  |  |  | 398 | M | L | EXCINUCLEASE ABC SUBUNIT B |
|  |  |  | 410 | R | L | EXCINUCLEASE ABC SUBUNIT B |
| 79 | 80 | RXA02736 | 312 | S | F | PUTATIVE OXPPCYCLE PROTEIN OPCA |
| 81 | 82 | RXA02742 | 179 | G | S | DNA/RNA HELICASE (DEAD/DEAH BOX FAMILY) |
| 83 | 84 | RXA02748 | 100 | P | S | SIGNAL RECOGNITION PARTICLE, SUBUNIT FFH/SRP54 |
|  |  |  | 164 | G | D | SIGNAL RECOGNITION PARTICLE, SUBUNIT FFH/SRP54 |
| 85 | 86 | RXA03070 | 249 | A | V | TRANSPOSASE |
| 87 | 88 | RXA03098 | 164 | S | N | DNA alkylation repair enzyme |
| 89 | 90 | RXA03206 | 98 | G | D | D-Tyr-tRNATyr deacylase |
| 91 | 92 | RXA03260 | 56 | S | F | TRANSPOSASE |
| 93 | 94 | RXA03394 | 11 | S | F | METHIONYL-TRNA SYNTHETASE (EC 6.1.1.10) |
| 95 | 96 | RXA03674 | 342 | V | I | ATP-DEPENDENT HELICASE HEPA |
| 97 | 98 | RXA03793 | 414 | A | V | RNA POLYMERASE SIGMA FACTOR RPOD |
| 99 | 100 | RXA06048 | 3 | L | F | PS1 PROTEIN PRECURSOR |
|  |  |  | 4 | L | P | PS1 PROTEIN PRECURSOR |
|  |  |  | 5 | T | S | PS1 PROTEIN PRECURSOR |
|  |  |  | 9 | A | T | PS1 PROTEIN PRECURSOR |
|  |  |  | 26 | I | V | PS1 PROTEIN PRECURSOR |
|  |  |  | 31 | S | T | PS1 PROTEIN PRECURSOR |
|  |  |  | 66 | S | N | PS1 PROTEIN PRECURSOR |
|  |  |  | 158 | N | D | PS1 PROTEIN PRECURSOR |
| 101 | 102 | RXA07005 | 339 | P | S | PROBABLE ATP-DEPENDENT HELICASE LHR (EC 3.6.1.—) |
| 103 | 104 | RXA07006 | 239 | P | L | EXODEOXYRIBONUCLEASE VII LARGE SUBUNIT (EC 3.1.11.6) |

We claim:

1. An isolated nucleic acid molecule encoding the amino acid sequence set forth in SEQ ID NO:14, wherein the amino acid residue at position 363 of SEQ ID NO:14 is any amino acid except alanine, or a complement thereof.

2. The isolated nucleic acid molecule of claim 1 wherein the amino acid residue at position 363 of SEQ ID NO:14 is threonine.

3. An isolated nucleic acid molecule which hybridizes to the complement of the nucleotide sequence set forth in SEQ ID NO:13 at 6X sodium chloride/sodium citrate (SSC) at 45° C. followed by one or more washes in 0.2 X SSC, 0.1% SDS at 50-65° C., wherein the nucleic acid molecule encodes any amino acid except alanine at the position corresponding to nucleotide residues 1187-1189 of SEQ ID NO:13, and wherein the nucleic acid molecule encodes a polypeptide which has a 60 kD chaperonin GroEL activity, or a complement thereof.

4. An isolated nucleic acid molecule comprising the nucleotide sequence set forth in SEQ ID NO:13, wherein the nucleic acid molecule comprises one or more nucleic acid modifications at nucleotide residues 1187-1189 of SEQ ID NO:13 such that nucleotide residues 1187-1189 of SEQ ID NO:13 encode any amino acid except alanine, or a complement thereof.

5. A vector comprising the nucleic acid molecule of claim 1, 3 or 4.

6. The vector of claim 5, which is an expression vector.

7. An isolated host cell, which is transfected with the vector of claim 6.

8. The host cell of claim 7, wherein expression of said nucleic acid molecule modulates the production of a fine chemical from said cell.

9. A method for preparing a fine chemical, comprising culturing the cell of claim 7 such that the fine chemical is produced.

10. The method of claim 7, wherein the fine chemical is an amino acid.

11. The method of claim 10, wherein said amino acid is lysine.

12. The host cell of claim 7, wherein said cell is a microorganism.

13. The host cell of claim 12, wherein said cell belongs to the genus *Corynebacterium* or *Brevibacterium*.

14. The host cell of claim 8, wherein said fine chemical is selected from the group consisting of organic acids, proteinogenic and nonproteinogenic amino acids, purine and pyrimidine bases, nucleosides, nucleotides, lipids, saturated and unsaturated fatty acids, diols, carbohydrates, aromatic compounds, vitamins, cofactors and enzymes.

15. The method of claim 9, wherein said cell belongs to the genus *Corynebacterium* or *Brevibacterium*.

16. The method of claim 9, wherein expression of the nucleic acid molecule from said vector results in modulation of production of said fine chemical.

17. A method for producing a fine chemical, comprising culturing a cell whose genomic DNA has been altered by the inclusion of a nucleic acid molecule of any one of claims 1, 3 or 4.

18. The nucleic acid molecule of claim 4, wherein nucleotide residues 1187-1189 of SEQ ID NO:13 encode threonine.

19. The nucleic acid molecule of claim 3, wherein the nucleic acid molecule encodes threonine at the position corresponding to nucleotide residues 1187-1189 of SEQ ID NO:13.

* * * * *

SEQUENCE LISTING

```
<160> NUMBER OF SEQ ID NOS: 104

<210> SEQ ID NO 1
<211> LENGTH: 1990
<212> TYPE: DNA
<213> ORGANISM: Corynebacterium glutamicum
<220> FEATURE:
<221> NAME/KEY: CDS
<222> LOCATION: (101)..(1960)
<223> OTHER INFORMATION: RXA00019

<400> SEQUENCE: 1
accggatacc ttatgaaaca cctggtgagc ggtgtgtttc accccaacaa ccgagtaaaa      60
tatatctagt actattttac gattgaaagt agattttcct atg acc gtt acc tca     115
                                              Met Thr Val Thr Ser
                                                1               5 cca gca gcg ctc gca ctc agc gac atg tcc tat gtg gac atc att aag     163
Pro Ala Ala Leu Ala Leu Ser Asp Met Ser Tyr Val Asp Ile Ile Lys
         10                  15                  20 aag aag cgc gga tgg aca acc gag ttt ttc cac agc acc atc aac acc     211
Lys Lys Arg Gly Trp Thr Thr Glu Phe Phe His Ser Thr Ile Asn Thr
```

|  |  |  |  |  |  |  |  |  |  |  |  |  |  |  |  |
|---|---|---|---|---|---|---|---|---|---|---|---|---|---|---|---|
|  |  | 25 |  |  |  |  | 30 |  |  |  |  | 35 |  |  |  |

```
ggt gaa acc acc aca ccg cta cca gac agc gac cgt gcc aca gca cta      259
Gly Glu Thr Thr Thr Pro Leu Pro Asp Ser Asp Arg Ala Thr Ala Leu
         40                  45                  50 atc cat gac cac atc acc aag gct caa gag ata acc atc atc acc gac      307
Ile His Asp His Ile Thr Lys Ala Gln Glu Ile Thr Ile Ile Thr Asp
 55                  60                  65 ttt gat atg gac ggt att tca gcc ggt gtc att gcc tat gca ggt ctt      355
Phe Asp Met Asp Gly Ile Ser Ala Gly Val Ile Ala Tyr Ala Gly Leu
 70                  75                  80                  85 gcc gaa ctg ggc gca cag gtc aat atg gtg gtg ccc gac tat cgt ggc      403
Ala Glu Leu Gly Ala Gln Val Asn Met Val Val Pro Asp Tyr Arg Gly
             90                  95                 100 gaa cga aat gtc aca gcc agc gat att gat cgt gcg cta gag ctc tac      451
Glu Arg Asn Val Thr Ala Ser Asp Ile Asp Arg Ala Leu Glu Leu Tyr
                105                 110                 115 cct gca acc tca ctc atc atc acc tgc gat gtc ggc atc ggc tcc cat      499
Pro Ala Thr Ser Leu Ile Ile Thr Cys Asp Val Gly Ile Gly Ser His
                120                 125                 130 gaa ggt att gcc cgt gct cac gaa cgc agt atc gcc gtc ctg gtc aca      547
Glu Gly Ile Ala Arg Ala His Glu Arg Ser Ile Ala Val Leu Val Thr
135                 140                 145 gat cac cac atg gag gtc gaa ccc tgc cag gcc gat gtg gtt ctt aac      595
Asp His His Met Glu Val Glu Pro Cys Gln Ala Asp Val Val Leu Asn
150                 155                 160                 165 ccc aac aga att gac tct gac tac ccc aac aaa gat att tgc ggt gcg      643
Pro Asn Arg Ile Asp Ser Asp Tyr Pro Asn Lys Asp Ile Cys Gly Ala
                170                 175                 180 cag gtc att ttc gcc aca ttg agt gac tat gca cgt cgt tat cgg gcg      691
Gln Val Ile Phe Ala Thr Leu Ser Asp Tyr Ala Arg Arg Tyr Arg Ala
                185                 190                 195 gac aag att atc gac att aat ttg ttg gct gtt ttc tca ggc att ggt      739
Asp Lys Ile Ile Asp Ile Asn Leu Leu Ala Val Phe Ser Gly Ile Gly
                200                 205                 210 gca ctc gcc gat gtc atg cct ctc acc cgt gac act cga cca aca gtg      787
Ala Leu Ala Asp Val Met Pro Leu Thr Arg Asp Thr Arg Pro Thr Val
215                 220                 225 aag cag gct att gcg ttg ctt cgg ctt gct atc cca caa gta agt aaa      835
Lys Gln Ala Ile Ala Leu Leu Arg Leu Ala Ile Pro Gln Val Ser Lys
230                 235                 240                 245 aac cgt ttc ggc ggt tgg gat acc tat gct gca cgc tct gtt aat cct      883
Asn Arg Phe Gly Gly Trp Asp Thr Tyr Ala Ala Arg Ser Val Asn Pro
                250                 255                 260 gat acg tcc aca ctc atg cat att gtc aat gcc agc cag cat gat cac      931
Asp Thr Ser Thr Leu Met His Ile Val Asn Ala Ser Gln His Asp His
                265                 270                 275 cgc ttc att gca gcc ttc caa ggc atc tca att ctt ctt ggt gaa ctg      979
Arg Phe Ile Ala Ala Phe Gln Gly Ile Ser Ile Leu Leu Gly Glu Leu
                280                 285                 290 att gcg caa aag aag cta gta aac atc gac aat att tct gag tca ttc      1027
Ile Ala Gln Lys Lys Leu Val Asn Ile Asp Asn Ile Ser Glu Ser Phe
                295                 300                 305 att ggc ttc act ctt ggt ccg atg ttt aac gct act cgt cgt gtt ggt      1075
Ile Gly Phe Thr Leu Gly Pro Met Phe Asn Ala Thr Arg Arg Val Gly
310                 315                 320                 325 ggc gac atg cac gat tca ttt ctc gtg ttt gcg ccc cat gcc gca cta      1123
Gly Asp Met His Asp Ser Phe Leu Val Phe Ala Pro His Ala Ala Leu
                330                 335                 340 gca tca cag ccg tcg atg aat cca aat cga cat gct gcg atc tct cgc      1171
```

```
Ala Ser Gln Pro Ser Met Asn Pro Asn Arg His Ala Ala Ile Ser Arg
            345                 350                 355 atc att gat aac aac gaa cgt cgc aaa gag ctc tcc aag tcc tct tat      1219
Ile Ile Asp Asn Asn Glu Arg Arg Lys Glu Leu Ser Lys Ser Ser Tyr
        360                 365                 370 gct gcc gta cac agc tca gat cag ccc tac gcg ccc ttt gtg tgg ctc      1267
Ala Ala Val His Ser Ser Asp Gln Pro Tyr Ala Pro Phe Val Trp Leu
375                 380                 385 tct gag gca cca agc ggc att ctt ggt ctc att gcc tca cag ctc act      1315
Ser Glu Ala Pro Ser Gly Ile Leu Gly Leu Ile Ala Ser Gln Leu Thr
390                 395                 400                 405 cgt gag tct gac gtg cct gcc att gtc att aat cca gat acc ttg tcc      1363
Arg Glu Ser Asp Val Pro Ala Ile Val Ile Asn Pro Asp Thr Leu Ser
                410                 415                 420 ggt tca gct cgc tca cct gag tgg gca ccg atc atc acc caa gta aac      1411
Gly Ser Ala Arg Ser Pro Glu Trp Ala Pro Ile Ile Thr Gln Val Asn
                425                 430                 435 acc ctc agc gca caa ggt cac ggc ggt att cat gct gca ggc cat gag      1459
Thr Leu Ser Ala Gln Gly His Gly Gly Ile His Ala Ala Gly His Glu
            440                 445                 450 tac gcc tgt ggt atg cgt ttt gat aac cat gat gac att gtg acc ttt      1507
Tyr Ala Cys Gly Met Arg Phe Asp Asn His Asp Asp Ile Val Thr Phe
455                 460                 465 gtt gca aca ctc gac gca ctc gat aaa aac acg cca cgg gaa gca cag      1555
Val Ala Thr Leu Asp Ala Leu Asp Lys Asn Thr Pro Arg Glu Ala Gln
470                 475                 480                 485 ccg gca gat ctg cat ttg gtt gac att gac cac gcg cgt cct gtg ctt      1603
Pro Ala Asp Leu His Leu Val Asp Ile Asp His Ala Arg Pro Val Leu
                490                 495                 500 gat aac ccc tca ctc acc caa gag ctc agt acg gtc gat gct gca gtg      1651
Asp Asn Pro Ser Leu Thr Gln Glu Leu Ser Thr Val Asp Ala Ala Val
                505                 510                 515 gat gct gca cag ttg ctt gtt ctc att gat cag ctt gat caa ctg cag      1699
Asp Ala Ala Gln Leu Leu Val Leu Ile Asp Gln Leu Asp Gln Leu Gln
            520                 525                 530 cca ttt gga cat ggt ttt acc tat ccg cgc atc gac gtg acg ttc agg      1747
Pro Phe Gly His Gly Phe Thr Tyr Pro Arg Ile Asp Val Thr Phe Arg
535                 540                 545 ccg gca gaa aca gaa ttc aag gtt atg ggt cag cac cat caa cat ctc      1795
Pro Ala Glu Thr Glu Phe Lys Val Met Gly Gln His His Gln His Leu
550                 555                 560                 565 aag gtg atc act cac tca ggg ttg acc tta ttg tgg tgg aat aag gct      1843
Lys Val Ile Thr His Ser Gly Leu Thr Leu Leu Trp Trp Asn Lys Ala
                570                 575                 580 cag cag ctc gat gag atc gca cag tct gaa tta gtc acc atg tct gtg      1891
Gln Gln Leu Asp Glu Ile Ala Gln Ser Glu Leu Val Thr Met Ser Val
            585                 590                 595 gag ctc gat gtc aat atg ttc cgt ggg ttt att tcc ccg caa ggc att      1939
Glu Leu Asp Val Asn Met Phe Arg Gly Phe Ile Ser Pro Gln Gly Ile
                600                 605                 610 gtc tct gcg tgc aca gtt atc tagcttggtt gcataagcac caaaaacaac         1990
Val Ser Ala Cys Thr Val Ile
            615                 620

<210> SEQ ID NO 2
<211> LENGTH: 620
<212> TYPE: PRT
<213> ORGANISM: Corynebacterium glutamicum

<400> SEQUENCE: 2
```

-continued

```
Met Thr Val Thr Ser Pro Ala Ala Leu Ala Leu Ser Asp Met Ser Tyr
 1               5                  10                  15

Val Asp Ile Ile Lys Lys Arg Gly Trp Thr Thr Glu Phe Phe His
             20                  25                  30

Ser Thr Ile Asn Thr Gly Glu Thr Thr Pro Leu Pro Asp Ser Asp
             35                  40                  45

Arg Ala Thr Ala Leu Ile His Asp His Ile Thr Lys Ala Gln Glu Ile
     50                  55                  60

Thr Ile Ile Thr Asp Phe Asp Met Asp Gly Ile Ser Ala Gly Val Ile
 65                  70                  75                  80

Ala Tyr Ala Gly Leu Ala Glu Leu Gly Ala Gln Val Asn Met Val Val
                 85                  90                  95

Pro Asp Tyr Arg Gly Glu Arg Asn Val Thr Ala Ser Asp Ile Asp Arg
                100                 105                 110

Ala Leu Glu Leu Tyr Pro Ala Thr Ser Leu Ile Ile Thr Cys Asp Val
             115                 120                 125

Gly Ile Gly Ser His Glu Gly Ile Ala Arg Ala His Glu Arg Ser Ile
         130                 135                 140

Ala Val Leu Val Thr Asp His His Met Glu Val Glu Pro Cys Gln Ala
145                 150                 155                 160

Asp Val Val Leu Asn Pro Asn Arg Ile Asp Ser Asp Tyr Pro Asn Lys
                 165                 170                 175

Asp Ile Cys Gly Ala Gln Val Ile Phe Ala Thr Leu Ser Asp Tyr Ala
             180                 185                 190

Arg Arg Tyr Arg Ala Asp Lys Ile Ile Asp Ile Asn Leu Leu Ala Val
         195                 200                 205

Phe Ser Gly Ile Gly Ala Leu Ala Asp Val Met Pro Leu Thr Arg Asp
210                 215                 220

Thr Arg Pro Thr Val Lys Gln Ala Ile Ala Leu Leu Arg Leu Ala Ile
225                 230                 235                 240

Pro Gln Val Ser Lys Asn Arg Phe Gly Gly Trp Asp Thr Tyr Ala Ala
                 245                 250                 255

Arg Ser Val Asn Pro Asp Thr Ser Thr Leu Met His Ile Val Asn Ala
             260                 265                 270

Ser Gln His Asp His Arg Phe Ile Ala Ala Phe Gln Gly Ile Ser Ile
         275                 280                 285

Leu Leu Gly Glu Leu Ile Ala Gln Lys Lys Leu Val Asn Ile Asp Asn
290                 295                 300

Ile Ser Glu Ser Phe Ile Gly Phe Thr Leu Gly Pro Met Phe Asn Ala
305                 310                 315                 320

Thr Arg Arg Val Gly Gly Asp Met His Asp Ser Phe Leu Val Phe Ala
                 325                 330                 335

Pro His Ala Ala Leu Ala Ser Gln Pro Ser Met Asn Pro Asn Arg His
             340                 345                 350

Ala Ala Ile Ser Arg Ile Ile Asp Asn Asn Glu Arg Arg Lys Glu Leu
         355                 360                 365

Ser Lys Ser Ser Tyr Ala Ala Val His Ser Ser Asp Gln Pro Tyr Ala
370                 375                 380

Pro Phe Val Trp Leu Ser Glu Ala Pro Ser Gly Ile Leu Gly Leu Ile
385                 390                 395                 400

Ala Ser Gln Leu Thr Arg Glu Ser Asp Val Pro Ala Ile Val Ile Asn
                 405                 410                 415

Pro Asp Thr Leu Ser Gly Ser Ala Arg Ser Pro Glu Trp Ala Pro Ile
```

-continued

```
              420             425             430
Ile Thr Gln Val Asn Thr Leu Ser Ala Gln Gly His Gly Ile His
        435                 440                 445

Ala Ala Gly His Glu Tyr Ala Cys Gly Met Arg Phe Asp Asn His Asp
        450                 455                 460

Asp Ile Val Thr Phe Val Ala Thr Leu Asp Ala Leu Asp Lys Asn Thr
465                 470                 475                 480

Pro Arg Glu Ala Gln Pro Ala Asp Leu His Leu Val Asp Ile Asp His
                485                 490                 495

Ala Arg Pro Val Leu Asp Asn Pro Ser Leu Thr Gln Glu Leu Ser Thr
        500                 505                 510

Val Asp Ala Ala Val Asp Ala Ala Gln Leu Leu Val Leu Ile Asp Gln
        515                 520                 525

Leu Asp Gln Leu Gln Pro Phe Gly His Gly Phe Thr Tyr Pro Arg Ile
        530                 535                 540

Asp Val Thr Phe Arg Pro Ala Glu Thr Glu Phe Lys Val Met Gly Gln
545                 550                 555                 560

His His Gln His Leu Lys Val Ile Thr His Ser Gly Leu Thr Leu Leu
                565                 570                 575

Trp Trp Asn Lys Ala Gln Gln Leu Asp Glu Ile Ala Gln Ser Glu Leu
        580                 585                 590

Val Thr Met Ser Val Glu Leu Asp Val Asn Met Phe Arg Gly Phe Ile
        595                 600                 605

Ser Pro Gln Gly Ile Val Ser Ala Cys Thr Val Ile
        610                 615                 620

<210> SEQ ID NO 3
<211> LENGTH: 2845
<212> TYPE: DNA
<213> ORGANISM: Corynebacterium glutamicum
<220> FEATURE:
<221> NAME/KEY: CDS
<222> LOCATION: (101)..(2815)
<223> OTHER INFORMATION: RXA00061

<400> SEQUENCE: 3
aatcaattgc agaactaacc cggttgtttc cgagccagtc tgaatgactg aaagcaatat      60
tagaccatca atgattagga atggaaatta ggggtctggt ttg ggt gaa tgt gtc      115
                                              Leu Gly Glu Cys Val
                                                1               5 gct aat ttt tcc act cgc cta cac tcg gga ggc gtg act gag aag act      163
Ala Asn Phe Ser Thr Arg Leu His Ser Gly Gly Val Thr Glu Lys Thr
            10                  15                  20 gac cag acc tta atg ctt atc gac ggc cac tcg atg gct ttc cgc gca      211
Asp Gln Thr Leu Met Leu Ile Asp Gly His Ser Met Ala Phe Arg Ala
        25                  30                  35 ttc ttt gct ttg ccg gct gag aat ttc tcc acg tcg ggc ggg cag gcc      259
Phe Phe Ala Leu Pro Ala Glu Asn Phe Ser Thr Ser Gly Gly Gln Ala
    40                  45                  50 acc aat gct gtc tat ggc ttt ctc tcg atg ctg tcc acg ttg ttg aag      307
Thr Asn Ala Val Tyr Gly Phe Leu Ser Met Leu Ser Thr Leu Leu Lys
55                  60                  65 gat gag cag cct act cat gtg gcg gtg gct ttc gat gtg ggg cgt aag      355
Asp Glu Gln Pro Thr His Val Ala Val Ala Phe Asp Val Gly Arg Lys
70                  75                  80                  85 acg ttc cgt acc gat atg ttc ccg gcg tat aag gcg cag cgt gaa gca      403
Thr Phe Arg Thr Asp Met Phe Pro Ala Tyr Lys Ala Gln Arg Glu Ala
            90                  95                  100
```

-continued

| | |
|---|---|
| acg cca cct gag ttt aag ggc cag gtg gaa atc ctc aag gag gtg ttg<br>Thr Pro Pro Glu Phe Lys Gly Gln Val Glu Ile Leu Lys Glu Val Leu<br>                105                    110                    115 | 451 |
| tcc act ttg gga att acg act att gag aaa atc gat ttt gag gct gat<br>Ser Thr Leu Gly Ile Thr Thr Ile Glu Lys Ile Asp Phe Glu Ala Asp<br>        120                    125                    130 | 499 |
| gat gtg atc gcc acg ttg tct gtg gcg gcg aaa cct tta ggc ttt aag<br>Asp Val Ile Ala Thr Leu Ser Val Ala Ala Lys Pro Leu Gly Phe Lys<br>135                    140                    145 | 547 |
| acg ctg att gtt acg ggt gac cgt gat tcc ttc cag ttg gtc aat gac<br>Thr Leu Ile Val Thr Gly Asp Arg Asp Ser Phe Gln Leu Val Asn Asp<br>150                    155                    160                    165 | 595 |
| acc acc acg gtg ttg tat ccg atg aag ggc gtg tct gtg ctg cac cgt<br>Thr Thr Thr Val Leu Tyr Pro Met Lys Gly Val Ser Val Leu His Arg<br>                    170                    175                    180 | 643 |
| ttc acg ccg gaa gca gtg gag gag aag tat gga ctg aca ccg agg cag<br>Phe Thr Pro Glu Ala Val Glu Glu Lys Tyr Gly Leu Thr Pro Arg Gln<br>                185                    190                    195 | 691 |
| tat ccg gag ttt gca gcg ctg cgt ggt gat cct tcc gat aac ttg cct<br>Tyr Pro Glu Phe Ala Ala Leu Arg Gly Asp Pro Ser Asp Asn Leu Pro<br>        200                    205                    210 | 739 |
| aat att cct ggc gtg ggc gag aag act gct acc aag tgg att gcc cag<br>Asn Ile Pro Gly Val Gly Glu Lys Thr Ala Thr Lys Trp Ile Ala Gln<br>215                    220                    225 | 787 |
| tat gaa act ttg gat aat ttg ctt gat cac gct gat gag atc aag ggc<br>Tyr Glu Thr Leu Asp Asn Leu Leu Asp His Ala Asp Glu Ile Lys Gly<br>230                    235                    240                    245 | 835 |
| aag gtt ggc gcc agc ctg cgt gag cgc att gag cag gtc cgg atg aac<br>Lys Val Gly Ala Ser Leu Arg Glu Arg Ile Glu Gln Val Arg Met Asn<br>                    250                    255                    260 | 883 |
| cgc aag ctc acg gag atg gtg aag gat ctg gag ctg ccg ctt ggt ccg<br>Arg Lys Leu Thr Glu Met Val Lys Asp Leu Glu Leu Pro Leu Gly Pro<br>                265                    270                    275 | 931 |
| gac gat ttt gag atg aag cct gtg cag gtt gcg gag gtt gcg gcg aag<br>Asp Asp Phe Glu Met Lys Pro Val Gln Val Ala Glu Val Ala Ala Lys<br>        280                    285                    290 | 979 |
| ttt gac gat ctg gag ttt ggt acc aat ttg cgt gag cgg gtg ctg gcg<br>Phe Asp Asp Leu Glu Phe Gly Thr Asn Leu Arg Glu Arg Val Leu Ala<br>295                    300                    305 | 1027 |
| gtg gtg aag gcc gag ggt tcc gct gcc ccc gtg gag gaa gtg gaa gcg<br>Val Val Lys Ala Glu Gly Ser Ala Ala Pro Val Glu Glu Val Glu Ala<br>310                    315                    320                    325 | 1075 |
| gaa cag gtt gtc gtc gat acg caa tct ttg gcg caa tgg ctg cct gct<br>Glu Gln Val Val Val Asp Thr Gln Ser Leu Ala Gln Trp Leu Pro Ala<br>                    330                    335                    340 | 1123 |
| agg gct ggc cag gcg ctt gct tta gcg ctg gct gga gtg gct aaa cct<br>Arg Ala Gly Gln Ala Leu Ala Leu Ala Leu Ala Gly Val Ala Lys Pro<br>                345                    350                    355 | 1171 |
| gct gct ggc gac acg tat gcg cta gcg att gcg gat acc aag cgc cat<br>Ala Ala Gly Asp Thr Tyr Ala Leu Ala Ile Ala Asp Thr Lys Arg His<br>        360                    365                    370 | 1219 |
| gcg gtg ttg gtt gat gtg gct gat att tca gcg gag gat gaa aag gcg<br>Ala Val Leu Val Asp Val Ala Asp Ile Ser Ala Glu Asp Glu Lys Ala<br>375                    380                    385 | 1267 |
| ctg gcc acg tgg ttg gcg tcg gaa gat cca aag atg ctg cac ggc gct<br>Leu Ala Thr Trp Leu Ala Ser Glu Asp Pro Lys Met Leu His Gly Ala<br>390                    395                    400                    405 | 1315 |
| aag gcc gcc tat cat atg ctc gct ggg cgc ggt ttt gag ctg cac ggc<br>Lys Ala Ala Tyr His Met Leu Ala Gly Arg Gly Phe Glu Leu His Gly | 1363 |

```
                          410                 415                 420
gtg gtg cat gac acg gcg atc gcg gca tac ttg ctg cgt ccg ggc caa          1411
Val Val His Asp Thr Ala Ile Ala Ala Tyr Leu Leu Arg Pro Gly Gln
            425                 430                 435 cgc acc tat gag ctt gcc gac gtc tac cag cgg cat ctt caa cga cag          1459
Arg Thr Tyr Glu Leu Ala Asp Val Tyr Gln Arg His Leu Gln Arg Gln
            440                 445                 450 ttg tct aca aac gac aat ggc ggc cag ctc acg ctg ctc gac gca gct          1507
Leu Ser Thr Asn Asp Asn Gly Gly Gln Leu Thr Leu Leu Asp Ala Ala
455                 460                 465 gat gac caa tcg ctt gtt gat gat gtc att gca atc ctt gag ctg tct          1555
Asp Asp Gln Ser Leu Val Asp Asp Val Ile Ala Ile Leu Glu Leu Ser
470                 475                 480                 485 gaa gaa ttg acc aaa cag ctt cag gag att caa gct ttt gag ctt tac          1603
Glu Glu Leu Thr Lys Gln Leu Gln Glu Ile Gln Ala Phe Glu Leu Tyr
            490                 495                 500 cat gac ctg gaa att ccg ctg tcg gga att ctg gcg cgc atg gag gcc          1651
His Asp Leu Glu Ile Pro Leu Ser Gly Ile Leu Ala Arg Met Glu Ala
            505                 510                 515 atc ggt atc gct gtt gat gtt gcc act ttg gaa gag cag ttg aag act          1699
Ile Gly Ile Ala Val Asp Val Ala Thr Leu Glu Glu Gln Leu Lys Thr
            520                 525                 530 ttc att ggt cag gtt gct cag gaa gag gaa gca gct cgc gag ctc gct          1747
Phe Ile Gly Gln Val Ala Gln Glu Glu Glu Ala Ala Arg Glu Leu Ala
535                 540                 545 gag gat cca acc ctg aat ctc tcg agc ccg aag cag ctg caa gtg gtg          1795
Glu Asp Pro Thr Leu Asn Leu Ser Ser Pro Lys Gln Leu Gln Val Val
550                 555                 560                 565 ctt ttt gag acg ttc gga atg ccg aaa acc aag aaa acc aag acc ggc          1843
Leu Phe Glu Thr Phe Gly Met Pro Lys Thr Lys Lys Thr Lys Thr Gly
            570                 575                 580 tac tct acg gct gcc gcg gaa att gaa gcc cta gcg atc aag aat ccg          1891
Tyr Ser Thr Ala Ala Ala Glu Ile Glu Ala Leu Ala Ile Lys Asn Pro
            585                 590                 595 cac cca ttc cta gat cac ctg ttg gca cac cgt cag tac caa aag atg          1939
His Pro Phe Leu Asp His Leu Leu Ala His Arg Gln Tyr Gln Lys Met
            600                 605                 610 aag acc act ctg gaa ggt ctc atc cgt gag gtg gct cct gat ggc cgt          1987
Lys Thr Thr Leu Glu Gly Leu Ile Arg Glu Val Ala Pro Asp Gly Arg
            615                 620                 625 att cac acc acc ttc aac cag acg gtg gcg tct acg gga cgt ttg tca          2035
Ile His Thr Thr Phe Asn Gln Thr Val Ala Ser Thr Gly Arg Leu Ser
630                 635                 640                 645 tcc act gat ccc aac ctg caa aac att cct gtg cgc act gag gct ggc          2083
Ser Thr Asp Pro Asn Leu Gln Asn Ile Pro Val Arg Thr Glu Ala Gly
            650                 655                 660 cga aag att cgt tcg gga ttc gtc gta ggc gag ggg tat gaa acc ttg          2131
Arg Lys Ile Arg Ser Gly Phe Val Val Gly Glu Gly Tyr Glu Thr Leu
            665                 670                 675 ctg act gcc gac tat tcg cag att gaa atg cgc gtg atg gct cac ctt          2179
Leu Thr Ala Asp Tyr Ser Gln Ile Glu Met Arg Val Met Ala His Leu
            680                 685                 690 tcc cag gac cca ggc ttg att gag gcg tac cgc gaa ggc gaa gac ctg          2227
Ser Gln Asp Pro Gly Leu Ile Glu Ala Tyr Arg Glu Gly Glu Asp Leu
695                 700                 705 cac aat tac gtg ggt tcc aag gtg ttt aat gtg ccc atc gat ggc gtg          2275
His Asn Tyr Val Gly Ser Lys Val Phe Asn Val Pro Ile Asp Gly Val
710                 715                 720                 725 acc cct gag ctg cgt cgc cag gtc aag gcc atg tct tac ggt ctg gtg          2323
```

```
Thr Pro Glu Leu Arg Arg Gln Val Lys Ala Met Ser Tyr Gly Leu Val
                730                 735                 740
tac ggc ttg tcc gcg ttt ggt ttg tct cag cag ctg agc att cct gct       2371
Tyr Gly Leu Ser Ala Phe Gly Leu Ser Gln Gln Leu Ser Ile Pro Ala
                745                 750                 755 ggc gaa gcg aag cag atc atg gag tcc tac ttc gag cgc ttc ggc gga       2419
Gly Glu Ala Lys Gln Ile Met Glu Ser Tyr Phe Glu Arg Phe Gly Gly
            760                 765                 770 gta cag cgc tac ctc cgg gag atc gtg gag gag gct cga aaa gct ggc       2467
Val Gln Arg Tyr Leu Arg Glu Ile Val Glu Glu Ala Arg Lys Ala Gly
        775                 780                 785 tac acg gaa acg ctg ttt ggg cgt cgt cgc tac ctg ccg gaa ctg acc       2515
Tyr Thr Glu Thr Leu Phe Gly Arg Arg Arg Tyr Leu Pro Glu Leu Thr
790                 795                 800                 805 tcg gat aac cgt gtc gct cgt gaa aac gct gaa cgt gcc gca ctg aac       2563
Ser Asp Asn Arg Val Ala Arg Glu Asn Ala Glu Arg Ala Ala Leu Asn
                810                 815                 820 gcc ccg att cag gga act gcc gca gac atc atc aag gtg gcc atg atc       2611
Ala Pro Ile Gln Gly Thr Ala Ala Asp Ile Ile Lys Val Ala Met Ile
            825                 830                 835 cgg gtg gac cgt tca ctc aag gaa gct gcc gtg aaa tct cgc gtg ctg       2659
Arg Val Asp Arg Ser Leu Lys Glu Ala Ala Val Lys Ser Arg Val Leu
        840                 845                 850 ctt cag gtg cat gat gaa ttg gtc gtg gaa gta gcg gcc ggt gag ttg       2707
Leu Gln Val His Asp Glu Leu Val Val Glu Val Ala Ala Gly Glu Leu
    855                 860                 865 gaa caa gtc cgt gag att ctg gaa cgc gaa atg gat aac gcc atc aag       2755
Glu Gln Val Arg Glu Ile Leu Glu Arg Glu Met Asp Asn Ala Ile Lys
870                 875                 880                 885 ctg tcc gtt cct ttg gaa gtt tca gct ggt gat ggc gtt aac tgg gat       2803
Leu Ser Val Pro Leu Glu Val Ser Ala Gly Asp Gly Val Asn Trp Asp
                890                 895                 900 gct gca gcg cac taagaggtaa ctgccttttc gtcgacgagc                      2845
Ala Ala Ala His
            905

<210> SEQ ID NO 4
<211> LENGTH: 905
<212> TYPE: PRT
<213> ORGANISM: Corynebacterium glutamicum

<400> SEQUENCE: 4

Leu Gly Glu Cys Val Ala Asn Phe Ser Thr Arg Leu His Ser Gly Gly
  1               5                  10                  15

Val Thr Glu Lys Thr Asp Gln Thr Leu Met Leu Ile Asp Gly His Ser
                 20                  25                  30

Met Ala Phe Arg Ala Phe Phe Ala Leu Pro Ala Glu Asn Phe Ser Thr
             35                  40                  45

Ser Gly Gly Gln Ala Thr Asn Ala Val Tyr Gly Phe Leu Ser Met Leu
         50                  55                  60

Ser Thr Leu Leu Lys Asp Glu Gln Pro Thr His Val Ala Val Ala Phe
 65                  70                  75                  80

Asp Val Gly Arg Lys Thr Phe Arg Thr Asp Met Phe Pro Ala Tyr Lys
                 85                  90                  95

Ala Gln Arg Glu Ala Thr Pro Pro Glu Phe Lys Gly Gln Val Glu Ile
            100                 105                 110

Leu Lys Glu Val Leu Ser Thr Leu Gly Ile Thr Thr Ile Glu Lys Ile
        115                 120                 125
```

-continued

```
Asp Phe Glu Ala Asp Asp Val Ile Ala Thr Leu Ser Val Ala Ala Lys
    130                 135                 140

Pro Leu Gly Phe Lys Thr Leu Ile Val Thr Gly Asp Arg Asp Ser Phe
145                 150                 155                 160

Gln Leu Val Asn Asp Thr Thr Val Leu Tyr Pro Met Lys Gly Val
                165                 170                 175

Ser Val Leu His Arg Phe Thr Pro Glu Ala Val Glu Glu Lys Tyr Gly
            180                 185                 190

Leu Thr Pro Arg Gln Tyr Pro Glu Phe Ala Ala Leu Arg Gly Asp Pro
        195                 200                 205

Ser Asp Asn Leu Pro Asn Ile Pro Gly Val Gly Glu Lys Thr Ala Thr
    210                 215                 220

Lys Trp Ile Ala Gln Tyr Glu Thr Leu Asp Asn Leu Leu Asp His Ala
225                 230                 235                 240

Asp Glu Ile Lys Gly Lys Val Gly Ala Ser Leu Arg Glu Arg Ile Glu
                245                 250                 255

Gln Val Arg Met Asn Arg Lys Leu Thr Glu Met Val Lys Asp Leu Glu
            260                 265                 270

Leu Pro Leu Gly Pro Asp Asp Phe Glu Met Lys Pro Val Gln Val Ala
        275                 280                 285

Glu Val Ala Ala Lys Phe Asp Asp Leu Glu Phe Gly Thr Asn Leu Arg
290                 295                 300

Glu Arg Val Leu Ala Val Val Lys Ala Glu Gly Ser Ala Ala Pro Val
305                 310                 315                 320

Glu Glu Val Glu Ala Glu Gln Val Val Asp Thr Gln Ser Leu Ala
                325                 330                 335

Gln Trp Leu Pro Ala Arg Ala Gly Gln Ala Leu Ala Leu Ala Leu Ala
        340                 345                 350

Gly Val Ala Lys Pro Ala Ala Gly Asp Thr Tyr Ala Leu Ala Ile Ala
    355                 360                 365

Asp Thr Lys Arg His Ala Val Leu Val Asp Val Ala Asp Ile Ser Ala
    370                 375                 380

Glu Asp Glu Lys Ala Leu Ala Thr Trp Leu Ala Ser Glu Asp Pro Lys
385                 390                 395                 400

Met Leu His Gly Ala Lys Ala Ala Tyr His Met Leu Ala Gly Arg Gly
                405                 410                 415

Phe Glu Leu His Gly Val Val His Asp Thr Ala Ile Ala Ala Tyr Leu
            420                 425                 430

Leu Arg Pro Gly Gln Arg Thr Tyr Glu Leu Ala Asp Val Tyr Gln Arg
        435                 440                 445

His Leu Gln Arg Gln Leu Ser Thr Asn Asp Asn Gly Gly Gln Leu Thr
    450                 455                 460

Leu Leu Asp Ala Ala Asp Asp Gln Ser Leu Val Asp Val Ile Ala
465                 470                 475                 480

Ile Leu Glu Leu Ser Glu Glu Leu Thr Lys Gln Leu Gln Glu Ile Gln
                485                 490                 495

Ala Phe Glu Leu Tyr His Asp Leu Glu Ile Pro Leu Ser Gly Ile Leu
            500                 505                 510

Ala Arg Met Glu Ala Ile Gly Ile Ala Val Asp Val Ala Thr Leu Glu
        515                 520                 525

Glu Gln Leu Lys Thr Phe Ile Gly Gln Val Ala Gln Glu Glu Glu Ala
    530                 535                 540

Ala Arg Glu Leu Ala Glu Asp Pro Thr Leu Asn Leu Ser Ser Pro Lys
```

```
                545                 550                 555                 560
Gln Leu Gln Val Val Leu Phe Glu Thr Phe Gly Met Pro Lys Thr Lys
                565                 570                 575
Lys Thr Lys Thr Gly Tyr Ser Thr Ala Ala Glu Ile Glu Ala Leu
            580                 585                 590
Ala Ile Lys Asn Pro His Pro Phe Leu Asp His Leu Leu Ala His Arg
            595                 600                 605
Gln Tyr Gln Lys Met Lys Thr Thr Leu Glu Gly Leu Ile Arg Glu Val
        610                 615                 620
Ala Pro Asp Gly Arg Ile His Thr Thr Phe Asn Gln Thr Val Ala Ser
625                 630                 635                 640
Thr Gly Arg Leu Ser Ser Thr Asp Pro Asn Leu Gln Asn Ile Pro Val
                645                 650                 655
Arg Thr Glu Ala Gly Arg Lys Ile Arg Ser Gly Phe Val Val Gly Glu
                660                 665                 670
Gly Tyr Glu Thr Leu Leu Thr Ala Asp Tyr Ser Gln Ile Glu Met Arg
            675                 680                 685
Val Met Ala His Leu Ser Gln Asp Pro Gly Leu Ile Glu Ala Tyr Arg
690                 695                 700
Glu Gly Glu Asp Leu His Asn Tyr Val Gly Ser Lys Val Phe Asn Val
705                 710                 715                 720
Pro Ile Asp Gly Val Thr Pro Glu Leu Arg Arg Gln Val Lys Ala Met
                725                 730                 735
Ser Tyr Gly Leu Val Tyr Gly Leu Ser Ala Phe Gly Leu Ser Gln Gln
            740                 745                 750
Leu Ser Ile Pro Ala Gly Glu Ala Lys Gln Ile Met Glu Ser Tyr Phe
        755                 760                 765
Glu Arg Phe Gly Gly Val Gln Arg Tyr Leu Arg Glu Ile Val Glu Glu
    770                 775                 780
Ala Arg Lys Ala Gly Tyr Thr Glu Thr Leu Phe Gly Arg Arg Arg Tyr
785                 790                 795                 800
Leu Pro Glu Leu Thr Ser Asp Asn Arg Val Ala Arg Glu Asn Ala Glu
                805                 810                 815
Arg Ala Leu Asn Ala Pro Ile Gln Gly Thr Ala Ala Asp Ile Ile
            820                 825                 830
Lys Val Ala Met Ile Arg Val Asp Arg Ser Leu Lys Glu Ala Ala Val
            835                 840                 845
Lys Ser Arg Val Leu Leu Gln Val His Asp Glu Leu Val Val Glu Val
        850                 855                 860
Ala Ala Gly Glu Leu Glu Gln Val Arg Glu Ile Leu Glu Arg Glu Met
865                 870                 875                 880
Asp Asn Ala Ile Lys Leu Ser Val Pro Leu Glu Val Ser Ala Gly Asp
                885                 890                 895
Gly Val Asn Trp Asp Ala Ala His
            900                 905

<210> SEQ ID NO 5
<211> LENGTH: 1621
<212> TYPE: DNA
<213> ORGANISM: Corynebacterium glutamicum
<220> FEATURE:
<221> NAME/KEY: CDS
<222> LOCATION: (101)..(1591)
<223> OTHER INFORMATION: RXA00209

<400> SEQUENCE: 5
```

```
acaagaccct cgatgctgcg gctgcgttgg accaagcgcc cgctgtcgag gatggacgtt     60
ttatggttcc gcagattctg ggtgagggcg actaataatt atg acc aac aag tac    115
                                            Met Thr Asn Lys Tyr
                                              1               5 ctg gtt gaa ggc tct gaa aac gag ctg acc aca aag acc gca gca gag    163
Leu Val Glu Gly Ser Glu Asn Glu Leu Thr Thr Lys Thr Ala Ala Glu
                10              15                  20 ctg gca ggt ctt att cat tcc cgc gag gta act tcc cgc gag gtt act    211
Leu Ala Gly Leu Ile His Ser Arg Glu Val Thr Ser Arg Glu Val Thr
            25                  30                  35 caa gcg cac cta gat cgc att gct gcg gtt gac ggc gat att cat gca    259
Gln Ala His Leu Asp Arg Ile Ala Ala Val Asp Gly Asp Ile His Ala
        40                  45                  50 ttt ctc cac gtt ggc cag gag gag gcc ctg aac gcg gcg gat gac gtc    307
Phe Leu His Val Gly Gln Glu Glu Ala Leu Asn Ala Ala Asp Asp Val
    55                  60                  65 gat aag cgt cta gac gct gga gag gca cct gcc tcg gct ttg gct ggc    355
Asp Lys Arg Leu Asp Ala Gly Glu Ala Pro Ala Ser Ala Leu Ala Gly
70                  75                  80                  85 gtg ccg ctt gcg ctg aag gat gtc ttt acc acc act gat gcg ccg acc    403
Val Pro Leu Ala Leu Lys Asp Val Phe Thr Thr Thr Asp Ala Pro Thr
                90                  95                 100 acg gcg gca tcg aag atg ctt gag ggc tac atg agc cct tat gac gcg    451
Thr Ala Ala Ser Lys Met Leu Glu Gly Tyr Met Ser Pro Tyr Asp Ala
            105                 110                 115 act gtg acc cgc aag atc cgt gag gct ggc atc cca att ttg ggt aag    499
Thr Val Thr Arg Lys Ile Arg Glu Ala Gly Ile Pro Ile Leu Gly Lys
        120                 125                 130 acc aac atg gat gag ttt gcg atg ggt tcc tcc act gag aac tcc gca    547
Thr Asn Met Asp Glu Phe Ala Met Gly Ser Ser Thr Glu Asn Ser Ala
    135                 140                 145 tac ggc cca acc cac aat ccg tgg gat ctg gag cgc acc gca ggt ggt    595
Tyr Gly Pro Thr His Asn Pro Trp Asp Leu Glu Arg Thr Ala Gly Gly
150                 155                 160                 165 tct ggt ggt ggc tct tca gct gct ctt gct gca ggt cag gcg cca ctt    643
Ser Gly Gly Gly Ser Ser Ala Ala Leu Ala Ala Gly Gln Ala Pro Leu
                170                 175                 180 gcg att ggt act gac act ggt gga tcc atc cgt cag cca gct gcg ctg    691
Ala Ile Gly Thr Asp Thr Gly Gly Ser Ile Arg Gln Pro Ala Ala Leu
            185                 190                 195 acc aac act gtc ggt gtg aag cca acc tac gga acc gta tcc cgt tac    739
Thr Asn Thr Val Gly Val Lys Pro Thr Tyr Gly Thr Val Ser Arg Tyr
        200                 205                 210 ggt ctg att gcg tgt gcg tcc tcc ctg gat cag ggt ggc cca acc gct    787
Gly Leu Ile Ala Cys Ala Ser Ser Leu Asp Gln Gly Gly Pro Thr Ala
    215                 220                 225 cgt act gtt ctg gat acc gcg ctt ttg cac gag gtt atc gca ggc cac    835
Arg Thr Val Leu Asp Thr Ala Leu Leu His Glu Val Ile Ala Gly His
230                 235                 240                 245 gac gct ttt gat gcg acc tcc gtg aat cgt ccg gtt gct cct gtt gtg    883
Asp Ala Phe Asp Ala Thr Ser Val Asn Arg Pro Val Ala Pro Val Val
                250                 255                 260 cag gct gcc cgt gaa ggc gcg aac ggt gac ctg aaa ggc gtg aag gtc    931
Gln Ala Ala Arg Glu Gly Ala Asn Gly Asp Leu Lys Gly Val Lys Val
            265                 270                 275 ggt gtg gtc aag cag ttc gac cgc gac ggc tac cag cct ggc gtg ctt    979
Gly Val Val Lys Gln Phe Asp Arg Asp Gly Tyr Gln Pro Gly Val Leu
        280                 285                 290
```

-continued

```
gag gca ttc cac gct tct gtt gag cag atg cgc tcc cag ggt gcg gaa     1027
Glu Ala Phe His Ala Ser Val Glu Gln Met Arg Ser Gln Gly Ala Glu
    295                 300                 305 atc gtc gag gtt gat tgc cct cac ttt gat gac gct ctt ggc gcg tac     1075
Ile Val Glu Val Asp Cys Pro His Phe Asp Asp Ala Leu Gly Ala Tyr
310                 315                 320                 325 tac ctg att ctt cct tgt gaa gtt tcc tcc aac ctc gcg cgt ttt gac     1123
Tyr Leu Ile Leu Pro Cys Glu Val Ser Ser Asn Leu Ala Arg Phe Asp
                330                 335                 340 ggc atg cgt tac ggt ttg cgc gct ggt gat gac gga act cgt tcc gcc     1171
Gly Met Arg Tyr Gly Leu Arg Ala Gly Asp Asp Gly Thr Arg Ser Ala
            345                 350                 355 gat gag gtc atg gcg tac acc cgt gcg cag gga ttc ggc cct gag gtt     1219
Asp Glu Val Met Ala Tyr Thr Arg Ala Gln Gly Phe Gly Pro Glu Val
        360                 365                 370 aag cgc cgt atc atc ctc ggc act tac gcg ttg tct gtt ggt tac tac     1267
Lys Arg Arg Ile Ile Leu Gly Thr Tyr Ala Leu Ser Val Gly Tyr Tyr
    375                 380                 385 gac gcg tac tac ctg cag gct cag cgc gtt cgt acc ctc att gca cag     1315
Asp Ala Tyr Tyr Leu Gln Ala Gln Arg Val Arg Thr Leu Ile Ala Gln
390                 395                 400                 405 gac ttc gcc aag gct tac gag cag gtc gac atc ttg gtg tcc cca acc     1363
Asp Phe Ala Lys Ala Tyr Glu Gln Val Asp Ile Leu Val Ser Pro Thr
                410                 415                 420 act cca acc acc gcg ttc aag ctg ggg gag aag gtc acc gat ccg ctg     1411
Thr Pro Thr Thr Ala Phe Lys Leu Gly Glu Lys Val Thr Asp Pro Leu
            425                 430                 435 gag atg tac aac ttc gac ttg tgc acc ctg cca ctg aac ctg gct ggt     1459
Glu Met Tyr Asn Phe Asp Leu Cys Thr Leu Pro Leu Asn Leu Ala Gly
        440                 445                 450 ctc gcg ggc atg tcc ctg cct tcc ggc ttg gca tca gat act ggt ctg     1507
Leu Ala Gly Met Ser Leu Pro Ser Gly Leu Ala Ser Asp Thr Gly Leu
    455                 460                 465 cct gtt ggt ttg cag ctg atg gct cct gct ttc cag gac gat cgt ctc     1555
Pro Val Gly Leu Gln Leu Met Ala Pro Ala Phe Gln Asp Asp Arg Leu
470                 475                 480                 485 tac cgc gtc ggc gct gct ttt gaa gct gga cgc aag taggttctaa          1601
Tyr Arg Val Gly Ala Ala Phe Glu Ala Gly Arg Lys
                490                 495 acccttttta agaaattggc                                               1621
```

<210> SEQ ID NO 6
<211> LENGTH: 497
<212> TYPE: PRT
<213> ORGANISM: Corynebacterium glutamicum

<400> SEQUENCE: 6

```
Met Thr Asn Lys Tyr Leu Val Glu Gly Ser Glu Asn Glu Leu Thr Thr
1               5                   10                  15

Lys Thr Ala Ala Glu Leu Ala Gly Leu Ile His Ser Arg Glu Val Thr
            20                  25                  30

Ser Arg Glu Val Thr Gln Ala His Leu Asp Arg Ile Ala Ala Val Asp
        35                  40                  45

Gly Asp Ile His Ala Phe Leu His Val Gly Gln Glu Glu Ala Leu Asn
    50                  55                  60

Ala Ala Asp Asp Val Asp Lys Arg Leu Asp Ala Gly Glu Ala Pro Ala
65                  70                  75                  80

Ser Ala Leu Ala Gly Val Pro Leu Ala Leu Lys Asp Val Phe Thr Thr
                85                  90                  95
```

-continued

```
Thr Asp Ala Pro Thr Thr Ala Ala Ser Lys Met Leu Glu Gly Tyr Met
            100                 105                 110

Ser Pro Tyr Asp Ala Thr Val Thr Arg Lys Ile Arg Glu Ala Gly Ile
        115                 120                 125

Pro Ile Leu Gly Lys Thr Asn Met Asp Glu Phe Ala Met Gly Ser Ser
    130                 135                 140

Thr Glu Asn Ser Ala Tyr Gly Pro Thr His Asn Pro Trp Asp Leu Glu
145                 150                 155                 160

Arg Thr Ala Gly Gly Ser Gly Gly Ser Ala Ala Leu Ala Ala
                165                 170                 175

Gly Gln Ala Pro Leu Ala Ile Gly Thr Asp Thr Gly Gly Ser Ile Arg
            180                 185                 190

Gln Pro Ala Ala Leu Thr Asn Thr Val Gly Val Lys Pro Thr Tyr Gly
        195                 200                 205

Thr Val Ser Arg Tyr Gly Leu Ile Ala Cys Ala Ser Ser Leu Asp Gln
    210                 215                 220

Gly Gly Pro Thr Ala Arg Thr Val Leu Asp Thr Ala Leu Leu His Glu
225                 230                 235                 240

Val Ile Ala Gly His Asp Ala Phe Asp Ala Thr Ser Val Asn Arg Pro
                245                 250                 255

Val Ala Pro Val Val Gln Ala Ala Arg Glu Gly Ala Asn Gly Asp Leu
            260                 265                 270

Lys Gly Val Lys Val Gly Val Val Lys Gln Phe Asp Arg Asp Gly Tyr
        275                 280                 285

Gln Pro Gly Val Leu Glu Ala Phe His Ala Ser Val Glu Gln Met Arg
    290                 295                 300

Ser Gln Gly Ala Glu Ile Val Glu Val Asp Cys Pro His Phe Asp Asp
305                 310                 315                 320

Ala Leu Gly Ala Tyr Tyr Leu Ile Leu Pro Cys Glu Val Ser Ser Asn
                325                 330                 335

Leu Ala Arg Phe Asp Gly Met Arg Tyr Gly Leu Arg Ala Gly Asp Asp
            340                 345                 350

Gly Thr Arg Ser Ala Asp Glu Val Met Ala Tyr Thr Arg Ala Gln Gly
        355                 360                 365

Phe Gly Pro Glu Val Lys Arg Ile Ile Leu Gly Thr Tyr Ala Leu
    370                 375                 380

Ser Val Gly Tyr Tyr Asp Ala Tyr Tyr Leu Gln Ala Gln Arg Val Arg
385                 390                 395                 400

Thr Leu Ile Ala Gln Asp Phe Ala Lys Ala Tyr Glu Gln Val Asp Ile
                405                 410                 415

Leu Val Ser Pro Thr Thr Pro Thr Thr Ala Phe Lys Leu Gly Glu Lys
            420                 425                 430

Val Thr Asp Pro Leu Glu Met Tyr Asn Phe Asp Leu Cys Thr Leu Pro
        435                 440                 445

Leu Asn Leu Ala Gly Leu Ala Gly Met Ser Leu Pro Ser Gly Leu Ala
    450                 455                 460

Ser Asp Thr Gly Leu Pro Val Gly Leu Gln Leu Met Ala Pro Ala Phe
465                 470                 475                 480

Gln Asp Asp Arg Leu Tyr Arg Val Gly Ala Ala Phe Glu Ala Gly Arg
                485                 490                 495

Lys
```

-continued

```
<210> SEQ ID NO 7
<211> LENGTH: 793
<212> TYPE: DNA
<213> ORGANISM: Corynebacterium glutamicum
<220> FEATURE:
<221> NAME/KEY: CDS
<222> LOCATION: (101)..(763)
<223> OTHER INFORMATION: RXA00211

<400> SEQUENCE: 7
tgagccaaaa tcaataaggt gttttcagc ctgaggtaaa aatacggtgg tactgtcgaa      60
accaatcatc ccctagtttt gaaaagaagg aagcgagcca atg tca ttc ctg atc     115
                                              Met Ser Phe Leu Ile
                                                1               5 cgc gtc ctg ttg tcc gac acc cca ggc agc ctc gcg tta ctc gct gaa     163
Arg Val Leu Leu Ser Asp Thr Pro Gly Ser Leu Ala Leu Leu Ala Glu
             10                  15                  20 gcc ctt ggg att gta gag gcc aat att caa tcc gtg gac gtg gtg gaa     211
Ala Leu Gly Ile Val Glu Ala Asn Ile Gln Ser Val Asp Val Val Glu
         25                  30                  35 cgc ttc ccc aat ggc acg gtc atg gac gat ctg gtg atc tcc atc cct     259
Arg Phe Pro Asn Gly Thr Val Met Asp Asp Leu Val Ile Ser Ile Pro
     40                  45                  50 cgc gat gtc atg gca gac acc atc atc acc gca gct gaa gaa gtc gac     307
Arg Asp Val Met Ala Asp Thr Ile Ile Thr Ala Ala Glu Glu Val Asp
 55                  60                  65 ggc gtg gag att gat tcc atc cgc cca ttc tcc ggg act gtt gac cgc     355
Gly Val Glu Ile Asp Ser Ile Arg Pro Phe Ser Gly Thr Val Asp Arg
 70                  75                  80                  85 cgc gga cag atc caa atg ctg gct gct gtt gct cac caa cgc cgc gat     403
Arg Gly Gln Ile Gln Met Leu Ala Ala Val Ala His Gln Arg Arg Asp
                 90                  95                 100 atc acc gca gcg atg gaa gaa atg gtc gat gtc atc ccc cgc acc atg     451
Ile Thr Ala Ala Met Glu Glu Met Val Asp Val Ile Pro Arg Thr Met
            105                 110                 115 acc tct ggt tgg gct ttg gtc att gat cta aaa gga ccc atc act cgc     499
Thr Ser Gly Trp Ala Leu Val Ile Asp Leu Lys Gly Pro Ile Thr Arg
        120                 125                 130 atc gct ggt tcc cta gca gcg ccc gaa gat gac ggc acc gtt ccg gag     547
Ile Ala Gly Ser Leu Ala Ala Pro Glu Asp Asp Gly Thr Val Pro Glu
    135                 140                 145 aac atc gtt ctc aaa gaa gct cgc atg ctc aac ccg gaa aac gat ccg     595
Asn Ile Val Leu Lys Glu Ala Arg Met Leu Asn Pro Glu Asn Asp Pro
150                 155                 160                 165 tgg att cca gag tcc tgg aca ctg ctt gat tct tcc ctt gcc atc gct     643
Trp Ile Pro Glu Ser Trp Thr Leu Leu Asp Ser Ser Leu Ala Ile Ala
                170                 175                 180 ccg atc ggc aag cac ggc ctg gct ctg att atc ggt cgc cct ggt ggc     691
Pro Ile Gly Lys His Gly Leu Ala Leu Ile Ile Gly Arg Pro Gly Gly
            185                 190                 195 cct gat ttc ttg gcc agc gaa gtg gag cac tta ggc caa gtc ggt gac     739
Pro Asp Phe Leu Ala Ser Glu Val Glu His Leu Gly Gln Val Gly Asp
        200                 205                 210 att atc gga gca atg ctt caa aaa taatctgagc tgtttaaaaa atgccccaag    793
Ile Ile Gly Ala Met Leu Gln Lys
    215                 220

<210> SEQ ID NO 8
<211> LENGTH: 221
<212> TYPE: PRT
<213> ORGANISM: Corynebacterium glutamicum
```

-continued

```
<400> SEQUENCE: 8

Met Ser Phe Leu Ile Arg Val Leu Leu Ser Asp Thr Pro Gly Ser Leu
 1               5                  10                  15

Ala Leu Leu Ala Glu Ala Leu Gly Ile Val Glu Ala Asn Ile Gln Ser
            20                  25                  30

Val Asp Val Glu Arg Phe Pro Asn Gly Thr Val Met Asp Asp Leu
        35                  40                  45

Val Ile Ser Ile Pro Arg Asp Val Met Ala Asp Thr Ile Ile Thr Ala
     50                  55                  60

Ala Glu Glu Val Asp Gly Val Glu Ile Asp Ser Ile Arg Pro Phe Ser
 65                  70                  75                  80

Gly Thr Val Asp Arg Arg Gly Gln Ile Gln Met Leu Ala Ala Val Ala
                85                  90                  95

His Gln Arg Arg Asp Ile Thr Ala Ala Met Glu Glu Met Val Asp Val
            100                 105                 110

Ile Pro Arg Thr Met Thr Ser Gly Trp Ala Leu Val Ile Asp Leu Lys
        115                 120                 125

Gly Pro Ile Thr Arg Ile Ala Gly Ser Leu Ala Ala Pro Glu Asp Asp
    130                 135                 140

Gly Thr Val Pro Glu Asn Ile Val Leu Lys Glu Ala Arg Met Leu Asn
145                 150                 155                 160

Pro Glu Asn Asp Pro Trp Ile Pro Glu Ser Trp Thr Leu Leu Asp Ser
                165                 170                 175

Ser Leu Ala Ile Ala Pro Ile Gly Lys His Gly Leu Ala Leu Ile Ile
            180                 185                 190

Gly Arg Pro Gly Gly Pro Asp Phe Leu Ala Ser Glu Val Glu His Leu
        195                 200                 205

Gly Gln Val Gly Asp Ile Ile Gly Ala Met Leu Gln Lys
    210                 215                 220

<210> SEQ ID NO 9
<211> LENGTH: 1543
<212> TYPE: DNA
<213> ORGANISM: Corynebacterium glutamicum
<220> FEATURE:
<221> NAME/KEY: CDS
<222> LOCATION: (101)..(1513)
<223> OTHER INFORMATION: RXA00314

<400> SEQUENCE: 9
acctgtaaac acttacggtt tgggcgaaat tgaagcggga gccaacctgc tcaacgtcgc      60
aaagaaagaa gcggtgccag caacaccata agttgaaacc ttg agt gtt cgc aca      115
                                           Leu Ser Val Arg Thr
                                             1               5 cag gtt aga cta ggg gac gtg act cta cgc atc ttt gac acc ggt acc      163
Gln Val Arg Leu Gly Asp Val Thr Leu Arg Ile Phe Asp Thr Gly Thr
             10                  15                  20 cgt acg ctt cga gat ttt aaa cct gtt caa cca ggt cat gcc tcg gtg      211
Arg Thr Leu Arg Asp Phe Lys Pro Val Gln Pro Gly His Ala Ser Val
         25                  30                  35 tac ctg tgt ggt gcc acc ccg caa tct tca ccc cac att gga cat gtt      259
Tyr Leu Cys Gly Ala Thr Pro Gln Ser Ser Pro His Ile Gly His Val
     40                  45                  50 cgt tca gca gta gcg ttt gat att ttg cgc cgc tgg ctc atg gct aag      307
Arg Ser Ala Val Ala Phe Asp Ile Leu Arg Arg Trp Leu Met Ala Lys
 55                  60                  65 gga ctt gat gtg gca ttt gtt cgc aat gtc act gat atc gat gac aag      355
```

|  |  |
|---|---|
| Gly Leu Asp Val Ala Phe Val Arg Asn Val Thr Asp Ile Asp Asp Lys<br>70               75                   80               85 | |
| att ctc acc aag gca tct gaa aat ggt cgc cct tgg tgg gaa tgg gtg<br>Ile Leu Thr Lys Ala Ser Glu Asn Gly Arg Pro Trp Trp Glu Trp Val<br>              90                   95                  100 | 403 |
| tcc acc tat gaa cgt gaa ttc acc tgg acg tac aac acg ttg ggt gtg<br>Ser Thr Tyr Glu Arg Glu Phe Thr Trp Thr Tyr Asn Thr Leu Gly Val<br>           105                      110                115 | 451 |
| ctt cct cca tca acg gag cct cgt gca aca ggc cac gtc act cag atg<br>Leu Pro Pro Ser Thr Glu Pro Arg Ala Thr Gly His Val Thr Gln Met<br>        120                      125                130 | 499 |
| att aag tac atg cag cgc ttg att gat aac ggc ttt gct tac gcc gtt<br>Ile Lys Tyr Met Gln Arg Leu Ile Asp Asn Gly Phe Ala Tyr Ala Val<br>135                140                  145 | 547 |
| gat ggc tct gtg tac ttt gat gtc gca gcg tgg tcc aag gct gaa gga<br>Asp Gly Ser Val Tyr Phe Asp Val Ala Ala Trp Ser Lys Ala Glu Gly<br>150                155                  160                165 | 595 |
| tct gac tat ggt tct ttg tcc gga aac cgt gtt gaa gat atg gag cag<br>Ser Asp Tyr Gly Ser Leu Ser Gly Asn Arg Val Glu Asp Met Glu Gln<br>                170                  175                180 | 643 |
| ggc gag ccc gat aac ttt ggt aag cgg ggg cca cag gac ttt gct ctg<br>Gly Glu Pro Asp Asn Phe Gly Lys Arg Gly Pro Gln Asp Phe Ala Leu<br>                185                  190                195 | 691 |
| tgg aag gct gcc aaa ccg ggt gag ccg tca tgg cca acc cct tgg gga<br>Trp Lys Ala Ala Lys Pro Gly Glu Pro Ser Trp Pro Thr Pro Trp Gly<br>        200                      205                210 | 739 |
| gac ggc cgg ccg ggt tgg cat ttg gaa tgc tct gcc atg gcc acc tac<br>Asp Gly Arg Pro Gly Trp His Leu Glu Cys Ser Ala Met Ala Thr Tyr<br>215                220                  225 | 787 |
| tat ttg ggt gag caa ttt gat att cac tgt ggt ggt ttg gat ctg caa<br>Tyr Leu Gly Glu Gln Phe Asp Ile His Cys Gly Gly Leu Asp Leu Gln<br>230                235                  240                245 | 835 |
| ttt cca cac cat gaa aat gaa att gcc cag gca cat gcg gct ggc gat<br>Phe Pro His His Glu Asn Glu Ile Ala Gln Ala His Ala Ala Gly Asp<br>                250                  255                260 | 883 |
| aaa ttt gcc aac tac tgg atg cac aat cac tgg gta aca atg gcc ggc<br>Lys Phe Ala Asn Tyr Trp Met His Asn His Trp Val Thr Met Ala Gly<br>                265                  270                275 | 931 |
| gag aaa atg tcc aag tct ttg ggc aat gtt ttg gct gtg ccg gaa atg<br>Glu Lys Met Ser Lys Ser Leu Gly Asn Val Leu Ala Val Pro Glu Met<br>        280                      285                290 | 979 |
| cta aag cag gtt cgt cct gtc gag ctt cgt tat tac ctt ggg tct gcc<br>Leu Lys Gln Val Arg Pro Val Glu Leu Arg Tyr Tyr Leu Gly Ser Ala<br>295                300                  305 | 1027 |
| cat tac cgt tcc gtc ctt gag tat tcc gag agc gct ttg agt gaa gct<br>His Tyr Arg Ser Val Leu Glu Tyr Ser Glu Ser Ala Leu Ser Glu Ala<br>310                315                  320                325 | 1075 |
| gcg gtg ggt tac cgt cgc att gag tct ttc ctt gag cgt gtg ggg gat<br>Ala Val Gly Tyr Arg Arg Ile Glu Ser Phe Leu Glu Arg Val Gly Asp<br>                330                  335                340 | 1123 |
| gtt gag gta ggc gag tgg acg cca ggt ttt gaa gtt gcg atg gat gag<br>Val Glu Val Gly Glu Trp Thr Pro Gly Phe Glu Val Ala Met Asp Glu<br>                345                  350                355 | 1171 |
| gat att gca gtt cct aag gct ttg gct gaa atc cat aac gct gtc cgc<br>Asp Ile Ala Val Pro Lys Ala Leu Ala Glu Ile His Asn Ala Val Arg<br>        360                      365                370 | 1219 |
| gag ggc aat gct gcc ttg gat aag ggt gat cgt gag gca gcg gag aag<br>Glu Gly Asn Ala Ala Leu Asp Lys Gly Asp Arg Glu Ala Ala Glu Lys<br>375                380                  385 | 1267 |

```
ctt gct tcc tcg gtt cgt gcg atg act ggc gtt ttg ggc ttc gac ccc      1315
Leu Ala Ser Ser Val Arg Ala Met Thr Gly Val Leu Gly Phe Asp Pro
390                 395                 400                 405 gtt gaa tgg ggt tca gat gca ggc gct gat ggc aag gca gat aag gcg      1363
Val Glu Trp Gly Ser Asp Ala Gly Ala Asp Gly Lys Ala Asp Lys Ala
            410                 415                 420 ctt gat gtg ctg att tct tcg gag ctt gag cgt cgt gca act gct cgt      1411
Leu Asp Val Leu Ile Ser Ser Glu Leu Glu Arg Arg Ala Thr Ala Arg
            425                 430                 435 gct gag aag aat tgg gcg gtt gct gat gag gtt cga gat cgt ctt gcc      1459
Ala Glu Lys Asn Trp Ala Val Ala Asp Glu Val Arg Asp Arg Leu Ala
            440                 445                 450 gat gct ggt att gag gtt gtg gat acc gca gat ggc gct aca tgg aaa      1507
Asp Ala Gly Ile Glu Val Val Asp Thr Ala Asp Gly Ala Thr Trp Lys
455                 460                 465 ttg cag taattacaga cactttaag gagataattt                              1543
Leu Gln
470

<210> SEQ ID NO 10
<211> LENGTH: 471
<212> TYPE: PRT
<213> ORGANISM: Corynebacterium glutamicum

<400> SEQUENCE: 10

Leu Ser Val Arg Thr Gln Val Arg Leu Gly Asp Val Thr Leu Arg Ile
 1               5                  10                  15

Phe Asp Thr Gly Thr Arg Thr Leu Arg Asp Phe Lys Pro Val Gln Pro
            20                  25                  30

Gly His Ala Ser Val Tyr Leu Cys Gly Ala Thr Pro Gln Ser Ser Pro
        35                  40                  45

His Ile Gly His Val Arg Ser Ala Val Ala Phe Asp Ile Leu Arg Arg
    50                  55                  60

Trp Leu Met Ala Lys Gly Leu Asp Val Ala Phe Val Arg Asn Val Thr
65                  70                  75                  80

Asp Ile Asp Asp Lys Ile Leu Thr Lys Ala Ser Glu Asn Gly Arg Pro
                85                  90                  95

Trp Trp Glu Trp Val Ser Thr Tyr Glu Arg Glu Phe Thr Trp Thr Tyr
            100                 105                 110

Asn Thr Leu Gly Val Leu Pro Pro Ser Thr Glu Pro Arg Ala Thr Gly
        115                 120                 125

His Val Thr Gln Met Ile Lys Tyr Met Gln Arg Leu Ile Asp Asn Gly
    130                 135                 140

Phe Ala Tyr Ala Val Asp Gly Ser Val Tyr Phe Asp Val Ala Ala Trp
145                 150                 155                 160

Ser Lys Ala Glu Gly Ser Asp Tyr Gly Ser Leu Ser Gly Asn Arg Val
                165                 170                 175

Glu Asp Met Glu Gln Gly Glu Pro Asp Asn Phe Gly Lys Arg Gly Pro
            180                 185                 190

Gln Asp Phe Ala Leu Trp Lys Ala Lys Pro Gly Glu Pro Ser Trp
        195                 200                 205

Pro Thr Pro Trp Gly Asp Gly Arg Pro Gly Trp His Leu Glu Cys Ser
    210                 215                 220

Ala Met Ala Thr Tyr Tyr Leu Gly Glu Gln Phe Asp Ile His Cys Gly
225                 230                 235                 240

Gly Leu Asp Leu Gln Phe Pro His His Glu Asn Glu Ile Ala Gln Ala
                245                 250                 255
```

His Ala Ala Gly Asp Lys Phe Ala Asn Tyr Trp Met His Asn His Trp
            260                 265                 270

Val Thr Met Ala Gly Glu Lys Met Ser Lys Ser Leu Gly Asn Val Leu
        275                 280                 285

Ala Val Pro Glu Met Leu Lys Gln Val Arg Pro Val Glu Leu Arg Tyr
    290                 295                 300

Tyr Leu Gly Ser Ala His Tyr Arg Ser Val Leu Glu Tyr Ser Glu Ser
305                 310                 315                 320

Ala Leu Ser Glu Ala Ala Val Gly Tyr Arg Arg Ile Glu Ser Phe Leu
                325                 330                 335

Glu Arg Val Gly Asp Val Glu Val Gly Glu Trp Thr Pro Gly Phe Glu
            340                 345                 350

Val Ala Met Asp Glu Asp Ile Ala Val Pro Lys Ala Leu Ala Glu Ile
        355                 360                 365

His Asn Ala Val Arg Glu Gly Asn Ala Ala Leu Asp Lys Gly Asp Arg
    370                 375                 380

Glu Ala Ala Glu Lys Leu Ala Ser Ser Val Arg Ala Met Thr Gly Val
385                 390                 395                 400

Leu Gly Phe Asp Pro Val Glu Trp Gly Ser Asp Ala Gly Ala Asp Gly
                405                 410                 415

Lys Ala Asp Lys Ala Leu Asp Val Leu Ile Ser Ser Glu Leu Glu Arg
            420                 425                 430

Arg Ala Thr Ala Arg Ala Glu Lys Asn Trp Ala Val Ala Asp Glu Val
        435                 440                 445

Arg Asp Arg Leu Ala Asp Ala Gly Ile Glu Val Val Asp Thr Ala Asp
    450                 455                 460

Gly Ala Thr Trp Lys Leu Gln
465                 470

<210> SEQ ID NO 11
<211> LENGTH: 1009
<212> TYPE: DNA
<213> ORGANISM: Corynebacterium glutamicum
<220> FEATURE:
<221> NAME/KEY: CDS
<222> LOCATION: (101)..(979)
<223> OTHER INFORMATION: RXA00458

<400> SEQUENCE: 11

```
cacccctgaa aacctcctca actatcccgg agtgatcatc tccaccgttc aggagaaccc      60
atccgaaaca tggcggcaag tgaacatcta atctagaaac atg gca gga cga tac     115
                                              Met Ala Gly Arg Tyr
                                                1               5 gca cca tca cca agc ggc gac ctt cac ttt ggc aac ctc cgc aca gca     163
Ala Pro Ser Pro Ser Gly Asp Leu His Phe Gly Asn Leu Arg Thr Ala
             10                  15                  20 ctg ctg gcc tgg ctg ttc gcg cgc tcc gaa gga aaa aaa ttc ctc atg     211
Leu Leu Ala Trp Leu Phe Ala Arg Ser Glu Gly Lys Lys Phe Leu Met
         25                  30                  35 cgg gtc gaa gac atc gat gaa caa cgc tca tcc aag gaa tcc gcc gaa     259
Arg Val Glu Asp Ile Asp Glu Gln Arg Ser Ser Lys Glu Ser Ala Glu
     40                  45                  50 agc caa ctc gca gac cta tcc gcc ctg ggt ctc gat tgg gat ggc gac     307
Ser Gln Leu Ala Asp Leu Ser Ala Leu Gly Leu Asp Trp Asp Gly Asp
 55                  60                  65 gtc ctc tac caa tcc aca cgc tac gac gcc tac cgc gca gcc ctt gaa     355
Val Leu Tyr Gln Ser Thr Arg Tyr Asp Ala Tyr Arg Ala Ala Leu Glu
```

```
                70                  75                  80                  85
aaa cta gac acc tac gaa tgt tat tgc tcg cgc cgg gac atc caa gaa      403
Lys Leu Asp Thr Tyr Glu Cys Tyr Cys Ser Arg Arg Asp Ile Gln Glu
                    90                  95                 100 gcc tcg cgg gca ccc cat gtg gct ccg gga gtg tat ccg gga acg tgt      451
Ala Ser Arg Ala Pro His Val Ala Pro Gly Val Tyr Pro Gly Thr Cys
                   105                 110                 115 agg gga ttg aag gag gag gaa cgc gtc gaa aag cgt gca acc ttg gct      499
Arg Gly Leu Lys Glu Glu Glu Arg Val Glu Lys Arg Ala Thr Leu Ala
                   120                 125                 130 gcg caa aac cgg cac ccc gcc atc cgc ctg cgc gcg cag gta acc tcg      547
Ala Gln Asn Arg His Pro Ala Ile Arg Leu Arg Ala Gln Val Thr Ser
135                 140                 145 ttt gat ttt cac gac cga ctt cgc ggc cca caa act ggc ccc gta gac      595
Phe Asp Phe His Asp Arg Leu Arg Gly Pro Gln Thr Gly Pro Val Asp
150                 155                 160                 165 gat ttc att ctg ctc cgc ggc ggg cag gaa ccc gga tgg gca tac aac      643
Asp Phe Ile Leu Leu Arg Gly Gly Gln Glu Pro Gly Trp Ala Tyr Asn
                   170                 175                 180 tta gct gtc gtc gtc gac gat gcc tac caa ggc gtt gac cag gta gtc      691
Leu Ala Val Val Val Asp Asp Ala Tyr Gln Gly Val Asp Gln Val Val
                   185                 190                 195 cgc ggc gac gac cta ctc gat tcc gcc gcg cgc caa gcc tac ctc ggc      739
Arg Gly Asp Asp Leu Leu Asp Ser Ala Ala Arg Gln Ala Tyr Leu Gly
                   200                 205                 210 tcg ctg ctg ggc acc ccc gcg ccc gaa tac att cac gtg ccg ctc gtg      787
Ser Leu Leu Gly Thr Pro Ala Pro Glu Tyr Ile His Val Pro Leu Val
215                 220                 225 ctc aac gcc cac ggc cag cgc ctc gcc aaa cgc gac ggg gca gtg acg      835
Leu Asn Ala His Gly Gln Arg Leu Ala Lys Arg Asp Gly Ala Val Thr
230                 235                 240                 245 ctt aaa gaa atg ctt atc gac gcc ccc ctc cac acc att ttc tcc cgc      883
Leu Lys Glu Met Leu Ile Asp Ala Pro Leu His Thr Ile Phe Ser Arg
                   250                 255                 260 ctc gca tca tcg ctc ggc tac gaa ggg gta aat tcc gca ccc caa ttg      931
Leu Ala Ser Ser Leu Gly Tyr Glu Gly Val Asn Ser Ala Pro Gln Leu
                   265                 270                 275 ttg gaa att ttc gac ccc aca acc ctc agc cgg gag ccg ttt att tac      979
Leu Glu Ile Phe Asp Pro Thr Thr Leu Ser Arg Glu Pro Phe Ile Tyr
                   280                 285                 290 tgaggctcag agggagggt cattccatct                                     1009
```

<210> SEQ ID NO 12
<211> LENGTH: 293
<212> TYPE: PRT
<213> ORGANISM: Corynebacterium glutamicum

<400> SEQUENCE: 12

```
Met Ala Gly Arg Tyr Ala Pro Ser Pro Ser Gly Asp Leu His Phe Gly
  1               5                  10                  15

Asn Leu Arg Thr Ala Leu Leu Ala Trp Leu Phe Ala Arg Ser Glu Gly
                 20                  25                  30

Lys Lys Phe Leu Met Arg Val Glu Asp Ile Asp Glu Gln Arg Ser Ser
             35                  40                  45

Lys Glu Ser Ala Glu Ser Gln Leu Ala Asp Leu Ser Ala Leu Gly Leu
         50                  55                  60

Asp Trp Asp Gly Asp Val Leu Tyr Gln Ser Thr Arg Tyr Asp Ala Tyr
 65                  70                  75                  80
```

```
Arg Ala Ala Leu Glu Lys Leu Asp Thr Tyr Glu Cys Tyr Cys Ser Arg
                85                  90                  95

Arg Asp Ile Gln Glu Ala Ser Arg Ala Pro His Val Ala Pro Gly Val
            100                 105                 110

Tyr Pro Gly Thr Cys Arg Gly Leu Lys Glu Glu Arg Val Glu Lys
        115                 120                 125

Arg Ala Thr Leu Ala Ala Gln Asn Arg His Pro Ala Ile Arg Leu Arg
    130                 135                 140

Ala Gln Val Thr Ser Phe Asp Phe His Asp Arg Leu Arg Gly Pro Gln
145                 150                 155                 160

Thr Gly Pro Val Asp Asp Phe Ile Leu Leu Arg Gly Gln Glu Pro
                165                 170                 175

Gly Trp Ala Tyr Asn Leu Ala Val Val Val Asp Asp Ala Tyr Gln Gly
            180                 185                 190

Val Asp Gln Val Val Arg Gly Asp Leu Leu Asp Ser Ala Ala Arg
        195                 200                 205

Gln Ala Tyr Leu Gly Ser Leu Leu Gly Thr Pro Ala Pro Glu Tyr Ile
    210                 215                 220

His Val Pro Leu Val Leu Asn Ala His Gly Gln Arg Leu Ala Lys Arg
225                 230                 235                 240

Asp Gly Ala Val Thr Leu Lys Glu Met Leu Ile Asp Ala Pro Leu His
                245                 250                 255

Thr Ile Phe Ser Arg Leu Ala Ser Ser Leu Gly Tyr Glu Gly Val Asn
            260                 265                 270

Ser Ala Pro Gln Leu Leu Glu Ile Phe Asp Pro Thr Thr Leu Ser Arg
        275                 280                 285

Glu Pro Phe Ile Tyr
    290

<210> SEQ ID NO 13
<211> LENGTH: 1744
<212> TYPE: DNA
<213> ORGANISM: Corynebacterium glutamicum
<220> FEATURE:
<221> NAME/KEY: CDS
<222> LOCATION: (101)..(1714)
<223> OTHER INFORMATION: RXA00493

<400> SEQUENCE: 13
cccgttacgg cggcaccgag atcaagttcg gtggcgtgga gtacttgctt ctctccgctc      60
gtgacatcct cgcaatcgtc gagaagtagg ggataagttc atg gca aag ctc att     115
                                             Met Ala Lys Leu Ile
                                               1               5 gct ttt gac cag gac gcc cgc gaa ggc att ctc cgg ggc gtt gac gct     163
Ala Phe Asp Gln Asp Ala Arg Glu Gly Ile Leu Arg Gly Val Asp Ala
            10                  15                  20 ctg gca aac gct gtc aag gta acc ctc ggc cca cgc ggc cgt aac gtg     211
Leu Ala Asn Ala Val Lys Val Thr Leu Gly Pro Arg Gly Arg Asn Val
        25                  30                  35 gtt ctt gat aag gca ttc ggc gga cct ctg gtc acc aac gac ggt gtc     259
Val Leu Asp Lys Ala Phe Gly Gly Pro Leu Val Thr Asn Asp Gly Val
    40                  45                  50 acc att gcc cgc gac atc gac ctt gag gat cct ttt gag aac ctc ggt     307
Thr Ile Ala Arg Asp Ile Asp Leu Glu Asp Pro Phe Glu Asn Leu Gly
55                  60                  65 gcg cag ctg gtg aag tcc gtt gct gtt aag acc aac gac atc gct ggt     355
Ala Gln Leu Val Lys Ser Val Ala Val Lys Thr Asn Asp Ile Ala Gly
        70                  75                  80                  85
```

```
gac ggc acc acg act gca act ctg ctt gct cag gca ctc att gct gaa      403
Asp Gly Thr Thr Thr Ala Thr Leu Leu Ala Gln Ala Leu Ile Ala Glu
             90                  95                 100 ggc ctg cgc aac gtt gct gct ggc gca aac cca atg gag ctc aac aag      451
Gly Leu Arg Asn Val Ala Ala Gly Ala Asn Pro Met Glu Leu Asn Lys
        105                 110                 115 ggt att tct gca gct gca gaa aag acc ttg gaa gag ttg aag gca cgc      499
Gly Ile Ser Ala Ala Ala Glu Lys Thr Leu Glu Glu Leu Lys Ala Arg
            120                 125                 130 gca acc gag gtg tct gac acc aag gaa atc gca aac gtc gct acc gtt      547
Ala Thr Glu Val Ser Asp Thr Lys Glu Ile Ala Asn Val Ala Thr Val
    135                 140                 145 tca tcc cgc gat gaa gtt gtc ggc gag atc gtt gct gca gcg atg gaa      595
Ser Ser Arg Asp Glu Val Val Gly Glu Ile Val Ala Ala Met Glu
150                 155                 160                 165 aag gtt ggc aag gac ggt gtc gtc acc gtt gag gag tcc cag tcc atc      643
Lys Val Gly Lys Asp Gly Val Val Thr Val Glu Glu Ser Gln Ser Ile
                170                 175                 180 gag act gct ctc gag gtc acc gaa ggt att tct ttc gac aag ggc tac      691
Glu Thr Ala Leu Glu Val Thr Glu Gly Ile Ser Phe Asp Lys Gly Tyr
            185                 190                 195 ctt tcc cct tat ttc atc aac gac aac gac act cag cag gct gtc ctg      739
Leu Ser Pro Tyr Phe Ile Asn Asp Asn Asp Thr Gln Gln Ala Val Leu
        200                 205                 210 gac aac cct gca gtg ctg ctt gtt cgc aac aag att tct tcc ctc cca      787
Asp Asn Pro Ala Val Leu Leu Val Arg Asn Lys Ile Ser Ser Leu Pro
    215                 220                 225 gac ttc ctc cca ttg ctg gag aag gtt gtg gag tcc aac cgt cct ttg      835
Asp Phe Leu Pro Leu Leu Glu Lys Val Val Glu Ser Asn Arg Pro Leu
230                 235                 240                 245 ctg atc atc gca gaa gac gtc gag ggc gag cct ttg cag acc ctg gtt      883
Leu Ile Ile Ala Glu Asp Val Glu Gly Glu Pro Leu Gln Thr Leu Val
                250                 255                 260 gtg aac tcc atc cgc aag acc atc aag gtc gtt gca gtg aag tcc cct      931
Val Asn Ser Ile Arg Lys Thr Ile Lys Val Val Ala Val Lys Ser Pro
            265                 270                 275 tac ttc ggt gac cga cgc aag gcg ttc atg gat gac ctg gct att gtc      979
Tyr Phe Gly Asp Arg Arg Lys Ala Phe Met Asp Asp Leu Ala Ile Val
        280                 285                 290 acc aag gca act gtc gtg gat cca gaa gtg ggc atc aac ctc aac gaa     1027
Thr Lys Ala Thr Val Val Asp Pro Glu Val Gly Ile Asn Leu Asn Glu
    295                 300                 305 gct ggc gaa gaa gtt ttc ggt acc gca cgc cgc atc acc gtt tcc aag     1075
Ala Gly Glu Glu Val Phe Gly Thr Ala Arg Arg Ile Thr Val Ser Lys
310                 315                 320                 325 gac gaa acc atc atc gtt gat ggt gca ggt tcc gca gaa gac gtt gaa     1123
Asp Glu Thr Ile Ile Val Asp Gly Ala Gly Ser Ala Glu Asp Val Glu
                330                 335                 340 gca cgt cgc ggc cag atc cgt cgc gaa atc gcc aac acc gat tcc acc     1171
Ala Arg Arg Gly Gln Ile Arg Arg Glu Ile Ala Asn Thr Asp Ser Thr
            345                 350                 355 tgg gat cgc gaa aag gca gaa gag cgt ttg gct aag ctc tcc ggt ggt     1219
Trp Asp Arg Glu Lys Ala Glu Glu Arg Leu Ala Lys Leu Ser Gly Gly
        360                 365                 370 att gct gtc atc cgc gtt ggt gca gca act gaa acc gaa gtc aac gac     1267
Ile Ala Val Ile Arg Val Gly Ala Ala Thr Glu Thr Glu Val Asn Asp
    375                 380                 385 cgc aag ctg cgt gtc gaa gat gcc atc aac gct gct cgc gca gca gca     1315
Arg Lys Leu Arg Val Glu Asp Ala Ile Asn Ala Ala Arg Ala Ala Ala
```

-continued

```
                390                 395                 400                 405
caa gaa ggc gtt atc gct ggt ggc ggt tcc gct ttg gtt cag atc gct       1363
Gln Glu Gly Val Ile Ala Gly Gly Gly Ser Ala Leu Val Gln Ile Ala
                410                 415                 420 gag act ctg aag gct tac gcc gaa gag ttc gaa ggc gac cag aag gtc       1411
Glu Thr Leu Lys Ala Tyr Ala Glu Glu Phe Glu Gly Asp Gln Lys Val
        425                 430                 435 ggc gtt cgc gca ctg gct act gct ttg ggc aag cca gcg tac tgg atc       1459
Gly Val Arg Ala Leu Ala Thr Ala Leu Gly Lys Pro Ala Tyr Trp Ile
            440                 445                 450 gcc tcc aac gca ggt ctt gac ggc tct gtt gtt gtt gca cgc act gct       1507
Ala Ser Asn Ala Gly Leu Asp Gly Ser Val Val Val Ala Arg Thr Ala
        455                 460                 465 gct ctg cca aac ggc gag ggc ttc aac gct gca act ttg gaa tac gga       1555
Ala Leu Pro Asn Gly Glu Gly Phe Asn Ala Ala Thr Leu Glu Tyr Gly
470                 475                 480                 485 aac ctg atc aac gac ggt gtc atc gac cca gtc aag gtc acc cat tcc       1603
Asn Leu Ile Asn Asp Gly Val Ile Asp Pro Val Lys Val Thr His Ser
                490                 495                 500 gca gta gtg aat gca acc tct gtt gca cgc atg gtt ctg acc act gag       1651
Ala Val Val Asn Ala Thr Ser Val Ala Arg Met Val Leu Thr Thr Glu
        505                 510                 515 gct tct gtt gtt gag aag cct gca gaa gaa gca gcc gat gca cat gca       1699
Ala Ser Val Val Glu Lys Pro Ala Glu Glu Ala Ala Asp Ala His Ala
            520                 525                 530 gga cat cat cac cac taaagttctg tgaaaaacac cgtggggcag                  1744
Gly His His His His
    535
```

<210> SEQ ID NO 14
<211> LENGTH: 538
<212> TYPE: PRT
<213> ORGANISM: Corynebacterium glutamicum

<400> SEQUENCE: 14

```
Met Ala Lys Leu Ile Ala Phe Asp Gln Asp Ala Arg Glu Gly Ile Leu
  1               5                  10                  15

Arg Gly Val Asp Ala Leu Ala Asn Ala Val Lys Val Thr Leu Gly Pro
             20                  25                  30

Arg Gly Arg Asn Val Val Leu Asp Lys Ala Phe Gly Gly Pro Leu Val
         35                  40                  45

Thr Asn Asp Gly Val Thr Ile Ala Arg Asp Ile Asp Leu Glu Asp Pro
     50                  55                  60

Phe Glu Asn Leu Gly Ala Gln Leu Val Lys Ser Val Ala Val Lys Thr
 65                  70                  75                  80

Asn Asp Ile Ala Gly Asp Gly Thr Thr Thr Ala Thr Leu Leu Ala Gln
                 85                  90                  95

Ala Leu Ile Ala Glu Gly Leu Arg Asn Val Ala Ala Gly Ala Asn Pro
            100                 105                 110

Met Glu Leu Asn Lys Gly Ile Ser Ala Ala Glu Lys Thr Leu Glu
        115                 120                 125

Glu Leu Lys Ala Arg Ala Thr Glu Val Ser Asp Thr Lys Glu Ile Ala
    130                 135                 140

Asn Val Ala Thr Val Ser Ser Arg Asp Glu Val Val Gly Glu Ile Val
145                 150                 155                 160

Ala Ala Ala Met Glu Lys Val Gly Lys Asp Gly Val Val Thr Val Glu
                165                 170                 175
```

-continued

Glu Ser Gln Ser Ile Glu Thr Ala Leu Glu Val Thr Glu Gly Ile Ser
                180                 185                 190
Phe Asp Lys Gly Tyr Leu Ser Pro Tyr Phe Ile Asn Asp Asn Asp Thr
            195                 200                 205
Gln Gln Ala Val Leu Asp Asn Pro Ala Val Leu Val Arg Asn Lys
    210                 215                 220
Ile Ser Ser Leu Pro Asp Phe Leu Pro Leu Leu Glu Lys Val Val Glu
225                 230                 235                 240
Ser Asn Arg Pro Leu Leu Ile Ile Ala Glu Asp Val Glu Gly Glu Pro
                245                 250                 255
Leu Gln Thr Leu Val Val Asn Ser Ile Arg Lys Thr Ile Lys Val Val
            260                 265                 270
Ala Val Lys Ser Pro Tyr Phe Gly Asp Arg Arg Lys Ala Phe Met Asp
        275                 280                 285
Asp Leu Ala Ile Val Thr Lys Ala Thr Val Val Asp Pro Glu Val Gly
    290                 295                 300
Ile Asn Leu Asn Glu Ala Gly Glu Val Phe Gly Thr Ala Arg Arg
305                 310                 315                 320
Ile Thr Val Ser Lys Asp Glu Thr Ile Ile Val Asp Gly Ala Gly Ser
                325                 330                 335
Ala Glu Asp Val Glu Ala Arg Arg Gly Gln Ile Arg Arg Glu Ile Ala
            340                 345                 350
Asn Thr Asp Ser Thr Trp Asp Arg Glu Lys Ala Glu Glu Arg Leu Ala
        355                 360                 365
Lys Leu Ser Gly Gly Ile Ala Val Ile Arg Val Gly Ala Ala Thr Glu
    370                 375                 380
Thr Glu Val Asn Asp Arg Lys Leu Arg Val Glu Asp Ala Ile Asn Ala
385                 390                 395                 400
Ala Arg Ala Ala Ala Gln Glu Gly Val Ile Ala Gly Gly Ser Ala
                405                 410                 415
Leu Val Gln Ile Ala Glu Thr Leu Lys Ala Tyr Ala Glu Glu Phe Glu
            420                 425                 430
Gly Asp Gln Lys Val Gly Val Arg Ala Leu Ala Thr Ala Leu Gly Lys
        435                 440                 445
Pro Ala Tyr Trp Ile Ala Ser Asn Ala Gly Leu Asp Gly Ser Val Val
    450                 455                 460
Val Ala Arg Thr Ala Ala Leu Pro Asn Gly Glu Gly Phe Asn Ala Ala
465                 470                 475                 480
Thr Leu Glu Tyr Gly Asn Leu Ile Asn Asp Gly Val Ile Asp Pro Val
                485                 490                 495
Lys Val Thr His Ser Ala Val Asn Ala Thr Ser Val Ala Arg Met
            500                 505                 510
Val Leu Thr Thr Glu Ala Ser Val Val Glu Lys Pro Ala Glu Glu Ala
        515                 520                 525
Ala Asp Ala His Ala Gly His His His
    530                 535

<210> SEQ ID NO 15
<211> LENGTH: 652
<212> TYPE: DNA
<213> ORGANISM: Corynebacterium glutamicum
<220> FEATURE:
<221> NAME/KEY: CDS
<222> LOCATION: (101)..(622)
<223> OTHER INFORMATION: RXA00588

-continued

<400> SEQUENCE: 15

```
tcatacatct tggccccgga aaaccggggc caatcttatg gctcaagtcg ctagttagcc      60
gatgatccac ctctactgtt ccccaggagg gtaagtaatt atg gca agt gta gat     115
                                            Met Ala Ser Val Asp
                                              1               5 aag caa tac atc acc cca gaa acc aag gcc aag ctg gag gaa gag ctc     163
Lys Gln Tyr Ile Thr Pro Glu Thr Lys Ala Lys Leu Glu Glu Glu Leu
                 10                  15                  20 aac gcc ctc atc gca cac cgc cct gca gtt gct gcg gaa atc aat gag     211
Asn Ala Leu Ile Ala His Arg Pro Ala Val Ala Ala Glu Ile Asn Glu
             25                  30                  35 cgc cgt gaa gaa ggc gac ctc aag gaa aac gct ggc tat gac gcc gct     259
Arg Arg Glu Glu Gly Asp Leu Lys Glu Asn Ala Gly Tyr Asp Ala Ala
         40                  45                  50 cgt gaa atg cag gac cag gaa gag gcc cgc atc aag cag atc tct gag     307
Arg Glu Met Gln Asp Gln Glu Glu Ala Arg Ile Lys Gln Ile Ser Glu
     55                  60                  65 ctg ctg gcc aac tcc acc act gag cgc gaa ggc atc atc gaa ggt gtc     355
Leu Leu Ala Asn Ser Thr Thr Glu Arg Glu Gly Ile Ile Glu Gly Val
 70                  75                  80                  85 gca aac gtt ggc tcc gtt gtt cac gtc tac tac gac ggc gac gag aac     403
Ala Asn Val Gly Ser Val Val His Val Tyr Tyr Asp Gly Asp Glu Asn
                 90                  95                 100 gac aag gaa acc ttc ctc atc ggt acc cgt gct ggc gct tcc gag aac     451
Asp Lys Glu Thr Phe Leu Ile Gly Thr Arg Ala Gly Ala Ser Glu Asn
            105                 110                 115 cca gat ctt gag acc tac tct gag cag tcc cca ctc ggc gct gca att     499
Pro Asp Leu Glu Thr Tyr Ser Glu Gln Ser Pro Leu Gly Ala Ala Ile
        120                 125                 130 ctc gga gct cag gaa ggc gac acc cgt cag tac acc gct cca aat ggt     547
Leu Gly Ala Gln Glu Gly Asp Thr Arg Gln Tyr Thr Ala Pro Asn Gly
    135                 140                 145 tcc gtt atc tcc gta act gtt gtt tct gca gaa cca tac aac tca gca     595
Ser Val Ile Ser Val Thr Val Val Ser Ala Glu Pro Tyr Asn Ser Ala
150                 155                 160                 165 aaa gcc gcg aca ctc cgc ggc aaa aac taaccaagga tttaaaagtc           642
Lys Ala Ala Thr Leu Arg Gly Lys Asn
                170 ttcaaaatga                                                          652

<210> SEQ ID NO 16
<211> LENGTH: 174
<212> TYPE: PRT
<213> ORGANISM: Corynebacterium glutamicum

<400> SEQUENCE: 16

Met Ala Ser Val Asp Lys Gln Tyr Ile Thr Pro Glu Thr Lys Ala Lys
  1               5                  10                  15

Leu Glu Glu Glu Leu Asn Ala Leu Ile Ala His Arg Pro Ala Val Ala
                 20                  25                  30

Ala Glu Ile Asn Glu Arg Arg Glu Glu Gly Asp Leu Lys Glu Asn Ala
             35                  40                  45

Gly Tyr Asp Ala Ala Arg Glu Met Gln Asp Gln Glu Glu Ala Arg Ile
         50                  55                  60

Lys Gln Ile Ser Glu Leu Leu Ala Asn Ser Thr Thr Glu Arg Glu Gly
 65                  70                  75                  80

Ile Ile Glu Gly Val Ala Asn Val Gly Ser Val Val His Val Tyr Tyr
                 85                  90                  95
```

-continued

```
Asp Gly Asp Glu Asn Asp Lys Glu Thr Phe Leu Ile Gly Thr Arg Ala
            100                 105                 110

Gly Ala Ser Glu Asn Pro Asp Leu Glu Thr Tyr Ser Glu Gln Ser Pro
        115                 120                 125

Leu Gly Ala Ala Ile Leu Gly Ala Gln Glu Gly Asp Thr Arg Gln Tyr
    130                 135                 140

Thr Ala Pro Asn Gly Ser Val Ile Ser Val Thr Val Ser Ala Glu
145                 150                 155                 160

Pro Tyr Asn Ser Ala Lys Ala Ala Thr Leu Arg Gly Lys Asn
                165                 170
```

<210> SEQ ID NO 17
<211> LENGTH: 1012
<212> TYPE: DNA
<213> ORGANISM: Corynebacterium glutamicum
<220> FEATURE:
<221> NAME/KEY: CDS
<222> LOCATION: (101)..(982)
<223> OTHER INFORMATION: RXA00669

<400> SEQUENCE: 17

```
tttactgcgg gcattttacg tatctgcacc ccgcccggct gcgctgagca gccgtaaagc         60
gtggggcgtg acgtcgaaaa gcaaaaaatg aaaggcagac atg gac aat tca acg         115
                                             Met Asp Asn Ser Thr
                                              1               5 gtg cga atc cgg ctg gat cta gcg tat gac ggc acg gat ttt cat ggc         163
Val Arg Ile Arg Leu Asp Leu Ala Tyr Asp Gly Thr Asp Phe His Gly
         10                  15                  20 tgg gcg aag cag ggg acc agc gat cta cgc acc gtg caa aaa gtg ttg         211
Trp Ala Lys Gln Gly Thr Ser Asp Leu Arg Thr Val Gln Lys Val Leu
     25                  30                  35 gaa gac aat ttg agc atg gtg ctg cgt gag act gtt gaa ttg act gtg         259
Glu Asp Asn Leu Ser Met Val Leu Arg Glu Thr Val Glu Leu Thr Val
 40                  45                  50 gcc ggg cga acc gat gcg ggg gtg cat gcg gcg ggc cag gtg gcg cac         307
Ala Gly Arg Thr Asp Ala Gly Val His Ala Ala Gly Gln Val Ala His
         55                  60                  65 ttt gat att ccg gca cac gct tta gag cag cgc agt att gat ggc gat         355
Phe Asp Ile Pro Ala His Ala Leu Glu Gln Arg Ser Ile Asp Gly Asp
 70                  75                  80                  85 cca agc aag ttg gtt cgg cgc ttg ggt cgg ttg ctg ccc gat gat att         403
Pro Ser Lys Leu Val Arg Arg Leu Gly Arg Leu Leu Pro Asp Asp Ile
                 90                  95                 100 cgg gtg cat ggc gta cgt ttt gcc gag ccc ggg ttt gat gcg cga ttt         451
Arg Val His Gly Val Arg Phe Ala Glu Pro Gly Phe Asp Ala Arg Phe
            105                 110                 115 tcc gcg atg cgc agg cac tac gtt tat cgc att acg acg cat ccc gcc         499
Ser Ala Met Arg Arg His Tyr Val Tyr Arg Ile Thr Thr His Pro Ala
        120                 125                 130 ggc gcg ctg cct acg cgc cgc cac gac acg gcg cag tgg cca aaa cct         547
Gly Ala Leu Pro Thr Arg Arg His Asp Thr Ala Gln Trp Pro Lys Pro
    135                 140                 145 gtc gaa cta gag cgg atg caa tta gcc gcc gat gca ctg ctg ggg ctg         595
Val Glu Leu Glu Arg Met Gln Leu Ala Ala Asp Ala Leu Leu Gly Leu
150                 155                 160                 165 cat gat ttt gtg gcg ttt tgc aaa gct aag cca cat gcg acg acg gtg         643
His Asp Phe Val Ala Phe Cys Lys Ala Lys Pro His Ala Thr Thr Val
                170                 175                 180 cgt gaa cta caa aaa ttt gcg tgg aaa gac gtc tcc act gac atc gaa         691
Arg Glu Leu Gln Lys Phe Ala Trp Lys Asp Val Ser Thr Asp Ile Glu
```

```
                                                                                  -continued Arg Glu Leu Gln Lys Phe Ala Trp Lys Asp Val Ser Thr Asp Ile Glu
            185                 190                 195 ccg cag gtg tat gaa gca cac gtg gtg gcc gat gct ttt tgc tgg tcg           739
Pro Gln Val Tyr Glu Ala His Val Val Ala Asp Ala Phe Cys Trp Ser
            200                 205                 210 atg gtg cgc tcg ctg gtc ggc tcc tgc atg gcc gtg ggc gaa gga cgc           787
Met Val Arg Ser Leu Val Gly Ser Cys Met Ala Val Gly Glu Gly Arg
        215                 220                 225 cgc gga tca ggg ttt act gca gaa ttg ctt gat gca agc gaa cgc agc           835
Arg Gly Ser Gly Phe Thr Ala Glu Leu Leu Asp Ala Ser Glu Arg Ser
230                 235                 240                 245 ccc atg gtt cca gta gca cct gcg aaa ggt ttg agc ttg gtt ggc gtg           883
Pro Met Val Pro Val Ala Pro Ala Lys Gly Leu Ser Leu Val Gly Val
                250                 255                 260 gat tat cct tcc gct gat aag tta cag gaa aga gcg ctg gaa acc cga           931
Asp Tyr Pro Ser Ala Asp Lys Leu Gln Glu Arg Ala Leu Glu Thr Arg
                265                 270                 275 gct gtt cgc gag ttt ccg gac gcg tcc gcg agc cta aaa cta gat gat           979
Ala Val Arg Glu Phe Pro Asp Ala Ser Ala Ser Leu Lys Leu Asp Asp
            280                 285                 290 gag taaaagggac taaactcgtc tctcgtatct                                     1012
Glu <210> SEQ ID NO 18
<211> LENGTH: 294
<212> TYPE: PRT
<213> ORGANISM: Corynebacterium glutamicum

<400> SEQUENCE: 18

Met Asp Asn Ser Thr Val Arg Ile Arg Leu Asp Leu Ala Tyr Asp Gly
1               5                   10                  15

Thr Asp Phe His Gly Trp Ala Lys Gln Gly Thr Ser Asp Leu Arg Thr
            20                  25                  30

Val Gln Lys Val Leu Glu Asp Asn Leu Ser Met Val Leu Arg Glu Thr
        35                  40                  45

Val Glu Leu Thr Val Ala Gly Arg Thr Asp Ala Gly Val His Ala Ala
    50                  55                  60

Gly Gln Val Ala His Phe Asp Ile Pro Ala His Ala Leu Glu Gln Arg
65                  70                  75                  80

Ser Ile Asp Gly Asp Pro Ser Lys Leu Val Arg Leu Gly Arg Leu
                85                  90                  95

Leu Pro Asp Ile Arg Val His Gly Val Arg Phe Ala Glu Pro Gly
            100                 105                 110

Phe Asp Ala Arg Phe Ser Ala Met Arg Arg His Tyr Val Tyr Arg Ile
        115                 120                 125

Thr Thr His Pro Ala Gly Ala Leu Pro Thr Arg Arg His Asp Thr Ala
    130                 135                 140

Gln Trp Pro Lys Pro Val Glu Leu Glu Arg Met Gln Leu Ala Ala Asp
145                 150                 155                 160

Ala Leu Leu Gly Leu His Asp Phe Val Ala Phe Cys Lys Ala Lys Pro
                165                 170                 175

His Ala Thr Thr Val Arg Glu Leu Gln Lys Phe Ala Trp Lys Asp Val
            180                 185                 190

Ser Thr Asp Ile Glu Pro Gln Val Tyr Glu Ala His Val Val Ala Asp
        195                 200                 205

Ala Phe Cys Trp Ser Met Val Arg Ser Leu Val Gly Ser Cys Met Ala
    210                 215                 220
```

Val Gly Glu Gly Arg Arg Gly Ser Gly Phe Thr Ala Glu Leu Leu Asp
225                 230                 235                 240

Ala Ser Glu Arg Ser Pro Met Val Pro Val Ala Pro Ala Lys Gly Leu
                245                 250                 255

Ser Leu Val Gly Val Asp Tyr Pro Ser Ala Asp Lys Leu Gln Glu Arg
                260                 265                 270

Ala Leu Glu Thr Arg Ala Val Arg Glu Phe Pro Asp Ala Ser Ala Ser
            275                 280                 285

Leu Lys Leu Asp Asp Glu
    290

<210> SEQ ID NO 19
<211> LENGTH: 3022
<212> TYPE: DNA
<213> ORGANISM: Corynebacterium glutamicum
<220> FEATURE:
<221> NAME/KEY: CDS
<222> LOCATION: (101)..(2992)
<223> OTHER INFORMATION: RXA01061

<400> SEQUENCE: 19

| | |
|---|---|
| gcagacaaga ctgagcagtc cgacggcgat aagcagtggt ttccacataa ttcttcaagt | 60 |
| ctatctactt attgagggga ggaagaattg ccctccacac atg aga tgt ccc gtg<br>                                                               Met Arg Cys Pro Val<br>                                                                         1              5 | 115 |
| tac cta cta cac tgt tta acc atg act aac ccg agc gaa ggc acc act<br>Tyr Leu Leu His Cys Leu Thr Met Thr Asn Pro Ser Glu Gly Thr Thr<br>                10                         15                         20 | 163 |
| ccc ctg gcg ttc cgt tat acc ccg gaa ctc gcc aac aag atc gaa ggt<br>Pro Leu Ala Phe Arg Tyr Thr Pro Glu Leu Ala Asn Lys Ile Glu Gly<br>                25                         30                         35 | 211 |
| gag tgg cag aat tac tgg act gac aac ggc aca ttc aac gca ccc aac<br>Glu Trp Gln Asn Tyr Trp Thr Asp Asn Gly Thr Phe Asn Ala Pro Asn<br>        40                         45                         50 | 259 |
| cca gtg ggt gat tta gcg cct gcg gac ggt aaa gca ctt cct gag gac<br>Pro Val Gly Asp Leu Ala Pro Ala Asp Gly Lys Ala Leu Pro Glu Asp<br> 55                         60                         65 | 307 |
| aag ctc ttt gtc cag gat atg ttc ccg tac cca tcc gga gct ggc ctg<br>Lys Leu Phe Val Gln Asp Met Phe Pro Tyr Pro Ser Gly Ala Gly Leu<br> 70                         75                        80                         85 | 355 |
| cac gta ggc cac cca ctc ggt tac atc gca acg gat gtt ttc gcc cgc<br>His Val Gly His Pro Leu Gly Tyr Ile Ala Thr Asp Val Phe Ala Arg<br>                        90                                95                      100 | 403 |
| tac aac cgc atg ctg ggc aag aac gtt ctg cac acc ttg ggc tat gac<br>Tyr Asn Arg Met Leu Gly Lys Asn Val Leu His Thr Leu Gly Tyr Asp<br>               105                       110                         115 | 451 |
| gcc ttc gga ctg cca gca gag cag tac gcg atc caa acc ggt aca cac<br>Ala Phe Gly Leu Pro Ala Glu Gln Tyr Ala Ile Gln Thr Gly Thr His<br>            120                       125                         130 | 499 |
| cca cgc acc acc acc atg gcc aac att gag aac atg aag cgc cag ctc<br>Pro Arg Thr Thr Thr Met Ala Asn Ile Glu Asn Met Lys Arg Gln Leu<br>135                        140                         145 | 547 |
| ggt gcg ctg ggt ctt ggc cat gat tcc cgt cgt gcg gtg gcc acc acg<br>Gly Ala Leu Gly Leu Gly His Asp Ser Arg Arg Ala Val Ala Thr Thr<br>150                        155                         160                         165 | 595 |
| gat cct gag ttc tac aag tgg act cag tgg atc ttc ctg cag att ttc<br>Asp Pro Glu Phe Tyr Lys Trp Thr Gln Trp Ile Phe Leu Gln Ile Phe<br>                    170                         175                        180 | 643 |
| aat tcg tgg ttc gat gca gag cag cag aag gca cgt ccc atc agt gag | 691 |

```
            Asn Ser Trp Phe Asp Ala Glu Gln Gln Lys Ala Arg Pro Ile Ser Glu
                        185                 190                 195 ctg att ccg ttg ctg gag tcc ggc gag ctg aag act aag gac ggg gcg          739
Leu Ile Pro Leu Leu Glu Ser Gly Glu Leu Lys Thr Lys Asp Gly Ala
        200                 205                 210 gat tac aac gcg ctg gga gac gtc gaa aag caa aaa gcg gtg gat gac          787
Asp Tyr Asn Ala Leu Gly Asp Val Glu Lys Gln Lys Ala Val Asp Asp
        215                 220                 225 tac cgc ctt gtt tat cgc tcg aac tcc acc gtg aac tgg tgc cca ggc          835
Tyr Arg Leu Val Tyr Arg Ser Asn Ser Thr Val Asn Trp Cys Pro Gly
230                 235                 240                 245 ttg ggc acc gtg ttg gca aac gag gaa gtg acc gcg gac ggc cgt tcc          883
Leu Gly Thr Val Leu Ala Asn Glu Glu Val Thr Ala Asp Gly Arg Ser
                250                 255                 260 gag cgt ggc aat ttc cct gtt ttc cgt aag aat ttg tcc cag tgg atg          931
Glu Arg Gly Asn Phe Pro Val Phe Arg Lys Asn Leu Ser Gln Trp Met
        265                 270                 275 atg cgc att acc gcg tac tcg gat cgt ctg atc gat gat ctg gag ctg          979
Met Arg Ile Thr Ala Tyr Ser Asp Arg Leu Ile Asp Asp Leu Glu Leu
        280                 285                 290 ctc gat tgg act gag aag gtc aag tcc atg cag cgt aac tgg att ggc         1027
Leu Asp Trp Thr Glu Lys Val Lys Ser Met Gln Arg Asn Trp Ile Gly
        295                 300                 305 cgt tcc cgc ggc gct gaa gtt gat ttc agt gca gag ggc gaa acc gtc         1075
Arg Ser Arg Gly Ala Glu Val Asp Phe Ser Ala Glu Gly Glu Thr Val
310                 315                 320                 325 acc gtg ttt acc acc cgc cca gat act ctg ttc ggc gcg acc tac atg         1123
Thr Val Phe Thr Thr Arg Pro Asp Thr Leu Phe Gly Ala Thr Tyr Met
                330                 335                 340 gtt ctt gca cct gag cat gag ctg gtc gac gtg ctg ctg gag aag gct         1171
Val Leu Ala Pro Glu His Glu Leu Val Asp Val Leu Leu Glu Lys Ala
        345                 350                 355 ggt tcc tac gag ggc gtt gat gcc cgt tgg acc aat ggc cag gcg agc         1219
Gly Ser Tyr Glu Gly Val Asp Ala Arg Trp Thr Asn Gly Gln Ala Ser
        360                 365                 370 cct gcg gaa gct gtc gct gca tac cgc gcc tcc atc gcc gcg aag tcc         1267
Pro Ala Glu Ala Val Ala Ala Tyr Arg Ala Ser Ile Ala Ala Lys Ser
375                 380                 385 gac ctg gag cgt cag gaa aac aag gaa aag acc ggc gtc ttc ctg ggc         1315
Asp Leu Glu Arg Gln Glu Asn Lys Glu Lys Thr Gly Val Phe Leu Gly
390                 395                 400                 405 gtt tac gcg acc aac cca gtc aac ggc gat cag atc aca gtg ttc atc         1363
Val Tyr Ala Thr Asn Pro Val Asn Gly Asp Gln Ile Thr Val Phe Ile
                410                 415                 420 gct gac tac gtt ctg acc ggc tac ggc acc ggc gcc atc atg gcg gtt         1411
Ala Asp Tyr Val Leu Thr Gly Tyr Gly Thr Gly Ala Ile Met Ala Val
        425                 430                 435 cct gct cac gac gag cgc gac tac gaa ttc gcc acc gtt ttg ggt ctg         1459
Pro Ala His Asp Glu Arg Asp Tyr Glu Phe Ala Thr Val Leu Gly Leu
        440                 445                 450 cct atc aag gaa gtt gtc gca ggt ggc aac atc gaa gag gct gct ttc         1507
Pro Ile Lys Glu Val Val Ala Gly Gly Asn Ile Glu Glu Ala Ala Phe
455                 460                 465 acc gaa tct ggc gaa gca gtc aac tct gcg aac gac aac ggc ctg gat         1555
Thr Glu Ser Gly Glu Ala Val Asn Ser Ala Asn Asp Asn Gly Leu Asp
470                 475                 480                 485 atc aac ggc ctt gcc aag gat gag gct att gcc aag acc atc gaa tgg         1603
Ile Asn Gly Leu Ala Lys Asp Glu Ala Ile Ala Lys Thr Ile Glu Trp
                490                 495                 500
```

```
ttg gaa gaa aag gaa ctt ggc cgc ggc acc atc cag tac aag ctg cgc        1651
Leu Glu Glu Lys Glu Leu Gly Arg Gly Thr Ile Gln Tyr Lys Leu Arg
        505                 510                 515 gac tgg ctg ttc gct cgc cag cgt tac tgg ggc gag cct ttc cca atc        1699
Asp Trp Leu Phe Ala Arg Gln Arg Tyr Trp Gly Glu Pro Phe Pro Ile
    520                 525                 530 gtc tac gac gaa aac ggc caa gca cat gct ctg cca gac tcc atg ctt        1747
Val Tyr Asp Glu Asn Gly Gln Ala His Ala Leu Pro Asp Ser Met Leu
535                 540                 545 cca gtc gag ctg cca gag gta gag gac tac aag cct gtc tcc ttc gac        1795
Pro Val Glu Leu Pro Glu Val Glu Asp Tyr Lys Pro Val Ser Phe Asp
550                 555                 560                 565 cct gaa gac gca gac tcc gag cct tcc cca ctg gct aag gcc cgc            1843
Pro Glu Asp Ala Asp Ser Glu Pro Ser Pro Leu Ala Lys Ala Arg
        570                 575                 580 gaa tgg gtt gag gtg gaa ctc gat ctc ggc gat ggc aag aag aag tac        1891
Glu Trp Val Glu Val Glu Leu Asp Leu Gly Asp Gly Lys Lys Lys Tyr
                585                 590                 595 acc cgc gac acc aac gtc atg cca cag tgg gca ggt tcc tcc tgg tac        1939
Thr Arg Asp Thr Asn Val Met Pro Gln Trp Ala Gly Ser Ser Trp Tyr
            600                 605                 610 cag ctg cgc tac gtc gat cca agc aac gat gag cag ttc tgc aac atc       1987
Gln Leu Arg Tyr Val Asp Pro Ser Asn Asp Glu Gln Phe Cys Asn Ile
        615                 620                 625 gaa aat gaa cgc tac tgg acc ggc cca cgc cca gaa acc cac gga cca        2035
Glu Asn Glu Arg Tyr Trp Thr Gly Pro Arg Pro Glu Thr His Gly Pro
630                 635                 640                 645 aac gat cca ggc ggc gta gac ctc tac gtc ggt ggc gtc gag cac gca        2083
Asn Asp Pro Gly Gly Val Asp Leu Tyr Val Gly Val Glu His Ala
        650                 655                 660 gtt ctc cac ctg ctc tac gca cgt ttc tgg cac aag gtc ctc ttc gac        2131
Val Leu His Leu Leu Tyr Ala Arg Phe Trp His Lys Val Leu Phe Asp
            665                 670                 675 ctg ggc cac gtc tcc tcc aag gag cca tac cgt cgc ctg tac aac cag        2179
Leu Gly His Val Ser Ser Lys Glu Pro Tyr Arg Arg Leu Tyr Asn Gln
        680                 685                 690 ggc tac atc cag gcc ttc gcc tac acc gat tcc cgt ggc gtc tac gtg        2227
Gly Tyr Ile Gln Ala Phe Ala Tyr Thr Asp Ser Arg Gly Val Tyr Val
    695                 700                 705 cct gcc gat gat gtc gaa gag aag gac gga aag ttc ttc tac cag ggc        2275
Pro Ala Asp Asp Val Glu Glu Lys Asp Gly Lys Phe Phe Tyr Gln Gly
710                 715                 720                 725 gaa gaa gtc aac cag gaa tac gga aag atg ggc aag tcc ctg aag aac        2323
Glu Glu Val Asn Gln Glu Tyr Gly Lys Met Gly Lys Ser Leu Lys Asn
            730                 735                 740 gcc gtt gcc cca gac gat atc tgc aac aac ttc ggt gct gac acc ctg        2371
Ala Val Ala Pro Asp Asp Ile Cys Asn Asn Phe Gly Ala Asp Thr Leu
        745                 750                 755 cgc gtt tac gag atg gcc atg gga cct ttg gac acc tcc cgt cca tgg        2419
Arg Val Tyr Glu Met Ala Met Gly Pro Leu Asp Thr Ser Arg Pro Trp
    760                 765                 770 gca acc aag gac gtc gtc ggt gcg cag cgc ttc ctc cag cgt ctg tgg        2467
Ala Thr Lys Asp Val Val Gly Ala Gln Arg Phe Leu Gln Arg Leu Trp
775                 780                 785 cgt ctc gtc gtc gat gaa aac acc ggc gaa gtg ctc act cgc gat gaa        2515
Arg Leu Val Val Asp Glu Asn Thr Gly Glu Val Leu Thr Arg Asp Glu
790                 795                 800                 805 gtc ctc acc gac gat gac aac aag caa ctg cac cgc acc atc gca ggc        2563
Val Leu Thr Asp Asp Asp Asn Lys Gln Leu His Arg Thr Ile Ala Gly
            810                 815                 820
```

-continued

```
gtc cgc gac gac tac acc aac ttg cgc gtt aac acc gtg gtt gcc aag      2611
Val Arg Asp Asp Tyr Thr Asn Leu Arg Val Asn Thr Val Val Ala Lys
            825                 830                 835 ctc atc gaa tac gtc aac tac ctg acc aaa aca tac cca gac acc atc      2659
Leu Ile Glu Tyr Val Asn Tyr Leu Thr Lys Thr Tyr Pro Asp Thr Ile
        840                 845                 850 cca gct ggc gca gtc ctg cca ctg atc gtc atg gtc tcc cct atc gca      2707
Pro Ala Gly Ala Val Leu Pro Leu Ile Val Met Val Ser Pro Ile Ala
    855                 860                 865 cca cac atc gcg gag gaa ctc tgg aag aag ctc ggc cac gac gac acc      2755
Pro His Ile Ala Glu Glu Leu Trp Lys Lys Leu Gly His Asp Asp Thr
870                 875                 880                 885 gtc acc tac gaa cca ttc ccc acc ttt gag gaa aaa tgg ctc acc gac      2803
Val Thr Tyr Glu Pro Phe Pro Thr Phe Glu Glu Lys Trp Leu Thr Asp
                890                 895                 900 gat gaa atc gaa ctg cca gtc cag gtc aac ggc aag gtc cgc ggt cgc      2851
Asp Glu Ile Glu Leu Pro Val Gln Val Asn Gly Lys Val Arg Gly Arg
            905                 910                 915 atc acc gtt gca gcc gac gcc agc cag gag cag gtc atc gag gca gcg      2899
Ile Thr Val Ala Ala Asp Ala Ser Gln Glu Gln Val Ile Glu Ala Ala
        920                 925                 930 ctt gcc gac gag aag gtg cag gag caa atc tcc ggc aag aac ctg atc      2947
Leu Ala Asp Glu Lys Val Gln Glu Gln Ile Ser Gly Lys Asn Leu Ile
    935                 940                 945 aag cag atc gtt gtt cca gga cgc atg gtt aac ctt gtg gtg aag          2992
Lys Gln Ile Val Val Pro Gly Arg Met Val Asn Leu Val Val Lys
950                 955                 960 taatcccct cggtttagat tccctagaa                                       3022

<210> SEQ ID NO 20
<211> LENGTH: 964
<212> TYPE: PRT
<213> ORGANISM: Corynebacterium glutamicum

<400> SEQUENCE: 20

Met Arg Cys Pro Val Tyr Leu Leu His Cys Leu Thr Met Thr Asn Pro
 1               5                  10                  15

Ser Glu Gly Thr Thr Pro Leu Ala Phe Arg Tyr Thr Pro Glu Leu Ala
                20                  25                  30

Asn Lys Ile Glu Gly Glu Trp Gln Asn Tyr Trp Thr Asp Asn Gly Thr
            35                  40                  45

Phe Asn Ala Pro Asn Pro Val Gly Asp Leu Ala Pro Asp Gly Lys
        50                  55                  60

Ala Leu Pro Glu Asp Lys Leu Phe Val Gln Asp Met Phe Pro Tyr Pro
 65                  70                  75                  80

Ser Gly Ala Gly Leu His Val Gly His Pro Leu Gly Tyr Ile Ala Thr
                85                  90                  95

Asp Val Phe Ala Arg Tyr Asn Arg Met Leu Gly Lys Asn Val Leu His
                100                 105                 110

Thr Leu Gly Tyr Asp Ala Phe Gly Leu Pro Ala Glu Gln Tyr Ala Ile
            115                 120                 125

Gln Thr Gly Thr His Pro Arg Thr Thr Met Ala Asn Ile Glu Asn
        130                 135                 140

Met Lys Arg Gln Leu Gly Ala Leu Gly Leu Gly His Asp Ser Arg Arg
145                 150                 155                 160

Ala Val Ala Thr Thr Asp Pro Glu Phe Tyr Lys Trp Thr Gln Trp Ile
                165                 170                 175
```

-continued

```
Phe Leu Gln Ile Phe Asn Ser Trp Phe Asp Ala Glu Gln Gln Lys Ala
            180                 185                 190
Arg Pro Ile Ser Glu Leu Ile Pro Leu Leu Glu Ser Gly Glu Leu Lys
            195                 200                 205
Thr Lys Asp Gly Ala Asp Tyr Asn Ala Leu Gly Asp Val Glu Lys Gln
            210                 215                 220
Lys Ala Val Asp Asp Tyr Arg Leu Val Tyr Arg Ser Asn Ser Thr Val
225                 230                 235                 240
Asn Trp Cys Pro Gly Leu Gly Thr Val Leu Ala Asn Glu Glu Val Thr
                    245                 250                 255
Ala Asp Gly Arg Ser Glu Arg Gly Asn Phe Pro Val Phe Arg Lys Asn
                260                 265                 270
Leu Ser Gln Trp Met Met Arg Ile Thr Ala Tyr Ser Asp Arg Leu Ile
            275                 280                 285
Asp Asp Leu Glu Leu Leu Asp Trp Thr Glu Lys Val Lys Ser Met Gln
            290                 295                 300
Arg Asn Trp Ile Gly Arg Ser Arg Gly Ala Glu Val Asp Phe Ser Ala
305                 310                 315                 320
Glu Gly Glu Thr Val Thr Val Phe Thr Thr Arg Pro Asp Thr Leu Phe
                    325                 330                 335
Gly Ala Thr Tyr Met Val Leu Ala Pro Glu His Glu Leu Val Asp Val
                340                 345                 350
Leu Leu Glu Lys Ala Gly Ser Tyr Glu Gly Val Asp Ala Arg Trp Thr
            355                 360                 365
Asn Gly Gln Ala Ser Pro Ala Glu Ala Val Ala Ala Tyr Arg Ala Ser
            370                 375                 380
Ile Ala Ala Lys Ser Asp Leu Glu Arg Gln Glu Asn Lys Glu Lys Thr
385                 390                 395                 400
Gly Val Phe Leu Gly Val Tyr Ala Thr Asn Pro Val Asn Gly Asp Gln
                    405                 410                 415
Ile Thr Val Phe Ile Ala Asp Tyr Val Leu Thr Gly Tyr Gly Thr Gly
                420                 425                 430
Ala Ile Met Ala Val Pro Ala His Asp Glu Arg Asp Tyr Glu Phe Ala
            435                 440                 445
Thr Val Leu Gly Leu Pro Ile Lys Glu Val Val Ala Gly Gly Asn Ile
            450                 455                 460
Glu Glu Ala Ala Phe Thr Glu Ser Gly Glu Ala Val Asn Ser Ala Asn
465                 470                 475                 480
Asp Asn Gly Leu Asp Ile Asn Gly Leu Ala Lys Asp Glu Ala Ile Ala
                    485                 490                 495
Lys Thr Ile Glu Trp Leu Glu Glu Lys Glu Leu Gly Arg Gly Thr Ile
                500                 505                 510
Gln Tyr Lys Leu Arg Asp Trp Leu Phe Ala Arg Gln Arg Tyr Trp Gly
            515                 520                 525
Glu Pro Phe Pro Ile Val Tyr Asp Glu Asn Gly Gln Ala His Ala Leu
            530                 535                 540
Pro Asp Ser Met Leu Pro Val Glu Leu Pro Glu Val Glu Asp Tyr Lys
545                 550                 555                 560
Pro Val Ser Phe Asp Pro Glu Asp Ala Asp Ser Glu Pro Ser Pro Pro
                    565                 570                 575
Leu Ala Lys Ala Arg Glu Trp Val Glu Val Glu Leu Asp Leu Gly Asp
                580                 585                 590
```

```
Gly Lys Lys Lys Tyr Thr Arg Asp Thr Asn Val Met Pro Gln Trp Ala
            595                 600                 605

Gly Ser Ser Trp Tyr Gln Leu Arg Tyr Val Asp Pro Ser Asn Asp Glu
    610                 615                 620

Gln Phe Cys Asn Ile Glu Asn Glu Arg Tyr Trp Thr Gly Pro Arg Pro
625                 630                 635                 640

Glu Thr His Gly Pro Asn Asp Pro Gly Gly Val Asp Leu Tyr Val Gly
                645                 650                 655

Gly Val Glu His Ala Val Leu His Leu Leu Tyr Ala Arg Phe Trp His
            660                 665                 670

Lys Val Leu Phe Asp Leu Gly His Val Ser Ser Lys Glu Pro Tyr Arg
        675                 680                 685

Arg Leu Tyr Asn Gln Gly Tyr Ile Gln Ala Phe Ala Tyr Thr Asp Ser
    690                 695                 700

Arg Gly Val Tyr Val Pro Ala Asp Asp Val Glu Glu Lys Asp Gly Lys
705                 710                 715                 720

Phe Phe Tyr Gln Gly Glu Val Asn Gln Glu Tyr Gly Lys Met Gly
                725                 730                 735

Lys Ser Leu Lys Asn Ala Val Ala Pro Asp Asp Ile Cys Asn Asn Phe
            740                 745                 750

Gly Ala Asp Thr Leu Arg Val Tyr Glu Met Ala Met Gly Pro Leu Asp
        755                 760                 765

Thr Ser Arg Pro Trp Ala Thr Lys Asp Val Val Gly Ala Gln Arg Phe
    770                 775                 780

Leu Gln Arg Leu Trp Arg Leu Val Val Asp Glu Asn Thr Gly Glu Val
785                 790                 795                 800

Leu Thr Arg Asp Glu Val Leu Thr Asp Asp Asn Lys Gln Leu His
                805                 810                 815

Arg Thr Ile Ala Gly Val Arg Asp Asp Tyr Thr Asn Leu Arg Val Asn
            820                 825                 830

Thr Val Val Ala Lys Leu Ile Glu Tyr Val Asn Tyr Leu Thr Lys Thr
        835                 840                 845

Tyr Pro Asp Thr Ile Pro Ala Gly Ala Val Leu Pro Leu Ile Val Met
    850                 855                 860

Val Ser Pro Ile Ala Pro His Ile Ala Glu Glu Leu Trp Lys Lys Leu
865                 870                 875                 880

Gly His Asp Asp Thr Val Thr Tyr Glu Pro Phe Pro Thr Phe Glu Glu
                885                 890                 895

Lys Trp Leu Thr Asp Asp Glu Ile Glu Leu Pro Val Gln Val Asn Gly
            900                 905                 910

Lys Val Arg Gly Arg Ile Thr Val Ala Ala Asp Ala Ser Gln Glu Gln
        915                 920                 925

Val Ile Glu Ala Ala Leu Ala Asp Glu Lys Val Gln Glu Gln Ile Ser
    930                 935                 940

Gly Lys Asn Leu Ile Lys Gln Ile Val Val Pro Gly Arg Met Val Asn
945                 950                 955                 960

Leu Val Val Lys

<210> SEQ ID NO 21
<211> LENGTH: 2248
<212> TYPE: DNA
<213> ORGANISM: Corynebacterium glutamicum
<220> FEATURE:
<221> NAME/KEY: CDS
<222> LOCATION: (101)..(2218)
```

<223> OTHER INFORMATION: RXA01277

<400> SEQUENCE: 21

```
gaccagccga atctacattc cttattctgc tggcgttaca attcagggcc aaacccgtat      60
gatgaaaaag acaccgggga atcggagtg cgcgtagatt ttg aaa acg gcc ggt        115
                                             Leu Lys Thr Ala Gly
                                               1               5 act act cgg ttc acg ttt acg tcg gct gat cca att gga ggc gcc ctc       163
Thr Thr Arg Phe Thr Phe Thr Ser Ala Asp Pro Ile Gly Gly Ala Leu
             10                  15                  20 gga agc cgc ctt aaa aaa cct gcc ggt caa aag atc act aac ctg aac       211
Gly Ser Arg Leu Lys Lys Pro Ala Gly Gln Lys Ile Thr Asn Leu Asn
         25                  30                  35 ttc atg act gat tac acg ttc ctc gaa gac att gac acc ccg gaa gcg       259
Phe Met Thr Asp Tyr Thr Phe Leu Glu Asp Ile Asp Thr Pro Glu Ala
     40                  45                  50 ctc gcg tgg gcg gaa aaa tgg tcg ggg gaa agc gtc gaa aag cta aaa       307
Leu Ala Trp Ala Glu Lys Trp Ser Gly Glu Ser Val Glu Lys Leu Lys
 55                  60                  65 agc cca gcc aag gac gcc ctg gaa gcc agg ctg ctg gct gcg ttg gac       355
Ser Pro Ala Lys Asp Ala Leu Glu Ala Arg Leu Leu Ala Ala Leu Asp
 70                  75                  80                  85 acc gat gat cgc att gcc tac gtg agc cgg cgc ggt gag aag ctg tac       403
Thr Asp Asp Arg Ile Ala Tyr Val Ser Arg Arg Gly Glu Lys Leu Tyr
                 90                  95                 100 aac ttt tgg cgg gac gcg cag cat ccg cgt gga gtg tgg cgc acg acc       451
Asn Phe Trp Arg Asp Ala Gln His Pro Arg Gly Val Trp Arg Thr Thr
             105                 110                 115 acg ttg gag tcg tat gaa agt gac cag ccg gag tgg gac gtg ctc att       499
Thr Leu Glu Ser Tyr Glu Ser Asp Gln Pro Glu Trp Asp Val Leu Ile
         120                 125                 130 gat gtg gat gcg ttg gcg gag gat gag ggc gaa aac tgg gta tgg aag       547
Asp Val Asp Ala Leu Ala Glu Asp Glu Gly Glu Asn Trp Val Trp Lys
     135                 140                 145 ggc gcg gtt gtg cgc tcg ccg gag ttt gat cgg gcg ttg gtg aag ttc       595
Gly Ala Val Val Arg Ser Pro Glu Phe Asp Arg Ala Leu Val Lys Phe
150                 155                 160                 165 tcg cgg ggc ggg gct gat gcg acg gtg att agg gag ttt gat ctg gcc       643
Ser Arg Gly Gly Ala Asp Ala Thr Val Ile Arg Glu Phe Asp Leu Ala
                 170                 175                 180 acg gct gct ttc gtg gat gat tcg ccg ttt gaa ttg gag gag gcg aag       691
Thr Ala Ala Phe Val Asp Asp Ser Pro Phe Glu Leu Glu Glu Ala Lys
             185                 190                 195 tcc gat gtc acg tgg gtt gat ctg gat acg ttg ctg gtg ggc acg gat       739
Ser Asp Val Thr Trp Val Asp Leu Asp Thr Leu Leu Val Gly Thr Asp
         200                 205                 210 acc ggc gag ggg tca ctg acg gat tct ggg tac ccg gcg cgg gtg ctc       787
Thr Gly Glu Gly Ser Leu Thr Asp Ser Gly Tyr Pro Ala Arg Val Leu
     215                 220                 225 acg tgg aag cgt ggg act ccg ctt gag cag gcg gag ttg ttc ttt gag       835
Thr Trp Lys Arg Gly Thr Pro Leu Glu Gln Ala Glu Leu Phe Phe Glu
230                 235                 240                 245 ggg tcg cgt cag gat gtg gcg act cat gcg tgg cgg gat tca aca cct       883
Gly Ser Arg Gln Asp Val Ala Thr His Ala Trp Arg Asp Ser Thr Pro
                 250                 255                 260 ggt ttt gag cgg acg ttt gtg tca agg tcg ttg gat ttc tat aat tcg       931
Gly Phe Glu Arg Thr Phe Val Ser Arg Ser Leu Asp Phe Tyr Asn Ser
             265                 270                 275 gag acg tcg ctg gaa acc gag ggt ggc ctg gtc aag ctt gat gtg ccg       979
```

-continued

```
                Glu Thr Ser Leu Glu Thr Glu Gly Gly Leu Val Lys Leu Asp Val Pro
                    280                 285                 290 acc gat tgc gat gtc att gtg aag aag cag tgg att ttt gtg agt cct          1027
Thr Asp Cys Asp Val Ile Val Lys Lys Gln Trp Ile Phe Val Ser Pro
    295                 300                 305 cgg acg gat ttc gct ggg att cca gca ggt ggc ttg gga gtg ctg ctg          1075
Arg Thr Asp Phe Ala Gly Ile Pro Ala Gly Gly Leu Gly Val Leu Leu
310                 315                 320                 325 tta aag gag ttc ctt gag ggc ggg cgc gat ttt cag cct gtg ttt acg          1123
Leu Lys Glu Phe Leu Glu Gly Gly Arg Asp Phe Gln Pro Val Phe Thr
                330                 335                 340 cct act gag tcg acg tcg ctg cag gga ttg gcc acg aca aag aat ttc          1171
Pro Thr Glu Ser Thr Ser Leu Gln Gly Leu Ala Thr Thr Lys Asn Phe
            345                 350                 355 ctg gtt tta acg ctc ctt aat aat gtc tcc aca gaa atc gtc aca gtg          1219
Leu Val Leu Thr Leu Leu Asn Asn Val Ser Thr Glu Ile Val Thr Val
        360                 365                 370 ccg ctc aat gat ccg aca acg gag cat gaa cac att gac ctc cca gag          1267
Pro Leu Asn Asp Pro Thr Thr Glu His Glu His Ile Asp Leu Pro Glu
    375                 380                 385 cat gtc acc gcg cat gtg gtt gct acc tcc ccg ttg gat ggc gat gaa          1315
His Val Thr Ala His Val Val Ala Thr Ser Pro Leu Asp Gly Asp Glu
390                 395                 400                 405 att tgg gtg cag gca gcg agt ttc acc gaa gcg cca acg ttg ctg cgt          1363
Ile Trp Val Gln Ala Ala Ser Phe Thr Glu Ala Pro Thr Leu Leu Arg
                410                 415                 420 gcg gag ctg cct ggt gcg ctt gag gct gtg aag aag gcg ccg ttg cag          1411
Ala Glu Leu Pro Gly Ala Leu Glu Ala Val Lys Lys Ala Pro Leu Gln
            425                 430                 435 ttt gaa aat gct ggt cag gag act cgt cag cat tgg gca acc tcg gcg          1459
Phe Glu Asn Ala Gly Gln Glu Thr Arg Gln His Trp Ala Thr Ser Ala
        440                 445                 450 gat gga acg aag att ccg tac ttt att aca gga gcc ttc gag gag gaa          1507
Asp Gly Thr Lys Ile Pro Tyr Phe Ile Thr Gly Ala Phe Glu Glu Glu
    455                 460                 465 cca caa aac acc ctg gtc cac gcc tac ggc ggc ttc gag gtt tcc ctt          1555
Pro Gln Asn Thr Leu Val His Ala Tyr Gly Gly Phe Glu Val Ser Leu
470                 475                 480                 485 acc cca agc cac tcc ccg acc cgc ggc atc gca tgg ttg gaa aag ggc          1603
Thr Pro Ser His Ser Pro Thr Arg Gly Ile Ala Trp Leu Glu Lys Gly
                490                 495                 500 tac tac ttt gtg gaa gcc aac ctg cgt ggt ggc ggt gaa ttc ggt ccg          1651
Tyr Tyr Phe Val Glu Ala Asn Leu Arg Gly Gly Gly Glu Phe Gly Pro
            505                 510                 515 gaa tgg cat tcg cag gca acc aag ctg aac cgc atg aag gtg tgg gag          1699
Glu Trp His Ser Gln Ala Thr Lys Leu Asn Arg Met Lys Val Trp Glu
        520                 525                 530 gat cac cgc gcg gtg ctc gcc gac ctt gtg gag cgc ggc tac gca acg          1747
Asp His Arg Ala Val Leu Ala Asp Leu Val Glu Arg Gly Tyr Ala Thr
    535                 540                 545 ccg gag cag att gcg att cgt ggc gga tcc aac ggt ggt ttg ctg aca          1795
Pro Glu Gln Ile Ala Ile Arg Gly Gly Ser Asn Gly Gly Leu Leu Thr
550                 555                 560                 565 agt ggc gcg tta act cag tac cca gaa gca ttc ggt gcg gca gtt gtg          1843
Ser Gly Ala Leu Thr Gln Tyr Pro Glu Ala Phe Gly Ala Ala Val Val
                570                 575                 580 cag gtg ccg ttg gct gat atg ttg cgc tat cac acc tgg tca gcg ggt          1891
Gln Val Pro Leu Ala Asp Met Leu Arg Tyr His Thr Trp Ser Ala Gly
            585                 590                 595
```

```
gct tcg tgg atg gcg gag tac ggc aac cct gac gat ccg gag gaa cgg      1939
Ala Ser Trp Met Ala Glu Tyr Gly Asn Pro Asp Asp Pro Glu Glu Arg
        600                 605                 610 gcg gtg att gag cag tac tcg ccg gtg cag gcg gtg gtg ggc gtc gag      1987
Ala Val Ile Glu Gln Tyr Ser Pro Val Gln Ala Val Val Gly Val Glu
        615                 620                 625 aag cga att tat cca ccc gca ttg gtg acg acc tca acc cgg gac gac      2035
Lys Arg Ile Tyr Pro Pro Ala Leu Val Thr Thr Ser Thr Arg Asp Asp
630                 635                 640                 645 cgc gtc cac ccc gcg cac gcg cgc ctt ttt gct caa gct ttg ctt gat      2083
Arg Val His Pro Ala His Ala Arg Leu Phe Ala Gln Ala Leu Leu Asp
                650                 655                 660 gcg ggc cag gcc gtg gat tac tac gaa aac acc gag ggc ggc cat gcc      2131
Ala Gly Gln Ala Val Asp Tyr Tyr Glu Asn Thr Glu Gly Gly His Ala
            665                 670                 675 ggc gcg gcg gat aac aag cag acc gcg ttt gtg gaa tcg ctg atc tac      2179
Gly Ala Ala Asp Asn Lys Gln Thr Ala Phe Val Glu Ser Leu Ile Tyr
        680                 685                 690 acc tgg atc gag aag act ttg gat cag cag ggt agc att taataccctat     2228
Thr Trp Ile Glu Lys Thr Leu Asp Gln Gln Gly Ser Ile
        695                 700                 705 gattatgcga aggctgcgct                                                 2248

<210> SEQ ID NO 22
<211> LENGTH: 706
<212> TYPE: PRT
<213> ORGANISM: Corynebacterium glutamicum

<400> SEQUENCE: 22

Leu Lys Thr Ala Gly Thr Thr Arg Phe Thr Phe Thr Ser Ala Asp Pro
 1               5                  10                  15

Ile Gly Gly Ala Leu Gly Ser Arg Leu Lys Lys Pro Ala Gly Gln Lys
            20                  25                  30

Ile Thr Asn Leu Asn Phe Met Thr Asp Tyr Thr Phe Leu Glu Asp Ile
        35                  40                  45

Asp Thr Pro Glu Ala Leu Ala Trp Ala Glu Lys Trp Ser Gly Glu Ser
    50                  55                  60

Val Glu Lys Leu Lys Ser Pro Ala Lys Asp Ala Leu Glu Ala Arg Leu
65                  70                  75                  80

Leu Ala Ala Leu Asp Thr Asp Arg Ile Ala Tyr Val Ser Arg Arg
                85                  90                  95

Gly Glu Lys Leu Tyr Asn Phe Trp Arg Asp Ala Gln His Pro Arg Gly
            100                 105                 110

Val Trp Arg Thr Thr Thr Leu Glu Ser Tyr Glu Ser Asp Gln Pro Glu
        115                 120                 125

Trp Asp Val Leu Ile Asp Val Asp Ala Leu Ala Glu Asp Glu Gly Glu
    130                 135                 140

Asn Trp Val Trp Lys Gly Ala Val Val Arg Ser Pro Glu Phe Asp Arg
145                 150                 155                 160

Ala Leu Val Lys Phe Ser Arg Gly Gly Ala Asp Ala Thr Val Ile Arg
                165                 170                 175

Glu Phe Asp Leu Ala Thr Ala Ala Phe Val Asp Ser Pro Phe Glu
            180                 185                 190

Leu Glu Glu Ala Lys Ser Asp Val Thr Trp Val Asp Leu Asp Thr Leu
        195                 200                 205

Leu Val Gly Thr Asp Thr Gly Glu Gly Ser Leu Thr Asp Ser Gly Tyr
    210                 215                 220
```

```
Pro Ala Arg Val Leu Thr Trp Lys Arg Gly Thr Pro Leu Glu Gln Ala
225                 230                 235                 240

Glu Leu Phe Phe Glu Gly Ser Arg Gln Asp Val Ala Thr His Ala Trp
            245                 250                 255

Arg Asp Ser Thr Pro Gly Phe Glu Arg Thr Phe Val Ser Arg Ser Leu
                260                 265                 270

Asp Phe Tyr Asn Ser Glu Thr Ser Leu Glu Thr Glu Gly Gly Leu Val
            275                 280                 285

Lys Leu Asp Val Pro Thr Asp Cys Asp Val Ile Val Lys Lys Gln Trp
290                 295                 300

Ile Phe Val Ser Pro Arg Thr Asp Phe Ala Gly Ile Pro Ala Gly Gly
305                 310                 315                 320

Leu Gly Val Leu Leu Lys Glu Phe Leu Glu Gly Gly Arg Asp Phe
            325                 330                 335

Gln Pro Val Phe Thr Pro Thr Glu Ser Thr Ser Leu Gln Gly Leu Ala
                340                 345                 350

Thr Thr Lys Asn Phe Leu Val Leu Thr Leu Leu Asn Asn Val Ser Thr
            355                 360                 365

Glu Ile Val Thr Val Pro Leu Asn Asp Pro Thr Thr Glu His Glu His
    370                 375                 380

Ile Asp Leu Pro Glu His Val Thr Ala His Val Val Ala Thr Ser Pro
385                 390                 395                 400

Leu Asp Gly Asp Glu Ile Trp Val Gln Ala Ala Ser Phe Thr Glu Ala
                405                 410                 415

Pro Thr Leu Leu Arg Ala Glu Leu Pro Gly Ala Leu Glu Ala Val Lys
                420                 425                 430

Lys Ala Pro Leu Gln Phe Glu Asn Ala Gly Gln Glu Thr Arg Gln His
            435                 440                 445

Trp Ala Thr Ser Ala Asp Gly Thr Lys Ile Pro Tyr Phe Ile Thr Gly
    450                 455                 460

Ala Phe Glu Glu Glu Pro Gln Asn Thr Leu Val His Ala Tyr Gly Gly
465                 470                 475                 480

Phe Glu Val Ser Leu Thr Pro Ser His Ser Pro Thr Arg Gly Ile Ala
                485                 490                 495

Trp Leu Glu Lys Gly Tyr Tyr Phe Val Glu Ala Asn Leu Arg Gly Gly
            500                 505                 510

Gly Glu Phe Gly Pro Glu Trp His Ser Gln Ala Thr Lys Leu Asn Arg
            515                 520                 525

Met Lys Val Trp Glu Asp His Arg Ala Val Leu Ala Asp Leu Val Glu
530                 535                 540

Arg Gly Tyr Ala Thr Pro Glu Gln Ile Ala Ile Arg Gly Gly Ser Asn
545                 550                 555                 560

Gly Gly Leu Leu Thr Ser Gly Ala Leu Thr Gln Tyr Pro Glu Ala Phe
                565                 570                 575

Gly Ala Ala Val Val Gln Val Pro Leu Ala Asp Met Leu Arg Tyr His
            580                 585                 590

Thr Trp Ser Ala Gly Ala Ser Trp Met Ala Glu Tyr Gly Asn Pro Asp
    595                 600                 605

Asp Pro Glu Glu Arg Ala Val Ile Glu Gln Tyr Ser Pro Val Gln Ala
            610                 615                 620

Val Val Gly Val Glu Lys Arg Ile Tyr Pro Pro Ala Leu Val Thr Thr
625                 630                 635                 640
```

-continued

```
Ser Thr Arg Asp Asp Arg Val His Pro Ala His Ala Arg Leu Phe Ala
            645                 650                 655

Gln Ala Leu Leu Asp Ala Gly Gln Ala Val Asp Tyr Tyr Glu Asn Thr
        660                 665                 670

Glu Gly Gly His Ala Gly Ala Ala Asp Asn Lys Gln Thr Ala Phe Val
    675                 680                 685

Glu Ser Leu Ile Tyr Thr Trp Ile Glu Lys Thr Leu Asp Gln Gln Gly
690                 695                 700

Ser Ile
705
```

<210> SEQ ID NO 23
<211> LENGTH: 2257
<212> TYPE: DNA
<213> ORGANISM: Corynebacterium glutamicum
<220> FEATURE:
<221> NAME/KEY: CDS
<222> LOCATION: (101)..(2227)
<223> OTHER INFORMATION: RXA01278

<400> SEQUENCE: 23

```
ttatccgtag gtgacaaact ttttaatact tgggtatctg tcatggatac cccggtaata    60
aataagtgaa ttaccgtaac caacaagttg gggtaccact gtg gca caa gaa gtg   115
                                            Val Ala Gln Glu Val
                                              1               5 ctt aag gat cta aac aag gtc cgc aac atc ggc atc atg gcg cac atc   163
Leu Lys Asp Leu Asn Lys Val Arg Asn Ile Gly Ile Met Ala His Ile
                10                  15                  20 gat gct ggt aag acc acg acc acc gaa cgc atc ctc ttc tac acc ggc   211
Asp Ala Gly Lys Thr Thr Thr Thr Glu Arg Ile Leu Phe Tyr Thr Gly
            25                  30                  35 atc aac cgt aag gtc ggt gag acc cac gac ggt ggc gca acc acc gac   259
Ile Asn Arg Lys Val Gly Glu Thr His Asp Gly Gly Ala Thr Thr Asp
        40                  45                  50 tgg atg gag cag gag aag gaa cgc ggc atc acc att acc tcc gcc gcg   307
Trp Met Glu Gln Glu Lys Glu Arg Gly Ile Thr Ile Thr Ser Ala Ala
    55                  60                  65 gtt acc tgt ttc tgg gat aac aac cag gtc aac atc att gac acc cct   355
Val Thr Cys Phe Trp Asp Asn Asn Gln Val Asn Ile Ile Asp Thr Pro
70                  75                  80                  85 ggc cac gtt gac ttc acc gtt gag gtt gag cgt tcc ctc cgc gtg ctt   403
Gly His Val Asp Phe Thr Val Glu Val Glu Arg Ser Leu Arg Val Leu
                90                  95                 100 gac ggc gca gtt gct gtg ttc gac ggc aag gaa ggc gtt gag cca cag   451
Asp Gly Ala Val Ala Val Phe Asp Gly Lys Glu Gly Val Glu Pro Gln
            105                 110                 115 tct gag cag gtt tgg cgt cag gct acc aag tac gac gtt cca cgt atc   499
Ser Glu Gln Val Trp Arg Gln Ala Thr Lys Tyr Asp Val Pro Arg Ile
        120                 125                 130 tgc ttc gtg aac aag atg gac aag ctc ggt gct gac ttc tac ttc acc   547
Cys Phe Val Asn Lys Met Asp Lys Leu Gly Ala Asp Phe Tyr Phe Thr
    135                 140                 145 gtt ggc acc atc gag gac cgc ctg ggt gca aag cca ttg gtt atg cag   595
Val Gly Thr Ile Glu Asp Arg Leu Gly Ala Lys Pro Leu Val Met Gln
150                 155                 160                 165 ctc cca atc ggt gct gag gac aac ttc gac ggc gtc atc gac ctt ctt   643
Leu Pro Ile Gly Ala Glu Asp Asn Phe Asp Gly Val Ile Asp Leu Leu
                170                 175                 180 gaa atg aag gca ctg acc tgg cgt gga gtt acc cca att ggt acc gaa   691
Glu Met Lys Ala Leu Thr Trp Arg Gly Val Thr Pro Ile Gly Thr Glu
```

|  |  |  |  |  |  |  |  |  |  |  |  |  |  |
|---|---|---|---|---|---|---|---|---|---|---|---|---|---|
|  |  |  | 185 |  |  |  | 190 |  |  |  | 195 |  |  |
| gct | acc | gtt | gag | gag | atc | cca | gca | gag | ctc | gca | gac | cgc | gca | gct | gag | 739 |
| Ala | Thr | Val | Glu | Glu | Ile | Pro | Ala | Glu | Leu | Ala | Asp | Arg | Ala | Ala | Glu |  |
|  |  | 200 |  |  |  | 205 |  |  |  | 210 |  |  |  |  | gct acc gtt gag gag atc cca gca gag ctc gca gac cgc gca gct gag    739
Ala Thr Val Glu Glu Ile Pro Ala Glu Leu Ala Asp Arg Ala Ala Glu
        200             205             210 tac cgt gag aag ctt ctc gag acc gtt gca gag tcc gac gaa gag ctc    787
Tyr Arg Glu Lys Leu Leu Glu Thr Val Ala Glu Ser Asp Glu Glu Leu
        215             220             225 atg gag aag tac ttc ggt ggc gaa gag ctc agc atc gct gag atc aag    835
Met Glu Lys Tyr Phe Gly Gly Glu Glu Leu Ser Ile Ala Glu Ile Lys
230             235             240             245 gca gct atc cgt aag atg gtt gtt aac tct gag atc tac cct gtt tac    883
Ala Ala Ile Arg Lys Met Val Val Asn Ser Glu Ile Tyr Pro Val Tyr
        250             255             260 tgt ggc acc gcc tac aag aac aag ggc atc cag cca ctg ctc gac gca    931
Cys Gly Thr Ala Tyr Lys Asn Lys Gly Ile Gln Pro Leu Leu Asp Ala
        265             270             275 gtc gtt gac ttc ctg cct tcc cca ctg gat ctc ggc gag acc aag ggc    979
Val Val Asp Phe Leu Pro Ser Pro Leu Asp Leu Gly Glu Thr Lys Gly
        280             285             290 act gac gtt aag gat cct gag aag gtt ctg acc cgt aag cct tcc gac   1027
Thr Asp Val Lys Asp Pro Glu Lys Val Leu Thr Arg Lys Pro Ser Asp
        295             300             305 gaa gag cca ctg tct gca ctt gca ttc aag att gca gct cac cca ttc   1075
Glu Glu Pro Leu Ser Ala Leu Ala Phe Lys Ile Ala Ala His Pro Phe
310             315             320             325 ttc ggt aag ctg acc ttc gtt cgt ctg tac tcc ggc aag gtt gag cca   1123
Phe Gly Lys Leu Thr Phe Val Arg Leu Tyr Ser Gly Lys Val Glu Pro
        330             335             340 ggc gag cag gtt ctt aac tcc acc aag aac aag aag gaa cgc att ggt   1171
Gly Glu Gln Val Leu Asn Ser Thr Lys Asn Lys Lys Glu Arg Ile Gly
        345             350             355 aag ctg ttc cag atg cac gcc aac aag gaa aac cct gtt gag gtt gca   1219
Lys Leu Phe Gln Met His Ala Asn Lys Glu Asn Pro Val Glu Val Ala
        360             365             370 cac gct ggt aac atc tac gcg ttc atc ggc ctg aag gac acc acc acc   1267
His Ala Gly Asn Ile Tyr Ala Phe Ile Gly Leu Lys Asp Thr Thr Thr
        375             380             385 ggt gac acc ctc tgt gac gca aac gct cca atc att ctt gag tcc atg   1315
Gly Asp Thr Leu Cys Asp Ala Asn Ala Pro Ile Ile Leu Glu Ser Met
390             395             400             405 gac ttc ccg gat cca gtt atc cag gtt gct att gag cct aag acc aag   1363
Asp Phe Pro Asp Pro Val Ile Gln Val Ala Ile Glu Pro Lys Thr Lys
        410             415             420 tct gac cag gag aag ctc ggc gta gct atc cag aag ctt gct gaa gaa   1411
Ser Asp Gln Glu Lys Leu Gly Val Ala Ile Gln Lys Leu Ala Glu Glu
        425             430             435 gac cca acc ttc acc gtt cac ttg gac gat gag tcc ggc cag acc gtc   1459
Asp Pro Thr Phe Thr Val His Leu Asp Asp Glu Ser Gly Gln Thr Val
        440             445             450 att ggc ggc atg ggc gag ctg cac ctc gat gtt ctt gtt gac cgc atg   1507
Ile Gly Gly Met Gly Glu Leu His Leu Asp Val Leu Val Asp Arg Met
455             460             465 aag cgc gag ttc aag gtt gag gca aac atc ggt gac cca cag gtt gct   1555
Lys Arg Glu Phe Lys Val Glu Ala Asn Ile Gly Asp Pro Gln Val Ala
470             475             480             485 tac cgt gag acc atc cgt aag cct gtt gag tcc ctc agc tac acc cac   1603
Tyr Arg Glu Thr Ile Arg Lys Pro Val Glu Ser Leu Ser Tyr Thr His
        490             495             500 aag aag cag act ggt ggt tcc ggt cag ttc gct aag gtc atc atc acc   1651

-continued

```
Lys Lys Gln Thr Gly Gly Ser Gly Gln Phe Ala Lys Val Ile Ile Thr
            505                 510                 515 att gag cct tac gca cct gag gca gac gag ctt gaa gag ggc gag tcc      1699
Ile Glu Pro Tyr Ala Pro Glu Ala Asp Glu Leu Glu Glu Gly Glu Ser
            520                 525                 530 gca atc tac aag ttc gag aac gct gtc acc ggt ggt cgt gtt cca cgt      1747
Ala Ile Tyr Lys Phe Glu Asn Ala Val Thr Gly Gly Arg Val Pro Arg
535                 540                 545 gaa tac atc cca tcc gtt gac gct ggt atc cag gac gca atg cag tac      1795
Glu Tyr Ile Pro Ser Val Asp Ala Gly Ile Gln Asp Ala Met Gln Tyr
550                 555                 560                 565 ggc ttc ctg gct ggc tac cca ctg gtt aac gtc aag gca acc ctt gaa      1843
Gly Phe Leu Ala Gly Tyr Pro Leu Val Asn Val Lys Ala Thr Leu Glu
            570                 575                 580 gat ggc gct tac cac gac gtt gac tcc tct gaa atg gcc ttc aag ctc      1891
Asp Gly Ala Tyr His Asp Val Asp Ser Ser Glu Met Ala Phe Lys Leu
            585                 590                 595 gcc ggt tcc cag gcg ttc aag gaa gct gtt gca aag gca aag cca gtc      1939
Ala Gly Ser Gln Ala Phe Lys Glu Ala Val Ala Lys Ala Lys Pro Val
            600                 605                 610 ctc ctc gag cca atc atg tcc gtt gaa atc acc act cct gag gag tac      1987
Leu Leu Glu Pro Ile Met Ser Val Glu Ile Thr Thr Pro Glu Glu Tyr
615                 620                 625 atg ggt gaa gtc atc ggt gac gtg aac tcc cgc cgt ggc cag atc gct      2035
Met Gly Glu Val Ile Gly Asp Val Asn Ser Arg Arg Gly Gln Ile Ala
630                 635                 640                 645 tcc atg gat gac cgt gca ggc gcc aag ctg gtt aag gct aag gtt cca      2083
Ser Met Asp Asp Arg Ala Gly Ala Lys Leu Val Lys Ala Lys Val Pro
            650                 655                 660 ctg tct cag atg ttc ggt tac gtc ggt gac ctt cgc tct aag acc cag      2131
Leu Ser Gln Met Phe Gly Tyr Val Gly Asp Leu Arg Ser Lys Thr Gln
            665                 670                 675 ggt cgt gca aac tac tcc atg gtc ttc gat tcc tac gct gag gtc cca      2179
Gly Arg Ala Asn Tyr Ser Met Val Phe Asp Ser Tyr Ala Glu Val Pro
            680                 685                 690 gcc aac gtt gcc gca gat gtt att gct gag cgc aac ggc acc gct tcc      2227
Ala Asn Val Ala Ala Asp Val Ile Ala Glu Arg Asn Gly Thr Ala Ser
            695                 700                 705 taaagatcgt ttagatccga aggaaaacgt                                     2257
```

<210> SEQ ID NO 24
<211> LENGTH: 709
<212> TYPE: PRT
<213> ORGANISM: Corynebacterium glutamicum

<400> SEQUENCE: 24

```
Val Ala Gln Glu Val Leu Lys Asp Leu Asn Lys Val Arg Asn Ile Gly
1               5                   10                  15

Ile Met Ala His Ile Asp Ala Gly Lys Thr Thr Thr Thr Glu Arg Ile
            20                  25                  30

Leu Phe Tyr Thr Gly Ile Asn Arg Lys Val Gly Glu Thr His Asp Gly
        35                  40                  45

Gly Ala Thr Thr Asp Trp Met Glu Gln Glu Lys Glu Arg Gly Ile Thr
    50                  55                  60

Ile Thr Ser Ala Ala Val Thr Cys Phe Trp Asp Asn Asn Gln Val Asn
65                  70                  75                  80

Ile Ile Asp Thr Pro Gly His Val Asp Phe Thr Val Glu Val Glu Arg
                85                  90                  95
```

-continued

```
Ser Leu Arg Val Leu Asp Gly Ala Val Ala Val Phe Asp Gly Lys Glu
            100                 105                 110

Gly Val Glu Pro Gln Ser Glu Gln Val Trp Arg Gln Ala Thr Lys Tyr
            115                 120                 125

Asp Val Pro Arg Ile Cys Phe Val Asn Lys Met Asp Lys Leu Gly Ala
            130                 135                 140

Asp Phe Tyr Phe Thr Val Gly Thr Ile Glu Asp Arg Leu Gly Ala Lys
145                 150                 155                 160

Pro Leu Val Met Gln Leu Pro Ile Gly Ala Glu Asp Asn Phe Asp Gly
                165                 170                 175

Val Ile Asp Leu Leu Glu Met Lys Ala Leu Thr Trp Arg Gly Val Thr
            180                 185                 190

Pro Ile Gly Thr Glu Ala Thr Val Glu Glu Ile Pro Ala Glu Leu Ala
            195                 200                 205

Asp Arg Ala Ala Glu Tyr Arg Glu Lys Leu Leu Glu Thr Val Ala Glu
            210                 215                 220

Ser Asp Glu Glu Leu Met Glu Lys Tyr Phe Gly Gly Glu Glu Leu Ser
225                 230                 235                 240

Ile Ala Glu Ile Lys Ala Ile Arg Lys Met Val Val Asn Ser Glu
                245                 250                 255

Ile Tyr Pro Val Tyr Cys Gly Thr Ala Tyr Lys Asn Lys Gly Ile Gln
            260                 265                 270

Pro Leu Leu Asp Ala Val Val Asp Phe Leu Pro Ser Pro Leu Asp Leu
            275                 280                 285

Gly Glu Thr Lys Gly Thr Asp Val Lys Asp Pro Glu Lys Val Leu Thr
            290                 295                 300

Arg Lys Pro Ser Asp Glu Glu Pro Leu Ser Ala Leu Ala Phe Lys Ile
305                 310                 315                 320

Ala Ala His Pro Phe Phe Gly Lys Leu Thr Phe Val Arg Leu Tyr Ser
                325                 330                 335

Gly Lys Val Glu Pro Gly Glu Gln Val Leu Asn Ser Thr Lys Asn Lys
            340                 345                 350

Lys Glu Arg Ile Gly Lys Leu Phe Gln Met His Ala Asn Lys Glu Asn
            355                 360                 365

Pro Val Glu Val His Ala Gly Asn Ile Tyr Ala Phe Ile Gly Leu
            370                 375                 380

Lys Asp Thr Thr Thr Gly Asp Thr Leu Cys Asp Ala Asn Ala Pro Ile
385                 390                 395                 400

Ile Leu Glu Ser Met Asp Phe Pro Asp Pro Val Ile Gln Val Ala Ile
                405                 410                 415

Glu Pro Lys Thr Lys Ser Asp Gln Glu Lys Leu Gly Val Ala Ile Gln
            420                 425                 430

Lys Leu Ala Glu Glu Asp Pro Thr Phe Thr Val His Leu Asp Asp Glu
            435                 440                 445

Ser Gly Gln Thr Val Ile Gly Gly Met Gly Glu Leu His Leu Asp Val
            450                 455                 460

Leu Val Asp Arg Met Lys Arg Glu Phe Lys Val Glu Ala Asn Ile Gly
465                 470                 475                 480

Asp Pro Gln Val Ala Tyr Arg Glu Thr Ile Arg Lys Pro Val Glu Ser
                485                 490                 495

Leu Ser Tyr Thr His Lys Lys Gln Thr Gly Gly Ser Gly Gln Phe Ala
            500                 505                 510

Lys Val Ile Ile Thr Ile Glu Pro Tyr Ala Pro Glu Ala Asp Glu Leu
```

-continued

```
                515                 520                 525
Glu Glu Gly Glu Ser Ala Ile Tyr Lys Phe Glu Asn Ala Val Thr Gly
        530                 535                 540

Gly Arg Val Pro Arg Glu Tyr Ile Pro Ser Val Asp Ala Gly Ile Gln
545                 550                 555                 560

Asp Ala Met Gln Tyr Gly Phe Leu Ala Gly Tyr Pro Leu Val Asn Val
                565                 570                 575

Lys Ala Thr Leu Glu Asp Gly Ala Tyr His Asp Val Asp Ser Ser Glu
                580                 585                 590

Met Ala Phe Lys Leu Ala Gly Ser Gln Ala Phe Lys Glu Ala Val Ala
                595                 600                 605

Lys Ala Lys Pro Val Leu Leu Glu Pro Ile Met Ser Val Glu Ile Thr
                610                 615                 620

Thr Pro Glu Glu Tyr Met Gly Glu Val Ile Gly Asp Val Asn Ser Arg
625                 630                 635                 640

Arg Gly Gln Ile Ala Ser Met Asp Asp Arg Ala Gly Ala Lys Leu Val
                645                 650                 655

Lys Ala Lys Val Pro Leu Ser Gln Met Phe Gly Tyr Val Gly Asp Leu
                660                 665                 670

Arg Ser Lys Thr Gln Gly Arg Ala Asn Tyr Ser Met Val Phe Asp Ser
                675                 680                 685

Tyr Ala Glu Val Pro Ala Asn Val Ala Ala Asp Val Ile Ala Glu Arg
                690                 695                 700

Asn Gly Thr Ala Ser
705
```

```
<210> SEQ ID NO 25
<211> LENGTH: 1318
<212> TYPE: DNA
<213> ORGANISM: Corynebacterium glutamicum
<220> FEATURE:
<221> NAME/KEY: CDS
<222> LOCATION: (101)..(1288)
<223> OTHER INFORMATION: RXA01284

<400> SEQUENCE: 25
atctgtgtgc tcagtcttcc aggctgctta tcacagtgaa agcaaaacca attcgtggct    60
gcgaaagtcg tagccaccac gaagtccagg aggacataca gtg gca aag gcg aag   115
                                              Val Ala Lys Ala Lys
                                                1               5 ttc gag cgt acc aag ccc cac gta aac atc ggc acc atc ggt cac gtt   163
Phe Glu Arg Thr Lys Pro His Val Asn Ile Gly Thr Ile Gly His Val
             10                  15                  20 gac cac ggt aag acc acc acc acc gcg gct atc acc aag gtt ctg gct   211
Asp His Gly Lys Thr Thr Thr Thr Ala Ala Ile Thr Lys Val Leu Ala
         25                  30                  35 gac act tac cct gag ctc aac gag gct ttc gcc ttc gac tcc atc gat   259
Asp Thr Tyr Pro Glu Leu Asn Glu Ala Phe Ala Phe Asp Ser Ile Asp
     40                  45                  50 aag gct cct gag gag aag gag cgt ggc atc acg atc aac atc tcc cac   307
Lys Ala Pro Glu Glu Lys Glu Arg Gly Ile Thr Ile Asn Ile Ser His
 55                  60                  65 gtt gag tac cag act gaa aag cgc cac tac gca cac gtt gac gct cca   355
Val Glu Tyr Gln Thr Glu Lys Arg His Tyr Ala His Val Asp Ala Pro
 70                  75                  80                  85 ggc cac gcc gac tac atc aag aac atg att acc ggc gct gct cag atg   403
Gly His Ala Asp Tyr Ile Lys Asn Met Ile Thr Gly Ala Ala Gln Met
                 90                  95                 100
```

-continued

```
gac ggc gca atc ctc gtt gtt gct gct acc gac ggc cca atg cct cag        451
Asp Gly Ala Ile Leu Val Val Ala Ala Thr Asp Gly Pro Met Pro Gln
            105                 110                 115 acc cgt gag cac gtt ctt ctt gct cgc cag gtt ggc gtt cct tac atc        499
Thr Arg Glu His Val Leu Leu Ala Arg Gln Val Gly Val Pro Tyr Ile
        120                 125                 130 ctc gtt gct ctt aac aag tgc gac atg gtt gag gat gag gaa atc atc        547
Leu Val Ala Leu Asn Lys Cys Asp Met Val Glu Asp Glu Glu Ile Ile
    135                 140                 145 gag ctc gtc gag atg gaa gtt cgt gaa ctt ctt gct gag cag gac tac        595
Glu Leu Val Glu Met Glu Val Arg Glu Leu Leu Ala Glu Gln Asp Tyr
150                 155                 160                 165 gac gaa gag gct cca att gtt cac atc tcc gct ctg aag gct ctt gag        643
Asp Glu Glu Ala Pro Ile Val His Ile Ser Ala Leu Lys Ala Leu Glu
                170                 175                 180 ggc gac gag aag tgg ggc aag cag atc ctt gag ctc atg cag gct tgc        691
Gly Asp Glu Lys Trp Gly Lys Gln Ile Leu Glu Leu Met Gln Ala Cys
            185                 190                 195 gat gac aac atc cct gac cca gtt cgt gag acc gac aag cca ttc ctc        739
Asp Asp Asn Ile Pro Asp Pro Val Arg Glu Thr Asp Lys Pro Phe Leu
        200                 205                 210 atg cct atc gag gac atc ttc acc atc acc ggt cgt ggc acc gtt gtt        787
Met Pro Ile Glu Asp Ile Phe Thr Ile Thr Gly Arg Gly Thr Val Val
    215                 220                 225 acc ggt cgt gtt gag cgc ggt acc ctg aac gtg aac gat gat gtt gac        835
Thr Gly Arg Val Glu Arg Gly Thr Leu Asn Val Asn Asp Asp Val Asp
230                 235                 240                 245 atc atc ggc atc aag gag aag tcc acc tcc acc acc gtt acc ggt atc        883
Ile Ile Gly Ile Lys Glu Lys Ser Thr Ser Thr Thr Val Thr Gly Ile
                250                 255                 260 gag atg ttc cgt aag ctt ctt gac tcc gct gag gct ggc gac aac tgt        931
Glu Met Phe Arg Lys Leu Leu Asp Ser Ala Glu Ala Gly Asp Asn Cys
            265                 270                 275 ggt ctg ctt ctc cgt ggt atc aag cgc gaa gat gtt gag cgt ggc cag        979
Gly Leu Leu Leu Arg Gly Ile Lys Arg Glu Asp Val Glu Arg Gly Gln
        280                 285                 290 gtt atc gtt aag cca ggc gct tac acc cct cac acc gag ttc gag ggc        1027
Val Ile Val Lys Pro Gly Ala Tyr Thr Pro His Thr Glu Phe Glu Gly
    295                 300                 305 tct gtc tac gtt ctg tcc aag gat gaa ggt ggc cgc cac acc cca ttc        1075
Ser Val Tyr Val Leu Ser Lys Asp Glu Gly Gly Arg His Thr Pro Phe
310                 315                 320                 325 ttc gac aac tac cgt cct cag ttc tac ttc cgc acc acc gac gtt acc        1123
Phe Asp Asn Tyr Arg Pro Gln Phe Tyr Phe Arg Thr Thr Asp Val Thr
                330                 335                 340 ggt gtt gtg aag ctt cca gag ggc acc gag atg gtc atg cct ggc gac        1171
Gly Val Val Lys Leu Pro Glu Gly Thr Glu Met Val Met Pro Gly Asp
            345                 350                 355 aac gtc gac atg tcc gtc acc ctg atc cag cct gtc gct atg gac gag        1219
Asn Val Asp Met Ser Val Thr Leu Ile Gln Pro Val Ala Met Asp Glu
        360                 365                 370 ggc ctg cgt ttc gct atc cgc gaa ggc tcc cgc acc gtt ggc gct ggt        1267
Gly Leu Arg Phe Ala Ile Arg Glu Gly Ser Arg Thr Val Gly Ala Gly
    375                 380                 385 cgt gtc acc aag atc atc aag taatttgatg ctctaactgt tgaggtcttt          1318
Arg Val Thr Lys Ile Ile Lys
390                 395
```

<210> SEQ ID NO 26

-continued

<211> LENGTH: 396
<212> TYPE: PRT
<213> ORGANISM: Corynebacterium glutamicum

<400> SEQUENCE: 26

```
Val Ala Lys Ala Lys Phe Glu Arg Thr Lys Pro His Val Asn Ile Gly
  1               5                  10                  15

Thr Ile Gly His Val Asp His Gly Lys Thr Thr Thr Ala Ala Ile
             20                  25                  30

Thr Lys Val Leu Ala Asp Thr Tyr Pro Glu Leu Asn Glu Ala Phe Ala
             35                  40                  45

Phe Asp Ser Ile Asp Lys Ala Pro Glu Glu Lys Glu Arg Gly Ile Thr
     50                  55                  60

Ile Asn Ile Ser His Val Glu Tyr Gln Thr Glu Lys Arg His Tyr Ala
 65                  70                  75                  80

His Val Asp Ala Pro Gly His Ala Asp Tyr Ile Lys Asn Met Ile Thr
                 85                  90                  95

Gly Ala Ala Gln Met Asp Gly Ala Ile Leu Val Val Ala Ala Thr Asp
                100                 105                 110

Gly Pro Met Pro Gln Thr Arg Glu His Val Leu Leu Ala Arg Gln Val
            115                 120                 125

Gly Val Pro Tyr Ile Leu Val Ala Leu Asn Lys Cys Asp Met Val Glu
        130                 135                 140

Asp Glu Glu Ile Ile Glu Leu Val Glu Met Glu Val Arg Glu Leu Leu
145                 150                 155                 160

Ala Glu Gln Asp Tyr Asp Glu Glu Ala Pro Ile Val His Ile Ser Ala
                165                 170                 175

Leu Lys Ala Leu Glu Gly Asp Glu Lys Trp Gly Lys Gln Ile Leu Glu
            180                 185                 190

Leu Met Gln Ala Cys Asp Asp Asn Ile Pro Asp Pro Val Arg Glu Thr
        195                 200                 205

Asp Lys Pro Phe Leu Met Pro Ile Glu Asp Ile Phe Thr Ile Thr Gly
    210                 215                 220

Arg Gly Thr Val Val Thr Gly Arg Val Glu Arg Gly Thr Leu Asn Val
225                 230                 235                 240

Asn Asp Asp Val Asp Ile Ile Gly Ile Lys Glu Lys Ser Thr Ser Thr
                245                 250                 255

Thr Val Thr Gly Ile Glu Met Phe Arg Lys Leu Leu Asp Ser Ala Glu
            260                 265                 270

Ala Gly Asp Asn Cys Gly Leu Leu Leu Arg Gly Ile Lys Arg Glu Asp
        275                 280                 285

Val Glu Arg Gly Gln Val Ile Val Lys Pro Gly Ala Tyr Thr Pro His
    290                 295                 300

Thr Glu Phe Glu Gly Ser Val Tyr Val Leu Ser Lys Asp Glu Gly Gly
305                 310                 315                 320

Arg His Thr Pro Phe Phe Asp Asn Tyr Arg Pro Gln Phe Tyr Phe Arg
                325                 330                 335

Thr Thr Asp Val Thr Gly Val Val Lys Leu Pro Glu Gly Thr Glu Met
            340                 345                 350

Val Met Pro Gly Asp Asn Val Asp Met Ser Val Thr Leu Ile Gln Pro
        355                 360                 365

Val Ala Met Asp Glu Gly Leu Arg Phe Ala Ile Arg Glu Gly Ser Arg
    370                 375                 380

Thr Val Gly Ala Gly Arg Val Thr Lys Ile Ile Lys
```

-continued

```
                385                 390                 395

<210> SEQ ID NO 27
<211> LENGTH: 3625
<212> TYPE: DNA
<213> ORGANISM: Corynebacterium glutamicum
<220> FEATURE:
<221> NAME/KEY: CDS
<222> LOCATION: (101)..(3595)
<223> OTHER INFORMATION: RXA01344

<400> SEQUENCE: 27
gggggatcgg gttcctcagc agaccaattg ctcaaaaata ccagcggtgt tgatctgcac      60
ttaatggcct tgaccagcca ggtgcaatta cccgcgtgag gtg ctg gaa gga ccc       115
                                            Val Leu Glu Gly Pro
                                              1               5 atc ttg gca gtc tcc cgc cag acc aag tca gtc gtc gat att ccc ggt       163
Ile Leu Ala Val Ser Arg Gln Thr Lys Ser Val Val Asp Ile Pro Gly
             10                  15                  20 gca ccg cag cgt tat tct ttc gcg aag gtg tcc gca ccc att gag gtg       211
Ala Pro Gln Arg Tyr Ser Phe Ala Lys Val Ser Ala Pro Ile Glu Val
         25                  30                  35 ccc ggg cta cta gat ctt caa ctg gat tct tac tcc tgg ctg att ggt       259
Pro Gly Leu Leu Asp Leu Gln Leu Asp Ser Tyr Ser Trp Leu Ile Gly
     40                  45                  50 acg cct gag tgg cgt gct cgt cag aag gaa gaa ttc ggc gag gga gcc       307
Thr Pro Glu Trp Arg Ala Arg Gln Lys Glu Glu Phe Gly Glu Gly Ala
 55                  60                  65 cgc gta acc agc ggc ctt gag aac att ctc gag gag ctc tcc cca atc       355
Arg Val Thr Ser Gly Leu Glu Asn Ile Leu Glu Glu Leu Ser Pro Ile
 70                  75                  80                  85 cag gat tac tct gga aac atg tcc ctg agc ctt tcg gag cca cgc ttc       403
Gln Asp Tyr Ser Gly Asn Met Ser Leu Ser Leu Ser Glu Pro Arg Phe
                 90                  95                 100 gaa gac gtc aag aac acc att gac gag gcg aaa gaa aag gac atc aac       451
Glu Asp Val Lys Asn Thr Ile Asp Glu Ala Lys Glu Lys Asp Ile Asn
            105                 110                 115 tac gcg gcg cca ctg tat gtg acc gcg gag ttc gtc aac aac acc acc       499
Tyr Ala Ala Pro Leu Tyr Val Thr Ala Glu Phe Val Asn Asn Thr Thr
        120                 125                 130 ggt gaa atc aag tct cag act gtc ttc atc ggc gat ttc cca atg atg       547
Gly Glu Ile Lys Ser Gln Thr Val Phe Ile Gly Asp Phe Pro Met Met
    135                 140                 145 acg gac aag gga acg ttc atc atc aac gga acc gaa cgc gtt gtg gtc       595
Thr Asp Lys Gly Thr Phe Ile Ile Asn Gly Thr Glu Arg Val Val Val
150                 155                 160                 165 agc cag ctc gtc cgc tcc ccg ggc gtg tac ttt gac cag acc atc gat       643
Ser Gln Leu Val Arg Ser Pro Gly Val Tyr Phe Asp Gln Thr Ile Asp
                170                 175                 180 aag tca act gag cgt cca ctg cac gcc gtg aag gtt att cct tcc cgt       691
Lys Ser Thr Glu Arg Pro Leu His Ala Val Lys Val Ile Pro Ser Arg
            185                 190                 195 ggt gct tgg ctt gag ttt gac gtc gat aag cgc gat tcg gtt ggt gtt       739
Gly Ala Trp Leu Glu Phe Asp Val Asp Lys Arg Asp Ser Val Gly Val
        200                 205                 210 cgt att gac cgc aag cgt cgc cag cca gtc acc gta ctg ctg aag gct       787
Arg Ile Asp Arg Lys Arg Arg Gln Pro Val Thr Val Leu Leu Lys Ala
    215                 220                 225 ctt ggc tgg acc act gag cag atc acc gag cgt ttc ggt ttc tct gaa       835
Leu Gly Trp Thr Thr Glu Gln Ile Thr Glu Arg Phe Gly Phe Ser Glu
230                 235                 240                 245
```

-continued

```
atc atg atg tcc acc ctc gag tcc gat ggt gta gca aac acc gat gag      883
Ile Met Met Ser Thr Leu Glu Ser Asp Gly Val Ala Asn Thr Asp Glu
            250                 255                 260 gca ttg ctg gag atc tac cgc aag cag cgt cca ggc gag cag cct acc      931
Ala Leu Leu Glu Ile Tyr Arg Lys Gln Arg Pro Gly Glu Gln Pro Thr
        265                 270                 275 cgc gac ctt gcg cag tcc ctc ctg gac aac agc ttc ttc cgt gca aag      979
Arg Asp Leu Ala Gln Ser Leu Leu Asp Asn Ser Phe Phe Arg Ala Lys
    280                 285                 290 cgc tac gac ctg gct cgc gtt ggt cgt tac aag atc aac cgc aag ctc     1027
Arg Tyr Asp Leu Ala Arg Val Gly Arg Tyr Lys Ile Asn Arg Lys Leu
295                 300                 305 ggc ctt ggt ggc gac cac gat ggt ttg atg act ctt act gaa gag gac     1075
Gly Leu Gly Gly Asp His Asp Gly Leu Met Thr Leu Thr Glu Glu Asp
310                 315                 320                 325 atc gca acc acc atc gag tac ctg gtg cgt ctg cac gca ggt gag cgc     1123
Ile Ala Thr Thr Ile Glu Tyr Leu Val Arg Leu His Ala Gly Glu Arg
        330                 335                 340 gtc atg act tct cca aat ggt gaa gag atc cca gtc gag acc gat gac     1171
Val Met Thr Ser Pro Asn Gly Glu Glu Ile Pro Val Glu Thr Asp Asp
    345                 350                 355 atc gac cac ttt ggt aac cgt cgt ctg cgt acc gtt ggc gaa ctg atc     1219
Ile Asp His Phe Gly Asn Arg Arg Leu Arg Thr Val Gly Glu Leu Ile
360                 365                 370 cag aac cag gtc cgt gtc ggc ctg tcc cgc atg gag cgc gtt gtt cgt     1267
Gln Asn Gln Val Arg Val Gly Leu Ser Arg Met Glu Arg Val Val Arg
    375                 380                 385 gag cgt atg acc acc cag gat gcg gag tcc att act cct act tcc ttg     1315
Glu Arg Met Thr Thr Gln Asp Ala Glu Ser Ile Thr Pro Thr Ser Leu
390                 395                 400                 405 atc aac gtt cgt cct gtc tct gca gct atc cgt gag ttc ttc gga act     1363
Ile Asn Val Arg Pro Val Ser Ala Ala Ile Arg Glu Phe Phe Gly Thr
        410                 415                 420 tcc cag ctg tct cag ttc atg gac cag aac aac tcc ctg tct ggt ttg     1411
Ser Gln Leu Ser Gln Phe Met Asp Gln Asn Asn Ser Leu Ser Gly Leu
    425                 430                 435 act cac aag cgt cgt ctg tcg gct ctg ggc ccg ggt ggt ctg tcc cgt     1459
Thr His Lys Arg Arg Leu Ser Ala Leu Gly Pro Gly Gly Leu Ser Arg
440                 445                 450 gag cgc gcc ggc atc gag gtt cga gac gtt cac cca tct cac tac ggc     1507
Glu Arg Ala Gly Ile Glu Val Arg Asp Val His Pro Ser His Tyr Gly
455                 460                 465 cgt atg tgc cca att gag act ccg gaa ggt cca aac att ggc ctg atc     1555
Arg Met Cys Pro Ile Glu Thr Pro Glu Gly Pro Asn Ile Gly Leu Ile
470                 475                 480                 485 ggt tcc ttg gct tcc tat gct cga gtg aac cca ttc ggt ttc att gag     1603
Gly Ser Leu Ala Ser Tyr Ala Arg Val Asn Pro Phe Gly Phe Ile Glu
        490                 495                 500 acc cca tac cgt cgc atc atc gac ggc aag ctg acc gac cag att gac     1651
Thr Pro Tyr Arg Arg Ile Ile Asp Gly Lys Leu Thr Asp Gln Ile Asp
    505                 510                 515 tac ctt acc gct gat gag gaa gac cgc ttc gtt gtt gcg cag gca aac     1699
Tyr Leu Thr Ala Asp Glu Glu Asp Arg Phe Val Val Ala Gln Ala Asn
520                 525                 530 acg cac tac gac gaa gag ggc aac atc acc gat gag acc gtc act gtt     1747
Thr His Tyr Asp Glu Glu Gly Asn Ile Thr Asp Glu Thr Val Thr Val
535                 540                 545 cgt ctg aag gac ggc gac atc gcc atg gtt ggc cgc aac gcg gtt gat     1795
Arg Leu Lys Asp Gly Asp Ile Ala Met Val Gly Arg Asn Ala Val Asp
```

-continued

| | | | | | | | | | | | | | | | |
|---|---|---|---|---|---|---|---|---|---|---|---|---|---|---|---|
| | 550 | | | | 555 | | | | 560 | | | | 565 | | |
| tac | atg | gac | gtt | tcc | cct | cgt | cag | atg | gtt | tct | gtt | ggt | acc | gcg | atg | 1843 |
| Tyr | Met | Asp | Val | Ser | Pro | Arg | Gln | Met | Val | Ser | Val | Gly | Thr | Ala | Met | |
| | | | | 570 | | | | | 575 | | | | | 580 | | |
| att | cca | ttc | ctg | gag | cac | gac | gat | gct | aac | cgt | gca | ctg | atg | ggc | gcg | 1891 |
| Ile | Pro | Phe | Leu | Glu | His | Asp | Asp | Ala | Asn | Arg | Ala | Leu | Met | Gly | Ala | |
| | | | | | 585 | | | | | 590 | | | | | 595 | |
| aac | atg | cag | aag | cag | gct | gtg | cca | ctg | att | cgt | gcc | gag | gct | cct | ttc | 1939 |
| Asn | Met | Gln | Lys | Gln | Ala | Val | Pro | Leu | Ile | Arg | Ala | Glu | Ala | Pro | Phe | |
| | | | 600 | | | | | 605 | | | | | 610 | | | |
| gtg | ggc | acc | ggt | atg | gag | cag | cgc | gca | gca | tac | gac | gcc | ggc | gac | ctg | 1987 |
| Val | Gly | Thr | Gly | Met | Glu | Gln | Arg | Ala | Ala | Tyr | Asp | Ala | Gly | Asp | Leu | |
| | | 615 | | | | | 620 | | | | | 625 | | | | |
| gtt | att | acc | cca | gtc | gca | ggt | gtg | gtg | gaa | aac | gtt | tca | gct | gac | ttc | 2035 |
| Val | Ile | Thr | Pro | Val | Ala | Gly | Val | Val | Glu | Asn | Val | Ser | Ala | Asp | Phe | |
| 630 | | | | | 635 | | | | | 640 | | | | | 645 | |
| atc | acc | atc | atg | gct | gat | gac | ggc | aag | cgc | gaa | acc | tac | ctg | ctg | cgt | 2083 |
| Ile | Thr | Ile | Met | Ala | Asp | Asp | Gly | Lys | Arg | Glu | Thr | Tyr | Leu | Leu | Arg | |
| | | | | 650 | | | | | 655 | | | | | 660 | | |
| aag | ttc | cag | cgc | acc | aac | cag | ggc | acc | agc | tac | aac | cag | aag | cct | ttg | 2131 |
| Lys | Phe | Gln | Arg | Thr | Asn | Gln | Gly | Thr | Ser | Tyr | Asn | Gln | Lys | Pro | Leu | |
| | | | 665 | | | | | 670 | | | | | 675 | | | |
| gtt | aac | ttg | ggc | gag | cgc | gtt | gaa | gct | ggc | cag | gtt | att | gct | gat | ggt | 2179 |
| Val | Asn | Leu | Gly | Glu | Arg | Val | Glu | Ala | Gly | Gln | Val | Ile | Ala | Asp | Gly | |
| | | 680 | | | | | 685 | | | | | 690 | | | | |
| cca | ggt | acc | ttc | aat | ggt | gaa | atg | tcc | ctt | ggc | cgt | aac | ctt | ctg | gtt | 2227 |
| Pro | Gly | Thr | Phe | Asn | Gly | Glu | Met | Ser | Leu | Gly | Arg | Asn | Leu | Leu | Val | |
| 695 | | | | | 700 | | | | | 705 | | | | | | |
| gcg | ttc | atg | cct | tgg | gaa | ggc | cac | aac | tac | gag | gat | gcg | atc | atc | ctc | 2275 |
| Ala | Phe | Met | Pro | Trp | Glu | Gly | His | Asn | Tyr | Glu | Asp | Ala | Ile | Ile | Leu | |
| 710 | | | | | 715 | | | | | 720 | | | | | 725 | |
| aac | cag | aac | atc | gtt | gag | cag | gac | atc | ttg | acc | tcg | atc | cac | atc | gag | 2323 |
| Asn | Gln | Asn | Ile | Val | Glu | Gln | Asp | Ile | Leu | Thr | Ser | Ile | His | Ile | Glu | |
| | | | | 730 | | | | | 735 | | | | | 740 | | |
| gag | cac | gag | atc | gat | gcc | cgc | gac | act | aag | ctt | ggc | gcc | gaa | gaa | atc | 2371 |
| Glu | His | Glu | Ile | Asp | Ala | Arg | Asp | Thr | Lys | Leu | Gly | Ala | Glu | Glu | Ile | |
| | | | 745 | | | | | 750 | | | | | 755 | | | |
| acc | cgc | gac | atc | cct | aat | gtg | tct | gaa | gaa | gtc | ctc | aag | gac | ctc | gac | 2419 |
| Thr | Arg | Asp | Ile | Pro | Asn | Val | Ser | Glu | Glu | Val | Leu | Lys | Asp | Leu | Asp | |
| | | 760 | | | | | 765 | | | | | 770 | | | | |
| gac | cgc | ggt | att | gtc | cgc | atc | ggt | gct | gat | gtt | cgt | gac | ggc | gac | atc | 2467 |
| Asp | Arg | Gly | Ile | Val | Arg | Ile | Gly | Ala | Asp | Val | Arg | Asp | Gly | Asp | Ile | |
| | 775 | | | | | 780 | | | | | 785 | | | | | |
| ctg | gtc | ggt | aag | gtc | acc | cct | aag | ggc | gag | acc | gag | ctc | acc | ccg | gaa | 2515 |
| Leu | Val | Gly | Lys | Val | Thr | Pro | Lys | Gly | Glu | Thr | Glu | Leu | Thr | Pro | Glu | |
| 790 | | | | | 795 | | | | | 800 | | | | | 805 | |
| gag | cgc | ttg | ctg | cgc | gca | atc | ttc | ggt | gag | aag | gcc | cgc | gaa | gtt | cgc | 2563 |
| Glu | Arg | Leu | Leu | Arg | Ala | Ile | Phe | Gly | Glu | Lys | Ala | Arg | Glu | Val | Arg | |
| | | | | 810 | | | | | 815 | | | | | 820 | | |
| gat | acc | tcc | atg | aag | gtg | cct | cac | ggt | gag | acc | ggc | aag | gtc | atc | ggc | 2611 |
| Asp | Thr | Ser | Met | Lys | Val | Pro | His | Gly | Glu | Thr | Gly | Lys | Val | Ile | Gly | |
| | | | 825 | | | | | 830 | | | | | 835 | | | |
| gtg | cgt | cac | ttc | tcc | cgc | gag | gac | gac | gac | gat | ctg | gct | cct | ggc | gtc | 2659 |
| Val | Arg | His | Phe | Ser | Arg | Glu | Asp | Asp | Asp | Asp | Leu | Ala | Pro | Gly | Val | |
| | | 840 | | | | | 845 | | | | | 850 | | | | |
| aac | gag | atg | atc | cgt | atc | tac | gtt | gct | cag | aag | cgt | aag | atc | cag | gac | 2707 |
| Asn | Glu | Met | Ile | Arg | Ile | Tyr | Val | Ala | Gln | Lys | Arg | Lys | Ile | Gln | Asp | |
| | 855 | | | | | 860 | | | | | 865 | | | | | |
| ggc | gat | aag | ctc | gct | ggc | cgc | cac | ggt | aac | aag | ggt | gtt | gtc | ggt | aaa | 2755 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Gly | Asp | Lys | Leu | Ala | Gly | Arg | His | Gly | Asn | Lys | Gly | Val | Val | Gly | Lys |      |
|     | 870 |     |     |     | 875 |     |     |     | 880 |     |     |     | 885 |     |     |      |
| att | ttg | cct | cag | gaa | gat | atg | cca | ttc | ctt | cca | gac | ggc | act | cct | gtt | 2803 |
| Ile | Leu | Pro | Gln | Glu | Asp | Met | Pro | Phe | Leu | Pro | Asp | Gly | Thr | Pro | Val |      |
|     |     |     |     |     | 890 |     |     |     | 895 |     |     |     | 900 |     |     |      |
| gac | atc | atc | ttg | aac | acc | cac | ggt | gtt | cca | cgt | cgt | atg | aac | att | ggt | 2851 |
| Asp | Ile | Ile | Leu | Asn | Thr | His | Gly | Val | Pro | Arg | Arg | Met | Asn | Ile | Gly |      |
|     |     |     | 905 |     |     |     | 910 |     |     |     | 915 |     |     |     |     |      |
| cag | gtt | ctt | gag | acc | cac | ctt | ggc | tgg | ctg | gca | tct | gct | ggt | tgg | tcc | 2899 |
| Gln | Val | Leu | Glu | Thr | His | Leu | Gly | Trp | Leu | Ala | Ser | Ala | Gly | Trp | Ser |      |
|     |     | 920 |     |     |     | 925 |     |     |     | 930 |     |     |     |     |     |      |
| gtg | gat | cct | gaa | gat | cct | gag | aac | gct | gag | ctc | gtc | aag | act | ctg | cct | 2947 |
| Val | Asp | Pro | Glu | Asp | Pro | Glu | Asn | Ala | Glu | Leu | Val | Lys | Thr | Leu | Pro |      |
|     | 935 |     |     |     | 940 |     |     |     | 945 |     |     |     |     |     |     |      |
| gca | gac | ctc | ctc | gag | gtt | cct | gct | ggt | tcc | ttg | act | gca | act | cct | gtg | 2995 |
| Ala | Asp | Leu | Leu | Glu | Val | Pro | Ala | Gly | Ser | Leu | Thr | Ala | Thr | Pro | Val |      |
| 950 |     |     |     | 955 |     |     |     | 960 |     |     |     | 965 |     |     |     |      |
| ttc | gac | ggt | gcg | tca | aac | gaa | gag | ctc | gca | ggc | ctg | ctc | gct | aat | tca | 3043 |
| Phe | Asp | Gly | Ala | Ser | Asn | Glu | Glu | Leu | Ala | Gly | Leu | Leu | Ala | Asn | Ser |      |
|     |     |     | 970 |     |     |     | 975 |     |     |     | 980 |     |     |     |     |      |
| cgt | cca | aac | cgc | gac | ggc | gac | gtc | atg | gtt | aac | gcg | gat | ggt | aaa | gca | 3091 |
| Arg | Pro | Asn | Arg | Asp | Gly | Asp | Val | Met | Val | Asn | Ala | Asp | Gly | Lys | Ala |      |
|     | 985 |     |     |     | 990 |     |     |     | 995 |     |     |     |     |     |     |      |
| acg | ctt | atc | gac | ggt | cgc | tcc | ggt | gag | cct | tac | ccg | tac | ccg | gtt | tcc | 3139 |
| Thr | Leu | Ile | Asp | Gly | Arg | Ser | Gly | Glu | Pro | Tyr | Pro | Tyr | Pro | Val | Ser |      |
| 1000 |    |     |     |     | 1005 |   |     |     |     | 1010 |  |     |     |     |     |      |
| atc | ggc | tac | atg | tac | atg | ctg | aag | ctg | cac | cac | ctc | gtt | gac | gag | aag | 3187 |
| Ile | Gly | Tyr | Met | Tyr | Met | Leu | Lys | Leu | His | His | Leu | Val | Asp | Glu | Lys |      |
|     | 1015 |   |     |     | 1020 |   |     |     | 1025 |  |     |     |     |     |     |      |
| atc | cac | gca | cgt | tcc | act | ggt | cct | tac | tcc | atg | att | acc | cag | cag | cca | 3235 |
| Ile | His | Ala | Arg | Ser | Thr | Gly | Pro | Tyr | Ser | Met | Ile | Thr | Gln | Gln | Pro |      |
| 1030 |   |     |     |     | 1035 |  |     |     | 1040 |  |     |     |     | 1045 |   |      |
| ctg | ggt | ggt | aaa | gca | cag | ttc | ggt | gga | cag | cgt | ttc | ggc | gaa | atg | gag | 3283 |
| Leu | Gly | Gly | Lys | Ala | Gln | Phe | Gly | Gly | Gln | Arg | Phe | Gly | Glu | Met | Glu |      |
|     |     |     | 1050 |  |     |     | 1055 |  |     |     | 1060 |  |     |     |     |      |
| gtg | tgg | gca | atg | cag | gca | tac | ggc | gct | gcc | tac | aca | ctt | cag | gag | ctg | 3331 |
| Val | Trp | Ala | Met | Gln | Ala | Tyr | Gly | Ala | Ala | Tyr | Thr | Leu | Gln | Glu | Leu |      |
|     |     |     | 1065 |  |     |     | 1070 |  |     |     | 1075 |  |     |     |     |      |
| ctg | acc | atc | aag | tct | gat | gac | gtg | gtt | ggc | cgt | gtc | aag | gtc | tac | gaa | 3379 |
| Leu | Thr | Ile | Lys | Ser | Asp | Asp | Val | Val | Gly | Arg | Val | Lys | Val | Tyr | Glu |      |
|     |     | 1080 |  |     |     | 1085 |  |     |     | 1090 |  |     |     |     |     |      |
| gca | att | gtg | aag | ggc | gag | aac | atc | ccg | gat | cca | ggt | att | cct | gag | tcc | 3427 |
| Ala | Ile | Val | Lys | Gly | Glu | Asn | Ile | Pro | Asp | Pro | Gly | Ile | Pro | Glu | Ser |      |
| 1095 |  |     |     |     | 1100 |  |     |     | 1105 |  |     |     |     |     |     |      |
| ttc | aag | gtt | ctc | ctc | aag | gag | ctc | cag | tcc | ttg | tgc | ctg | aac | gtg | gag | 3475 |
| Phe | Lys | Val | Leu | Leu | Lys | Glu | Leu | Gln | Ser | Leu | Cys | Leu | Asn | Val | Glu |      |
| 1110 |  |     |     | 1115 |  |     |     | 1120 |  |     |     | 1125 |   |     |     |      |
| gtt | ctc | tcc | gca | gac | ggc | act | cca | atg | gag | ctc | gcg | ggt | gac | gac | gac | 3523 |
| Val | Leu | Ser | Ala | Asp | Gly | Thr | Pro | Met | Glu | Leu | Ala | Gly | Asp | Asp | Asp |      |
|     |     |     | 1130 |  |     |     | 1135 |  |     |     | 1140 |  |     |     |     |      |
| gac | ttc | gat | cag | gca | ggc | gcc | tca | ctt | ggc | atc | aac | ctg | tcc | cgt | gac | 3571 |
| Asp | Phe | Asp | Gln | Ala | Gly | Ala | Ser | Leu | Gly | Ile | Asn | Leu | Ser | Arg | Asp |      |
|     |     |     | 1145 |  |     |     | 1150 |  |     |     | 1155 |  |     |     |     |      |
| gag | cgt | tcc | gac | gcc | gac | acc | gca | tagcagatca | gaaaacaacc | gctagaaatc |   |     |     |     |     | 3625 |
| Glu | Arg | Ser | Asp | Ala | Asp | Thr | Ala |     |     |     |     |     |     |     |     |      |
|     |     | 1160 |  |     |     | 1165 |  |     |     |     |     |     |     |     |     |      |

<210> SEQ ID NO 28
<211> LENGTH: 1165
<212> TYPE: PRT

<213> ORGANISM: Corynebacterium glutamicum

<400> SEQUENCE: 28

| | | | | | | | | | | | | | | |
|---|---|---|---|---|---|---|---|---|---|---|---|---|---|---|
| Val | Leu | Glu | Gly | Pro | Ile | Leu | Ala | Val | Ser | Arg | Gln | Thr | Lys | Ser | Val |
| 1 | | | | 5 | | | | | 10 | | | | | 15 | |
| Val | Asp | Ile | Pro | Gly | Ala | Pro | Gln | Arg | Tyr | Ser | Phe | Ala | Lys | Val | Ser |
| | | | 20 | | | | | 25 | | | | | 30 | | |
| Ala | Pro | Ile | Glu | Val | Pro | Gly | Leu | Leu | Asp | Leu | Gln | Leu | Asp | Ser | Tyr |
| | | | 35 | | | | | 40 | | | | | 45 | | |
| Ser | Trp | Leu | Ile | Gly | Thr | Pro | Glu | Trp | Arg | Ala | Arg | Gln | Lys | Glu | Glu |
| | | 50 | | | | | 55 | | | | | 60 | | | |
| Phe | Gly | Glu | Gly | Ala | Arg | Val | Thr | Ser | Gly | Leu | Glu | Asn | Ile | Leu | Glu |
| 65 | | | | | 70 | | | | | 75 | | | | | 80 |
| Glu | Leu | Ser | Pro | Ile | Gln | Asp | Tyr | Ser | Gly | Asn | Met | Ser | Leu | Ser | Leu |
| | | | | 85 | | | | | 90 | | | | | 95 | |
| Ser | Glu | Pro | Arg | Phe | Glu | Asp | Val | Lys | Asn | Thr | Ile | Asp | Glu | Ala | Lys |
| | | | 100 | | | | | 105 | | | | | 110 | | |
| Glu | Lys | Asp | Ile | Asn | Tyr | Ala | Ala | Pro | Leu | Tyr | Val | Thr | Ala | Glu | Phe |
| | | | 115 | | | | | 120 | | | | | 125 | | |
| Val | Asn | Asn | Thr | Thr | Gly | Glu | Ile | Lys | Ser | Gln | Thr | Val | Phe | Ile | Gly |
| | | 130 | | | | | 135 | | | | | 140 | | | |
| Asp | Phe | Pro | Met | Met | Thr | Asp | Lys | Gly | Thr | Phe | Ile | Ile | Asn | Gly | Thr |
| 145 | | | | | 150 | | | | | 155 | | | | | 160 |
| Glu | Arg | Val | Val | Ser | Gln | Leu | Val | Arg | Ser | Pro | Gly | Val | Tyr | Phe | |
| | | | | 165 | | | | | 170 | | | | | 175 | |
| Asp | Gln | Thr | Ile | Asp | Lys | Ser | Thr | Glu | Arg | Pro | Leu | His | Ala | Val | Lys |
| | | | 180 | | | | | 185 | | | | | 190 | | |
| Val | Ile | Pro | Ser | Arg | Gly | Ala | Trp | Leu | Glu | Phe | Asp | Val | Asp | Lys | Arg |
| | | | 195 | | | | | 200 | | | | | 205 | | |
| Asp | Ser | Val | Gly | Val | Arg | Ile | Asp | Arg | Lys | Arg | Gln | Pro | Val | Thr | |
| | | 210 | | | | | 215 | | | | | 220 | | | |
| Val | Leu | Leu | Lys | Ala | Leu | Gly | Trp | Thr | Thr | Glu | Gln | Ile | Thr | Glu | Arg |
| 225 | | | | | 230 | | | | | 235 | | | | | 240 |
| Phe | Gly | Phe | Ser | Glu | Ile | Met | Met | Ser | Thr | Leu | Glu | Ser | Asp | Gly | Val |
| | | | | 245 | | | | | 250 | | | | | 255 | |
| Ala | Asn | Thr | Asp | Glu | Ala | Leu | Leu | Glu | Ile | Tyr | Arg | Lys | Gln | Arg | Pro |
| | | | 260 | | | | | 265 | | | | | 270 | | |
| Gly | Glu | Gln | Pro | Thr | Arg | Asp | Leu | Ala | Gln | Ser | Leu | Leu | Asp | Asn | Ser |
| | | | 275 | | | | | 280 | | | | | 285 | | |
| Phe | Phe | Arg | Ala | Lys | Arg | Tyr | Asp | Leu | Ala | Arg | Val | Gly | Arg | Tyr | Lys |
| | | 290 | | | | | 295 | | | | | 300 | | | |
| Ile | Asn | Arg | Lys | Leu | Gly | Leu | Gly | Gly | Asp | His | Asp | Gly | Leu | Met | Thr |
| 305 | | | | | 310 | | | | | 315 | | | | | 320 |
| Leu | Thr | Glu | Glu | Asp | Ile | Ala | Thr | Thr | Ile | Glu | Tyr | Leu | Val | Arg | Leu |
| | | | | 325 | | | | | 330 | | | | | 335 | |
| His | Ala | Gly | Glu | Arg | Val | Met | Thr | Ser | Pro | Asn | Gly | Glu | Glu | Ile | Pro |
| | | | 340 | | | | | 345 | | | | | 350 | | |
| Val | Glu | Thr | Asp | Asp | Ile | Asp | His | Phe | Gly | Asn | Arg | Arg | Leu | Arg | Thr |
| | | | 355 | | | | | 360 | | | | | 365 | | |
| Val | Gly | Glu | Leu | Ile | Gln | Asn | Gln | Val | Arg | Val | Gly | Leu | Ser | Arg | Met |
| | | 370 | | | | | 375 | | | | | 380 | | | |
| Glu | Arg | Val | Val | Arg | Glu | Arg | Met | Thr | Thr | Gln | Asp | Ala | Glu | Ser | Ile |
| 385 | | | | | 390 | | | | | 395 | | | | | 400 |

-continued

```
Thr Pro Thr Ser Leu Ile Asn Val Arg Pro Val Ser Ala Ala Ile Arg
                405                 410                 415
Glu Phe Phe Gly Thr Ser Gln Leu Ser Gln Phe Met Asp Gln Asn Asn
            420                 425                 430
Ser Leu Ser Gly Leu Thr His Lys Arg Arg Leu Ser Ala Leu Gly Pro
        435                 440                 445
Gly Gly Leu Ser Arg Glu Arg Ala Gly Ile Glu Val Arg Asp Val His
    450                 455                 460
Pro Ser His Tyr Gly Arg Met Cys Pro Ile Glu Thr Pro Glu Gly Pro
465                 470                 475                 480
Asn Ile Gly Leu Ile Gly Ser Leu Ala Ser Tyr Ala Arg Val Asn Pro
                485                 490                 495
Phe Gly Phe Ile Glu Thr Pro Tyr Arg Arg Ile Ile Asp Gly Lys Leu
            500                 505                 510
Thr Asp Gln Ile Asp Tyr Leu Thr Ala Asp Glu Glu Asp Arg Phe Val
        515                 520                 525
Val Ala Gln Ala Asn Thr His Tyr Asp Glu Glu Gly Asn Ile Thr Asp
    530                 535                 540
Glu Thr Val Thr Val Arg Leu Lys Asp Gly Asp Ile Ala Met Val Gly
545                 550                 555                 560
Arg Asn Ala Val Asp Tyr Met Asp Val Ser Pro Arg Gln Met Val Ser
                565                 570                 575
Val Gly Thr Ala Met Ile Pro Phe Leu Glu His Asp Asp Ala Asn Arg
            580                 585                 590
Ala Leu Met Gly Ala Asn Met Gln Lys Gln Ala Val Pro Leu Ile Arg
        595                 600                 605
Ala Glu Ala Pro Phe Val Gly Thr Gly Met Glu Gln Arg Ala Ala Tyr
    610                 615                 620
Asp Ala Gly Asp Leu Val Ile Thr Pro Val Ala Gly Val Val Glu Asn
625                 630                 635                 640
Val Ser Ala Asp Phe Ile Thr Ile Met Ala Asp Asp Gly Lys Arg Glu
                645                 650                 655
Thr Tyr Leu Leu Arg Lys Phe Gln Arg Thr Asn Gln Gly Thr Ser Tyr
            660                 665                 670
Asn Gln Lys Pro Leu Val Asn Leu Gly Glu Arg Val Glu Ala Gly Gln
        675                 680                 685
Val Ile Ala Asp Gly Pro Gly Thr Phe Asn Gly Glu Met Ser Leu Gly
    690                 695                 700
Arg Asn Leu Leu Val Ala Phe Met Pro Trp Glu Gly His Asn Tyr Glu
705                 710                 715                 720
Asp Ala Ile Ile Leu Asn Gln Asn Ile Val Glu Gln Asp Ile Leu Thr
                725                 730                 735
Ser Ile His Ile Glu Glu His Glu Ile Asp Ala Arg Asp Thr Lys Leu
            740                 745                 750
Gly Ala Glu Glu Ile Thr Arg Asp Ile Pro Asn Val Ser Glu Glu Val
        755                 760                 765
Leu Lys Asp Leu Asp Asp Arg Gly Ile Val Arg Ile Gly Ala Asp Val
770                 775                 780
Arg Asp Gly Asp Ile Leu Val Gly Lys Val Thr Pro Lys Gly Glu Thr
785                 790                 795                 800
Glu Leu Thr Pro Glu Glu Arg Leu Leu Arg Ala Ile Phe Gly Glu Lys
            805                 810                 815
Ala Arg Glu Val Arg Asp Thr Ser Met Lys Val Pro His Gly Glu Thr
```

820                 825                 830
Gly Lys Val Ile Gly Val Arg His Phe Ser Arg Glu Asp Asp Asp
        835                 840                 845

Leu Ala Pro Gly Val Asn Glu Met Ile Arg Ile Tyr Val Ala Gln Lys
    850                 855                 860

Arg Lys Ile Gln Asp Gly Asp Lys Leu Ala Gly Arg His Gly Asn Lys
865                 870                 875                 880

Gly Val Val Gly Lys Ile Leu Pro Gln Glu Asp Met Pro Phe Leu Pro
                885                 890                 895

Asp Gly Thr Pro Val Asp Ile Ile Leu Asn Thr His Gly Val Pro Arg
            900                 905                 910

Arg Met Asn Ile Gly Gln Val Leu Glu Thr His Leu Gly Trp Leu Ala
        915                 920                 925

Ser Ala Gly Trp Ser Val Asp Pro Glu Asp Pro Glu Asn Ala Glu Leu
    930                 935                 940

Val Lys Thr Leu Pro Ala Asp Leu Leu Glu Val Pro Ala Gly Ser Leu
945                 950                 955                 960

Thr Ala Thr Pro Val Phe Asp Gly Ala Ser Asn Glu Glu Leu Ala Gly
                965                 970                 975

Leu Leu Ala Asn Ser Arg Pro Asn Arg Asp Gly Asp Val Met Val Asn
            980                 985                 990

Ala Asp Gly Lys Ala Thr Leu Ile Asp Gly Arg Ser Gly Glu Pro Tyr
        995                 1000                1005

Pro Tyr Pro Val Ser Ile Gly Tyr Met Tyr Met Leu Lys Leu His His
    1010                1015                1020

Leu Val Asp Glu Lys Ile His Ala Arg Ser Thr Gly Pro Tyr Ser Met
1025                1030                1035                1040

Ile Thr Gln Gln Pro Leu Gly Gly Lys Ala Gln Phe Gly Gly Gln Arg
                1045                1050                1055

Phe Gly Glu Met Glu Val Trp Ala Met Gln Ala Tyr Gly Ala Ala Tyr
            1060                1065                1070

Thr Leu Gln Glu Leu Leu Thr Ile Lys Ser Asp Asp Val Val Gly Arg
        1075                1080                1085

Val Lys Val Tyr Glu Ala Ile Val Lys Gly Glu Asn Ile Pro Asp Pro
    1090                1095                1100

Gly Ile Pro Glu Ser Phe Lys Val Leu Leu Lys Glu Leu Gln Ser Leu
1105                1110                1115                1120

Cys Leu Asn Val Glu Val Leu Ser Ala Asp Gly Thr Pro Met Glu Leu
                1125                1130                1135

Ala Gly Asp Asp Asp Phe Asp Gln Ala Gly Ala Ser Leu Gly Ile
            1140                1145                1150

Asn Leu Ser Arg Asp Glu Arg Ser Asp Ala Asp Thr Ala
        1155                1160                1165

<210> SEQ ID NO 29
<211> LENGTH: 1582
<212> TYPE: DNA
<213> ORGANISM: Corynebacterium glutamicum
<220> FEATURE:
<221> NAME/KEY: CDS
<222> LOCATION: (101)..(1552)
<223> OTHER INFORMATION: RXA01345

<400> SEQUENCE: 29
cataacctca ttgaacatgc aaaactaatg cttttggggg gtatgcataa attcgtttcg        60

```
                                                       -continued
ttccactgca cagcccgaaa atgctgctag ggtcaagttc atg cgt ttt gga ctt        115
                                            Met Arg Phe Gly Leu
                                             1               5 gac ttg gga act acc cgc aca atc gcg gcc gcc gtg gac cgc gga aac        163
Asp Leu Gly Thr Thr Arg Thr Ile Ala Ala Ala Val Asp Arg Gly Asn
            10                  15                  20 tat ccc atc gtc act gtg gaa gat tct tta ggc gac acc cac gat ttc        211
Tyr Pro Ile Val Thr Val Glu Asp Ser Leu Gly Asp Thr His Asp Phe
                25                  30                  35 att cca tct gtg gtg gcc ctc aag gca gat agg att gtc gcg ggt tgg        259
Ile Pro Ser Val Val Ala Leu Lys Ala Asp Arg Ile Val Ala Gly Trp
        40                  45                  50 gat gct att gag gtt ggg cag gac cac cct tcc ttc gta cgt tct ttc        307
Asp Ala Ile Glu Val Gly Gln Asp His Pro Ser Phe Val Arg Ser Phe
    55                  60                  65 aaa cgc cta ctc tct gaa ccc aat gtc acg gaa gcc acc ccg gtc tac        355
Lys Arg Leu Leu Ser Glu Pro Asn Val Thr Glu Ala Thr Pro Val Tyr
70                  75                  80                  85 ttg ggc gat cat gta cac cct ttg ggc gcc gtc ctg gag gct ttt gcg        403
Leu Gly Asp His Val His Pro Leu Gly Ala Val Leu Glu Ala Phe Ala
                90                  95                 100 gaa aac gtg gtc act gcg ctg cgt gca ttt cag acg caa ttg gga gat        451
Glu Asn Val Val Thr Ala Leu Arg Ala Phe Gln Thr Gln Leu Gly Asp
            105                 110                 115 acc tcc ccg atc gaa gta gtc att ggt gtg ccc gcc aac tcc cac agc        499
Thr Ser Pro Ile Glu Val Val Ile Gly Val Pro Ala Asn Ser His Ser
        120                 125                 130 gcc cag cga ctg ctc acc atg tcc gcc ttc agc gcc aca ggc atc acc        547
Ala Gln Arg Leu Leu Thr Met Ser Ala Phe Ser Ala Thr Gly Ile Thr
    135                 140                 145 gtt gtc ggt ttg gtc aat gag ccc agc gcc gca gct ttc gag tac acc        595
Val Val Gly Leu Val Asn Glu Pro Ser Ala Ala Ala Phe Glu Tyr Thr
150                 155                 160                 165 cac cgc cac gcc cgc acc tta aac tcc aag cgc caa gcc atc gtg gtt        643
His Arg His Ala Arg Thr Leu Asn Ser Lys Arg Gln Ala Ile Val Val
                170                 175                 180 tat gat ttg gga ggc gga aca ttc gac tcc tcg ctc atc cgc atc gac        691
Tyr Asp Leu Gly Gly Gly Thr Phe Asp Ser Ser Leu Ile Arg Ile Asp
            185                 190                 195 ggc acc cac cac gag gtt gtg tcc tcc att ggc att tca cgc ctt ggt        739
Gly Thr His His Glu Val Val Ser Ser Ile Gly Ile Ser Arg Leu Gly
        200                 205                 210 ggc gat gat ttc gat gaa atc ctc ctc caa tgc gcg ctc aag gcc gca        787
Gly Asp Asp Phe Asp Glu Ile Leu Leu Gln Cys Ala Leu Lys Ala Ala
215                 220                 225 ggc aga cag cac gat gcg ttt ggc aag cgt gct aaa aac acg ctt ctc        835
Gly Arg Gln His Asp Ala Phe Gly Lys Arg Ala Lys Asn Thr Leu Leu
230                 235                 240                 245 gac gaa tcc cgc aac gcg aag gaa gct ctt gtt ccg caa tcc cgt cgc        883
Asp Glu Ser Arg Asn Ala Lys Glu Ala Leu Val Pro Gln Ser Arg Arg
                250                 255                 260 ttg gtt cta gaa att ggc gac gac gac atc acc gtt cca gtg aac aag        931
Leu Val Leu Glu Ile Gly Asp Asp Asp Ile Thr Val Pro Val Asn Lys
            265                 270                 275 ttc tac gag gct gcc act ccc ctg gtg gaa aaa tcc ttg tcc atc atg        979
Phe Tyr Glu Ala Ala Thr Pro Leu Val Glu Lys Ser Leu Ser Ile Met
        280                 285                 290 gaa ccc ctc atc ggc gtc gat gat ctt aaa gat tcc gac atc gca ggc       1027
Glu Pro Leu Ile Gly Val Asp Asp Leu Lys Asp Ser Asp Ile Ala Gly
295                 300                 305
```

```
atc tac ctt gtt ggt gga gga tcc tcg ctc cca ctc gtt tcc agg ttg    1075
Ile Tyr Leu Val Gly Gly Gly Ser Ser Leu Pro Leu Val Ser Arg Leu
310                 315                 320                 325 ctc cgc gag cgt ttc ggc cgc gtt gtc cac cgc tcc cca ttc ccc tca    1123
Leu Arg Glu Arg Phe Gly Arg Val Val His Arg Ser Pro Phe Pro Ser
                330                 335                 340 ggt tcc act gcg gtg ggt ctg gcc atc gcg gct gac cct tcc tct ggt    1171
Gly Ser Thr Ala Val Gly Leu Ala Ile Ala Ala Asp Pro Ser Ser Gly
            345                 350                 355 ttc cac cta agg gac cgc gtt gcg cga ggc atc ggt gtg ttc cgt gag    1219
Phe His Leu Arg Asp Arg Val Ala Arg Gly Ile Gly Val Phe Arg Glu
        360                 365                 370 cac gat tct ggt cgt gcc gtg agc ttt gac ccg ctg atc gcc ccg gac    1267
His Asp Ser Gly Arg Ala Val Ser Phe Asp Pro Leu Ile Ala Pro Asp
    375                 380                 385 acc gat tct gcg acc gtg gcg aaa cga tgc tac aag gcg gtg cac aac    1315
Thr Asp Ser Ala Thr Val Ala Lys Arg Cys Tyr Lys Ala Val His Asn
390                 395                 400                 405 att ggt tgg ttc agg ttc gtg gaa tac tcc acc gtg tcc gag gat ggc    1363
Ile Gly Trp Phe Arg Phe Val Glu Tyr Ser Thr Val Ser Glu Asp Gly
                410                 415                 420 agc ccc gga gat att tcc ctg ctc agt gaa atc aag att cct ttt gat    1411
Ser Pro Gly Asp Ile Ser Leu Leu Ser Glu Ile Lys Ile Pro Phe Asp
            425                 430                 435 agc tcc atc acc gat gtg gat gct acc gag att tca cgt ttc gat ggc    1459
Ser Ser Ile Thr Asp Val Asp Ala Thr Glu Ile Ser Arg Phe Asp Gly
        440                 445                 450 cca gaa gta gaa gaa acc atc aca gtc aat gac aac ggc gtg gct tcc    1507
Pro Glu Val Glu Glu Thr Ile Thr Val Asn Asp Asn Gly Val Ala Ser
    455                 460                 465 att tcc atc aag ata ctc ggc ggc gtt acc gtc gag cac aca att        1552
Ile Ser Ile Lys Ile Leu Gly Gly Val Thr Val Glu His Thr Ile
470                 475                 480 tagttaccat tttggtgctg gtggagtcca                                   1582

<210> SEQ ID NO 30
<211> LENGTH: 484
<212> TYPE: PRT
<213> ORGANISM: Corynebacterium glutamicum

<400> SEQUENCE: 30

Met Arg Phe Gly Leu Asp Leu Gly Thr Thr Arg Thr Ile Ala Ala Ala
1               5                   10                  15

Val Asp Arg Gly Asn Tyr Pro Ile Val Thr Val Glu Asp Ser Leu Gly
                20                  25                  30

Asp Thr His Asp Phe Ile Pro Ser Val Val Ala Leu Lys Ala Asp Arg
            35                  40                  45

Ile Val Ala Gly Trp Asp Ala Ile Glu Val Gly Gln Asp His Pro Ser
        50                  55                  60

Phe Val Arg Ser Phe Lys Arg Leu Leu Ser Glu Pro Asn Val Thr Glu
65                  70                  75                  80

Ala Thr Pro Val Tyr Leu Gly Asp His Val His Pro Leu Gly Ala Val
                85                  90                  95

Leu Glu Ala Phe Ala Glu Asn Val Thr Ala Leu Arg Ala Phe Gln
            100                 105                 110

Thr Gln Leu Gly Asp Thr Ser Pro Ile Glu Val Val Ile Gly Val Pro
        115                 120                 125
```

```
Ala Asn Ser His Ser Ala Gln Arg Leu Leu Thr Met Ser Ala Phe Ser
    130                 135                 140

Ala Thr Gly Ile Thr Val Val Gly Leu Val Asn Glu Pro Ser Ala Ala
145                 150                 155                 160

Ala Phe Glu Tyr Thr His Arg His Ala Arg Thr Leu Asn Ser Lys Arg
                165                 170                 175

Gln Ala Ile Val Val Tyr Asp Leu Gly Gly Thr Phe Asp Ser Ser
            180                 185                 190

Leu Ile Arg Ile Asp Gly Thr His His Glu Val Val Ser Ser Ile Gly
    195                 200                 205

Ile Ser Arg Leu Gly Gly Asp Asp Phe Asp Glu Ile Leu Leu Gln Cys
210                 215                 220

Ala Leu Lys Ala Ala Gly Arg Gln His Asp Ala Phe Gly Lys Arg Ala
225                 230                 235                 240

Lys Asn Thr Leu Leu Asp Glu Ser Arg Asn Ala Lys Glu Ala Leu Val
                245                 250                 255

Pro Gln Ser Arg Arg Leu Val Leu Glu Ile Gly Asp Asp Ile Thr
                260                 265                 270

Val Pro Val Asn Lys Phe Tyr Glu Ala Ala Thr Pro Leu Val Glu Lys
    275                 280                 285

Ser Leu Ser Ile Met Glu Pro Leu Ile Gly Val Asp Asp Leu Lys Asp
290                 295                 300

Ser Asp Ile Ala Gly Ile Tyr Leu Val Gly Gly Ser Ser Leu Pro
305                 310                 315                 320

Leu Val Ser Arg Leu Leu Arg Glu Arg Phe Gly Arg Val His Arg
                325                 330                 335

Ser Pro Phe Pro Ser Gly Ser Thr Ala Val Gly Leu Ala Ile Ala Ala
                340                 345                 350

Asp Pro Ser Ser Gly Phe His Leu Arg Asp Arg Val Ala Arg Gly Ile
                355                 360                 365

Gly Val Phe Arg Glu His Asp Ser Gly Arg Ala Val Ser Phe Asp Pro
    370                 375                 380

Leu Ile Ala Pro Asp Thr Asp Ser Ala Thr Val Ala Lys Arg Cys Tyr
385                 390                 395                 400

Lys Ala Val His Asn Ile Gly Trp Phe Arg Phe Val Glu Tyr Ser Thr
                405                 410                 415

Val Ser Glu Asp Gly Ser Pro Gly Asp Ile Ser Leu Leu Ser Glu Ile
                420                 425                 430

Lys Ile Pro Phe Asp Ser Ser Ile Thr Asp Val Asp Ala Thr Glu Ile
            435                 440                 445

Ser Arg Phe Asp Gly Pro Glu Val Glu Glu Thr Ile Thr Val Asn Asp
    450                 455                 460

Asn Gly Val Ala Ser Ile Ser Ile Lys Ile Leu Gly Gly Val Thr Val
465                 470                 475                 480

Glu His Thr Ile

<210> SEQ ID NO 31
<211> LENGTH: 1123
<212> TYPE: DNA
<213> ORGANISM: Corynebacterium glutamicum
<220> FEATURE:
<221> NAME/KEY: CDS
<222> LOCATION: (101)..(1093)
<223> OTHER INFORMATION: RXA01404
<220> FEATURE:
<221> NAME/KEY: unsure
```

<222> LOCATION: 12 .. 12
<223> OTHER INFORMATION: All occurrences of n indicate any nucleotide

<400> SEQUENCE: 31

```
gtggatccgg tnttgtgatc cactacgcaa ttggagcgct ccaacacaag ctatatttgt      60
ttaaatgtcc tgtcaatagt tcaagagaaa atcacagaag atg agc aca tcc cgc      115
                                              Met Ser Thr Ser Arg
                                              1               5 ccc aca att tat gac gtc gcc aaa gcc gca ggc gtc tcc aaa tcc ttg      163
Pro Thr Ile Tyr Asp Val Ala Lys Ala Ala Gly Val Ser Lys Ser Leu
             10                  15                  20 gtt tct ctc gtg ctt cgc ggc tcc ccc aac gtg agc aaa gaa tcc gaa      211
Val Ser Leu Val Leu Arg Gly Ser Pro Asn Val Ser Lys Glu Ser Glu
         25                  30                  35 gcc gcg gtc aag acc gcg ata aaa aag ctc aac tac cag cca aat cgc      259
Ala Ala Val Lys Thr Ala Ile Lys Lys Leu Asn Tyr Gln Pro Asn Arg
     40                  45                  50 gcc gca tca gac ctt gcg gcc aag cgc acg cag ctc att gca gtg ctt      307
Ala Ala Ser Asp Leu Ala Ala Lys Arg Thr Gln Leu Ile Ala Val Leu
 55                  60                  65 atc gac gac tac tcc aac ccg tgg ttc atc gac ctg att caa agc ctc      355
Ile Asp Asp Tyr Ser Asn Pro Trp Phe Ile Asp Leu Ile Gln Ser Leu
 70                  75                  80                  85 agc gat gtg ctc acc ccc aag ggg tac cga ctg tcc gtc att gac tca      403
Ser Asp Val Leu Thr Pro Lys Gly Tyr Arg Leu Ser Val Ile Asp Ser
                 90                  95                 100 tta acc tct caa gcc ggc acc gat ccc att acc agt gca cta tca atg      451
Leu Thr Ser Gln Ala Gly Thr Asp Pro Ile Thr Ser Ala Leu Ser Met
            105                 110                 115 cgc ccc gat gga atc atc atc gcc caa gac atc ccc gat ttc act gtc      499
Arg Pro Asp Gly Ile Ile Ile Ala Gln Asp Ile Pro Asp Phe Thr Val
        120                 125                 130 ccc gat tcc cta ccc cca ttt gtc atc gca ggc acc aga atc acc caa      547
Pro Asp Ser Leu Pro Pro Phe Val Ile Ala Gly Thr Arg Ile Thr Gln
    135                 140                 145 gcc agc acc cat gat tca gtg gcc aac gat gac ttc cgg ggc gca gaa      595
Ala Ser Thr His Asp Ser Val Ala Asn Asp Asp Phe Arg Gly Ala Glu
150                 155                 160                 165 ata gcc aca aaa cac ctc atc gat ctt gga cac acc cac atc gcc cac      643
Ile Ala Thr Lys His Leu Ile Asp Leu Gly His Thr His Ile Ala His
                170                 175                 180 cta cgc gtg gga agc ggc gct ggc tta cga cgc ttc gaa agc ttt gag      691
Leu Arg Val Gly Ser Gly Ala Gly Leu Arg Arg Phe Glu Ser Phe Glu
            185                 190                 195 gca acc atg cgt gca cat ggc ctg gag ccg ctt tcc aac gat tac ctc      739
Ala Thr Met Arg Ala His Gly Leu Glu Pro Leu Ser Asn Asp Tyr Leu
        200                 205                 210 ggc ccc gcc gtt gag cac gcc ggg tac acc gaa acc ctc gca cta ctc      787
Gly Pro Ala Val Glu His Ala Gly Tyr Thr Glu Thr Leu Ala Leu Leu
    215                 220                 225 aaa gag cac ccg gag gtc acc gcc att ttc tcc tca aac gac atc acc      835
Lys Glu His Pro Glu Val Thr Ala Ile Phe Ser Ser Asn Asp Ile Thr
230                 235                 240                 245 gcc atc gga gca ctc ggt gcc gcc cgt gaa cta ggt tta cgc gta cct      883
Ala Ile Gly Ala Leu Gly Ala Ala Arg Glu Leu Gly Leu Arg Val Pro
                250                 255                 260 gaa gat cta tca ata atc gga tat gac aac act ccc ctc gcc caa acc      931
Glu Asp Leu Ser Ile Ile Gly Tyr Asp Asn Thr Pro Leu Ala Gln Thr
            265                 270                 275
```

```
                                                          -continued cga ctg atc aac ctc acc acc atc gac gac aac agc atc ggc gtc ggc      979
Arg Leu Ile Asn Leu Thr Thr Ile Asp Asp Asn Ser Ile Gly Val Gly
        280                 285                 290 tac aac gcc gct ctc ttg ttg ctg agc atg ctt gat ccc gag gca ccc     1027
Tyr Asn Ala Ala Leu Leu Leu Leu Ser Met Leu Asp Pro Glu Ala Pro
295                 300                 305 cac ccg gag atc atg cat acg ttg cag ccc tcg ctg att gaa cgg ggc     1075
His Pro Glu Ile Met His Thr Leu Gln Pro Ser Leu Ile Glu Arg Gly
310                 315                 320                 325 acg tgc gcg cca cgt gga tagctacccc aaatacttgg acttcctaat            1123
Thr Cys Ala Pro Arg Gly
                330
```

<210> SEQ ID NO 32
<211> LENGTH: 331
<212> TYPE: PRT
<213> ORGANISM: Corynebacterium glutamicum

<400> SEQUENCE: 32

```
Met Ser Thr Ser Arg Pro Thr Ile Tyr Asp Val Ala Lys Ala Ala Gly
  1               5                  10                  15

Val Ser Lys Ser Leu Val Ser Leu Val Leu Arg Gly Ser Pro Asn Val
             20                  25                  30

Ser Lys Glu Ser Glu Ala Ala Val Lys Thr Ala Ile Lys Lys Leu Asn
         35                  40                  45

Tyr Gln Pro Asn Arg Ala Ala Ser Asp Leu Ala Ala Lys Arg Thr Gln
     50                  55                  60

Leu Ile Ala Val Leu Ile Asp Asp Tyr Ser Asn Pro Trp Phe Ile Asp
 65                  70                  75                  80

Leu Ile Gln Ser Leu Ser Asp Val Leu Thr Pro Lys Gly Tyr Arg Leu
                 85                  90                  95

Ser Val Ile Asp Ser Leu Thr Ser Gln Ala Gly Thr Asp Pro Ile Thr
            100                 105                 110

Ser Ala Leu Ser Met Arg Pro Asp Gly Ile Ile Ala Gln Asp Ile
        115                 120                 125

Pro Asp Phe Thr Val Pro Asp Ser Leu Pro Pro Phe Val Ile Ala Gly
    130                 135                 140

Thr Arg Ile Thr Gln Ala Ser Thr His Asp Ser Val Ala Asn Asp Asp
145                 150                 155                 160

Phe Arg Gly Ala Glu Ile Ala Thr Lys His Leu Ile Asp Leu Gly His
                165                 170                 175

Thr His Ile Ala His Leu Arg Val Gly Ser Gly Ala Gly Leu Arg Arg
            180                 185                 190

Phe Glu Ser Phe Glu Ala Thr Met Arg Ala His Gly Leu Glu Pro Leu
        195                 200                 205

Ser Asn Asp Tyr Leu Gly Pro Ala Val Glu His Ala Gly Tyr Thr Glu
    210                 215                 220

Thr Leu Ala Leu Leu Lys Glu His Pro Glu Val Thr Ala Ile Phe Ser
225                 230                 235                 240

Ser Asn Asp Ile Thr Ala Ile Gly Ala Leu Gly Ala Ala Arg Glu Leu
                245                 250                 255

Gly Leu Arg Val Pro Glu Asp Leu Ser Ile Ile Gly Tyr Asp Asn Thr
            260                 265                 270

Pro Leu Ala Gln Thr Arg Leu Ile Asn Leu Thr Thr Ile Asp Asp Asn
        275                 280                 285

Ser Ile Gly Val Gly Tyr Asn Ala Ala Leu Leu Leu Leu Ser Met Leu
```

```
                  290                 295                 300
Asp Pro Glu Ala Pro His Pro Glu Ile Met His Thr Leu Gln Pro Ser
305                 310                 315                 320

Leu Ile Glu Arg Gly Thr Cys Ala Pro Arg Gly
                325                 330

<210> SEQ ID NO 33
<211> LENGTH: 502
<212> TYPE: DNA
<213> ORGANISM: Corynebacterium glutamicum
<220> FEATURE:
<221> NAME/KEY: CDS
<222> LOCATION: (101)..(472)
<223> OTHER INFORMATION: RXA01431

<400> SEQUENCE: 33
caccgcagct ggttccggtt gccgcgcagc gatcgatgca gagcattacc tagcttctct      60
ggcctaattc acagttagcc ttaaaccaaa ccatgtacca atg aat gtc gga ttc      115
                                              Met Asn Val Gly Phe
                                               1               5 ccc agg agt ccc gtc att gtt aat tta gga gaa acc atg agc aat gtt      163
Pro Arg Ser Pro Val Ile Val Asn Leu Gly Glu Thr Met Ser Asn Val
                 10                  15                  20 gtt gca gta acc gag cag acc ttc aag tcc acc gtc atc gat tcc gac      211
Val Ala Val Thr Glu Gln Thr Phe Lys Ser Thr Val Ile Asp Ser Asp
             25                  30                  35 aag cca gtc atc gtt gac ttc tgg gca gaa tgg tgt ggc ccc tgc aag      259
Lys Pro Val Ile Val Asp Phe Trp Ala Glu Trp Cys Gly Pro Cys Lys
         40                  45                  50 aag ctc agc ccc atc att gag gaa atc gca ggc gag tac ggc gac aag      307
Lys Leu Ser Pro Ile Ile Glu Glu Ile Ala Gly Glu Tyr Gly Asp Lys
     55                  60                  65 gca gtc gtt gcc agc gtc gac gtc gat gca gag cgt acc ttg ggt gcc      355
Ala Val Val Ala Ser Val Asp Val Asp Ala Glu Arg Thr Leu Gly Ala
 70                  75                  80                  85 atg ttc cag att atg tcg att cct tct gtt ctc att ttc aaa aat ggt      403
Met Phe Gln Ile Met Ser Ile Pro Ser Val Leu Ile Phe Lys Asn Gly
                 90                  95                 100 gca aaa gtc gag gaa ttt gtc ggt ctg cgc ccc aag aac gaa att gtg      451
Ala Lys Val Glu Glu Phe Val Gly Leu Arg Pro Lys Asn Glu Ile Val
            105                 110                 115 gaa aaa cta gag aag cac ctc tagctggtat tcttactgca gtcacgtgga          502
Glu Lys Leu Glu Lys His Leu
        120

<210> SEQ ID NO 34
<211> LENGTH: 124
<212> TYPE: PRT
<213> ORGANISM: Corynebacterium glutamicum

<400> SEQUENCE: 34

Met Asn Val Gly Phe Pro Arg Ser Pro Val Ile Val Asn Leu Gly Glu
 1               5                  10                  15

Thr Met Ser Asn Val Val Ala Val Thr Glu Gln Thr Phe Lys Ser Thr
                 20                  25                  30

Val Ile Asp Ser Asp Lys Pro Val Ile Val Asp Phe Trp Ala Glu Trp
             35                  40                  45

Cys Gly Pro Cys Lys Lys Leu Ser Pro Ile Ile Glu Glu Ile Ala Gly
         50                  55                  60

Glu Tyr Gly Asp Lys Ala Val Val Ala Ser Val Asp Val Asp Ala Glu
```

```
                65                  70                  75                  80
Arg Thr Leu Gly Ala Met Phe Gln Ile Met Ser Ile Pro Ser Val Leu
                        85                  90                  95

Ile Phe Lys Asn Gly Ala Lys Val Glu Glu Phe Val Gly Leu Arg Pro
                100                 105                 110

Lys Asn Glu Ile Val Glu Lys Leu Glu Lys His Leu
        115                 120

<210> SEQ ID NO 35
<211> LENGTH: 1495
<212> TYPE: DNA
<213> ORGANISM: Corynebacterium glutamicum
<220> FEATURE:
<221> NAME/KEY: CDS
<222> LOCATION: (101)..(1465)
<223> OTHER INFORMATION: RXA01438

<400> SEQUENCE: 35
ccattagcag tcgcaccccg ataggagtcg aatctacaag tggaaccccc gctcacatac          60
tccacatttt ttagaacccc tttaaggaat cgaactttat atg tct cgc cct ttg          115
                                              Met Ser Arg Pro Leu
                                               1               5 cgt gtt gcc gtt gtc ggt gca ggt cca gca gga atc tac gcg tct gat          163
Arg Val Ala Val Val Gly Ala Gly Pro Ala Gly Ile Tyr Ala Ser Asp
            10                  15                  20 ttg ttg atg aaa tcc gac acg gac gtg cag att gat ctt ttt gaa cgt          211
Leu Leu Met Lys Ser Asp Thr Asp Val Gln Ile Asp Leu Phe Glu Arg
        25                  30                  35 atg cca gcg cct ttc ggt ttg atc cgt tat ggt gtt gcg cct gat cac          259
Met Pro Ala Pro Phe Gly Leu Ile Arg Tyr Gly Val Ala Pro Asp His
    40                  45                  50 cct cgc atc aag ggc atc gtg aag tcc ctg cac aat gtg atg gac aag          307
Pro Arg Ile Lys Gly Ile Val Lys Ser Leu His Asn Val Met Asp Lys
55                  60                  65 gag cag ctg cgt ttc ttg ggc aac att gag gtc ggc aag gac atc act          355
Glu Gln Leu Arg Phe Leu Gly Asn Ile Glu Val Gly Lys Asp Ile Thr
70                  75                  80                  85 gtt gag gag ttg cgt gag ttt tat gac gcg atc gtg ttc tcc act ggc          403
Val Glu Glu Leu Arg Glu Phe Tyr Asp Ala Ile Val Phe Ser Thr Gly
            90                  95                 100 gct act ggc gac cag gat ctt cgg gtt cca ggt tct gat ctg gaa ggt          451
Ala Thr Gly Asp Gln Asp Leu Arg Val Pro Gly Ser Asp Leu Glu Gly
        105                 110                 115 tcg tgg ggc gct ggc gag ttc gtt ggt ttc tat gat ggc aac ccg aac          499
Ser Trp Gly Ala Gly Glu Phe Val Gly Phe Tyr Asp Gly Asn Pro Asn
    120                 125                 130 ttt gaa cgc aac tgg gat ctt tct gct gag aag gta gcg gtt gtt ggt          547
Phe Glu Arg Asn Trp Asp Leu Ser Ala Glu Lys Val Ala Val Val Gly
135                 140                 145 gtc ggt aac gtg gcg ttg gac gtt gct cgt att ttg gcg aag act ggc          595
Val Gly Asn Val Ala Leu Asp Val Ala Arg Ile Leu Ala Lys Thr Gly
150                 155                 160                 165 gat gag ctg cta gtt act gaa atc cct gac aat gtc tat gag agc ttg          643
Asp Glu Leu Leu Val Thr Glu Ile Pro Asp Asn Val Tyr Glu Ser Leu
            170                 175                 180 gct aag aat cag gct aag gaa gtg cac gtt ttt ggt cgt cgt gga cct          691
Ala Lys Asn Gln Ala Lys Glu Val His Val Phe Gly Arg Arg Gly Pro
        185                 190                 195 gct cag gcg aag ttc act ccg ttg gag ctg aag gaa ctt gac cat tcc          739
Ala Gln Ala Lys Phe Thr Pro Leu Glu Leu Lys Glu Leu Asp His Ser
```

```
                    200                 205                 210
gac acc atc gag gtg atc gtg aac cct gag gac att gat tac gat gca          787
Asp Thr Ile Glu Val Ile Val Asn Pro Glu Asp Ile Asp Tyr Asp Ala
    215                 220                 225 gct tcg gag cag gct cgt cgt gat tcc aag tct cag gac ctc gtg tgc          835
Ala Ser Glu Gln Ala Arg Arg Asp Ser Lys Ser Gln Asp Leu Val Cys
230                 235                 240                 245 cag act ttg gaa agc tac gcg atg cgc gat cct aag ggc gct cct cac          883
Gln Thr Leu Glu Ser Tyr Ala Met Arg Asp Pro Lys Gly Ala Pro His
                250                 255                 260 aag ctg ttc att cac ttc ttt gag tcc cca gtg gag atc ctc ggt gag          931
Lys Leu Phe Ile His Phe Phe Glu Ser Pro Val Glu Ile Leu Gly Glu
            265                 270                 275 gac ggc aag gtt gtt ggc ctc aag act gag cgt act cag ctg gac ggc          979
Asp Gly Lys Val Val Gly Leu Lys Thr Glu Arg Thr Gln Leu Asp Gly
        280                 285                 290 aac ggt ggc gtg act ggc acc ggc gag ttc aag acc tgg gat atg cag         1027
Asn Gly Gly Val Thr Gly Thr Gly Glu Phe Lys Thr Trp Asp Met Gln
    295                 300                 305 tca gtt tac cgc gcg gta ggt tac cgt tct gat gcg atc gag ggt gtt         1075
Ser Val Tyr Arg Ala Val Gly Tyr Arg Ser Asp Ala Ile Glu Gly Val
310                 315                 320                 325 cct ttt gac gat gag cgc gcg gtt gtc ccc aac gac ggc ggc cac atc         1123
Pro Phe Asp Asp Glu Arg Ala Val Val Pro Asn Asp Gly Gly His Ile
                330                 335                 340 atc gat cct gag gtc ggc tcc ccc atc act ggc ctg tac gcc act ggc         1171
Ile Asp Pro Glu Val Gly Ser Pro Ile Thr Gly Leu Tyr Ala Thr Gly
            345                 350                 355 tgg atc aag cgt ggc cca att gga ctg atc ggc aac acc aag tcc gac         1219
Trp Ile Lys Arg Gly Pro Ile Gly Leu Ile Gly Asn Thr Lys Ser Asp
        360                 365                 370 gcc aag gaa acc act gag atg ctg ctt gct gat cac gct gct ggt tct         1267
Ala Lys Glu Thr Thr Glu Met Leu Leu Ala Asp His Ala Ala Gly Ser
    375                 380                 385 ttg cct gcg cct gca aag cct gag ttg gag tcc atc att gag ttc ctc         1315
Leu Pro Ala Pro Ala Lys Pro Glu Leu Glu Ser Ile Ile Glu Phe Leu
390                 395                 400                 405 gat gag cgc aag gtt gcg ttc acc aca tgg gat ggc tgg cac ctg ctg         1363
Asp Glu Arg Lys Val Ala Phe Thr Thr Trp Asp Gly Trp His Leu Leu
                410                 415                 420 gat gct gcg gag cgc gcg ctg ggt gag cct gag ggc cgc gag cgc aag         1411
Asp Ala Ala Glu Arg Ala Leu Gly Glu Pro Glu Gly Arg Glu Arg Lys
            425                 430                 435 aag atc gtt gag tgg aat gac atg gtg cgc cat gct cgt cca gaa tac         1459
Lys Ile Val Glu Trp Asn Asp Met Val Arg His Ala Arg Pro Glu Tyr
        440                 445                 450 gac atc taaagtcgct taaagcctca aaaaagggcg                                 1495
Asp Ile
    455

<210> SEQ ID NO 36
<211> LENGTH: 455
<212> TYPE: PRT
<213> ORGANISM: Corynebacterium glutamicum

<400> SEQUENCE: 36

Met Ser Arg Pro Leu Arg Val Ala Val Gly Ala Gly Pro Ala Gly
 1               5                  10                  15

Ile Tyr Ala Ser Asp Leu Leu Met Lys Ser Asp Thr Asp Val Gln Ile
                20                  25                  30
```

```
Asp Leu Phe Glu Arg Met Pro Ala Pro Phe Gly Leu Ile Arg Tyr Gly
         35                  40                  45

Val Ala Pro Asp His Pro Arg Ile Lys Gly Ile Val Lys Ser Leu His
     50                  55                  60

Asn Val Met Asp Lys Glu Gln Leu Arg Phe Leu Gly Asn Ile Glu Val
 65                  70                  75                  80

Gly Lys Asp Ile Thr Val Glu Glu Leu Arg Glu Phe Tyr Asp Ala Ile
                 85                  90                  95

Val Phe Ser Thr Gly Ala Thr Gly Asp Gln Asp Leu Arg Val Pro Gly
                100                 105                 110

Ser Asp Leu Glu Gly Ser Trp Gly Ala Gly Glu Phe Val Gly Phe Tyr
        115                 120                 125

Asp Gly Asn Pro Asn Phe Glu Arg Asn Trp Asp Leu Ser Ala Glu Lys
    130                 135                 140

Val Ala Val Gly Val Gly Asn Val Ala Leu Asp Val Ala Arg Ile
145                 150                 155                 160

Leu Ala Lys Thr Gly Asp Glu Leu Leu Val Thr Glu Ile Pro Asp Asn
                165                 170                 175

Val Tyr Glu Ser Leu Ala Lys Asn Gln Ala Lys Glu Val His Val Phe
                180                 185                 190

Gly Arg Gly Pro Ala Gln Ala Lys Phe Thr Pro Leu Glu Leu Lys
        195                 200                 205

Glu Leu Asp His Ser Asp Thr Ile Glu Val Ile Val Asn Pro Glu Asp
    210                 215                 220

Ile Asp Tyr Asp Ala Ala Ser Glu Gln Ala Arg Arg Asp Ser Lys Ser
225                 230                 235                 240

Gln Asp Leu Val Cys Gln Thr Leu Glu Ser Tyr Ala Met Arg Asp Pro
                245                 250                 255

Lys Gly Ala Pro His Lys Leu Phe Ile His Phe Phe Glu Ser Pro Val
                260                 265                 270

Glu Ile Leu Gly Glu Asp Gly Lys Val Val Gly Leu Lys Thr Glu Arg
    275                 280                 285

Thr Gln Leu Asp Gly Asn Gly Gly Val Thr Gly Thr Gly Glu Phe Lys
    290                 295                 300

Thr Trp Asp Met Gln Ser Val Tyr Arg Ala Val Gly Tyr Arg Ser Asp
305                 310                 315                 320

Ala Ile Glu Gly Val Pro Phe Asp Asp Glu Arg Ala Val Val Pro Asn
                325                 330                 335

Asp Gly Gly His Ile Ile Asp Pro Glu Val Gly Ser Pro Ile Thr Gly
                340                 345                 350

Leu Tyr Ala Thr Gly Trp Ile Lys Arg Gly Pro Ile Gly Leu Ile Gly
        355                 360                 365

Asn Thr Lys Ser Asp Ala Lys Glu Thr Thr Glu Met Leu Leu Ala Asp
    370                 375                 380

His Ala Ala Gly Ser Leu Pro Ala Pro Ala Lys Pro Glu Leu Glu Ser
385                 390                 395                 400

Ile Ile Glu Phe Leu Asp Glu Arg Lys Val Ala Phe Thr Thr Trp Asp
                405                 410                 415

Gly Trp His Leu Leu Asp Ala Ala Glu Arg Ala Leu Gly Glu Pro Glu
                420                 425                 430

Gly Arg Glu Arg Lys Lys Ile Val Glu Trp Asn Asp Met Val Arg His
        435                 440                 445
```

```
Ala Arg Pro Glu Tyr Asp Ile
    450             455

<210> SEQ ID NO 37
<211> LENGTH: 1021
<212> TYPE: DNA
<213> ORGANISM: Corynebacterium glutamicum
<220> FEATURE:
<221> NAME/KEY: CDS
<222> LOCATION: (101)..(991)
<223> OTHER INFORMATION: RXA01490

<400> SEQUENCE: 37
cacaccaatg gtgactactg atccttgaag atcagccgga acgctgtcta gtccactcca         60
aatatccact gttttagact acggcataga ctcaacagac atg aat gct cct gcc         115
                                              Met Asn Ala Pro Ala
                                                1               5 cct aaa cct gga ctc gtg atc gtc gac aag ccc gcc gga atg aca tcc         163
Pro Lys Pro Gly Leu Val Ile Val Asp Lys Pro Ala Gly Met Thr Ser
             10                  15                  20 cat gac gtg gtg tcc aaa ttg cgc cgc gca ttt tcc acc cgc aaa gta         211
His Asp Val Val Ser Lys Leu Arg Arg Ala Phe Ser Thr Arg Lys Val
         25                  30                  35 ggc cac gca ggc acc ctc gac ccc atg gca acc ggc gtg tta gtc gtc         259
Gly His Ala Gly Thr Leu Asp Pro Met Ala Thr Gly Val Leu Val Val
     40                  45                  50 gga att gag cgc gga acc cgc ttc ctg gca cac atg gtg gcc tcc acc         307
Gly Ile Glu Arg Gly Thr Arg Phe Leu Ala His Met Val Ala Ser Thr
 55                  60                  65 aaa gcc tac gac gcc acc att cga ctc ggc gcc gcc acc agc acc gat         355
Lys Ala Tyr Asp Ala Thr Ile Arg Leu Gly Ala Ala Thr Ser Thr Asp
 70                  75                  80                  85 gat gca gaa ggc gag gtt atc tcc aca aca gac gca tcc ggc ctc gac         403
Asp Ala Glu Gly Glu Val Ile Ser Thr Thr Asp Ala Ser Gly Leu Asp
                 90                  95                 100 cac agc acc atc ctt gct gaa atc gtc aac ctc acc ggc gac atc atg         451
His Ser Thr Ile Leu Ala Glu Ile Val Asn Leu Thr Gly Asp Ile Met
            105                 110                 115 caa aaa ccc acc aaa gtc tcc gcc atc aaa atc gac ggc aaa cgc gcc         499
Gln Lys Pro Thr Lys Val Ser Ala Ile Lys Ile Asp Gly Lys Arg Ala
        120                 125                 130 cac gaa cgc gtc cgc gac ggc gaa gaa gta gac att ccc gca cgt ccc         547
His Glu Arg Val Arg Asp Gly Glu Glu Val Asp Ile Pro Ala Arg Pro
    135                 140                 145 gtc acc gtc agc gtc ttt gac gtg ctc gac tac cac gtc gac ggt gaa         595
Val Thr Val Ser Val Phe Asp Val Leu Asp Tyr His Val Asp Gly Glu
150                 155                 160                 165 ttt tat gac tta gat gtg cgc gtc cac tgc tcc tcc ggc acc tac atc         643
Phe Tyr Asp Leu Asp Val Arg Val His Cys Ser Ser Gly Thr Tyr Ile
                170                 175                 180 cgc gcg ctc gcc cgc gac ctc ggc aac gct ttg cag gtc ggc ggc cac         691
Arg Ala Leu Ala Arg Asp Leu Gly Asn Ala Leu Gln Val Gly Gly His
            185                 190                 195 ctg acc gcg ctt agg cgc aca gag gtc ggc cct ttt acg ctt aac gac         739
Leu Thr Ala Leu Arg Arg Thr Glu Val Gly Pro Phe Thr Leu Asn Asp
        200                 205                 210 gcg acc ccc ctc tcc aaa ctc caa gag aat cca gaa ctc tcc ctc aac         787
Ala Thr Pro Leu Ser Lys Leu Gln Glu Asn Pro Glu Leu Ser Leu Asn
    215                 220                 225 ctc gac cag gca ctc acc cgc agt tac cca gtc ctt gac atc acc gaa         835
Leu Asp Gln Ala Leu Thr Arg Ser Tyr Pro Val Leu Asp Ile Thr Glu
```

```
                230                 235                 240                 245
gac gaa ggc gtt gac ctg tcc atg ggc aaa tgg ttg gaa cct cgc gga          883
Asp Glu Gly Val Asp Leu Ser Met Gly Lys Trp Leu Glu Pro Arg Gly
                    250                 255                 260 ctg aaa ggc gtc cac gct gca gta aca cca tca gga aaa gcc gtg gcg          931
Leu Lys Gly Val His Ala Ala Val Thr Pro Ser Gly Lys Ala Val Ala
                265                 270                 275 ctc atc gaa gaa aag ggc aaa cgc ctg gcc acc gtg ttt gtt gct cac          979
Leu Ile Glu Glu Lys Gly Lys Arg Leu Ala Thr Val Phe Val Ala His
                280                 285                 290 ccc aac act ctt tagttggtct gccagaagcc gatttaagag                         1021
Pro Asn Thr Leu
    295

<210> SEQ ID NO 38
<211> LENGTH: 297
<212> TYPE: PRT
<213> ORGANISM: Corynebacterium glutamicum

<400> SEQUENCE: 38

Met Asn Ala Pro Ala Pro Lys Pro Gly Leu Val Ile Val Asp Lys Pro
1               5                   10                  15

Ala Gly Met Thr Ser His Asp Val Ser Lys Leu Arg Arg Ala Phe
            20                  25                  30

Ser Thr Arg Lys Val Gly His Ala Gly Thr Leu Asp Pro Met Ala Thr
        35                  40                  45

Gly Val Leu Val Gly Ile Glu Arg Gly Thr Arg Phe Leu Ala His
    50                  55                  60

Met Val Ala Ser Thr Lys Ala Tyr Asp Ala Thr Ile Arg Leu Gly Ala
65                  70                  75                  80

Ala Thr Ser Thr Asp Asp Ala Glu Gly Glu Val Ile Ser Thr Thr Asp
                85                  90                  95

Ala Ser Gly Leu Asp His Ser Thr Ile Leu Ala Glu Ile Val Asn Leu
            100                 105                 110

Thr Gly Asp Ile Met Gln Lys Pro Thr Lys Val Ser Ala Ile Lys Ile
        115                 120                 125

Asp Gly Lys Arg Ala His Glu Arg Val Arg Asp Gly Glu Glu Val Asp
    130                 135                 140

Ile Pro Ala Arg Pro Val Thr Val Ser Val Phe Asp Val Leu Asp Tyr
145                 150                 155                 160

His Val Asp Gly Glu Phe Tyr Asp Leu Asp Val Arg Val His Cys Ser
                165                 170                 175

Ser Gly Thr Tyr Ile Arg Ala Leu Ala Arg Asp Leu Gly Asn Ala Leu
            180                 185                 190

Gln Val Gly Gly His Leu Thr Ala Leu Arg Arg Thr Glu Val Gly Pro
        195                 200                 205

Phe Thr Leu Asn Asp Ala Thr Pro Leu Ser Lys Leu Gln Glu Asn Pro
    210                 215                 220

Glu Leu Ser Leu Asn Leu Asp Gln Ala Leu Thr Arg Ser Tyr Pro Val
225                 230                 235                 240

Leu Asp Ile Thr Glu Asp Glu Gly Val Asp Leu Ser Met Gly Lys Trp
                245                 250                 255

Leu Glu Pro Arg Gly Leu Lys Gly Val His Ala Ala Val Thr Pro Ser
            260                 265                 270

Gly Lys Ala Val Ala Leu Ile Glu Glu Lys Gly Lys Arg Leu Ala Thr
        275                 280                 285
```

```
                Val Phe Val Ala His Pro Asn Thr Leu
                    290                 295

<210> SEQ ID NO 39
<211> LENGTH: 1441
<212> TYPE: DNA
<213> ORGANISM: Corynebacterium glutamicum
<220> FEATURE:
<221> NAME/KEY: CDS
<222> LOCATION: (101)..(1411)
<223> OTHER INFORMATION: RXA01493

<400> SEQUENCE: 39
cctgctgcag gctataccgc tcgtggtacg gaaatcgaag ccctcgatac gttgattgaa      60
gcaaccgtta ccttggggga gtctttgcga agctcggcgc atg tcg atg tct aac     115
                                            Met Ser Met Ser Asn
                                              1               5 aac gac ttt gag cat gag tcc cat gat gtt tct gca aag cag atc ttc     163
Asn Asp Phe Glu His Glu Ser His Asp Val Ser Ala Lys Gln Ile Phe
                10                  15                  20 ggg ctc gcg ttc ccc gca ctg ggt gtt cta gct gcg atg ccg ctg tat     211
Gly Leu Ala Phe Pro Ala Leu Gly Val Leu Ala Ala Met Pro Leu Tyr
            25                  30                  35 ctc ttg ttg gat aca gcg gtt gtt ggc act ttg ggt ggc ttc gaa ttg     259
Leu Leu Leu Asp Thr Ala Val Val Gly Thr Leu Gly Gly Phe Glu Leu
        40                  45                  50 gct gcg ttg ggc gca gca aca aca att caa gct caa gtg aca aca cag     307
Ala Ala Leu Gly Ala Ala Thr Thr Ile Gln Ala Gln Val Thr Thr Gln
    55                  60                  65 ctg aca ttc ttg tcc tat gga act acc gcg aga tca tcg aga att ttc     355
Leu Thr Phe Leu Ser Tyr Gly Thr Thr Ala Arg Ser Ser Arg Ile Phe
70                  75                  80                  85 gga atg ggt gat cgc cgg gga gca att gcc gaa ggt gtg caa gca acc     403
Gly Met Gly Asp Arg Arg Gly Ala Ile Ala Glu Gly Val Gln Ala Thr
                90                  95                 100 tgg gtg gca ctc ttt gta ggc ttg ggc atc tta acg ctg atg ctc att     451
Trp Val Ala Leu Phe Val Gly Leu Gly Ile Leu Thr Leu Met Leu Ile
            105                 110                 115 gga gcc ccg act ttc gcg ttg tgg ctc agt ggt gat gaa gct cta gcc     499
Gly Ala Pro Thr Phe Ala Leu Trp Leu Ser Gly Asp Glu Ala Leu Ala
        120                 125                 130 caa gaa gca ggg cat tgg ctc cgg gtc gct gct ttt gcg gtg cca cta     547
Gln Glu Ala Gly His Trp Leu Arg Val Ala Ala Phe Ala Val Pro Leu
    135                 140                 145 att ctc atg atc atg gct ggc aac ggt tgg tta aga ggt att caa aac     595
Ile Leu Met Ile Met Ala Gly Asn Gly Trp Leu Arg Gly Ile Gln Asn
150                 155                 160                 165 acc aag ctg cca ctc tat ttc acc ttg gcg gga gtc atc ccc ggc gcg     643
Thr Lys Leu Pro Leu Tyr Phe Thr Leu Ala Gly Val Ile Pro Gly Ala
                170                 175                 180 atc ttg att ccg ata ttc gtg gct aag ttt gga ctt gtg ggc tct gcc     691
Ile Leu Ile Pro Ile Phe Val Ala Lys Phe Gly Leu Val Gly Ser Ala
            185                 190                 195 tgg gca aac ctc att gca gaa gca att act gct tcg ctg ttt ttg ggt     739
Trp Ala Asn Leu Ile Ala Glu Ala Ile Thr Ala Ser Leu Phe Leu Gly
        200                 205                 210 gca ttg atc aag cac cac gaa ggt tcg tgg aag ccg agc tgg acg gtg     787
Ala Leu Ile Lys His His Glu Gly Ser Trp Lys Pro Ser Trp Thr Val
    215                 220                 225 atg aaa aat cag ttg gtt ctt gga cgt gat ttg atc atg cgg tca atg     835
```

```
                Met Lys Asn Gln Leu Val Leu Gly Arg Asp Leu Ile Met Arg Ser Met
                230                 235                 240                 245 tcg ttc cag gtt gct ttt ctt tcc gcg gcc gct gtg gct gca cga ttt               883
Ser Phe Gln Val Ala Phe Leu Ser Ala Ala Ala Val Ala Ala Arg Phe
                250                 255                 260 ggc acg gca tcc ttg gcg gcc cac cag gtg ttg ctt cag ctg tgg aat               931
Gly Thr Ala Ser Leu Ala Ala His Gln Val Leu Leu Gln Leu Trp Asn
                265                 270                 275 ttc atc aca ttg gtg ctg gat tct cta gct atc gcg gcg cag acc tta               979
Phe Ile Thr Leu Val Leu Asp Ser Leu Ala Ile Ala Ala Gln Thr Leu
                280                 285                 290 act ggt gca gcc ctg ggc gct gga act gcg aag gtc gcc cgc agg gtg              1027
Thr Gly Ala Ala Leu Gly Ala Gly Thr Ala Lys Val Ala Arg Arg Val
                295                 300                 305 ggt aat cag gtg att aag tac tct ctg att ttc gct ggt ggc tta ggt              1075
Gly Asn Gln Val Ile Lys Tyr Ser Leu Ile Phe Ala Gly Gly Leu Gly
310                 315                 320                 325 ttg gtg ttc gtg gtc tta cac tcg tgg att ccg cgt att ttc act cag              1123
Leu Val Phe Val Val Leu His Ser Trp Ile Pro Arg Ile Phe Thr Gln
                330                 335                 340 gac gcc gac gtt tta gat gcg att gct tcc ccg tgg tgg atc atg gtc              1171
Asp Ala Asp Val Leu Asp Ala Ile Ala Ser Pro Trp Trp Ile Met Val
                345                 350                 355 gcg atg atc att ttg ggt ggc att gtc ttt gct att gat ggt gtg ctg              1219
Ala Met Ile Ile Leu Gly Gly Ile Val Phe Ala Ile Asp Gly Val Leu
                360                 365                 370 ttg ggt gct gct gac gcg gtg ttc ctc cga aat gcc tct atc ttg gcg              1267
Leu Gly Ala Ala Asp Ala Val Phe Leu Arg Asn Ala Ser Ile Leu Ala
375                 380                 385 gtt gtg gtc gga ttc tta cca ggc gtc tgg att tcc tat gca tta gat              1315
Val Val Val Gly Phe Leu Pro Gly Val Trp Ile Ser Tyr Ala Leu Asp
390                 395                 400                 405 gca ggg ctg aca ggc gtg tgg tgt ggt ttg ctg gcg ttt att ctg atc              1363
Ala Gly Leu Thr Gly Val Trp Cys Gly Leu Leu Ala Phe Ile Leu Ile
                410                 415                 420 cga cta ttt gcg gtg att tgg cgg ttt aag tct atg aag tgg gcg cgt              1411
Arg Leu Phe Ala Val Ile Trp Arg Phe Lys Ser Met Lys Trp Ala Arg
                425                 430                 435 tagcttcggc gcgtggcaaa ccacatttgc                                              1441

<210> SEQ ID NO 40
<211> LENGTH: 437
<212> TYPE: PRT
<213> ORGANISM: Corynebacterium glutamicum

<400> SEQUENCE: 40

Met Ser Met Ser Asn Asn Asp Phe Glu His Glu Ser His Asp Val Ser
 1               5                  10                  15

Ala Lys Gln Ile Phe Gly Leu Ala Phe Pro Ala Leu Gly Val Leu Ala
                20                  25                  30

Ala Met Pro Leu Tyr Leu Leu Leu Asp Thr Ala Val Val Gly Thr Leu
            35                  40                  45

Gly Gly Phe Glu Leu Ala Ala Leu Gly Ala Ala Thr Thr Ile Gln Ala
        50                  55                  60

Gln Val Thr Thr Gln Leu Thr Phe Leu Ser Tyr Gly Thr Thr Ala Arg
65                  70                  75                  80

Ser Ser Arg Ile Phe Gly Met Gly Asp Arg Arg Gly Ala Ile Ala Glu
                85                  90                  95
```

```
Gly Val Gln Ala Thr Trp Val Ala Leu Phe Val Gly Leu Gly Ile Leu
            100                 105                 110

Thr Leu Met Leu Ile Gly Ala Pro Thr Phe Ala Leu Trp Leu Ser Gly
        115                 120                 125

Asp Glu Ala Leu Ala Gln Glu Ala Gly His Trp Leu Arg Val Ala Ala
    130                 135                 140

Phe Ala Val Pro Leu Ile Leu Met Ile Met Ala Gly Asn Gly Trp Leu
145                 150                 155                 160

Arg Gly Ile Gln Asn Thr Lys Leu Pro Leu Tyr Phe Thr Leu Ala Gly
                165                 170                 175

Val Ile Pro Gly Ala Ile Leu Ile Pro Ile Phe Val Ala Lys Phe Gly
            180                 185                 190

Leu Val Gly Ser Ala Trp Ala Asn Leu Ile Ala Glu Ala Ile Thr Ala
        195                 200                 205

Ser Leu Phe Leu Gly Ala Leu Ile Lys His His Glu Gly Ser Trp Lys
    210                 215                 220

Pro Ser Trp Thr Val Met Lys Asn Gln Leu Val Leu Gly Arg Asp Leu
225                 230                 235                 240

Ile Met Arg Ser Met Ser Phe Gln Val Ala Phe Leu Ser Ala Ala Ala
                245                 250                 255

Val Ala Ala Arg Phe Gly Thr Ala Ser Leu Ala Ala His Gln Val Leu
            260                 265                 270

Leu Gln Leu Trp Asn Phe Ile Thr Leu Val Leu Asp Ser Leu Ala Ile
        275                 280                 285

Ala Ala Gln Thr Leu Thr Gly Ala Ala Leu Gly Ala Gly Thr Ala Lys
    290                 295                 300

Val Ala Arg Arg Val Gly Asn Gln Val Ile Lys Tyr Ser Leu Ile Phe
305                 310                 315                 320

Ala Gly Gly Leu Gly Leu Val Phe Val Leu His Ser Trp Ile Pro
                325                 330                 335

Arg Ile Phe Thr Gln Asp Ala Asp Val Leu Asp Ala Ile Ala Ser Pro
            340                 345                 350

Trp Trp Ile Met Val Ala Met Ile Ile Leu Gly Gly Ile Val Phe Ala
        355                 360                 365

Ile Asp Gly Val Leu Leu Gly Ala Ala Asp Ala Val Phe Leu Arg Asn
    370                 375                 380

Ala Ser Ile Leu Ala Val Val Gly Phe Leu Pro Gly Val Trp Ile
385                 390                 395                 400

Ser Tyr Ala Leu Asp Ala Gly Leu Thr Gly Val Trp Cys Gly Leu Leu
                405                 410                 415

Ala Phe Ile Leu Ile Arg Leu Phe Ala Val Ile Trp Arg Phe Lys Ser
            420                 425                 430

Met Lys Trp Ala Arg
        435

<210> SEQ ID NO 41
<211> LENGTH: 2056
<212> TYPE: DNA
<213> ORGANISM: Corynebacterium glutamicum
<220> FEATURE:
<221> NAME/KEY: CDS
<222> LOCATION: (101)..(2026)
<223> OTHER INFORMATION: RXA01559

<400> SEQUENCE: 41
ctttctcgct cgtgtcgcac tcacccacgc cacctggcgt gggtgagtgg cgcatggagt    60
```

-continued

```
gggtgggcgt cgacaagcgt ggttgtctgg ttgattggaa ttg aag gag act ttc      115
                                            Leu Lys Glu Thr Phe
                                              1               5 ttg gct cgg caa aaa aag agt gcc gct agc gcc tgg gaa cga tgg cca      163
Leu Ala Arg Gln Lys Lys Ser Ala Ala Ser Ala Trp Glu Arg Trp Pro
             10                  15                  20 aaa cgc gca ata gcg ttg ttt gtg ctc atc gtc gtt ggt gtt tat gcg      211
Lys Arg Ala Ile Ala Leu Phe Val Leu Ile Val Val Gly Val Tyr Ala
         25                  30                  35 ttg gtg ctg ttg aca ggc gat cgt tct gcc aca cca aaa ttg ggt att      259
Leu Val Leu Leu Thr Gly Asp Arg Ser Ala Thr Pro Lys Leu Gly Ile
     40                  45                  50 gat ctg caa ggc gga acc cga gtg acc ctc gtg ccg cag ggg cag gat      307
Asp Leu Gln Gly Gly Thr Arg Val Thr Leu Val Pro Gln Gly Gln Asp
 55                  60                  65 cca act cag gac cag ctg aat cag gca cgc acc att ctg gaa aac cgt      355
Pro Thr Gln Asp Gln Leu Asn Gln Ala Arg Thr Ile Leu Glu Asn Arg
             70                  75                  80              85 gtg aac ggc atg ggc gtt tca ggt gca agc gtg gtc gct gac ggt aac      403
Val Asn Gly Met Gly Val Ser Gly Ala Ser Val Val Ala Asp Gly Asn
             90                  95                 100 acg ctg gtg atc act gtt ccc ggg gaa aat acc gca cag gcg caa tcc      451
Thr Leu Val Ile Thr Val Pro Gly Glu Asn Thr Ala Gln Ala Gln Ser
            105                 110                 115 cta gga cag acc tcc cag ctg ctg ttc cgt ccc gtt ggt cag gca gga      499
Leu Gly Gln Thr Ser Gln Leu Leu Phe Arg Pro Val Gly Gln Ala Gly
            120                 125                 130 atg ccc gat atg acc acg ttg atg cca gag ctg gaa gag atg gcc aac      547
Met Pro Asp Met Thr Thr Leu Met Pro Glu Leu Glu Glu Met Ala Asn
135                 140                 145 agg tgg gtt gaa tac ggc gtc atc acc gaa gag cag gca aat gcc tcc      595
Arg Trp Val Glu Tyr Gly Val Ile Thr Glu Glu Gln Ala Asn Ala Ser
150                 155                 160                 165 ttg gag gaa atg aac acc gct gtt gca tcg acc act gcg gtg gaa ggc      643
Leu Glu Glu Met Asn Thr Ala Val Ala Ser Thr Thr Ala Val Glu Gly
                170                 175                 180 gaa gaa gca act gag cca gaa ccc gtc acc gtg tcg gcg acc cct atg      691
Glu Glu Ala Thr Glu Pro Glu Pro Val Thr Val Ser Ala Thr Pro Met
                185                 190                 195 gat gag cca gcc aac tcc att gag gca aca cag cga cgc cag gaa atc      739
Asp Glu Pro Ala Asn Ser Ile Glu Ala Thr Gln Arg Arg Gln Glu Ile
                200                 205                 210 acg gac atg ctg cgc acc gac cgc cag tcc acc gat ccc act gtc cag      787
Thr Asp Met Leu Arg Thr Asp Arg Gln Ser Thr Asp Pro Thr Val Gln
215                 220                 225 atc gct gca agt tct ttg atg cag tgc acc act gat gag atg gat cct      835
Ile Ala Ala Ser Ser Leu Met Gln Cys Thr Thr Asp Glu Met Asp Pro
230                 235                 240                 245 ttg gcc ggc acc gat gat cca cgc ctg cca ttg gtg gca tgt gat cca      883
Leu Ala Gly Thr Asp Asp Pro Arg Leu Pro Leu Val Ala Cys Asp Pro
                250                 255                 260 gct gta ggt ggc gtg tat gta ctt gat cct gca cct ttg ctc aac ggc      931
Ala Val Gly Gly Val Tyr Val Leu Asp Pro Ala Pro Leu Leu Asn Gly
                265                 270                 275 gaa acc gat gag gaa aat ggt gcg cgc cta acc ggt aat gag atc gat      979
Glu Thr Asp Glu Glu Asn Gly Ala Arg Leu Thr Gly Asn Glu Ile Asp
                280                 285                 290 acc aac cgt ccc atc acc ggt gga ttc aac gcc cag tcc ggc cag atg      1027
Thr Asn Arg Pro Ile Thr Gly Gly Phe Asn Ala Gln Ser Gly Gln Met
```

-continued

```
                  295                 300                 305
gaa atc agc ttt gcc ttc aaa tcc ggc gat ggg gaa gaa ggc tct gca    1075
Glu Ile Ser Phe Ala Phe Lys Ser Gly Asp Gly Glu Glu Gly Ser Ala
310             315                 320                 325 act tgg tcc tct ctg acc agc cag tac ctg cag cag cag atc gcc atc    1123
Thr Trp Ser Ser Leu Thr Ser Gln Tyr Leu Gln Gln Gln Ile Ala Ile
            330                 335                 340 acc ctg gac tct cag gtg att tct gca ccc gtg att cag tca gca acc    1171
Thr Leu Asp Ser Gln Val Ile Ser Ala Pro Val Ile Gln Ser Ala Thr
        345                 350                 355 cct gtg ggt tct gca aca tcc atc acc ggt gac ttc act caa act gaa    1219
Pro Val Gly Ser Ala Thr Ser Ile Thr Gly Asp Phe Thr Gln Thr Glu
    360                 365                 370 gcc caa gat ctg gcg aac aac ctg cgc tac ggt gca ttg ccc ctg agc    1267
Ala Gln Asp Leu Ala Asn Asn Leu Arg Tyr Gly Ala Leu Pro Leu Ser
375                 380                 385 ttc gca ggt gaa aac ggc gag cgc ggc gga act acc acc gtt ccg        1315
Phe Ala Gly Glu Asn Gly Glu Arg Gly Gly Thr Thr Thr Val Pro
390                 395                 400                 405 cca tca cta ggc gca gca tcc ttg aag gcc gga ctg atc gca ggc atc    1363
Pro Ser Leu Gly Ala Ala Ser Leu Lys Ala Gly Leu Ile Ala Gly Ile
            410                 415                 420 gtc ggc atc gcg ctg gtc gcc atc ttc gtg ttc gcc tac tac cgc gtc    1411
Val Gly Ile Ala Leu Val Ala Ile Phe Val Phe Ala Tyr Tyr Arg Val
        425                 430                 435 ttc gga ttc gtt tcc ctg ttc acc ctg ttt gcc gca ggc gtg ttg gtc    1459
Phe Gly Phe Val Ser Leu Phe Thr Leu Phe Ala Ala Gly Val Leu Val
    440                 445                 450 tac ggc ctt ctg gta ctg ctg gga cgc tgg atc gga tat tcc cta gac    1507
Tyr Gly Leu Leu Val Leu Leu Gly Arg Trp Ile Gly Tyr Ser Leu Asp
455                 460                 465 ctt gct ggt atc gcc ggt ttg atc atc ggt atc ggt acc acc gcc gac    1555
Leu Ala Gly Ile Ala Gly Leu Ile Ile Gly Ile Gly Thr Thr Ala Asp
470                 475                 480                 485 tcc ttc gtg gtg ttc tat gag cgc atc aag gat gag atc cgt gaa gga    1603
Ser Phe Val Val Phe Tyr Glu Arg Ile Lys Asp Glu Ile Arg Glu Gly
            490                 495                 500 aga tcc ttt aga tct gca gta cct cgt gca tgg gaa agc gcc aag cgc    1651
Arg Ser Phe Arg Ser Ala Val Pro Arg Ala Trp Glu Ser Ala Lys Arg
        505                 510                 515 acc atc gtc aca ggc aac atg gtc act ttg ctc ggc gct atc gtg att    1699
Thr Ile Val Thr Gly Asn Met Val Thr Leu Leu Gly Ala Ile Val Ile
    520                 525                 530 tac ttg ctc gcg gtc ggc gaa gtc aag ggc ttt gcc ttc acc ctg ggt    1747
Tyr Leu Leu Ala Val Gly Glu Val Lys Gly Phe Ala Phe Thr Leu Gly
535                 540                 545 ctg acc acc gta ttc gat ctc gtt gtc acc ttc ctg atc acg gca cca    1795
Leu Thr Thr Val Phe Asp Leu Val Val Thr Phe Leu Ile Thr Ala Pro
550                 555                 560                 565 ctg gtt atc ctg gca tca cgc aac cca ttc ttt gcc aag tca tcg gtc    1843
Leu Val Ile Leu Ala Ser Arg Asn Pro Phe Phe Ala Lys Ser Ser Val
            570                 575                 580 aac ggc atg gga cga gtg atg aag ctc gtt gaa gaa cgc cgc gcc aac    1891
Asn Gly Met Gly Arg Val Met Lys Leu Val Glu Glu Arg Arg Ala Asn
        585                 590                 595 ggt gaa ttg gat gag cct gag tac ctg aaa aag atc cat gcc aag aat    1939
Gly Glu Leu Asp Glu Pro Glu Tyr Leu Lys Lys Ile His Ala Lys Asn
    600                 605                 610 gcg gca gct gat aag gct tcc act gac aat tct tcc act gac aat tct    1987
```

-continued

```
Ala Ala Ala Asp Lys Ala Ser Thr Asp Asn Ser Ser Thr Asp Asn Ser
            615                 620                 625 gaa gca cct ggc acc gat acg aac caa gag gag gag aag tagccatgac        2036
Glu Ala Pro Gly Thr Asp Thr Asn Gln Glu Glu Glu Lys
630                 635                 640 tgattcccag actgaatcac                                                 2056

<210> SEQ ID NO 42
<211> LENGTH: 642
<212> TYPE: PRT
<213> ORGANISM: Corynebacterium glutamicum

<400> SEQUENCE: 42

Leu Lys Glu Thr Phe Leu Ala Arg Gln Lys Lys Ser Ala Ala Ser Ala
1               5                   10                  15

Trp Glu Arg Trp Pro Lys Arg Ala Ile Ala Leu Phe Val Leu Ile Val
                20                  25                  30

Val Gly Val Tyr Ala Leu Val Leu Leu Thr Gly Asp Arg Ser Ala Thr
            35                  40                  45

Pro Lys Leu Gly Ile Asp Leu Gln Gly Gly Thr Arg Val Thr Leu Val
        50                  55                  60

Pro Gln Gly Gln Asp Pro Thr Gln Asp Gln Leu Asn Gln Ala Arg Thr
65                  70                  75                  80

Ile Leu Glu Asn Arg Val Asn Gly Met Gly Val Ser Gly Ala Ser Val
                85                  90                  95

Val Ala Asp Gly Asn Thr Leu Val Ile Thr Val Pro Gly Glu Asn Thr
            100                 105                 110

Ala Gln Ala Gln Ser Leu Gly Gln Thr Ser Gln Leu Leu Phe Arg Pro
        115                 120                 125

Val Gly Gln Ala Gly Met Pro Asp Met Thr Thr Leu Met Pro Glu Leu
130                 135                 140

Glu Glu Met Ala Asn Arg Trp Val Glu Tyr Gly Val Ile Thr Glu Glu
145                 150                 155                 160

Gln Ala Asn Ala Ser Leu Glu Glu Met Asn Thr Ala Val Ala Ser Thr
                165                 170                 175

Thr Ala Val Glu Gly Glu Glu Ala Thr Glu Pro Glu Pro Val Thr Val
            180                 185                 190

Ser Ala Thr Pro Met Asp Glu Pro Ala Asn Ser Ile Glu Ala Thr Gln
        195                 200                 205

Arg Arg Gln Glu Ile Thr Asp Met Leu Arg Thr Asp Arg Gln Ser Thr
210                 215                 220

Asp Pro Thr Val Gln Ile Ala Ala Ser Ser Leu Met Gln Cys Thr Thr
225                 230                 235                 240

Asp Glu Met Asp Pro Leu Ala Gly Thr Asp Pro Arg Leu Pro Leu
                245                 250                 255

Val Ala Cys Asp Pro Ala Val Gly Gly Val Tyr Val Leu Asp Pro Ala
            260                 265                 270

Pro Leu Leu Asn Gly Glu Thr Asp Glu Glu Asn Gly Ala Arg Leu Thr
        275                 280                 285

Gly Asn Glu Ile Asp Thr Asn Arg Pro Ile Thr Gly Phe Asn Ala
290                 295                 300

Gln Ser Gly Gln Met Glu Ile Ser Phe Ala Phe Lys Ser Gly Asp Gly
305                 310                 315                 320

Glu Glu Gly Ser Ala Thr Trp Ser Ser Leu Thr Ser Gln Tyr Leu Gln
                325                 330                 335
```

-continued

```
Gln Gln Ile Ala Ile Thr Leu Asp Ser Gln Val Ile Ser Ala Pro Val
            340                 345                 350
Ile Gln Ser Ala Thr Pro Val Gly Ser Ala Thr Ser Ile Thr Gly Asp
        355                 360                 365
Phe Thr Gln Thr Glu Ala Gln Asp Leu Ala Asn Asn Leu Arg Tyr Gly
    370                 375                 380
Ala Leu Pro Leu Ser Phe Ala Gly Glu Asn Gly Glu Arg Gly Gly Thr
385                 390                 395                 400
Thr Thr Thr Val Pro Pro Ser Leu Gly Ala Ala Ser Leu Lys Ala Gly
                405                 410                 415
Leu Ile Ala Gly Ile Val Gly Ile Ala Leu Val Ala Ile Phe Val Phe
            420                 425                 430
Ala Tyr Tyr Arg Val Phe Gly Phe Val Ser Leu Phe Thr Leu Phe Ala
        435                 440                 445
Ala Gly Val Leu Val Tyr Gly Leu Leu Val Leu Leu Gly Arg Trp Ile
    450                 455                 460
Gly Tyr Ser Leu Asp Leu Ala Gly Ile Ala Gly Leu Ile Ile Gly Ile
465                 470                 475                 480
Gly Thr Thr Ala Asp Ser Phe Val Val Phe Tyr Glu Arg Ile Lys Asp
                485                 490                 495
Glu Ile Arg Glu Gly Arg Ser Phe Arg Ser Ala Val Pro Arg Ala Trp
            500                 505                 510
Glu Ser Ala Lys Arg Thr Ile Val Thr Gly Asn Met Val Thr Leu Leu
        515                 520                 525
Gly Ala Ile Val Ile Tyr Leu Leu Ala Val Gly Glu Val Lys Gly Phe
    530                 535                 540
Ala Phe Thr Leu Gly Leu Thr Thr Val Phe Asp Leu Val Val Thr Phe
545                 550                 555                 560
Leu Ile Thr Ala Pro Leu Val Ile Leu Ala Ser Arg Asn Pro Phe Phe
                565                 570                 575
Ala Lys Ser Ser Val Asn Gly Met Gly Arg Val Met Lys Leu Val Glu
            580                 585                 590
Glu Arg Arg Ala Asn Gly Glu Leu Asp Glu Pro Glu Tyr Leu Lys Lys
        595                 600                 605
Ile His Ala Lys Asn Ala Ala Ala Asp Lys Ala Ser Thr Asp Asn Ser
    610                 615                 620
Ser Thr Asp Asn Ser Glu Ala Pro Gly Thr Asp Thr Asn Gln Glu Glu
625                 630                 635                 640
Glu Lys
```

<210> SEQ ID NO 43
<211> LENGTH: 1909
<212> TYPE: DNA
<213> ORGANISM: Corynebacterium glutamicum
<220> FEATURE:
<221> NAME/KEY: CDS
<222> LOCATION: (101)..(1879)
<223> OTHER INFORMATION: RXA01596

<400> SEQUENCE: 43

```
tcccaggtca gcgggtaat tcgaaaacca ttcgaacaat tttcgaggat ttagaaaaaa      60
cgttcgcata aattgttaga actgatgtac actttgaggc atg ctc gta gac att     115
                                              Met Leu Val Asp Ile
                                                1               5 gct att gag aac ctc gga gtt att cca gcg gcc tca gct gag ttc agc     163
```

```
                Ala Ile Glu Asn Leu Gly Val Ile Pro Ala Ala Ser Ala Glu Phe Ser
                             10                  15                  20 tca ggt tta aca gtg ctc acc ggt gag acc ggc gcc gga aag acc atg             211
Ser Gly Leu Thr Val Leu Thr Gly Glu Thr Gly Ala Gly Lys Thr Met
             25                  30                  35 gta gtg aca ggt tta cgc ctg tta tcc ggc ggt cgc gcc gac gct tca             259
Val Val Thr Gly Leu Arg Leu Leu Ser Gly Gly Arg Ala Asp Ala Ser
         40                  45                  50 cgc gtg cgc aca gga tcc cct caa gct gtt gtg gag ggg cgc ttt gtt             307
Arg Val Arg Thr Gly Ser Pro Gln Ala Val Val Glu Gly Arg Phe Val
     55                  60                  65 acg caa ggc gtg ccc tgc gac att gtc gaa cgt gca acc gga atc gtt             355
Thr Gln Gly Val Pro Cys Asp Ile Val Glu Arg Ala Thr Gly Ile Val
 70                  75                  80                  85 tcg aac gcc gga ggt gcc gca gat gaa aat gga gag ttt tta gct gtc             403
Ser Asn Ala Gly Gly Ala Ala Asp Glu Asn Gly Glu Phe Leu Ala Val
                 90                  95                 100 cgt tcc gtc ggc gcc aac ggc cgt tca aaa gct cat ctc ggt ggt cgc             451
Arg Ser Val Gly Ala Asn Gly Arg Ser Lys Ala His Leu Gly Gly Arg
            105                 110                 115 tcc gta cct gcg gca acg ctg tcc gag ttc tct gat gag ctg ttg acc             499
Ser Val Pro Ala Ala Thr Leu Ser Glu Phe Ser Asp Glu Leu Leu Thr
        120                 125                 130 atc cac ggt caa aat gac caa ctc cgg ttg ctc tcc cca gaa cgc caa             547
Ile His Gly Gln Asn Asp Gln Leu Arg Leu Leu Ser Pro Glu Arg Gln
135                 140                 145 cta gag gcg ctt gat cgt ttt gat cca gag ctg gcc caa ctg cgc aaa             595
Leu Glu Ala Leu Asp Arg Phe Asp Pro Glu Leu Ala Gln Leu Arg Lys
150                 155                 160                 165 aac tac aac gcc aag tac ctc act tgg aag tcc ttg gat aaa gat ctg             643
Asn Tyr Asn Ala Lys Tyr Leu Thr Trp Lys Ser Leu Asp Lys Asp Leu
            170                 175                 180 cag aag cgc ctg agt agt agg cga gag ctg gct caa gaa gtc gat cgc             691
Gln Lys Arg Leu Ser Ser Arg Arg Glu Leu Ala Gln Glu Val Asp Arg
        185                 190                 195 ctg caa ttc gcg att aat gag atc gag gaa gtc tcg cca cag cca ggc             739
Leu Gln Phe Ala Ile Asn Glu Ile Glu Glu Val Ser Pro Gln Pro Gly
    200                 205                 210 gaa gac gcc gaa ctg gtt gag cag atc cgc agg ctc cag gac gtg gac             787
Glu Asp Ala Glu Leu Val Glu Gln Ile Arg Arg Leu Gln Asp Val Asp
215                 220                 225 acc ctg cgg gag caa gct gca acc gca ttg gct gcg att gat ggt gcc             835
Thr Leu Arg Glu Gln Ala Ala Thr Ala Leu Ala Ala Ile Asp Gly Ala
230                 235                 240                 245 ggc tct ctc agc gac gcc atg ggt ggt tcc ggc ggc ttt gat gaa tcc             883
Gly Ser Leu Ser Asp Ala Met Gly Gly Ser Gly Gly Phe Asp Glu Ser
            250                 255                 260 cag gag tca gcc tct gac cag ctc ggc cag gcg gag tcc gcg ctg gca             931
Gln Glu Ser Ala Ser Asp Gln Leu Gly Gln Ala Glu Ser Ala Leu Ala
        265                 270                 275 ggc agt gat gac tca aag ctg aaa gat att gcc gtt cag ctt gcg gaa             979
Gly Ser Asp Asp Ser Lys Leu Lys Asp Ile Ala Val Gln Leu Ala Glu
    280                 285                 290 atc acc agc cag ctc agc caa gtg tcc atg gaa ttg gcc ggg ttc ctc             1027
Ile Thr Ser Gln Leu Ser Gln Val Ser Met Glu Leu Gly Gly Phe Leu
295                 300                 305 tct gat ctc ccc gca gac ccc caa gca ctc gat gac atg ctc acc cgc             1075
Ser Asp Leu Pro Ala Asp Pro Gln Ala Leu Asp Asp Met Leu Thr Arg
310                 315                 320                 325
```

| | | | | | | | | | | | | | | | | |
|---|---|---|---|---|---|---|---|---|---|---|---|---|---|---|---|---|
| caa | cag | caa | ttg | aaa | ctg | ctc | acg | cgt | aaa | tac | gct | gca | gat | att | gac | 1123 |
| Gln | Gln | Gln | Leu | Lys | Leu | Leu | Thr | Arg | Lys | Tyr | Ala | Ala | Asp | Ile | Asp | |
| | | | 330 | | | | | 335 | | | | | 340 | | | |
| ggc | gtg | att | gag | tgg | cag | cgg | aaa | gcc | caa | atc | cgc | cta | gac | agc | att | 1171 |
| Gly | Val | Ile | Glu | Trp | Gln | Arg | Lys | Ala | Gln | Ile | Arg | Leu | Asp | Ser | Ile | |
| | | 345 | | | | | 350 | | | | | 355 | | | | |
| gac | att | tcc | tcc | gaa | gcg | ctt | gac | aag | ctg | aaa | gaa | gac | gcg | aaa | aag | 1219 |
| Asp | Ile | Ser | Ser | Glu | Ala | Leu | Asp | Lys | Leu | Lys | Glu | Asp | Ala | Lys | Lys | |
| | | 360 | | | | | 365 | | | | | 370 | | | | |
| gcg | cag | gcc | tcc | atg | atg | cgt | gcc | gct | aag | aag | ctt | tca | gct | gtc | cgt | 1267 |
| Ala | Gln | Ala | Ser | Met | Met | Arg | Ala | Ala | Lys | Lys | Leu | Ser | Ala | Val | Arg | |
| | 375 | | | | | 380 | | | | | 385 | | | | | |
| gca | aag | gca | gca | acc | aag | ttg | ggg | aca | act | gtc | acc | gag | gag | ctt | cag | 1315 |
| Ala | Lys | Ala | Ala | Thr | Lys | Leu | Gly | Thr | Thr | Val | Thr | Glu | Glu | Leu | Gln | |
| 390 | | | | | 395 | | | | | 400 | | | | | 405 | |
| ggc | ctg | gcc | atg | caa | aaa | gcc | cgc | ttt | gag | gtt | gct | ttg | acc | tcc | att | 1363 |
| Gly | Leu | Ala | Met | Gln | Lys | Ala | Arg | Phe | Glu | Val | Ala | Leu | Thr | Ser | Ile | |
| | | | 410 | | | | | 415 | | | | | 420 | | | |
| gag | gcg | tgc | gcc | agc | ggt | atc | gac | cag | gtg | gaa | ttc | cag | ctc | gca | gca | 1411 |
| Glu | Ala | Cys | Ala | Ser | Gly | Ile | Asp | Gln | Val | Glu | Phe | Gln | Leu | Ala | Ala | |
| | | 425 | | | | | 430 | | | | | 435 | | | | |
| aat | gcc | ttt | gca | cag | cct | cgt | cca | ctt | gca | tcc | tct | gcg | tct | ggt | ggt | 1459 |
| Asn | Ala | Phe | Ala | Gln | Pro | Arg | Pro | Leu | Ala | Ser | Ser | Ala | Ser | Gly | Gly | |
| | | 440 | | | | | 445 | | | | | 450 | | | | |
| gaa | ctt | tcc | cgc | gtt | atg | ttg | gcg | ctc | gag | gtg | atc | ttg | gct | gct | gga | 1507 |
| Glu | Leu | Ser | Arg | Val | Met | Leu | Ala | Leu | Glu | Val | Ile | Leu | Ala | Ala | Gly | |
| | 455 | | | | | 460 | | | | | 465 | | | | | |
| acc | acg | ggc | acc | acc | ttg | gtg | ttc | gac | gag | gtt | gat | gca | ggt | gtg | ggc | 1555 |
| Thr | Thr | Gly | Thr | Thr | Leu | Val | Phe | Asp | Glu | Val | Asp | Ala | Gly | Val | Gly | |
| 470 | | | | | 475 | | | | | 480 | | | | | 485 | |
| gga | cgc | gca | gcg | gtg | gaa | atc | ggt | cgc | cgc | ctg | gcc | cgc | ctt | gcc | acc | 1603 |
| Gly | Arg | Ala | Ala | Val | Glu | Ile | Gly | Arg | Arg | Leu | Ala | Arg | Leu | Ala | Thr | |
| | | | 490 | | | | | 495 | | | | | 500 | | | |
| aaa | aac | caa | gtc | atc | gtg | gtc | acc | cat | ctc | cca | cag | gtc | gct | gct | tac | 1651 |
| Lys | Asn | Gln | Val | Ile | Val | Val | Thr | His | Leu | Pro | Gln | Val | Ala | Ala | Tyr | |
| | | | 505 | | | | | 510 | | | | | 515 | | | |
| gcc | gac | acg | cac | ctg | cac | gtt | gcc | aag | aat | gta | gga | gaa | gcc | tcc | gtg | 1699 |
| Ala | Asp | Thr | His | Leu | His | Val | Ala | Lys | Asn | Val | Gly | Glu | Ala | Ser | Val | |
| | | 520 | | | | | 525 | | | | | 530 | | | | |
| acc | tca | gga | gtg | gag | tca | ctg | acc | ttc | gac | cga | cgc | gtg | gaa | gag | ctc | 1747 |
| Thr | Ser | Gly | Val | Glu | Ser | Leu | Thr | Phe | Asp | Arg | Arg | Val | Glu | Glu | Leu | |
| | 535 | | | | | 540 | | | | | 545 | | | | | |
| tcc | cgc | atg | ctc | gct | ggc | ctc | gac | gac | acc | gcc | acc | ggc | cga | gcc | cac | 1795 |
| Ser | Arg | Met | Leu | Ala | Gly | Leu | Asp | Asp | Thr | Ala | Thr | Gly | Arg | Ala | His | |
| 550 | | | | | 555 | | | | | 560 | | | | | 565 | |
| gca | acg | gag | ctg | ctc | gag | cgt | gca | cag | cgt | gaa | aag | gaa | gat | att | aac | 1843 |
| Ala | Thr | Glu | Leu | Leu | Glu | Arg | Ala | Gln | Arg | Glu | Lys | Glu | Asp | Ile | Asn | |
| | | | 570 | | | | | 575 | | | | | 580 | | | |
| gag | gag | cga | gta | gaa | cca | ctt | ctc | gcc | gcc | agt | gca | taagagtttt | | | | 1889 |
| Glu | Glu | Arg | Val | Glu | Pro | Leu | Leu | Ala | Ala | Ser | Ala | | | | | |
| | | 585 | | | | | 590 | | | | | | | | | | cttggaattt tttaggcgcg 1909

<210> SEQ ID NO 44
<211> LENGTH: 593
<212> TYPE: PRT
<213> ORGANISM: Corynebacterium glutamicum

<400> SEQUENCE: 44

Met Leu Val Asp Ile Ala Ile Glu Asn Leu Gly Val Ile Pro Ala Ala

-continued

```
   1               5              10              15
Ser Ala Glu Phe Ser Ser Gly Leu Thr Val Leu Thr Gly Glu Thr Gly
             20                  25                  30
Ala Gly Lys Thr Met Val Val Thr Gly Leu Arg Leu Leu Ser Gly Gly
             35                  40                  45
Arg Ala Asp Ala Ser Arg Val Arg Thr Gly Ser Pro Gln Ala Val Val
             50                  55                  60
Glu Gly Arg Phe Val Thr Gln Gly Val Pro Cys Asp Ile Val Glu Arg
 65                  70                  75                  80
Ala Thr Gly Ile Val Ser Asn Ala Gly Ala Ala Asp Glu Asn Gly
                 85                  90                  95
Glu Phe Leu Ala Val Arg Ser Val Gly Ala Asn Gly Arg Ser Lys Ala
                100                 105                 110
His Leu Gly Gly Arg Ser Val Pro Ala Ala Thr Leu Ser Glu Phe Ser
                115                 120                 125
Asp Glu Leu Leu Thr Ile His Gly Gln Asn Asp Gln Leu Arg Leu Leu
    130                 135                 140
Ser Pro Glu Arg Gln Leu Glu Ala Leu Asp Arg Phe Asp Pro Glu Leu
145                 150                 155                 160
Ala Gln Leu Arg Lys Asn Tyr Asn Ala Lys Tyr Leu Thr Trp Lys Ser
                165                 170                 175
Leu Asp Lys Asp Leu Gln Lys Arg Leu Ser Ser Arg Arg Glu Leu Ala
                180                 185                 190
Gln Glu Val Asp Arg Leu Gln Phe Ala Ile Asn Glu Ile Glu Val
                195                 200                 205
Ser Pro Gln Pro Gly Glu Asp Ala Glu Leu Val Glu Gln Ile Arg Arg
    210                 215                 220
Leu Gln Asp Val Asp Thr Leu Arg Glu Gln Ala Ala Thr Ala Leu Ala
225                 230                 235                 240
Ala Ile Asp Gly Ala Gly Ser Leu Ser Asp Ala Met Gly Gly Ser Gly
                245                 250                 255
Gly Phe Asp Glu Ser Gln Glu Ser Ala Ser Asp Gln Leu Gly Gln Ala
                260                 265                 270
Glu Ser Ala Leu Ala Gly Ser Asp Asp Ser Lys Leu Lys Asp Ile Ala
    275                 280                 285
Val Gln Leu Ala Glu Ile Thr Ser Gln Leu Ser Gln Val Ser Met Glu
    290                 295                 300
Leu Gly Gly Phe Leu Ser Asp Leu Pro Ala Asp Pro Gln Ala Leu Asp
305                 310                 315                 320
Asp Met Leu Thr Arg Gln Gln Leu Lys Leu Leu Thr Arg Lys Tyr
                325                 330                 335
Ala Ala Asp Ile Asp Gly Val Ile Glu Trp Gln Arg Lys Ala Gln Ile
                340                 345                 350
Arg Leu Asp Ser Ile Asp Ile Ser Glu Ala Leu Asp Lys Leu Lys
                355                 360                 365
Glu Asp Ala Lys Lys Ala Gln Ala Ser Met Met Arg Ala Ala Lys Lys
    370                 375                 380
Leu Ser Ala Val Arg Ala Lys Ala Ala Thr Lys Leu Gly Thr Thr Val
385                 390                 395                 400
Thr Glu Glu Leu Gln Gly Leu Ala Met Gln Lys Ala Arg Phe Glu Val
                405                 410                 415
Ala Leu Thr Ser Ile Glu Ala Cys Ala Ser Gly Ile Asp Gln Val Glu
                420                 425                 430
```

```
Phe Gln Leu Ala Ala Asn Ala Phe Ala Gln Pro Arg Pro Leu Ala Ser
        435                 440                 445
Ser Ala Ser Gly Gly Glu Leu Ser Arg Val Met Leu Ala Leu Glu Val
        450                 455                 460
Ile Leu Ala Ala Gly Thr Thr Gly Thr Thr Leu Val Phe Asp Glu Val
465                 470                 475                 480
Asp Ala Gly Val Gly Gly Arg Ala Val Glu Ile Gly Arg Arg Leu
                485                 490                 495
Ala Arg Leu Ala Thr Lys Asn Gln Val Ile Val Thr His Leu Pro
        500                 505                 510
Gln Val Ala Ala Tyr Ala Asp Thr His Leu His Val Ala Lys Asn Val
        515                 520                 525
Gly Glu Ala Ser Val Thr Ser Gly Val Glu Ser Leu Thr Phe Asp Arg
        530                 535                 540
Arg Val Glu Glu Leu Ser Arg Met Leu Ala Gly Leu Asp Asp Thr Ala
545                 550                 555                 560
Thr Gly Arg Ala His Ala Thr Glu Leu Leu Glu Arg Ala Gln Arg Glu
                565                 570                 575
Lys Glu Asp Ile Asn Glu Glu Arg Val Glu Pro Leu Leu Ala Ala Ser
        580                 585                 590
Ala
```

<210> SEQ ID NO 45
<211> LENGTH: 265
<212> TYPE: DNA
<213> ORGANISM: Corynebacterium glutamicum
<220> FEATURE:
<221> NAME/KEY: CDS
<222> LOCATION: (101)..(235)
<223> OTHER INFORMATION: RXA01651

<400> SEQUENCE: 45

```
caatctctaa ggagaaagtt tatgacaaat aggacctgac ccctgtttgg tagacaccta    60
acatcccaac attctgggac agaaaggtaa cctacctatc atg cca acc aag acc     115
                                              Met Pro Thr Lys Thr
                                                1               5 tac tcc gag gag ttc aaa cgc gac gcc gtt gct ttg tac gag aac tcc    163
Tyr Ser Glu Glu Phe Lys Arg Asp Ala Val Ala Leu Tyr Glu Asn Ser
             10                  15                  20 gat ggg gcc tca ctc caa cag atc gcc aac gat ctc ggc atc aac cga    211
Asp Gly Ala Ser Leu Gln Gln Ile Ala Asn Asp Leu Gly Ile Asn Arg
         25                  30                  35 gta acc ctg aaa aac ttc gat caa taaatacggt gcgcatgcct caaccaacac    265
Val Thr Leu Lys Asn Phe Asp Gln
         40              45
```

<210> SEQ ID NO 46
<211> LENGTH: 45
<212> TYPE: PRT
<213> ORGANISM: Corynebacterium glutamicum

<400> SEQUENCE: 46

```
Met Pro Thr Lys Thr Tyr Ser Glu Glu Phe Lys Arg Asp Ala Val Ala
  1               5                  10                  15

Leu Tyr Glu Asn Ser Asp Gly Ala Ser Leu Gln Gln Ile Ala Asn Asp
             20                  25                  30

Leu Gly Ile Asn Arg Val Thr Leu Lys Asn Phe Asp Gln
         35                  40              45
```

```
<210> SEQ ID NO 47
<211> LENGTH: 538
<212> TYPE: DNA
<213> ORGANISM: Corynebacterium glutamicum
<220> FEATURE:
<221> NAME/KEY: CDS
<222> LOCATION: (101)..(508)
<223> OTHER INFORMATION: RXA01710

<400> SEQUENCE: 47
tctcggcgct aatctggttt attggtgata tccgagccaa gggaactccg agctcaccca        60
ttaccactga tccaacgcac gaccatcttg agaggacagc atg aca gac ttc aaa        115
                                             Met Thr Asp Phe Lys
                                               1               5 ctc atc agc gat acc gag tgg cgc gaa cgc ctc acc ccg cag gaa ttc        163
Leu Ile Ser Asp Thr Glu Trp Arg Glu Arg Leu Thr Pro Gln Glu Phe
               10                  15                  20 cat gtc ctc cgc gaa gcc ggc acc gaa cca cct cac gtc ggt gaa tac        211
His Val Leu Arg Glu Ala Gly Thr Glu Pro Pro His Val Gly Glu Tyr
           25                  30                  35 acc aac acc acc acc gaa ggt gtg tac tcc tgt cgc gcc tgt ggt gaa        259
Thr Asn Thr Thr Thr Glu Gly Val Tyr Ser Cys Arg Ala Cys Gly Glu
       40                  45                  50 gag tta ttc cgc tcc acc gag aag ttt gaa tcc cac tgc ggt tgg cct        307
Glu Leu Phe Arg Ser Thr Glu Lys Phe Glu Ser His Cys Gly Trp Pro
55                  60                  65 tcc ttc ttc tcc cca ctt gct ggc gac aaa atc att gag aag gaa gat        355
Ser Phe Phe Ser Pro Leu Ala Gly Asp Lys Ile Ile Glu Lys Glu Asp
 70                  75                  80                  85 ctt tcc ctc ggt atg cgt cgc gtt gag att ctg tgc gct aac tgc ggc        403
Leu Ser Leu Gly Met Arg Arg Val Glu Ile Leu Cys Ala Asn Cys Gly
                 90                  95                 100 tct cac atg ggt cac gtc ttc gaa ggc gaa ggc tac gac acc ccc acc        451
Ser His Met Gly His Val Phe Glu Gly Glu Gly Tyr Asp Thr Pro Thr
            105                 110                 115 gat ctt cgt tac tgc att aac tcc atc agc ttg aag ctg gaa gaa aag        499
Asp Leu Arg Tyr Cys Ile Asn Ser Ile Ser Leu Lys Leu Glu Glu Lys
        120                 125                 130 cca gtt tcc taagcttccg agcacgaaac gagccttggc                           538
Pro Val Ser
    135

<210> SEQ ID NO 48
<211> LENGTH: 136
<212> TYPE: PRT
<213> ORGANISM: Corynebacterium glutamicum

<400> SEQUENCE: 48

Met Thr Asp Phe Lys Leu Ile Ser Asp Thr Glu Trp Arg Glu Arg Leu
  1               5                  10                  15

Thr Pro Gln Glu Phe His Val Leu Arg Glu Ala Gly Thr Glu Pro Pro
                 20                  25                  30

His Val Gly Glu Tyr Thr Asn Thr Thr Thr Glu Gly Val Tyr Ser Cys
             35                  40                  45

Arg Ala Cys Gly Glu Glu Leu Phe Arg Ser Thr Glu Lys Phe Glu Ser
         50                  55                  60

His Cys Gly Trp Pro Ser Phe Phe Ser Pro Leu Ala Gly Asp Lys Ile
 65                  70                  75                  80

Ile Glu Lys Glu Asp Leu Ser Leu Gly Met Arg Arg Val Glu Ile Leu
```

-continued

```
                        85                  90                  95
Cys Ala Asn Cys Gly Ser His Met Gly His Val Phe Glu Gly Glu Gly
            100                 105                 110
Tyr Asp Thr Pro Thr Asp Leu Arg Tyr Cys Ile Asn Ser Ile Ser Leu
            115                 120                 125
Lys Leu Glu Glu Lys Pro Val Ser
130                 135

<210> SEQ ID NO 49
<211> LENGTH: 1417
<212> TYPE: DNA
<213> ORGANISM: Corynebacterium glutamicum
<220> FEATURE:
<221> NAME/KEY: CDS
<222> LOCATION: (101)..(1387)
<223> OTHER INFORMATION: RXA01852

<400> SEQUENCE: 49
aaccaccacc atgcgtgcag aacgcactgg taacccttc ttgctggcac tgtagggcta      60
agttccgtac tacttcttcg aataggtatc gttaataatc gtg agt caa aac aag     115
                                              Val Ser Gln Asn Lys
                                                1               5 tcc aag tct gaa aag ctt cag tca ttt gct gca ccc aag ggt gtt cct     163
Ser Lys Ser Glu Lys Leu Gln Ser Phe Ala Ala Pro Lys Gly Val Pro
            10                  15                  20 gat tac gcc cca cca aaa tct gca gcg ttt tta gca gtc cgt gat gcc     211
Asp Tyr Ala Pro Pro Lys Ser Ala Ala Phe Leu Ala Val Arg Asp Ala
        25                  30                  35 ttt gtt aat caa gca cat aag gcc ggg ttt gag cat att gag ctg ccg     259
Phe Val Asn Gln Ala His Lys Ala Gly Phe Glu His Ile Glu Leu Pro
    40                  45                  50 atc ttt gaa gac acc ggc ttg ttt gcg cgt ggt gtt ggt gag tcc act     307
Ile Phe Glu Asp Thr Gly Leu Phe Ala Arg Gly Val Gly Glu Ser Thr
55                  60                  65 gac gta gtg agc aag gaa atg tac acc ttc gct gat cgt ggc gag cgc     355
Asp Val Val Ser Lys Glu Met Tyr Thr Phe Ala Asp Arg Gly Glu Arg
    70                  75                  80                  85 tct gtc acg ctg cgc cca gaa ggc act gca ggc gtg atg cgt gca gtt     403
Ser Val Thr Leu Arg Pro Glu Gly Thr Ala Gly Val Met Arg Ala Val
                90                  95                 100 att gaa cac agc ctg gac cgt gga cag ctt ccc gta aag ctg aac tac     451
Ile Glu His Ser Leu Asp Arg Gly Gln Leu Pro Val Lys Leu Asn Tyr
            105                 110                 115 gcc gga cca ttc ttc cgt tat gag cgt cct cag gca ggg cgt tac cgt     499
Ala Gly Pro Phe Phe Arg Tyr Glu Arg Pro Gln Ala Gly Arg Tyr Arg
        120                 125                 130 cag ctt cag caa gta ggc gta gag gca att ggt gtg gat gat cca gcg     547
Gln Leu Gln Gln Val Gly Val Glu Ala Ile Gly Val Asp Asp Pro Ala
    135                 140                 145 ctt gat gcg gag atc att gcg ctt gct gat cgt tct tac cgc agc ttg     595
Leu Asp Ala Glu Ile Ile Ala Leu Ala Asp Arg Ser Tyr Arg Ser Leu
150                 155                 160                 165 ggg ctg cag gat ttc cgt ctg gag ctc acc agc ttg ggt gat cgt cac     643
Gly Leu Gln Asp Phe Arg Leu Glu Leu Thr Ser Leu Gly Asp Arg His
                170                 175                 180 tgc cgt ccc gag tat cgt cag aag ctg cag gat ttc ttg ttt gca ctt     691
Cys Arg Pro Glu Tyr Arg Gln Lys Leu Gln Asp Phe Leu Phe Ala Leu
            185                 190                 195 cct ttg gat gag gaa acc cgc aag cgc gca gag atc aac cca ctt cgg     739
Pro Leu Asp Glu Glu Thr Arg Lys Arg Ala Glu Ile Asn Pro Leu Arg
```

-continued

```
             200                 205                 210
gtg ttg gat gat aag cgt cct gaa gtc caa gag atg act gcg gat gca       787
Val Leu Asp Asp Lys Arg Pro Glu Val Gln Glu Met Thr Ala Asp Ala
    215                 220                 225 cca ttg atg ctg gat cac ctt gat gca gag tgc cgt gag cac ttt gaa       835
Pro Leu Met Leu Asp His Leu Asp Ala Glu Cys Arg Glu His Phe Glu
230                 235                 240                 245 aca gtg act ggt ttg ctc gat gac atg ggt gtt cca tat gtg att aac       883
Thr Val Thr Gly Leu Leu Asp Asp Met Gly Val Pro Tyr Val Ile Asn
                250                 255                 260 cca cgc atg gtt cgt ggt ttg gat tac tac acc aag act tgt ttt gag       931
Pro Arg Met Val Arg Gly Leu Asp Tyr Tyr Thr Lys Thr Cys Phe Glu
            265                 270                 275 ttc gtt cac gat ggc ctg ggc gca cag tct ggc att ggt ggc ggc gga       979
Phe Val His Asp Gly Leu Gly Ala Gln Ser Gly Ile Gly Gly Gly Gly
        280                 285                 290 cgc tac gac ggt ctg atg gca cag ctt ggc gga cag gat ctg tct ggc      1027
Arg Tyr Asp Gly Leu Met Ala Gln Leu Gly Gly Gln Asp Leu Ser Gly
    295                 300                 305 atc ggc tat ggc ctg ggt gtg gat cgc acc atg ttg gct ctg gaa gct      1075
Ile Gly Tyr Gly Leu Gly Val Asp Arg Thr Met Leu Ala Leu Glu Ala
310                 315                 320                 325 gaa ggt gtg act gtt ggt gct gag cgt cgc gtt gat gtg tac ggc gtt      1123
Glu Gly Val Thr Val Gly Ala Glu Arg Arg Val Asp Val Tyr Gly Val
                330                 335                 340 cca ctg ggc aag gat gct aag aag gct ctt gct gga atc gtg aac acg      1171
Pro Leu Gly Lys Asp Ala Lys Lys Ala Leu Ala Gly Ile Val Asn Thr
            345                 350                 355 ctg cgc gct gcg ggt att tcc acc gat atg tct tac ggc gac cgt ggc      1219
Leu Arg Ala Ala Gly Ile Ser Thr Asp Met Ser Tyr Gly Asp Arg Gly
        360                 365                 370 ctg aag ggt gcc atg aag ggc gct gac cgc tcc aac gcg ttg tac acc      1267
Leu Lys Gly Ala Met Lys Gly Ala Asp Arg Ser Asn Ala Leu Tyr Thr
    375                 380                 385 ttg gtg ctg ggc gag cag gag ctg gag aac aac acc atc gcg gtg aag      1315
Leu Val Leu Gly Glu Gln Glu Leu Glu Asn Asn Thr Ile Ala Val Lys
390                 395                 400                 405 gat atg cgt gcg cat gag cag cac gat gtc gca ttg gac gag gtt gtg      1363
Asp Met Arg Ala His Glu Gln His Asp Val Ala Leu Asp Glu Val Val
                410                 415                 420 gcc ttt ttg cag ggg aaa ctt att taaataattc ataagtaaaa aaccgtcaat     1417
Ala Phe Leu Gln Gly Lys Leu Ile
            425
```

<210> SEQ ID NO 50
<211> LENGTH: 429
<212> TYPE: PRT
<213> ORGANISM: Corynebacterium glutamicum

<400> SEQUENCE: 50

```
Val Ser Gln Asn Lys Ser Lys Ser Glu Lys Leu Gln Ser Phe Ala Ala
  1               5                  10                  15

Pro Lys Gly Val Pro Asp Tyr Ala Pro Lys Ser Ala Ala Phe Leu
                 20                  25                  30

Ala Val Arg Asp Ala Phe Val Asn Gln Ala His Lys Ala Gly Phe Glu
             35                  40                  45

His Ile Glu Leu Pro Ile Phe Glu Asp Thr Gly Leu Phe Ala Arg Gly
         50                  55                  60

Val Gly Glu Ser Thr Asp Val Val Ser Lys Glu Met Tyr Thr Phe Ala
```

```
                65                  70                  75                  80
Asp Arg Gly Glu Arg Ser Val Thr Leu Arg Pro Glu Gly Thr Ala Gly
                    85                  90                  95

Val Met Arg Ala Val Ile Glu His Ser Leu Asp Arg Gly Gln Leu Pro
                100                 105                 110

Val Lys Leu Asn Tyr Ala Gly Pro Phe Phe Arg Tyr Glu Arg Pro Gln
            115                 120                 125

Ala Gly Arg Tyr Arg Gln Leu Gln Gln Val Gly Val Glu Ala Ile Gly
        130                 135                 140

Val Asp Asp Pro Ala Leu Asp Ala Glu Ile Ile Ala Leu Ala Asp Arg
145                 150                 155                 160

Ser Tyr Arg Ser Leu Gly Leu Gln Asp Phe Arg Leu Glu Leu Thr Ser
                165                 170                 175

Leu Gly Asp Arg His Cys Arg Pro Glu Tyr Arg Gln Lys Leu Gln Asp
            180                 185                 190

Phe Leu Phe Ala Leu Pro Leu Asp Glu Thr Arg Lys Arg Ala Glu
        195                 200                 205

Ile Asn Pro Leu Arg Val Leu Asp Asp Lys Arg Pro Glu Val Gln Glu
    210                 215                 220

Met Thr Ala Asp Ala Pro Leu Met Leu Asp His Leu Asp Ala Glu Cys
225                 230                 235                 240

Arg Glu His Phe Glu Thr Val Thr Gly Leu Leu Asp Asp Met Gly Val
                245                 250                 255

Pro Tyr Val Ile Asn Pro Arg Met Val Arg Gly Leu Asp Tyr Tyr Thr
            260                 265                 270

Lys Thr Cys Phe Glu Phe Val His Asp Gly Leu Gly Ala Gln Ser Gly
        275                 280                 285

Ile Gly Gly Gly Arg Tyr Asp Gly Leu Met Ala Gln Leu Gly Gly
    290                 295                 300

Gln Asp Leu Ser Gly Ile Gly Tyr Gly Leu Gly Val Asp Arg Thr Met
305                 310                 315                 320

Leu Ala Leu Glu Ala Glu Gly Val Thr Val Gly Ala Glu Arg Arg Val
                325                 330                 335

Asp Val Tyr Gly Val Pro Leu Gly Lys Asp Ala Lys Lys Ala Leu Ala
            340                 345                 350

Gly Ile Val Asn Thr Leu Arg Ala Ala Gly Ile Ser Thr Asp Met Ser
        355                 360                 365

Tyr Gly Asp Arg Gly Leu Lys Gly Ala Met Lys Gly Ala Asp Arg Ser
    370                 375                 380

Asn Ala Leu Tyr Thr Leu Val Leu Gly Glu Gln Glu Leu Glu Asn Asn
385                 390                 395                 400

Thr Ile Ala Val Lys Asp Met Arg Ala His Glu Gln His Asp Val Ala
                405                 410                 415

Leu Asp Glu Val Val Ala Phe Leu Gln Gly Lys Leu Ile
            420                 425
```

<210> SEQ ID NO 51
<211> LENGTH: 955
<212> TYPE: DNA
<213> ORGANISM: Corynebacterium glutamicum
<220> FEATURE:
<221> NAME/KEY: CDS
<222> LOCATION: (101)..(925)
<223> OTHER INFORMATION: RXA01913

<400> SEQUENCE: 51

```
acctgtacga tcactttta gacgggcggg tagggctact gtgccctaac ctaagcttgt      60
aaagcattaa ttatccatac ataaggagga tcgccccgta atg gcg aac tac acc     115
                                              Met Ala Asn Tyr Thr
                                               1               5 gct gcg gat gtt aag aag ctc cgc gaa ctc acc ggt tcc ggc atg ctc     163
Ala Ala Asp Val Lys Lys Leu Arg Glu Leu Thr Gly Ser Gly Met Leu
             10              15                  20 gat tgc aag aag gct ctg gag gag tcc gct ggc gac ttc gac aag gct     211
Asp Cys Lys Lys Ala Leu Glu Glu Ser Ala Gly Asp Phe Asp Lys Ala
         25              30              35 gtt gag atc ctg cgc gtc aag ggc gca aag gac gtc gga aag cgt gca     259
Val Glu Ile Leu Arg Val Lys Gly Ala Lys Asp Val Gly Lys Arg Ala
         40              45              50 gag cgt aac gct acc gaa ggt ctc gtt gca gtt tct ggc aac acc atg     307
Glu Arg Asn Ala Thr Glu Gly Leu Val Ala Val Ser Gly Asn Thr Met
     55              60              65 gtc gag gtc aac tct gag acc gac ttc gtt gca aag aac tct gac ttc     355
Val Glu Val Asn Ser Glu Thr Asp Phe Val Ala Lys Asn Ser Asp Phe
 70              75              80              85 aag gaa ttc gct gca aag gtt gca gac gca gca gca gct gca aag gct     403
Lys Glu Phe Ala Ala Lys Val Ala Asp Ala Ala Ala Ala Ala Lys Ala
             90              95             100 aac tcc cag gaa gag ctc gca gca gtt gac gtg gac gga cag acc gca     451
Asn Ser Gln Glu Glu Leu Ala Ala Val Asp Val Asp Gly Gln Thr Ala
        105             110             115 gac gca gct ctg cag gag ttc tcc gca aag atc ggc gag aag ctt gag     499
Asp Ala Ala Leu Gln Glu Phe Ser Ala Lys Ile Gly Glu Lys Leu Glu
        120             125             130 ctt cgt cgc gca gta acc ctc gag ggc gac aag acc gct gtt tac ctc     547
Leu Arg Arg Ala Val Thr Leu Glu Gly Asp Lys Thr Ala Val Tyr Leu
        135             140             145 cac cag cgt tcc gct gac ctg cca cca gca gtt ggc gtt ttg gtt gct     595
His Gln Arg Ser Ala Asp Leu Pro Pro Ala Val Gly Val Leu Val Ala
150             155             160             165 ttc acc ggt gaa ggt gaa gca gct gag gca gct gca cgt cag gct gca     643
Phe Thr Gly Glu Gly Glu Ala Ala Glu Ala Ala Ala Arg Gln Ala Ala
            170             175             180 atg cag att gct gct ctg aag gct tct tac ctc acc cgt gag gac gtt     691
Met Gln Ile Ala Ala Leu Lys Ala Ser Tyr Leu Thr Arg Glu Asp Val
        185             190             195 cct gca gag atc atc gag aag gag cgc tcc atc gct gag cag atc act     739
Pro Ala Glu Ile Ile Glu Lys Glu Arg Ser Ile Ala Glu Gln Ile Thr
        200             205             210 cgc gaa gag ggc aag cca gag cag gct atc cct aag atc gtt gag ggt     787
Arg Glu Glu Gly Lys Pro Glu Gln Ala Ile Pro Lys Ile Val Glu Gly
        215             220             225 cgt ttg aat ggc ttc tac aag gag aac gta ctt ctt gag cag tcc tcg     835
Arg Leu Asn Gly Phe Tyr Lys Glu Asn Val Leu Leu Glu Gln Ser Ser
230             235             240             245 gta gct gac agc aag aag acc gtt aag gct ctt ctg gac gag gct ggc     883
Val Ala Asp Ser Lys Lys Thr Val Lys Ala Leu Leu Asp Glu Ala Gly
            250             255             260 gtt acc gtc acc tcc ttc gct cgc ttc gag gtc ggc cag gct             925
Val Thr Val Thr Ser Phe Ala Arg Phe Glu Val Gly Gln Ala
            265             270             275 taaggccact tgaaggttgt gggtgggtgt                                    955
```

<210> SEQ ID NO 52

<211> LENGTH: 275
<212> TYPE: PRT
<213> ORGANISM: Corynebacterium glutamicum

<400> SEQUENCE: 52

```
Met Ala Asn Tyr Thr Ala Ala Asp Val Lys Lys Leu Arg Glu Leu Thr
  1               5                  10                  15
Gly Ser Gly Met Leu Asp Cys Lys Lys Ala Leu Glu Glu Ser Ala Gly
             20                  25                  30
Asp Phe Asp Lys Ala Val Glu Ile Leu Arg Val Lys Gly Ala Lys Asp
         35                  40                  45
Val Gly Lys Arg Ala Glu Arg Asn Ala Thr Glu Gly Leu Val Ala Val
     50                  55                  60
Ser Gly Asn Thr Met Val Glu Val Asn Ser Glu Thr Asp Phe Val Ala
 65                  70                  75                  80
Lys Asn Ser Asp Phe Lys Glu Phe Ala Lys Val Ala Asp Ala Ala
                 85                  90                  95
Ala Ala Ala Lys Ala Asn Ser Gln Glu Glu Leu Ala Ala Val Asp Val
            100                 105                 110
Asp Gly Gln Thr Ala Asp Ala Ala Leu Gln Glu Phe Ser Ala Lys Ile
        115                 120                 125
Gly Glu Lys Leu Glu Leu Arg Arg Ala Val Thr Leu Glu Gly Asp Lys
    130                 135                 140
Thr Ala Val Tyr Leu His Gln Arg Ser Ala Asp Leu Pro Pro Ala Val
145                 150                 155                 160
Gly Val Leu Val Ala Phe Thr Gly Glu Gly Glu Ala Ala Glu Ala Ala
                165                 170                 175
Ala Arg Gln Ala Ala Met Gln Ile Ala Ala Leu Lys Ala Ser Tyr Leu
            180                 185                 190
Thr Arg Glu Asp Val Pro Ala Glu Ile Ile Glu Lys Glu Arg Ser Ile
        195                 200                 205
Ala Glu Gln Ile Thr Arg Glu Glu Gly Lys Pro Glu Gln Ala Ile Pro
    210                 215                 220
Lys Ile Val Glu Gly Arg Leu Asn Gly Phe Tyr Lys Glu Asn Val Leu
225                 230                 235                 240
Leu Glu Gln Ser Ser Val Ala Asp Ser Lys Lys Thr Val Lys Ala Leu
                245                 250                 255
Leu Asp Glu Ala Gly Val Thr Val Thr Ser Phe Ala Arg Phe Glu Val
            260                 265                 270
Gly Gln Ala
        275
```

<210> SEQ ID NO 53
<211> LENGTH: 1747
<212> TYPE: DNA
<213> ORGANISM: Corynebacterium glutamicum
<220> FEATURE:
<221> NAME/KEY: CDS
<222> LOCATION: (101)..(1717)
<223> OTHER INFORMATION: RXA02145

<400> SEQUENCE: 53

```
cactgccaca gctgccaatt accgttgatg aagagggcta cctcatcgcc gctggtaact    60
tcattgagcc actcggccct gcattctggg agcgtaagtc atg agt cta gct acc    115
                                             Met Ser Leu Ala Thr
                                               1               5 gtg gga aac aat ctt gat tcc cgt tac acc atg gcg tcg ggt atc cgt    163
```

```
                Val Gly Asn Asn Leu Asp Ser Arg Tyr Thr Met Ala Ser Gly Ile Arg
                             10                  15                  20 cgc cag atc aac aag gtc ttc cca act cac tgg tcc ttc atg ctc ggc         211
Arg Gln Ile Asn Lys Val Phe Pro Thr His Trp Ser Phe Met Leu Gly
                25                  30                  35 gag att gcg ctt tac agc ttc atc gtc ttg ctg ctg act ggt gtc tac         259
Glu Ile Ala Leu Tyr Ser Phe Ile Val Leu Leu Leu Thr Gly Val Tyr
            40                  45                  50 ctg acc ctg ttc ttc gac cca tca atc acc aag gtc att tat gac ggc         307
Leu Thr Leu Phe Phe Asp Pro Ser Ile Thr Lys Val Ile Tyr Asp Gly
        55                  60                  65 ggc tac ctc cca ctg aac ggt gtg gag atg tcc cgt gca tac gca act         355
Gly Tyr Leu Pro Leu Asn Gly Val Glu Met Ser Arg Ala Tyr Ala Thr
70                  75                  80                  85 gcg ttg gat att tcc ttc gag gtt cgc ggt ggt ctg ttc atc cgc cag         403
Ala Leu Asp Ile Ser Phe Glu Val Arg Gly Gly Leu Phe Ile Arg Gln
                90                  95                 100 atg cac cac tgg gca gcc ctg ctg ttc gtt gta tcc atg ctg gtt cac         451
Met His His Trp Ala Ala Leu Leu Phe Val Val Ser Met Leu Val His
                105                 110                 115 atg ctc cgt att ttc ttc acc ggt gcg ttc cgt cgc cca cgt gaa gca         499
Met Leu Arg Ile Phe Phe Thr Gly Ala Phe Arg Arg Pro Arg Glu Ala
        120                 125                 130 aac tgg atc atc ggt gtt gtt ctg atc atc ctg ggt atg gct gaa ggc         547
Asn Trp Ile Ile Gly Val Val Leu Ile Ile Leu Gly Met Ala Glu Gly
135                 140                 145 ttc atg ggt tac tcc ctg cct gat gac ctg ctc tct ggt gtt ggt ctt         595
Phe Met Gly Tyr Ser Leu Pro Asp Asp Leu Leu Ser Gly Val Gly Leu
150                 155                 160                 165 cga atc atg tcc gcc atc atc gtt ggt ctt ccg atc ata ggt acc tgg         643
Arg Ile Met Ser Ala Ile Ile Val Gly Leu Pro Ile Ile Gly Thr Trp
                170                 175                 180 atg cac tgg ctg atc ttc ggt gga gac ttc cca tcc gat ctg atg ctg         691
Met His Trp Leu Ile Phe Gly Gly Asp Phe Pro Ser Asp Leu Met Leu
                185                 190                 195 gac cgc ttc tac atc gca cac gtt cta atc atc cca gct atc ctg ctt         739
Asp Arg Phe Tyr Ile Ala His Val Leu Ile Ile Pro Ala Ile Leu Leu
        200                 205                 210 ggc ttg atc gca gct cac ctg gca ctt gtt tgg tac cag aag cac acc         787
Gly Leu Ile Ala Ala His Leu Ala Leu Val Trp Tyr Gln Lys His Thr
215                 220                 225 cag ttc cca ggc gct ggc cgc act gag aac aac gtg atc ggt atc cga         835
Gln Phe Pro Gly Ala Gly Arg Thr Glu Asn Asn Val Ile Gly Ile Arg
230                 235                 240                 245 atc atg cct ctg ttc gca gtt aag gct gtt gct ttc ggc ctc atc gtc         883
Ile Met Pro Leu Phe Ala Val Lys Ala Val Ala Phe Gly Leu Ile Val
                250                 255                 260 ttc ggt ttc ctc gca ctg ctt gct ggt gtc acc acc att aac gca att         931
Phe Gly Phe Leu Ala Leu Leu Ala Gly Val Thr Thr Ile Asn Ala Ile
            265                 270                 275 tgg aat ctt gga ccg tac aac cct tca cag gtg tct gct ggt tcc cag         979
Trp Asn Leu Gly Pro Tyr Asn Pro Ser Gln Val Ser Ala Gly Ser Gln
        280                 285                 290 cct gac gtt tac atg ctg tgg aca gat ggt gct gct cgt gtc atg ccg        1027
Pro Asp Val Tyr Met Leu Trp Thr Asp Gly Ala Ala Arg Val Met Pro
    295                 300                 305 gca tgg gag ctc tac ctc ggt aac tac act att cca gca gtc ttc tgg        1075
Ala Trp Glu Leu Tyr Leu Gly Asn Tyr Thr Ile Pro Ala Val Phe Trp
310                 315                 320                 325
```

```
gtt gct gtg atg ctg ggt atc ctc gtg gtt ctg ctt gtg act tac cca      1123
Val Ala Val Met Leu Gly Ile Leu Val Val Leu Leu Val Thr Tyr Pro
            330                 335                 340 ttc att gag cgt aag ttc acc ggc gac gat gca cac cac aac ttg ctg      1171
Phe Ile Glu Arg Lys Phe Thr Gly Asp Asp Ala His His Asn Leu Leu
                345                 350                 355 cag cgt cct cgc gat gtt cca gtc cgc acc tca ctc ggt gtc atg gcg      1219
Gln Arg Pro Arg Asp Val Pro Val Arg Thr Ser Leu Gly Val Met Ala
            360                 365                 370 ctt gtc ttc tac atc ctg ctt acc gtt tct ggt ggt aac gat gtt tac      1267
Leu Val Phe Tyr Ile Leu Leu Thr Val Ser Gly Gly Asn Asp Val Tyr
        375                 380                 385 gca atg cag ttc cat gtt tca ctg aac gcg atg acc tgg atc ggt cgt      1315
Ala Met Gln Phe His Val Ser Leu Asn Ala Met Thr Trp Ile Gly Arg
390                 395                 400                 405 atc ggc ctc atc gtt gga cca gct att gca tac ttc atc act tac cga      1363
Ile Gly Leu Ile Val Gly Pro Ala Ile Ala Tyr Phe Ile Thr Tyr Arg
                410                 415                 420 ctg tgc atc ggc ttg cag cgc tct gac cgc gag gtc ctg gag cac ggc      1411
Leu Cys Ile Gly Leu Gln Arg Ser Asp Arg Glu Val Leu Glu His Gly
            425                 430                 435 atc gag acc ggt atc atc aag cag atg cca aat ggt gcc ttc att gaa      1459
Ile Glu Thr Gly Ile Ile Lys Gln Met Pro Asn Gly Ala Phe Ile Glu
        440                 445                 450 gtt cac cag cca ctt ggc cca gtt gat gac cat ggt cac cca atc cca      1507
Val His Gln Pro Leu Gly Pro Val Asp Asp His Gly His Pro Ile Pro
    455                 460                 465 ctg cca tac gct ggc gct gcg gtt cca aag cag atg aac cag ctt ggt      1555
Leu Pro Tyr Ala Gly Ala Ala Val Pro Lys Gln Met Asn Gln Leu Gly
470                 475                 480                 485 tac gct gag gtt gaa acc cgc ggt gga ttc ttc gga cct gat cca gaa      1603
Tyr Ala Glu Val Glu Thr Arg Gly Gly Phe Phe Gly Pro Asp Pro Glu
                490                 495                 500 gac atc cgt gcg aag gct aag gaa att gag cac gca aac cac att gag      1651
Asp Ile Arg Ala Lys Ala Lys Glu Ile Glu His Ala Asn His Ile Glu
            505                 510                 515 gaa gcg aac act ctt cgt gca ctc aac gag gca aac att gag cgt gac      1699
Glu Ala Asn Thr Leu Arg Ala Leu Asn Glu Ala Asn Ile Glu Arg Asp
        520                 525                 530 aag aat gag ggc aag aac tagtttctag gacttcatct ctgaaactcc             1747
Lys Asn Glu Gly Lys Asn
    535

<210> SEQ ID NO 54
<211> LENGTH: 539
<212> TYPE: PRT
<213> ORGANISM: Corynebacterium glutamicum

<400> SEQUENCE: 54

Met Ser Leu Ala Thr Val Gly Asn Asn Leu Asp Ser Arg Tyr Thr Met
 1               5                  10                  15

Ala Ser Gly Ile Arg Arg Gln Ile Asn Lys Val Phe Pro Thr His Trp
            20                  25                  30

Ser Phe Met Leu Gly Glu Ile Ala Leu Tyr Ser Phe Ile Val Leu Leu
        35                  40                  45

Leu Thr Gly Val Tyr Leu Thr Leu Phe Phe Asp Pro Ser Ile Thr Lys
    50                  55                  60

Val Ile Tyr Asp Gly Gly Tyr Leu Pro Leu Asn Gly Val Glu Met Ser
65                  70                  75                  80
```

-continued

```
Arg Ala Tyr Ala Thr Ala Leu Asp Ile Ser Phe Glu Val Arg Gly Gly
                 85                  90                  95

Leu Phe Ile Arg Gln Met His His Trp Ala Ala Leu Leu Phe Val Val
            100                 105                 110

Ser Met Leu Val His Met Leu Arg Ile Phe Phe Thr Gly Ala Phe Arg
        115                 120                 125

Arg Pro Arg Glu Ala Asn Trp Ile Ile Gly Val Val Leu Ile Ile Leu
130                 135                 140

Gly Met Ala Glu Gly Phe Met Gly Tyr Ser Leu Pro Asp Asp Leu Leu
145                 150                 155                 160

Ser Gly Val Gly Leu Arg Ile Met Ser Ala Ile Val Gly Leu Pro
                165                 170                 175

Ile Ile Gly Thr Trp Met His Trp Leu Ile Phe Gly Gly Asp Phe Pro
            180                 185                 190

Ser Asp Leu Met Leu Asp Arg Phe Tyr Ile Ala His Val Leu Ile Ile
        195                 200                 205

Pro Ala Ile Leu Leu Gly Leu Ile Ala Ala His Leu Ala Leu Val Trp
    210                 215                 220

Tyr Gln Lys His Thr Gln Phe Pro Gly Ala Gly Arg Thr Glu Asn Asn
225                 230                 235                 240

Val Ile Gly Ile Arg Ile Met Pro Leu Phe Ala Val Lys Ala Val Ala
                245                 250                 255

Phe Gly Leu Ile Val Phe Gly Phe Leu Ala Leu Leu Ala Gly Val Thr
            260                 265                 270

Thr Ile Asn Ala Ile Trp Asn Leu Gly Pro Tyr Asn Pro Ser Gln Val
        275                 280                 285

Ser Ala Gly Ser Gln Pro Asp Val Tyr Met Leu Trp Thr Asp Gly Ala
    290                 295                 300

Ala Arg Val Met Pro Ala Trp Glu Leu Tyr Leu Gly Asn Tyr Thr Ile
305                 310                 315                 320

Pro Ala Val Phe Trp Val Ala Val Met Leu Gly Ile Leu Val Val Leu
                325                 330                 335

Leu Val Thr Tyr Pro Phe Ile Glu Arg Lys Phe Thr Gly Asp Asp Ala
            340                 345                 350

His His Asn Leu Leu Gln Arg Pro Arg Asp Val Pro Val Arg Thr Ser
        355                 360                 365

Leu Gly Val Met Ala Leu Val Phe Tyr Ile Leu Leu Thr Val Ser Gly
    370                 375                 380

Gly Asn Asp Val Tyr Ala Met Gln Phe His Val Ser Leu Asn Ala Met
385                 390                 395                 400

Thr Trp Ile Gly Arg Ile Gly Leu Ile Val Gly Pro Ala Ile Ala Tyr
                405                 410                 415

Phe Ile Thr Tyr Arg Leu Cys Ile Gly Leu Gln Arg Ser Asp Arg Glu
            420                 425                 430

Val Leu Glu His Gly Ile Glu Thr Gly Ile Ile Lys Gln Met Pro Asn
        435                 440                 445

Gly Ala Phe Ile Glu Val His Gln Pro Leu Gly Pro Val Asp Asp His
    450                 455                 460

Gly His Pro Ile Pro Leu Pro Tyr Ala Gly Ala Val Pro Lys Gln
465                 470                 475                 480

Met Asn Gln Leu Gly Tyr Ala Glu Val Glu Thr Arg Gly Gly Phe Phe
                485                 490                 495

Gly Pro Asp Pro Glu Asp Ile Arg Ala Lys Ala Lys Glu Ile Glu His
```

```
                500             505             510
Ala Asn His Ile Glu Glu Ala Asn Thr Leu Arg Ala Leu Asn Glu Ala
            515             520             525

Asn Ile Glu Arg Asp Lys Asn Glu Gly Lys Asn
    530             535

<210> SEQ ID NO 55
<211> LENGTH: 448
<212> TYPE: DNA
<213> ORGANISM: Corynebacterium glutamicum
<220> FEATURE:
<221> NAME/KEY: CDS
<222> LOCATION: (101)..(418)
<223> OTHER INFORMATION: RXA02236

<400> SEQUENCE: 55
gcaggctgac atccttggta ttaaccaggt gtaccctcga tttctggata ctttggtatt      60
ccttttgtca ctaaaaacca cacgataacg gaggaacccc gtg gcc ctt cca cag     115
                                             Val Ala Leu Pro Gln
                                               1               5 ttg act gat gag cag cgc aag gca gcg ctt gct aag gca gca gag gca     163
Leu Thr Asp Glu Gln Arg Lys Ala Ala Leu Ala Lys Ala Ala Glu Ala
             10                  15                  20 cgc aag gca cgc gca gag ctc aaa gag aac ctg aag cgc ggc aac act     211
Arg Lys Ala Arg Ala Glu Leu Lys Glu Asn Leu Lys Arg Gly Asn Thr
         25                  30                  35 aac ctc agg gaa gtt ctg gac aag gct gag tct gac gag atc atc ggc     259
Asn Leu Arg Glu Val Leu Asp Lys Ala Glu Ser Asp Glu Ile Ile Gly
     40                  45                  50 aag acc aag gtc tcc gct ctc ctc gag gct ctc cct aag gtt ggc aag     307
Lys Thr Lys Val Ser Ala Leu Leu Glu Ala Leu Pro Lys Val Gly Lys
 55                  60                  65 gtc aag gca aag gag att atg gac gag ctg ggc att gct cag acc cgt     355
Val Lys Ala Lys Glu Ile Met Asp Glu Leu Gly Ile Ala Gln Thr Arg
 70                  75                  80                  85 cgt ctt cgt gga ctg ggt gac cgt cag cgt cgc gca ctt ctc gag cgt     403
Arg Leu Arg Gly Leu Gly Asp Arg Gln Arg Arg Ala Leu Leu Glu Arg
             90                  95                 100 ttc ggc ttc gag gat taattcttca gtgtcgggcg ataaccaact                  448
Phe Gly Phe Glu Asp
            105

<210> SEQ ID NO 56
<211> LENGTH: 106
<212> TYPE: PRT
<213> ORGANISM: Corynebacterium glutamicum

<400> SEQUENCE: 56

Val Ala Leu Pro Gln Leu Thr Asp Glu Gln Arg Lys Ala Ala Leu Ala
  1               5                  10                  15

Lys Ala Ala Glu Ala Arg Lys Ala Arg Ala Glu Leu Lys Glu Asn Leu
                 20                  25                  30

Lys Arg Gly Asn Thr Asn Leu Arg Glu Val Leu Asp Lys Ala Glu Ser
             35                  40                  45

Asp Glu Ile Ile Gly Lys Thr Lys Val Ser Ala Leu Leu Glu Ala Leu
         50                  55                  60

Pro Lys Val Gly Lys Val Lys Ala Lys Glu Ile Met Asp Glu Leu Gly
 65                  70                  75                  80

Ile Ala Gln Thr Arg Arg Leu Arg Gly Leu Gly Asp Arg Gln Arg Arg
                 85                  90                  95
```

```
Ala Leu Leu Glu Arg Phe Gly Phe Glu Asp
            100                 105

<210> SEQ ID NO 57
<211> LENGTH: 1003
<212> TYPE: DNA
<213> ORGANISM: Corynebacterium glutamicum
<220> FEATURE:
<221> NAME/KEY: CDS
<222> LOCATION: (101)..(973)
<223> OTHER INFORMATION: RXA02267

<400> SEQUENCE: 57
tgcgctcggc aagtgttttg cttatcgacg tctccccaca taacaatccc aactcgaagc      60
accaacgatt caagccttat cagtttgta caggaaaata gtg caa aaa tgg ggt        115
                                          Val Gln Lys Trp Gly
                                            1               5 tta agc ttc gtg gag agg att gtc atc atg aac aac gtg caa cag ttt      163
Leu Ser Phe Val Glu Arg Ile Val Ile Met Asn Asn Val Gln Gln Phe
            10                  15                  20 cat cga ttt ttt gat gat tcc gca gtc tat tat ccc tgc ttc gtc ccg      211
His Arg Phe Phe Asp Asp Ser Ala Val Tyr Tyr Pro Cys Phe Val Pro
        25                  30                  35 ctt gac cga gcc atc ggc gaa cac ttt gat cgt cag aac aaa ccg atg      259
Leu Asp Arg Ala Ile Gly Glu His Phe Asp Arg Gln Asn Lys Pro Met
    40                  45                  50 tcc aga ttc atc gga acg ctc att ctg ccg tta gcc aaa ctg gaa gaa      307
Ser Arg Phe Ile Gly Thr Leu Ile Leu Pro Leu Ala Lys Leu Glu Glu
55                  60                  65 gcc gcc caa tac acc ggc gat gaa gtc ctt cgc gtg tcg gca gta atc      355
Ala Ala Gln Tyr Thr Gly Asp Glu Val Leu Arg Val Ser Ala Val Ile
 70                  75                  80                  85 agt act gat ggg ctc gct gat ctg cga agg gat ttt tac gaa ctc ccc      403
Ser Thr Asp Gly Leu Ala Asp Leu Arg Arg Asp Phe Tyr Glu Leu Pro
                90                  95                 100 aac atc gac atc gcc tcg gtg gaa atc aag ctg gtc ggc gca gcc ctc      451
Asn Ile Asp Ile Ala Ser Val Glu Ile Lys Leu Val Gly Ala Ala Leu
            105                 110                 115 acc aac acc gct tgg ttg gga gat gtg gaa aaa ctc atc caa caa cat      499
Thr Asn Thr Ala Trp Leu Gly Asp Val Glu Lys Leu Ile Gln Gln His
        120                 125                 130 cgc aac act ttc gta tgg gtt gag att ccg aca gcc ctg gtc acc gca      547
Arg Asn Thr Phe Val Trp Val Glu Ile Pro Thr Ala Leu Val Thr Ala
    135                 140                 145 gat att gtc cga aaa ctc cgc cac atg gga gct ggc ctg aaa tac aga      595
Asp Ile Val Arg Lys Leu Arg His Met Gly Ala Gly Leu Lys Tyr Arg
150                 155                 160                 165 act gga ggt gat agg gaa gag ctc ttc ccc tca ccg cag gac ttg gtc      643
Thr Gly Gly Asp Arg Glu Glu Leu Phe Pro Ser Pro Gln Asp Leu Val
                170                 175                 180 act gtg ctg cgc acc gcc atc gat gct gca ttg ccg ttt aaa ctc act      691
Thr Val Leu Arg Thr Ala Ile Asp Ala Ala Leu Pro Phe Lys Leu Thr
            185                 190                 195 gca ggc ctg cat cgt gct ctc agg tat cgt gac gag aaa acc ggc cga      739
Ala Gly Leu His Arg Ala Leu Arg Tyr Arg Asp Glu Lys Thr Gly Arg
        200                 205                 210 ctt cac ttc gga ttc ctc aac att gca gcc gcc gtg gcg aca ctt cgt      787
Leu His Phe Gly Phe Leu Asn Ile Ala Ala Ala Val Ala Thr Leu Arg
    215                 220                 225 gct gga aaa ggc gag gca gag gca ctg aag atc ctt gaa ggc gat gat      835
Ala Gly Lys Gly Glu Ala Glu Ala Leu Lys Ile Leu Glu Gly Asp Asp
```

-continued

```
Ala Gly Lys Gly Glu Ala Glu Ala Leu Lys Ile Leu Glu Gly Asp Asp
230                 235                 240                 245 gcc gct ccg ctt att cac gca cta caa agc ggc gaa aac tgg cgg gat    883
Ala Ala Pro Leu Ile His Ala Leu Gln Ser Gly Glu Asn Trp Arg Asp
                250                 255                 260 tcc ttc cgc agc ttc agt acc tgc aat gtt gtt gaa cca ctc aac act    931
Ser Phe Arg Ser Phe Ser Thr Cys Asn Val Val Glu Pro Leu Asn Thr
265                 270                 275 ctg att gat ctt gat gtg ttg gcg gaa gga gac gta cat ccc            973
Leu Ile Asp Leu Asp Val Leu Ala Glu Gly Asp Val His Pro
        280                 285                 290 taaggatcga cgctagttag atcggttttt                                   1003
```

<210> SEQ ID NO 58
<211> LENGTH: 291
<212> TYPE: PRT
<213> ORGANISM: Corynebacterium glutamicum

<400> SEQUENCE: 58

```
Val Gln Lys Trp Gly Leu Ser Phe Val Glu Arg Ile Val Ile Met Asn
1               5                   10                  15

Asn Val Gln Gln Phe His Arg Phe Asp Asp Ser Ala Val Tyr Tyr
            20                  25                  30

Pro Cys Phe Val Pro Leu Asp Arg Ala Ile Gly Glu His Phe Asp Arg
        35                  40                  45

Gln Asn Lys Pro Met Ser Arg Phe Ile Gly Thr Leu Ile Leu Pro Leu
    50                  55                  60

Ala Lys Leu Glu Glu Ala Ala Gln Tyr Thr Gly Asp Glu Val Leu Arg
65                  70                  75                  80

Val Ser Ala Val Ile Ser Thr Asp Gly Leu Ala Asp Leu Arg Arg Asp
                85                  90                  95

Phe Tyr Glu Leu Pro Asn Ile Asp Ile Ala Ser Val Glu Ile Lys Leu
            100                 105                 110

Val Gly Ala Ala Leu Thr Asn Thr Ala Trp Leu Gly Asp Val Glu Lys
        115                 120                 125

Leu Ile Gln Gln His Arg Asn Thr Phe Val Trp Val Glu Ile Pro Thr
    130                 135                 140

Ala Leu Val Thr Ala Asp Ile Val Arg Lys Leu Arg His Met Gly Ala
145                 150                 155                 160

Gly Leu Lys Tyr Arg Thr Gly Gly Asp Arg Glu Glu Leu Phe Pro Ser
                165                 170                 175

Pro Gln Asp Leu Val Thr Val Leu Arg Thr Ala Ile Asp Ala Ala Leu
            180                 185                 190

Pro Phe Lys Leu Thr Ala Gly Leu His Arg Ala Leu Arg Tyr Arg Asp
        195                 200                 205

Glu Lys Thr Gly Arg Leu His Phe Gly Phe Leu Asn Ile Ala Ala Ala
    210                 215                 220

Val Ala Thr Leu Arg Ala Gly Lys Gly Glu Ala Glu Ala Leu Lys Ile
225                 230                 235                 240

Leu Glu Gly Asp Asp Ala Ala Pro Leu Ile His Ala Leu Gln Ser Gly
                245                 250                 255

Glu Asn Trp Arg Asp Ser Phe Arg Ser Phe Ser Thr Cys Asn Val Val
            260                 265                 270

Glu Pro Leu Asn Thr Leu Ile Asp Leu Asp Val Leu Ala Glu Gly Asp
        275                 280                 285
```

```
Val His Pro
    290

<210> SEQ ID NO 59
<211> LENGTH: 1984
<212> TYPE: DNA
<213> ORGANISM: Corynebacterium glutamicum
<220> FEATURE:
<221> NAME/KEY: CDS
<222> LOCATION: (101)..(1954)
<223> OTHER INFORMATION: RXA02280

<400> SEQUENCE: 59
ggtcgaggtg tcgtagatgt caatgagctt cgcgattgcg tcatcgatcg ttgttgcttc      60
catgcgcacc acactatctt tctgcacgcc ctgatgccct gtg gat tca aaa ctg      115
                                             Val Asp Ser Lys Leu
                                              1               5 tgc ttt tat agg cgt atg caa gaa tcc tca cgt gat aat ttc caa gtt      163
Cys Phe Tyr Arg Arg Met Gln Glu Ser Ser Arg Asp Asn Phe Gln Val
                 10                  15                  20 gac ctc ggc ggc gtt gtt gat ctt ttg agt cgc cac att tat tcc ggt      211
Asp Leu Gly Gly Val Val Asp Leu Leu Ser Arg His Ile Tyr Ser Gly
             25                  30                  35 ccg agg gtg tat gtg cgt gag ttg ctg cag aat gcg gtt gat gct tgt      259
Pro Arg Val Tyr Val Arg Glu Leu Leu Gln Asn Ala Val Asp Ala Cys
         40                  45                  50 act gca cgt tct gaa cag ggt gag gag ggc tac gag ccg agt att cgt      307
Thr Ala Arg Ser Glu Gln Gly Glu Glu Gly Tyr Glu Pro Ser Ile Arg
     55                  60                  65 att cgg ccg gtg acc aag gat cgt gcc acg ttt tca ctg gtt gat aat      355
Ile Arg Pro Val Thr Lys Asp Arg Ala Thr Phe Ser Leu Val Asp Asn
 70                  75                  80                  85 ggt acg ggc ctg acc gcg cag gag gcg cgg gaa ttg ctg gcg acg gtg      403
Gly Thr Gly Leu Thr Ala Gln Glu Ala Arg Glu Leu Leu Ala Thr Val
                 90                  95                 100 ggg cgg acg tcg aaa cgc gat gaa ttc ggt ctg cag cgg gaa ggt cgc      451
Gly Arg Thr Ser Lys Arg Asp Glu Phe Gly Leu Gln Arg Glu Gly Arg
            105                 110                 115 ctg ggg caa ttt ggc atc ggg ctg ctt agt tgt ttc atg gtg gcg gat      499
Leu Gly Gln Phe Gly Ile Gly Leu Leu Ser Cys Phe Met Val Ala Asp
        120                 125                 130 gag atc acc atg gtg tcg cat gcg gag ggt gcg tcg gcg att cgg tgg      547
Glu Ile Thr Met Val Ser His Ala Glu Gly Ala Ser Ala Ile Arg Trp
    135                 140                 145 act ggt cat gcg gat ggc acc ttt aac ctg gag att ctt ggg gat gac      595
Thr Gly His Ala Asp Gly Thr Phe Asn Leu Glu Ile Leu Gly Asp Asp
150                 155                 160                 165 gca acg gat gtc att ccg gtg ggc acg act gtg cac ctg act ccg cgc      643
Ala Thr Asp Val Ile Pro Val Gly Thr Thr Val His Leu Thr Pro Arg
                170                 175                 180 cct gat gag cgc acg ttg ctg acg gaa aat tcc gtg gtc acc att gct      691
Pro Asp Glu Arg Thr Leu Leu Thr Glu Asn Ser Val Val Thr Ile Ala
            185                 190                 195 agt aat tat ggc cgt tac ctg ccg att cct att gtg gtg cag ggt gag      739
Ser Asn Tyr Gly Arg Tyr Leu Pro Ile Pro Ile Val Val Gln Gly Glu
        200                 205                 210 aaa aac acc acc atc act aca tcg ccg gtg ttt gca aag gat act gat      787
Lys Asn Thr Thr Ile Thr Thr Ser Pro Val Phe Ala Lys Asp Thr Asp
    215                 220                 225 cag cag cac agg ctg tat gcc ggc cgg gag cgc ctt ggt aaa act cct      835
Gln Gln His Arg Leu Tyr Ala Gly Arg Glu Arg Leu Gly Lys Thr Pro
```

```
                    230                 235                 240                 245
ttt gat gtc atc gat ctc acc ggt cct ggc atc gag ggt gtg gct tat      883
Phe Asp Val Ile Asp Leu Thr Gly Pro Gly Ile Glu Gly Val Ala Tyr
                    250                 255                 260 gta ttg ccg gag gcc cag gct ccg cat atg tcc agg cgt cac agt att      931
Val Leu Pro Glu Ala Gln Ala Pro His Met Ser Arg Arg His Ser Ile
                265                 270                 275 tat gtc aac cgc atg ttg gtc tct gat ggg cct tcc acg gtg ctg ccc      979
Tyr Val Asn Arg Met Leu Val Ser Asp Gly Pro Ser Thr Val Leu Pro
            280                 285                 290 aac tgg gcg ttc ttt gtg gaa tgt gaa atc aat tca acc gat ttg gaa     1027
Asn Trp Ala Phe Phe Val Glu Cys Glu Ile Asn Ser Thr Asp Leu Glu
    295                 300                 305 ccc acc gca tcg cgt gaa gcg ctc atg gat gac acc gcg ttc gcg gca     1075
Pro Thr Ala Ser Arg Glu Ala Leu Met Asp Asp Thr Ala Phe Ala Ala
310                 315                 320                 325 acc agg gaa cat atc ggt gag tgc att aaa tcg tgg ctg att aat ctc     1123
Thr Arg Glu His Ile Gly Glu Cys Ile Lys Ser Trp Leu Ile Asn Leu
                330                 335                 340 gcc atg acc aag cct cac cgc gtg cgg gaa ttt act gcg att cat gat     1171
Ala Met Thr Lys Pro His Arg Val Arg Glu Phe Thr Ala Ile His Asp
            345                 350                 355 ctt gcc ctg cgc gag ctg tgc caa tcg gac gcg gac ctg gct gaa acc     1219
Leu Ala Leu Arg Glu Leu Cys Gln Ser Asp Ala Asp Leu Ala Glu Thr
    360                 365                 370 atg ttg ggt ctt ctc acc ttg gag acc tcc cgt ggt cgc atc tcg atc     1267
Met Leu Gly Leu Leu Thr Leu Glu Thr Ser Arg Gly Arg Ile Ser Ile
375                 380                 385 ggt gag atc acc acg ttg tcc atc acc gag gat gtg tcg ctg cag ctg     1315
Gly Glu Ile Thr Thr Leu Ser Ile Thr Glu Asp Val Ser Leu Gln Leu
390                 395                 400                 405 gct acc acg ttg gat gat ttc agg cag ctc aac acc att gcg cgc ccg     1363
Ala Thr Thr Leu Asp Asp Phe Arg Gln Leu Asn Thr Ile Ala Arg Pro
                410                 415                 420 gac acc ttg att att aat ggc ggc tac att cac gac agc gat ctg gct     1411
Asp Thr Leu Ile Ile Asn Gly Gly Tyr Ile His Asp Ser Asp Leu Ala
            425                 430                 435 cgg ctc att ccc gtt cac tac cca ccg ctt acg gta tct act gct gac     1459
Arg Leu Ile Pro Val His Tyr Pro Pro Leu Thr Val Ser Thr Ala Asp
    440                 445                 450 ctg cgc gaa tcc atg gat ctg atg gag ctt ccg ccg ctg cag gac att     1507
Leu Arg Glu Ser Met Asp Leu Met Glu Leu Pro Pro Leu Gln Asp Ile
455                 460                 465 gag aaa gcc aag gca ctg gat gcg cag gtc acg gaa tca ttg aag gat     1555
Glu Lys Ala Lys Ala Leu Asp Ala Gln Val Thr Glu Ser Leu Lys Asp
470                 475                 480                 485 ttt cag atc aag ggc gca acg agg gtt ttt gaa ccc gca gat gtt cct     1603
Phe Gln Ile Lys Gly Ala Thr Arg Val Phe Glu Pro Ala Asp Val Pro
                490                 495                 500 gcc gtg gtg atc att gat tcc aag gcg cag gcc tca cgg gat cgc aat     1651
Ala Val Val Ile Ile Asp Ser Lys Ala Gln Ala Ser Arg Asp Arg Asn
            505                 510                 515 gaa aca caa agc gca acc act gat cgt tgg gct gac att ttg gca acg     1699
Glu Thr Gln Ser Ala Thr Thr Asp Arg Trp Ala Asp Ile Leu Ala Thr
    520                 525                 530 gtg gat aac acg ttg agc cgt caa aca gcc aac att cca cag gat cag     1747
Val Asp Asn Thr Leu Ser Arg Gln Thr Ala Asn Ile Pro Gln Asp Gln
535                 540                 545 gga ctg tcg gcg ttg tgc ttg aat tgg aac aat tcg ctg gtc agg aaa     1795
```

```
Gly Leu Ser Ala Leu Cys Leu Asn Trp Asn Asn Ser Leu Val Arg Lys
550                 555                 560                 565 ttg gcg tcc act gat gac acc gcc gtg gtg tcg cgc acg gtg cgt ttg      1843
Leu Ala Ser Thr Asp Asp Thr Ala Val Val Ser Arg Thr Val Arg Leu
                570                 575                 580 ctc tac gtt cag gca ttg ttg tcc agc aag agg cca ctg cgg gtg aag      1891
Leu Tyr Val Gln Ala Leu Leu Ser Ser Lys Arg Pro Leu Arg Val Lys
                585                 590                 595 gaa cgc gcg ctg ctt aat gat tcg ctg gca gat ctg gtt tct ttg tct      1939
Glu Arg Ala Leu Leu Asn Asp Ser Leu Ala Asp Leu Val Ser Leu Ser
                600                 605                 610 ttg tca tcc gat atc taagacaatc ctccgctaat ctcgagggca                 1984
Leu Ser Ser Asp Ile
            615

<210> SEQ ID NO 60
<211> LENGTH: 618
<212> TYPE: PRT
<213> ORGANISM: Corynebacterium glutamicum

<400> SEQUENCE: 60

Val Asp Ser Lys Leu Cys Phe Tyr Arg Arg Met Gln Glu Ser Ser Arg
 1               5                  10                  15

Asp Asn Phe Gln Val Asp Leu Gly Gly Val Val Asp Leu Leu Ser Arg
                20                  25                  30

His Ile Tyr Ser Gly Pro Arg Val Tyr Val Arg Glu Leu Leu Gln Asn
            35                  40                  45

Ala Val Asp Ala Cys Thr Ala Arg Ser Glu Gln Gly Glu Glu Gly Tyr
        50                  55                  60

Glu Pro Ser Ile Arg Ile Arg Pro Val Thr Lys Asp Arg Ala Thr Phe
 65                 70                  75                  80

Ser Leu Val Asp Asn Gly Thr Gly Leu Thr Ala Gln Glu Ala Arg Glu
                85                  90                  95

Leu Leu Ala Thr Val Gly Arg Thr Ser Lys Arg Asp Glu Phe Gly Leu
            100                 105                 110

Gln Arg Glu Gly Arg Leu Gly Gln Phe Gly Ile Gly Leu Leu Ser Cys
        115                 120                 125

Phe Met Val Ala Asp Glu Ile Thr Met Val Ser His Ala Glu Gly Ala
130                 135                 140

Ser Ala Ile Arg Trp Thr Gly His Ala Asp Gly Thr Phe Asn Leu Glu
145                 150                 155                 160

Ile Leu Gly Asp Asp Ala Thr Asp Val Ile Pro Val Gly Thr Thr Val
                165                 170                 175

His Leu Thr Pro Arg Pro Asp Glu Arg Thr Leu Leu Thr Glu Asn Ser
            180                 185                 190

Val Val Thr Ile Ala Ser Asn Tyr Gly Arg Tyr Leu Pro Ile Pro Ile
        195                 200                 205

Val Val Gln Gly Glu Lys Asn Thr Thr Ile Thr Thr Ser Pro Val Phe
    210                 215                 220

Ala Lys Asp Thr Asp Gln Gln His Arg Leu Tyr Ala Gly Arg Glu Arg
225                 230                 235                 240

Leu Gly Lys Thr Pro Phe Asp Val Ile Asp Leu Thr Gly Pro Gly Ile
                245                 250                 255

Glu Gly Val Ala Tyr Val Leu Pro Glu Ala Gln Ala Pro His Met Ser
            260                 265                 270

Arg Arg His Ser Ile Tyr Val Asn Arg Met Leu Val Ser Asp Gly Pro
```

```
                 275                 280                 285
Ser Thr Val Leu Pro Asn Trp Ala Phe Phe Val Glu Cys Glu Ile Asn
    290                 295                 300

Ser Thr Asp Leu Glu Pro Thr Ala Ser Arg Glu Ala Leu Met Asp Asp
305                 310                 315                 320

Thr Ala Phe Ala Ala Thr Arg Glu His Ile Gly Glu Cys Ile Lys Ser
                325                 330                 335

Trp Leu Ile Asn Leu Ala Met Thr Lys Pro His Arg Val Arg Glu Phe
                340                 345                 350

Thr Ala Ile His Asp Leu Ala Leu Arg Glu Leu Cys Gln Ser Asp Ala
                355                 360                 365

Asp Leu Ala Glu Thr Met Leu Gly Leu Leu Thr Leu Glu Thr Ser Arg
    370                 375                 380

Gly Arg Ile Ser Ile Gly Glu Ile Thr Thr Leu Ser Ile Thr Glu Asp
385                 390                 395                 400

Val Ser Leu Gln Leu Ala Thr Thr Leu Asp Asp Phe Arg Gln Leu Asn
                405                 410                 415

Thr Ile Ala Arg Pro Asp Thr Leu Ile Ile Asn Gly Gly Tyr Ile His
                420                 425                 430

Asp Ser Asp Leu Ala Arg Leu Ile Pro Val His Tyr Pro Pro Leu Thr
                435                 440                 445

Val Ser Thr Ala Asp Leu Arg Glu Ser Met Asp Leu Met Glu Leu Pro
    450                 455                 460

Pro Leu Gln Asp Ile Glu Lys Ala Lys Ala Leu Asp Ala Gln Val Thr
465                 470                 475                 480

Glu Ser Leu Lys Asp Phe Gln Ile Lys Gly Ala Thr Arg Val Phe Glu
                485                 490                 495

Pro Ala Asp Val Pro Ala Val Val Ile Ile Asp Ser Lys Ala Gln Ala
                500                 505                 510

Ser Arg Asp Arg Asn Glu Thr Gln Ser Ala Thr Thr Asp Arg Trp Ala
                515                 520                 525

Asp Ile Leu Ala Thr Val Asp Asn Thr Leu Ser Arg Gln Thr Ala Asn
530                 535                 540

Ile Pro Gln Asp Gln Gly Leu Ser Ala Leu Cys Leu Asn Trp Asn Asn
545                 550                 555                 560

Ser Leu Val Arg Lys Leu Ala Ser Thr Asp Thr Ala Val Val Ser
                565                 570                 575

Arg Thr Val Arg Leu Leu Tyr Val Gln Ala Leu Leu Ser Ser Lys Arg
                580                 585                 590

Pro Leu Arg Val Lys Glu Arg Ala Leu Leu Asn Asp Ser Leu Ala Asp
                595                 600                 605

Leu Val Ser Leu Ser Leu Ser Ser Asp Ile
    610                 615

<210> SEQ ID NO 61
<211> LENGTH: 1792
<212> TYPE: DNA
<213> ORGANISM: Corynebacterium glutamicum
<220> FEATURE:
<221> NAME/KEY: CDS
<222> LOCATION: (101)..(1762)
<223> OTHER INFORMATION: RXA02388

<400> SEQUENCE: 61
ttcgggagag caacggtggg tttagcaccg tggaggattt actgcaggtc aagggggattg    60
```

-continued

| | |
|---|---|
| ggccctcaaa gtttgagcag atctctggat tggtgtcccc atg att gag gtg cgt<br>                                                                                          Met Ile Glu Val Arg<br>                                                                                           1                  5 | 115 |
| ttg gtt ccg gtg gcg gct gtg atg tgg atg gct gtc gct gcg ttg att<br>Leu Val Pro Val Ala Ala Val Met Trp Met Ala Val Ala Ala Leu Ile<br>                 10                        15                        20 | 163 |
| atc agt ggt tcg tgg gtg ttg tcg gtg ggg att gtt ggc atc gcg atc<br>Ile Ser Gly Ser Trp Val Leu Ser Val Gly Ile Val Gly Ile Ala Ile<br>                 25                        30                        35 | 211 |
| att gct gct tgt gtg ttt aaa cac tgg ggt caa gct gtg gtg ata gct<br>Ile Ala Ala Cys Val Phe Lys His Trp Gly Gln Ala Val Val Ile Ala<br>                 40                        45                        50 | 259 |
| gca ctg ggc gtt ggt gcc gta gtg atg gct gcg ttg aga atc agc agc<br>Ala Leu Gly Val Gly Ala Val Val Met Ala Ala Leu Arg Ile Ser Ser<br>      55                        60                        65 | 307 |
| gcg aag gca ttt gaa gca ccg caa acc tgg gtg ggt acc gca gaa acc<br>Ala Lys Ala Phe Glu Ala Pro Gln Thr Trp Val Gly Thr Ala Glu Thr<br>70                        75                        80                        85 | 355 |
| atc aag ttt tta gac agc ggt gat caa cta atc ggt ttg aga gta gaa<br>Ile Lys Phe Leu Asp Ser Gly Asp Gln Leu Ile Gly Leu Arg Val Glu<br>                 90                        95                       100 | 403 |
| ggc tat cca gcg ccg att cca gtg ttt tac tct ggt agc gac acc att<br>Gly Tyr Pro Ala Pro Ile Pro Val Phe Tyr Ser Gly Ser Asp Thr Ile<br>                105                      110                      115 | 451 |
| gag aaa gcc tct ctc att gca gtg tcc ggt cgg att aaa cca gat agt<br>Glu Lys Ala Ser Leu Ile Ala Val Ser Gly Arg Ile Lys Pro Asp Ser<br>        120                     125                      130 | 499 |
| ttc cct ggg gtg ggt gat ctg acc att tcc act gaa gac att gat cag<br>Phe Pro Gly Val Gly Asp Leu Thr Ile Ser Thr Glu Asp Ile Asp Gln<br>135                        140                        145 | 547 |
| ttg gaa ccg acc act ggt tat agc gca tgg gtg aac cag gtg cgt gac<br>Leu Glu Pro Thr Thr Gly Tyr Ser Ala Trp Val Asn Gln Val Arg Asp<br>150                        155                        160                        165 | 595 |
| ggg ttt tcc caa gcc gtg gaa gaa acc gtg ggg gag tct tcc cgt gga<br>Gly Phe Ser Gln Ala Val Glu Glu Thr Val Gly Glu Ser Ser Arg Gly<br>                170                      175                      180 | 643 |
| ctg att cca ggc atg gtg ttg ggg gat acg cgg ttg cag ggg tca att<br>Leu Ile Pro Gly Met Val Leu Gly Asp Thr Arg Leu Gln Gly Ser Ile<br>                185                      190                      195 | 691 |
| gaa gcc caa acc tat att gat acg ggg ttg tct cac ctg tca gct gtt<br>Glu Ala Gln Thr Tyr Ile Asp Thr Gly Leu Ser His Leu Ser Ala Val<br>        200                     205                      210 | 739 |
| agt gga agc aat gta gcc att gtg gtg tcc tct gtg gtg gtg ttg tcg<br>Ser Gly Ser Asn Val Ala Ile Val Val Ser Ser Val Val Val Leu Ser<br>215                        220                        225 | 787 |
| tat ttt ctc acc gct ggg cca cgc atc agg gtg gtg gcg tca ttg ctg<br>Tyr Phe Leu Thr Ala Gly Pro Arg Ile Arg Val Val Ala Ser Leu Leu<br>230                        235                        240                        245 | 835 |
| tcc tta gtt att ttt gtc tcc ctc gtg ggg ttt gaa cca agt gtg ctt<br>Ser Leu Val Ile Phe Val Ser Leu Val Gly Phe Glu Pro Ser Val Leu<br>                250                      255                      260 | 883 |
| cgt gct tcg gtc aca ggc atc gtg ggg ctt ctg gca atc atc aac tct<br>Arg Ala Ser Val Thr Gly Ile Val Gly Leu Leu Ala Ile Ile Asn Ser<br>                 265                     270                      275 | 931 |
| tct cgg atg gag ccg atg cat ggg ttg agt ctt tcg gtg att tgc tta<br>Ser Arg Met Glu Pro Met His Gly Leu Ser Leu Ser Val Ile Cys Leu<br>        280                     285                      290 | 979 |
| ctg ttt tat gat tcc aac ctg gcg gtg cat tac gga ttc tta ctc tcg<br>Leu Phe Tyr Asp Ser Asn Leu Ala Val His Tyr Gly Phe Leu Leu Ser<br>295                        300                        305 | 1027 |

-continued

```
tgt gca gca act gct ggc att gtg atg ctt caa cca ctg ctg tac cgt      1075
Cys Ala Ala Thr Ala Gly Ile Val Met Leu Gln Pro Leu Leu Tyr Arg
310                 315                 320                 325 gcc atc ggt cca cca ctg gcg gtg tgg aaa gta cca gac atc gtg gtg      1123
Ala Ile Gly Pro Pro Leu Ala Val Trp Lys Val Pro Asp Ile Val Val
        330                 335                 340 cgc gct ttc gcg gtg tcc att gcc gct gat ctg gtg acc atc ccg att      1171
Arg Ala Phe Ala Val Ser Ile Ala Ala Asp Leu Val Thr Ile Pro Ile
            345                 350                 355 atc gct ctg atg gct cgc caa ata tcc ctc gtg gca gtg ctg gcc aac      1219
Ile Ala Leu Met Ala Arg Gln Ile Ser Leu Val Ala Val Leu Ala Asn
                360                 365                 370 gtg ttg gtt gaa tta gct gtt cca ccc atc acg ttg ctt ggg ttg att      1267
Val Leu Val Glu Leu Ala Val Pro Pro Ile Thr Leu Leu Gly Leu Ile
375                 380                 385 gcc gtg ctg gca agc ctt ctt ccc tgg cca gtg gaa tac cca ctc ttg      1315
Ala Val Leu Ala Ser Leu Leu Pro Trp Pro Val Glu Tyr Pro Leu Leu
390                 395                 400                 405 aaa atc att gag ccc ttc acc tgg tgg att cat cac gtg gcc aag tgg      1363
Lys Ile Ile Glu Pro Phe Thr Trp Trp Ile His His Val Ala Lys Trp
        410                 415                 420 tgc caa caa tta ccc aat tcg acg ctg gaa ata agt gct ggt tgg gca      1411
Cys Gln Gln Leu Pro Asn Ser Thr Leu Glu Ile Ser Ala Gly Trp Ala
            425                 430                 435 ggg att gcc tgg gcg tgt atg gca gcg gtg tgg gtg gtg gtg att atc      1459
Gly Ile Ala Trp Ala Cys Met Ala Ala Val Trp Val Val Val Ile Ile
                440                 445                 450 tac aaa gga tat gtg cgc acc ctt gca gtg tgt tgt gtc tgc ttc ttt      1507
Tyr Lys Gly Tyr Val Arg Thr Leu Ala Val Cys Cys Val Cys Phe Phe
455                 460                 465 ctt ttc ggc gcg tgg aat aac aga ctg cca gcc caa ata gat ccg aca      1555
Leu Phe Gly Ala Trp Asn Asn Arg Leu Pro Ala Gln Ile Asp Pro Thr
470                 475                 480                 485 gag ctg cgg ttt gtc atc atc gcc gat gat tct gag ctc act gat gtg      1603
Glu Leu Arg Phe Val Ile Ile Ala Asp Asp Ser Glu Leu Thr Asp Val
        490                 495                 500 ccc gaa cat gca gaa ttg atc atc gtg gaa gac ccc cac ggc agc atg      1651
Pro Glu His Ala Glu Leu Ile Ile Val Glu Asp Pro His Gly Ser Met
            505                 510                 515 tcc gat cgc ccc atc gtc acc aga gaa gga atc cct gtg ctg tat cca      1699
Ser Asp Arg Pro Ile Val Thr Arg Glu Gly Ile Pro Val Leu Tyr Pro
                520                 525                 530 tac cgc gat ggg gag gtc agc ctt cat att gat ggc acc cag cat gca      1747
Tyr Arg Asp Gly Glu Val Ser Leu His Ile Asp Gly Thr Gln His Ala
535                 540                 545 gcg gac ggg aga ttt taacgacact tgtggcacga tggtcacgtg               1792
Ala Asp Gly Arg Phe
550

<210> SEQ ID NO 62
<211> LENGTH: 554
<212> TYPE: PRT
<213> ORGANISM: Corynebacterium glutamicum

<400> SEQUENCE: 62

Met Ile Glu Val Arg Leu Val Pro Val Ala Ala Val Met Trp Met Ala
1               5                   10                  15

Val Ala Ala Leu Ile Ile Ser Gly Ser Trp Val Leu Ser Val Gly Ile
            20                  25                  30
```

-continued

```
Val Gly Ile Ala Ile Ile Ala Ala Cys Val Phe Lys His Trp Gly Gln
             35                  40                  45

Ala Val Val Ile Ala Ala Leu Gly Val Gly Ala Val Val Met Ala Ala
 50                  55                  60

Leu Arg Ile Ser Ser Ala Lys Ala Phe Glu Ala Pro Gln Thr Trp Val
 65                  70                  75                  80

Gly Thr Ala Glu Thr Ile Lys Phe Leu Asp Ser Gly Asp Gln Leu Ile
                 85                  90                  95

Gly Leu Arg Val Glu Gly Tyr Pro Ala Pro Ile Pro Val Phe Tyr Ser
                100                 105                 110

Gly Ser Asp Thr Ile Glu Lys Ala Ser Leu Ile Ala Val Ser Gly Arg
             115                 120                 125

Ile Lys Pro Asp Ser Phe Pro Gly Val Gly Asp Leu Thr Ile Ser Thr
130                 135                 140

Glu Asp Ile Asp Gln Leu Glu Pro Thr Thr Gly Tyr Ser Ala Trp Val
145                 150                 155                 160

Asn Gln Val Arg Asp Gly Phe Ser Gln Ala Val Glu Thr Val Gly
                165                 170                 175

Glu Ser Ser Arg Gly Leu Ile Pro Gly Met Val Leu Gly Asp Thr Arg
             180                 185                 190

Leu Gln Gly Ser Ile Glu Ala Gln Thr Tyr Ile Asp Thr Gly Leu Ser
             195                 200                 205

His Leu Ser Ala Val Ser Gly Ser Asn Val Ala Ile Val Ser Ser
             210                 215                 220

Val Val Val Leu Ser Tyr Phe Leu Thr Ala Gly Pro Arg Ile Arg Val
225                 230                 235                 240

Val Ala Ser Leu Leu Ser Leu Val Ile Phe Val Ser Leu Val Gly Phe
                 245                 250                 255

Glu Pro Ser Val Leu Arg Ala Ser Val Thr Gly Ile Val Gly Leu Leu
                 260                 265                 270

Ala Ile Ile Asn Ser Ser Arg Met Glu Pro Met His Gly Leu Ser Leu
             275                 280                 285

Ser Val Ile Cys Leu Leu Phe Tyr Asp Ser Asn Leu Ala Val His Tyr
             290                 295                 300

Gly Phe Leu Leu Ser Cys Ala Ala Thr Ala Gly Ile Val Met Leu Gln
305                 310                 315                 320

Pro Leu Leu Tyr Arg Ala Ile Gly Pro Pro Leu Ala Val Trp Lys Val
                 325                 330                 335

Pro Asp Ile Val Val Arg Ala Phe Ala Val Ser Ile Ala Ala Asp Leu
                 340                 345                 350

Val Thr Ile Pro Ile Ile Ala Leu Met Ala Arg Gln Ile Ser Leu Val
             355                 360                 365

Ala Val Leu Ala Asn Val Leu Val Glu Leu Ala Val Pro Pro Ile Thr
 370                 375                 380

Leu Leu Gly Leu Ile Ala Val Leu Ala Ser Leu Leu Pro Trp Pro Val
385                 390                 395                 400

Glu Tyr Pro Leu Leu Lys Ile Ile Glu Pro Phe Thr Trp Trp Ile His
                 405                 410                 415

His Val Ala Lys Trp Cys Gln Gln Leu Pro Asn Ser Thr Leu Glu Ile
             420                 425                 430

Ser Ala Gly Trp Ala Gly Ile Ala Trp Ala Cys Met Ala Ala Val Trp
             435                 440                 445

Val Val Val Ile Ile Tyr Lys Gly Tyr Val Arg Thr Leu Ala Val Cys
```

```
                  450             455             460
     Cys Val Cys Phe Phe Leu Phe Gly Ala Trp Asn Asn Arg Leu Pro Ala
     465                 470                 475                 480

Gln Ile Asp Pro Thr Glu Leu Arg Phe Val Ile Ile Ala Asp Asp Ser
                     485                 490                 495

Glu Leu Thr Asp Val Pro Glu His Ala Glu Leu Ile Ile Val Glu Asp
                 500                 505                 510

Pro His Gly Ser Met Ser Asp Arg Pro Ile Val Thr Arg Glu Gly Ile
             515                 520                 525

Pro Val Leu Tyr Pro Tyr Arg Asp Gly Glu Val Ser Leu His Ile Asp
         530                 535                 540

Gly Thr Gln His Ala Ala Asp Gly Arg Phe
     545                 550

<210> SEQ ID NO 63
<211> LENGTH: 2977
<212> TYPE: DNA
<213> ORGANISM: Corynebacterium glutamicum
<220> FEATURE:
<221> NAME/KEY: CDS
<222> LOCATION: (101)..(2947)
<223> OTHER INFORMATION: RXA02416

<400> SEQUENCE: 63
agtcatgtgg ttcagactag cggaaacacc ttgttcgatg ctatgttcga aggtgtattt      60
tttgaagcga caaaaatcga ttttgaaggg cagttgagca ttg gct gat cgc ctc      115
                                              Leu Ala Asp Arg Leu
                                                1               5 gta gtg cgc gga gcg cgt gaa cat aac cta aaa ggc gtg gat att gat     163
Val Val Arg Gly Ala Arg Glu His Asn Leu Lys Gly Val Asp Ile Asp
                 10                  15                  20 ttg cca cgc gac tcg atg gtg gtg ttc acc ggc ctg tca ggt tcc ggt     211
Leu Pro Arg Asp Ser Met Val Val Phe Thr Gly Leu Ser Gly Ser Gly
             25                  30                  35 aaa tca tca ctg gcc ttt gac acc atc ttt gcg gaa ggc cag cgc cgt     259
Lys Ser Ser Leu Ala Phe Asp Thr Ile Phe Ala Glu Gly Gln Arg Arg
         40                  45                  50 tac gtg gag tcg ttg tcc agt tac gcc cgc atg ttc ttg ggg cag atg     307
Tyr Val Glu Ser Leu Ser Ser Tyr Ala Arg Met Phe Leu Gly Gln Met
     55                  60                  65 gac aag ccg gac gtg gat ttg att gat gga tta tcc cca gcg gtc tcc     355
Asp Lys Pro Asp Val Asp Leu Ile Asp Gly Leu Ser Pro Ala Val Ser
 70                  75                  80                  85 att gac caa aaa tcc acc aac cgc aac cct cgg tcc aca gtc ggt acc     403
Ile Asp Gln Lys Ser Thr Asn Arg Asn Pro Arg Ser Thr Val Gly Thr
                 90                  95                 100 atc acg gaa gtc tat gac tac ctg cgt ctt ctg tac gcc cgc gct ggt     451
Ile Thr Glu Val Tyr Asp Tyr Leu Arg Leu Leu Tyr Ala Arg Ala Gly
            105                 110                 115 acc gca cac tgc cca gtg tgt gat gcc cgc gtg gag cgt caa acc ccc     499
Thr Ala His Cys Pro Val Cys Asp Ala Arg Val Glu Arg Gln Thr Pro
        120                 125                 130 cag cag atg gtg gac caa atc ctt ggc atg gag gag gga ctg aag ttc     547
Gln Gln Met Val Asp Gln Ile Leu Gly Met Glu Glu Gly Leu Lys Phe
    135                 140                 145 caa atc ctt gcg cct gtg gtg cgt acc cgt aaa ggt gag ttc gtt gat     595
Gln Ile Leu Ala Pro Val Val Arg Thr Arg Lys Gly Glu Phe Val Asp
150                 155                 160                 165 ctt ttc gca gat ctt gca tcc caa ggt tat tcc cgc gtg cgg gtt gat     643
Leu Phe Ala Asp Leu Ala Ser Gln Gly Tyr Ser Arg Val Arg Val Asp
```

-continued

| | | |
|---|---|---|
| Leu Phe Ala Asp Leu Ala Ser Gln Gly Tyr Ser Arg Val Arg Val Asp<br>170 175 180 | | |
| ggg gaa gtg cac cag ctc tcg gat cct cca aag cta gaa aag cag atc<br>Gly Glu Val His Gln Leu Ser Asp Pro Pro Lys Leu Glu Lys Gln Ile<br>185 190 195 | | 691 |
| aag cac gat att gat gtt gtg gtt gac cgt ctg cag gta aaa gcc agc<br>Lys His Asp Ile Asp Val Val Val Asp Arg Leu Gln Val Lys Ala Ser<br>200 205 210 | | 739 |
| caa aag cag cgc ctg aca gac tct atg gaa acc gca ctt cgc ctg gcc<br>Gln Lys Gln Arg Leu Thr Asp Ser Met Glu Thr Ala Leu Arg Leu Ala<br>215 220 225 | | 787 |
| gat ggc gtg gct gtg ctg gag ttc gtt ggc ctg gag gaa gat gat ccg<br>Asp Gly Val Ala Val Leu Glu Phe Val Gly Leu Glu Glu Asp Asp Pro<br>230 235 240 245 | | 835 |
| aat agg ctt cgt cga ttc tct gaa aag atg agc tgc cct aac ggt cac<br>Asn Arg Leu Arg Arg Phe Ser Glu Lys Met Ser Cys Pro Asn Gly His<br>250 255 260 | | 883 |
| gcg ttg acg gtt gat gag ctg gag cct cgt gct ttt tcc ttc aac tct<br>Ala Leu Thr Val Asp Glu Leu Glu Pro Arg Ala Phe Ser Phe Asn Ser<br>265 270 275 | | 931 |
| cct tat ggc gcg tgt cct gcc tgt gat ggc ttg ggt gtg cgc acc gaa<br>Pro Tyr Gly Ala Cys Pro Ala Cys Asp Gly Leu Gly Val Arg Thr Glu<br>280 285 290 | | 979 |
| gtt gat att gat ctg atc atc cca gat cca gat gca cct gca act aaa<br>Val Asp Ile Asp Leu Ile Ile Pro Asp Pro Asp Ala Pro Ala Thr Lys<br>295 300 305 | | 1027 |
| gcg gtt cag ccc tgg aac tcc agc cca aac cac tct tac ttt gaa aag<br>Ala Val Gln Pro Trp Asn Ser Ser Pro Asn His Ser Tyr Phe Glu Lys<br>310 315 320 325 | | 1075 |
| ctc att gaa ggc ctg gcg aaa gcc ctc gga ttt gat ccg gaa act ccg<br>Leu Ile Glu Gly Leu Ala Lys Ala Leu Gly Phe Asp Pro Glu Thr Pro<br>330 335 340 | | 1123 |
| tac agt gag ctc acc gca gct caa aag aag gct ctg gtc tat gga tcg<br>Tyr Ser Glu Leu Thr Ala Ala Gln Lys Lys Ala Leu Val Tyr Gly Ser<br>345 350 355 | | 1171 |
| aag gaa gaa gta agc gtt cga tac aag aac cgc tac gga cgc gtg cgt<br>Lys Glu Glu Val Ser Val Arg Tyr Lys Asn Arg Tyr Gly Arg Val Arg<br>360 365 370 | | 1219 |
| tct tgg act gcg cct ttt gaa ggt gtc atg ggc tac ttt gat cgc aag<br>Ser Trp Thr Ala Pro Phe Glu Gly Val Met Gly Tyr Phe Asp Arg Lys<br>375 380 385 | | 1267 |
| ttg gag cag act gat tcc gaa acc caa aaa gac cga ctg ttg ggc tac<br>Leu Glu Gln Thr Asp Ser Glu Thr Gln Lys Asp Arg Leu Leu Gly Tyr<br>390 395 400 405 | | 1315 |
| acc cgt gaa gtg ccc tgc cca acc tgt aaa ggc gca cgc ctc aag ccg<br>Thr Arg Glu Val Pro Cys Pro Thr Cys Lys Gly Ala Arg Leu Lys Pro<br>410 415 420 | | 1363 |
| gaa atc ttg gcc gtt cgc cta gac tcc gga agc cat gga gcg ttg tcc<br>Glu Ile Leu Ala Val Arg Leu Asp Ser Gly Ser His Gly Ala Leu Ser<br>425 430 435 | | 1411 |
| att gct gga cta acc gcg ctg tcg gtg cat gaa gca ttc gag ttt ttg<br>Ile Ala Gly Leu Thr Ala Leu Ser Val His Glu Ala Phe Glu Phe Leu<br>440 445 450 | | 1459 |
| gat aac ctc aca ctg ggc aag cgc gag gaa atg atc gcg gga gct gtg<br>Asp Asn Leu Thr Leu Gly Lys Arg Glu Glu Met Ile Ala Gly Ala Val<br>455 460 465 | | 1507 |
| ctg aag gaa att cac gcc cgc ctg aaa ttc ctg ctt gac gtg ggc ctt<br>Leu Lys Glu Ile His Ala Arg Leu Lys Phe Leu Leu Asp Val Gly Leu<br>470 475 480 485 | | 1555 |

| | |
|---|---:|
| tcc tac ctc acc ctt gat cgc gcc gca ggc acc ctg tct ggt ggt gaa<br>Ser Tyr Leu Thr Leu Asp Arg Ala Ala Gly Thr Leu Ser Gly Gly Glu<br>490                        495                      500 | 1603 |
| gcg cag cgt atc cgc ctg gct act caa att ggt tcc ggt ctg gct ggt<br>Ala Gln Arg Ile Arg Leu Ala Thr Gln Ile Gly Ser Gly Leu Ala Gly<br>505                     510                     515 | 1651 |
| gtg ctc tac gtc ttg gat gag cca tcc att ggt ctg cac caa cgt gac<br>Val Leu Tyr Val Leu Asp Glu Pro Ser Ile Gly Leu His Gln Arg Asp<br>520                       525                     530 | 1699 |
| aac cag cgc ttg atc act acc ctt gag cat ctc cga gat atc gga aac<br>Asn Gln Arg Leu Ile Thr Thr Leu Glu His Leu Arg Asp Ile Gly Asn<br>535                     540                     545 | 1747 |
| acg ctc att gtt gtg gaa cac gat gaa gac acc atc agg cgc gca gat<br>Thr Leu Ile Val Val Glu His Asp Glu Asp Thr Ile Arg Arg Ala Asp<br>550                     555                     560                     565 | 1795 |
| tgg ctc gtg gat att ggt cct cga gct ggt gaa ttt ggt ggc gaa gtg<br>Trp Leu Val Asp Ile Gly Pro Arg Ala Gly Glu Phe Gly Gly Glu Val<br>570                     575                     580 | 1843 |
| gtc tac caa ggt gag ccg aag ggc att ttg gac tgc gaa gaa tcc ctc<br>Val Tyr Gln Gly Glu Pro Lys Gly Ile Leu Asp Cys Glu Glu Ser Leu<br>585                     590                     595 | 1891 |
| aca ggt gct tac ttg tct ggt cgt cga acc ctg ggt gtt cct gat act<br>Thr Gly Ala Tyr Leu Ser Gly Arg Arg Thr Leu Gly Val Pro Asp Thr<br>600                     605                     610 | 1939 |
| cgc cgt gag atc gac aaa gag cga cag ctc aag gtg gtt ggt gct agg<br>Arg Arg Glu Ile Asp Lys Glu Arg Gln Leu Lys Val Val Gly Ala Arg<br>615                     620                     625 | 1987 |
| gaa aat aac ctg cag ggc atc gat gtg aaa atc cca ctg ggt gtg ctg<br>Glu Asn Asn Leu Gln Gly Ile Asp Val Lys Ile Pro Leu Gly Val Leu<br>630                     635                     640                     645 | 2035 |
| tgc tgc atc act ggt gtg tcg gga tct ggt aaa tcc acg ctg gtc aat<br>Cys Cys Ile Thr Gly Val Ser Gly Ser Gly Lys Ser Thr Leu Val Asn<br>650                     655                     660 | 2083 |
| cag att ttg gcc aag gtt ctg gcc aac aaa ctc aac cgc gca cgc caa<br>Gln Ile Leu Ala Lys Val Leu Ala Asn Lys Leu Asn Arg Ala Arg Gln<br>665                     670                     675 | 2131 |
| gtg cct ggt cgc gca aag cgg gtg gaa ggc ctc gag cac ttg gat aag<br>Val Pro Gly Arg Ala Lys Arg Val Glu Gly Leu Glu His Leu Asp Lys<br>680                     685                     690 | 2179 |
| ttg gtc caa gtg gat cag tcg cca att ggt cgt act cca cgt tca aac<br>Leu Val Gln Val Asp Gln Ser Pro Ile Gly Arg Thr Pro Arg Ser Asn<br>695                     700                     705 | 2227 |
| cca gcg acg tac acg ggt gtg ttt gat aaa gtc cgt aac ctt ttt gcc<br>Pro Ala Thr Tyr Thr Gly Val Phe Asp Lys Val Arg Asn Leu Phe Ala<br>710                     715                     720                     725 | 2275 |
| gag acc act gaa gcg aag gtc cgc ggt tac aag cct ggc cgc ttc tcc<br>Glu Thr Thr Glu Ala Lys Val Arg Gly Tyr Lys Pro Gly Arg Phe Ser<br>730                     735                     740 | 2323 |
| ttc aat att aag ggt gga cgc tgc gaa gca tgt cag ggc gat ggc acg<br>Phe Asn Ile Lys Gly Gly Arg Cys Glu Ala Cys Gln Gly Asp Gly Thr<br>745                     750                     755 | 2371 |
| ctg aag atc gaa atg aac ttc ctg ccc gac gtg tat gtt ccg tgt gaa<br>Leu Lys Ile Glu Met Asn Phe Leu Pro Asp Val Tyr Val Pro Cys Glu<br>760                     765                     770 | 2419 |
| gtc tgt gat ggt cag cgc tac aac cgc gag acc ctc gag gtg aag tac<br>Val Cys Asp Gly Gln Arg Tyr Asn Arg Glu Thr Leu Glu Val Lys Tyr<br>775                     780                     785 | 2467 |
| aag ggc aaa aac atc gct gaa gta ttg ggc atg ccg atc tct gag gct<br>Lys Gly Lys Asn Ile Ala Glu Val Leu Gly Met Pro Ile Ser Glu Ala<br>790                     795                     800                     805 | 2515 |

```
gcg gac ttc ttt gag ccc atc acc tca att cac cga tac cta gca acg    2563
Ala Asp Phe Phe Glu Pro Ile Thr Ser Ile His Arg Tyr Leu Ala Thr
            810                 815                 820 ctg gtt gat gtc ggc ctt ggc tat gtc cgt ttg ggc cag gca gca aca    2611
Leu Val Asp Val Gly Leu Gly Tyr Val Arg Leu Gly Gln Ala Ala Thr
        825                 830                 835 acc ttg tct ggt ggt gaa gcc cag cgt gtg aaa ctt gcc gct gag ctg    2659
Thr Leu Ser Gly Gly Glu Ala Gln Arg Val Lys Leu Ala Ala Glu Leu
    840                 845                 850 cag aag cgt tcc aac ggt cgc acc gtt tac atc ctc gat gag cca act    2707
Gln Lys Arg Ser Asn Gly Arg Thr Val Tyr Ile Leu Asp Glu Pro Thr
855                 860                 865 act ggt ttg cac ttt gaa gat att cgc aaa ctc atg atg gtg atc gaa    2755
Thr Gly Leu His Phe Glu Asp Ile Arg Lys Leu Met Met Val Ile Glu
870                 875                 880                 885 ggc ctg gtg gac aag ggt aac tcc gtg atc atc atc gag cac aac ctc    2803
Gly Leu Val Asp Lys Gly Asn Ser Val Ile Ile Ile Glu His Asn Leu
            890                 895                 900 gac gtg atc aag gct gcc gac tgg atc gtg gac atg ggt cca gag ggc    2851
Asp Val Ile Lys Ala Ala Asp Trp Ile Val Asp Met Gly Pro Glu Gly
        905                 910                 915 gga agc ggc ggt gga acc gtg gtc gct gaa gga acc cca gag caa gtt    2899
Gly Ser Gly Gly Gly Thr Val Val Ala Glu Gly Thr Pro Glu Gln Val
    920                 925                 930 gct gaa gtt gcg ggt tcc tac acc ggc caa ttc ctt aaa gag ttg ttg    2947
Ala Glu Val Ala Gly Ser Tyr Thr Gly Gln Phe Leu Lys Glu Leu Leu
935                 940                 945 taggagaaga tgagggcttt tcatgggaag                                   2977

<210> SEQ ID NO 64
<211> LENGTH: 949
<212> TYPE: PRT
<213> ORGANISM: Corynebacterium glutamicum

<400> SEQUENCE: 64

Leu Ala Asp Arg Leu Val Val Arg Gly Ala Arg Glu His Asn Leu Lys
1               5                   10                  15

Gly Val Asp Ile Asp Leu Pro Arg Asp Ser Met Val Val Phe Thr Gly
            20                  25                  30

Leu Ser Gly Ser Gly Lys Ser Ser Leu Ala Phe Asp Thr Ile Phe Ala
        35                  40                  45

Glu Gly Gln Arg Arg Tyr Val Glu Ser Leu Ser Ser Tyr Ala Arg Met
    50                  55                  60

Phe Leu Gly Gln Met Asp Lys Pro Asp Val Asp Leu Ile Asp Gly Leu
65                  70                  75                  80

Ser Pro Ala Val Ser Ile Asp Gln Lys Ser Thr Asn Arg Asn Pro Arg
                85                  90                  95

Ser Thr Val Gly Thr Ile Thr Glu Val Tyr Asp Tyr Leu Arg Leu Leu
            100                 105                 110

Tyr Ala Arg Ala Gly Thr Ala His Cys Pro Val Cys Asp Ala Arg Val
        115                 120                 125

Glu Arg Gln Thr Pro Gln Gln Met Val Asp Gln Ile Leu Gly Met Glu
    130                 135                 140

Glu Gly Leu Lys Phe Gln Ile Leu Ala Pro Val Val Arg Thr Arg Lys
145                 150                 155                 160

Gly Glu Phe Val Asp Leu Phe Ala Asp Leu Ala Ser Gln Gly Tyr Ser
                165                 170                 175
```

```
Arg Val Arg Val Asp Gly Glu Val His Gln Leu Ser Asp Pro Pro Lys
            180                 185                 190
Leu Glu Lys Gln Ile Lys His Asp Ile Asp Val Val Asp Arg Leu
        195                 200                 205
Gln Val Lys Ala Ser Gln Lys Gln Arg Leu Thr Asp Ser Met Glu Thr
    210                 215                 220
Ala Leu Arg Leu Ala Asp Gly Val Ala Val Leu Glu Phe Val Gly Leu
225                 230                 235                 240
Glu Glu Asp Asp Pro Asn Arg Leu Arg Arg Phe Ser Glu Lys Met Ser
                245                 250                 255
Cys Pro Asn Gly His Ala Leu Thr Val Asp Glu Leu Glu Pro Arg Ala
            260                 265                 270
Phe Ser Phe Asn Ser Pro Tyr Gly Ala Cys Pro Ala Cys Asp Gly Leu
        275                 280                 285
Gly Val Arg Thr Glu Val Asp Ile Asp Leu Ile Ile Pro Asp Pro Asp
    290                 295                 300
Ala Pro Ala Thr Lys Ala Val Gln Pro Trp Asn Ser Ser Pro Asn His
305                 310                 315                 320
Ser Tyr Phe Glu Lys Leu Ile Glu Gly Leu Ala Lys Ala Leu Gly Phe
                325                 330                 335
Asp Pro Glu Thr Pro Tyr Ser Glu Leu Thr Ala Ala Gln Lys Lys Ala
            340                 345                 350
Leu Val Tyr Gly Ser Lys Glu Glu Val Ser Val Arg Tyr Lys Asn Arg
        355                 360                 365
Tyr Gly Arg Val Arg Ser Trp Thr Ala Pro Phe Glu Gly Val Met Gly
    370                 375                 380
Tyr Phe Asp Arg Lys Leu Glu Gln Thr Asp Ser Glu Thr Gln Lys Asp
385                 390                 395                 400
Arg Leu Leu Gly Tyr Thr Arg Glu Val Pro Cys Pro Thr Cys Lys Gly
                405                 410                 415
Ala Arg Leu Lys Pro Glu Ile Leu Ala Val Arg Leu Asp Ser Gly Ser
            420                 425                 430
His Gly Ala Leu Ser Ile Ala Gly Leu Thr Ala Leu Ser Val His Glu
        435                 440                 445
Ala Phe Glu Phe Leu Asp Asn Leu Thr Leu Gly Lys Arg Glu Glu Met
    450                 455                 460
Ile Ala Gly Ala Val Leu Lys Glu Ile His Ala Arg Leu Lys Phe Leu
465                 470                 475                 480
Leu Asp Val Gly Leu Ser Tyr Leu Thr Leu Asp Arg Ala Ala Gly Thr
                485                 490                 495
Leu Ser Gly Gly Glu Ala Gln Arg Ile Arg Leu Ala Thr Gln Ile Gly
            500                 505                 510
Ser Gly Leu Ala Gly Val Leu Tyr Val Leu Asp Glu Pro Ser Ile Gly
        515                 520                 525
Leu His Gln Arg Asp Asn Gln Arg Leu Ile Thr Thr Leu Glu His Leu
    530                 535                 540
Arg Asp Ile Gly Asn Thr Leu Ile Val Val Glu His Asp Glu Asp Thr
545                 550                 555                 560
Ile Arg Arg Ala Asp Trp Leu Val Asp Ile Gly Pro Arg Ala Gly Glu
                565                 570                 575
Phe Gly Gly Glu Val Val Tyr Gln Gly Glu Pro Lys Gly Ile Leu Asp
            580                 585                 590
```

-continued

```
Cys Glu Glu Ser Leu Thr Gly Ala Tyr Leu Ser Gly Arg Arg Thr Leu
        595                 600                 605

Gly Val Pro Asp Thr Arg Arg Glu Ile Asp Lys Glu Arg Gln Leu Lys
610                 615                 620

Val Val Gly Ala Arg Glu Asn Asn Leu Gln Gly Ile Asp Val Lys Ile
625                 630                 635                 640

Pro Leu Gly Val Leu Cys Cys Ile Thr Gly Val Ser Gly Ser Gly Lys
                645                 650                 655

Ser Thr Leu Val Asn Gln Ile Leu Ala Lys Val Leu Ala Asn Lys Leu
            660                 665                 670

Asn Arg Ala Arg Gln Val Pro Gly Arg Ala Lys Arg Val Glu Gly Leu
        675                 680                 685

Glu His Leu Asp Lys Leu Val Gln Val Asp Gln Ser Pro Ile Gly Arg
    690                 695                 700

Thr Pro Arg Ser Asn Pro Ala Thr Tyr Thr Gly Val Phe Asp Lys Val
705                 710                 715                 720

Arg Asn Leu Phe Ala Glu Thr Thr Glu Ala Lys Val Arg Gly Tyr Lys
                725                 730                 735

Pro Gly Arg Phe Ser Phe Asn Ile Lys Gly Gly Arg Cys Glu Ala Cys
            740                 745                 750

Gln Gly Asp Gly Thr Leu Lys Ile Glu Met Asn Phe Leu Pro Asp Val
        755                 760                 765

Tyr Val Pro Cys Glu Val Cys Asp Gly Gln Arg Tyr Asn Arg Glu Thr
    770                 775                 780

Leu Glu Val Lys Tyr Lys Gly Lys Asn Ile Ala Glu Val Leu Gly Met
785                 790                 795                 800

Pro Ile Ser Glu Ala Ala Asp Phe Phe Glu Pro Ile Thr Ser Ile His
                805                 810                 815

Arg Tyr Leu Ala Thr Leu Val Asp Val Gly Leu Gly Tyr Val Arg Leu
            820                 825                 830

Gly Gln Ala Ala Thr Thr Leu Ser Gly Gly Glu Ala Gln Arg Val Lys
        835                 840                 845

Leu Ala Ala Glu Leu Gln Lys Arg Ser Asn Gly Arg Thr Val Tyr Ile
    850                 855                 860

Leu Asp Glu Pro Thr Thr Gly Leu His Phe Glu Asp Ile Arg Lys Leu
865                 870                 875                 880

Met Met Val Ile Glu Gly Leu Val Asp Lys Gly Asn Ser Val Ile Ile
                885                 890                 895

Ile Glu His Asn Leu Asp Val Ile Lys Ala Ala Asp Trp Ile Val Asp
            900                 905                 910

Met Gly Pro Glu Gly Gly Ser Gly Gly Gly Thr Val Val Ala Glu Gly
        915                 920                 925

Thr Pro Glu Gln Val Ala Glu Val Ala Gly Ser Tyr Thr Gly Gln Phe
    930                 935                 940

Leu Lys Glu Leu Leu
945

<210> SEQ ID NO 65
<211> LENGTH: 697
<212> TYPE: DNA
<213> ORGANISM: Corynebacterium glutamicum
<220> FEATURE:
<221> NAME/KEY: CDS
<222> LOCATION: (101)..(667)
<223> OTHER INFORMATION: RXA02418
```

```
<400> SEQUENCE: 65
gacacggact agtgcccgtg tataactctt gaaagtcaga tctcccgttc atcctagatg      60
atgaacgggt ttttggtctg catagggca  atcacctcaa gtg gtt cgg tac gtc     115
                                              Val Val Arg Tyr Val
                                                1               5 aaa ttt tcc cgc act gct aac aga gga gtc cac atc agc gct gaa gct     163
Lys Phe Ser Arg Thr Ala Asn Arg Gly Val His Ile Ser Ala Glu Ala
             10                  15                  20 cgc att aat gag cgc atc cga gtt ccc gaa gtc cgc ctt gtc gga cct     211
Arg Ile Asn Glu Arg Ile Arg Val Pro Glu Val Arg Leu Val Gly Pro
         25                  30                  35 aac ggt gag caa gta ggc atc gtc cgt atc gaa gat gcc cgc aag ctc     259
Asn Gly Glu Gln Val Gly Ile Val Arg Ile Glu Asp Ala Arg Lys Leu
     40                  45                  50 gca ttc gac gca gac cta gac ctg gtc gag gtc gca ccc aac gcc aaa     307
Ala Phe Asp Ala Asp Leu Asp Leu Val Glu Val Ala Pro Asn Ala Lys
 55                  60                  65 cct cca gtc tgc aag atc atg gac tac gga aag ttc aag tac gaa gcg     355
Pro Pro Val Cys Lys Ile Met Asp Tyr Gly Lys Phe Lys Tyr Glu Ala
 70                  75                  80                  85 gcc caa aag gct cgt gag tca cgc aag aat cag cag cag acc gtg gtc     403
Ala Gln Lys Ala Arg Glu Ser Arg Lys Asn Gln Gln Gln Thr Val Val
                 90                  95                 100 aaa gag caa aag ctt cgt ccc aag atc gat gat cat gat tat gag acg     451
Lys Glu Gln Lys Leu Arg Pro Lys Ile Asp Asp His Asp Tyr Glu Thr
             105                 110                 115 aag aag aac aat gtg atc cga ttc ctt gaa aag gga tca aag gtc aaa     499
Lys Lys Asn Asn Val Ile Arg Phe Leu Glu Lys Gly Ser Lys Val Lys
         120                 125                 130 gtc acg atc atg ttc cgt ggt cgt gag cag gct cgc cca gag ctt ggc     547
Val Thr Ile Met Phe Arg Gly Arg Glu Gln Ala Arg Pro Glu Leu Gly
 135                 140                 145 tac agg ctc ctc gag cga ctg gca aac gat gtc gta gat ttt ggc atc     595
Tyr Arg Leu Leu Glu Arg Leu Ala Asn Asp Val Val Asp Phe Gly Ile
150                 155                 160                 165 gtg gaa acc cgc gca aag cag gac gga cga aac atg aca atg gtt ctc     643
Val Glu Thr Arg Ala Lys Gln Asp Gly Arg Asn Met Thr Met Val Leu
                 170                 175                 180 ggt ccg gtg cgc aag ggc aag aaa taatcacgaa tagggtttaa ggacaacttt    697
Gly Pro Val Arg Lys Gly Lys Lys
                 185

<210> SEQ ID NO 66
<211> LENGTH: 189
<212> TYPE: PRT
<213> ORGANISM: Corynebacterium glutamicum

<400> SEQUENCE: 66

Val Val Arg Tyr Val Lys Phe Ser Arg Thr Ala Asn Arg Gly Val His
  1               5                  10                  15

Ile Ser Ala Glu Ala Arg Ile Asn Glu Arg Ile Arg Val Pro Glu Val
             20                  25                  30

Arg Leu Val Gly Pro Asn Gly Glu Gln Val Gly Ile Val Arg Ile Glu
         35                  40                  45

Asp Ala Arg Lys Leu Ala Phe Asp Ala Asp Leu Asp Leu Val Glu Val
     50                  55                  60

Ala Pro Asn Ala Lys Pro Pro Val Cys Lys Ile Met Asp Tyr Gly Lys
 65                  70                  75                  80
```

```
Phe Lys Tyr Glu Ala Ala Gln Lys Ala Arg Glu Ser Arg Lys Asn Gln
                85                  90                  95

Gln Gln Thr Val Val Lys Glu Gln Lys Leu Arg Pro Lys Ile Asp Asp
            100                 105                 110

His Asp Tyr Glu Thr Lys Lys Asn Asn Val Ile Arg Phe Leu Glu Lys
        115                 120                 125

Gly Ser Lys Val Lys Val Thr Ile Met Phe Arg Gly Arg Glu Gln Ala
    130                 135                 140

Arg Pro Glu Leu Gly Tyr Arg Leu Leu Glu Arg Leu Ala Asn Asp Val
145                 150                 155                 160

Val Asp Phe Gly Ile Val Glu Thr Arg Ala Lys Gln Asp Gly Arg Asn
                165                 170                 175

Met Thr Met Val Leu Gly Pro Val Arg Lys Gly Lys Lys
                180                 185
```

<210> SEQ ID NO 67
<211> LENGTH: 2419
<212> TYPE: DNA
<213> ORGANISM: Corynebacterium glutamicum
<220> FEATURE:
<221> NAME/KEY: CDS
<222> LOCATION: (101)..(2389)
<223> OTHER INFORMATION: RXA02429

<400> SEQUENCE: 67

```
tcttacccac cagtgcaatg taggtcacgt cgtatcacgt ctgagggtga ttgagtaggg      60
ttaaacagat gaattcattt agctcaccgg aggtataacc gtg gcc ggt ttt gat     115
                                             Val Ala Gly Phe Asp
                                               1               5 tgg ttt tgg aag gcc ctt ggc ggc aaa tcg ggc aga aac caa aaa cgt     163
Trp Phe Trp Lys Ala Leu Gly Gly Lys Ser Gly Arg Asn Gln Lys Arg
             10                  15                  20 agc gtg gca att gtc aat cag gta gaa aac cat gca gcg gaa tta gac     211
Ser Val Ala Ile Val Asn Gln Val Glu Asn His Ala Ala Glu Leu Asp
         25                  30                  35 gcg ctg gat gat gtt gca ttg gcg cag cgt gcc aag gat cta gcc agt     259
Ala Leu Asp Asp Val Ala Leu Ala Gln Arg Ala Lys Asp Leu Ala Ser
     40                  45                  50 ggt gga cgc att gac aat cat gcg gaa ttc ctc gcc att ttg ggt gtg     307
Gly Gly Arg Ile Asp Asn His Ala Glu Phe Leu Ala Ile Leu Gly Val
 55                  60                  65 gca tcg cag cgg aca ttg ggg ctg aag ccg tat ccg gtg caa tca cag     355
Ala Ser Gln Arg Thr Leu Gly Leu Lys Pro Tyr Pro Val Gln Ser Gln
 70                  75                  80                  85 gcg gtg ttg cgt ctc att gaa ggc gat gtg gtg cac atg gct acc ggt     403
Ala Val Leu Arg Leu Ile Glu Gly Asp Val Val His Met Ala Thr Gly
             90                  95                 100 gag ggc aag act ttg gtg ggc gcg atg gcg gcc acc ggt ctg ggg ttg     451
Glu Gly Lys Thr Leu Val Gly Ala Met Ala Ala Thr Gly Leu Gly Leu
         105                 110                 115 atg ggc aag cga gtc cat tcg att acc gtc aat gat tat ttg gcg gtg     499
Met Gly Lys Arg Val His Ser Ile Thr Val Asn Asp Tyr Leu Ala Val
     120                 125                 130 cgc gat gcc gaa tgg atg cgg cca ttg gtc gaa ttt ttc ggt ctg agc     547
Arg Asp Ala Glu Trp Met Arg Pro Leu Val Glu Phe Phe Gly Leu Ser
 135                 140                 145 gtg gcg agc atc agc gag aag atg gat gca ggg gag cgt cga caa gca     595
Val Ala Ser Ile Ser Glu Lys Met Asp Ala Gly Glu Arg Arg Gln Ala
150                 155                 160                 165
```

```
tat aaa gcc gca att gtc tac gga cct gtc aat gaa atc ggc ttt gac      643
Tyr Lys Ala Ala Ile Val Tyr Gly Pro Val Asn Glu Ile Gly Phe Asp
            170                 175                 180 gtg ctg cgt gat cag cta att acc cgg cgc gaa gac gcc gtg cag cat      691
Val Leu Arg Asp Gln Leu Ile Thr Arg Arg Glu Asp Ala Val Gln His
        185                 190                 195 ggc gcc gac gtc gcg att atc gat gag gcc gat tcc gtg ctt gtc gac      739
Gly Ala Asp Val Ala Ile Ile Asp Glu Ala Asp Ser Val Leu Val Asp
    200                 205                 210 gag gcc ctg gtg cca ctc gtc ctc gcc ggc aac cag ccc ggc cat gcg      787
Glu Ala Leu Val Pro Leu Val Leu Ala Gly Asn Gln Pro Gly His Ala
215                 220                 225 ccg cgc ggc aaa atc acc gat gtg gtg cgc tcg ttg aaa gaa aac gac      835
Pro Arg Gly Lys Ile Thr Asp Val Val Arg Ser Leu Lys Glu Asn Asp
230                 235                 240                 245 gat tac acc atc gac gat gat cgt cgc aac gtc ttc ctc acc gac aag      883
Asp Tyr Thr Ile Asp Asp Asp Arg Arg Asn Val Phe Leu Thr Asp Lys
                250                 255                 260 ggt gcc gcc aaa tta gag cag cag ctg ggc atc agc agc ctc tac gac      931
Gly Ala Ala Lys Leu Glu Gln Gln Leu Gly Ile Ser Ser Leu Tyr Asp
            265                 270                 275 gat gag cac gtc ggc tcg acg ctc gtg cag gtc aac ctc gcc ctc cac      979
Asp Glu His Val Gly Ser Thr Leu Val Gln Val Asn Leu Ala Leu His
        280                 285                 290 gcg cag gca ctg ctc atc cgc gac atc cac tac atc gtc cgc gac agc     1027
Ala Gln Ala Leu Leu Ile Arg Asp Ile His Tyr Ile Val Arg Asp Ser
    295                 300                 305 aag gtc ttg ctt atc gac gcc tcc cgc ggc cgt gtc gcc gac ctg cag     1075
Lys Val Leu Leu Ile Asp Ala Ser Arg Gly Arg Val Ala Asp Leu Gln
310                 315                 320                 325 cgc tgg ccc gac ggc ctg caa gca gca gtg gag gcc aag gaa ggt ctc     1123
Arg Trp Pro Asp Gly Leu Gln Ala Ala Val Glu Ala Lys Glu Gly Leu
                330                 335                 340 gcg gtt tct gaa ggc ggc aag atc ctt gac acc atc aca ctt cag gcg     1171
Ala Val Ser Glu Gly Gly Lys Ile Leu Asp Thr Ile Thr Leu Gln Ala
            345                 350                 355 ttg att ggt cgc tac cca atg gca tgc ggc atg aca ggt acc gcc gtg     1219
Leu Ile Gly Arg Tyr Pro Met Ala Cys Gly Met Thr Gly Thr Ala Val
        360                 365                 370 gag gca acc gat cag cta cgc acc ttc tat gac ttg cat gtt tct gtc     1267
Glu Ala Thr Asp Gln Leu Arg Thr Phe Tyr Asp Leu His Val Ser Val
    375                 380                 385 att gag cgc aat cat ccg ctg aag cgc ttt gat gaa gct gac cgt atc     1315
Ile Glu Arg Asn His Pro Leu Lys Arg Phe Asp Glu Ala Asp Arg Ile
390                 395                 400                 405 tac gcc acc atg gcg gag aaa aac cgc gcc atc atc gat gaa atc gca     1363
Tyr Ala Thr Met Ala Glu Lys Asn Arg Ala Ile Ile Asp Glu Ile Ala
                410                 415                 420 ctc ctt cac agc acg ggg cag cca gtc ctg gtg ggt acc cac gat gtg     1411
Leu Leu His Ser Thr Gly Gln Pro Val Leu Val Gly Thr His Asp Val
            425                 430                 435 gca gag tcg gaa gaa ctc gcc act gca ctg cgt gaa ctc aac atc gaa     1459
Ala Glu Ser Glu Glu Leu Ala Thr Ala Leu Arg Glu Leu Asn Ile Glu
        440                 445                 450 gta agc gtt ctc aac gcc aag aat gat gcc gaa gaa gcc cag atc atc     1507
Val Ser Val Leu Asn Ala Lys Asn Asp Ala Glu Glu Ala Gln Ile Ile
    455                 460                 465 gca gag gct ggc gat att gga cga gtg acc gtt tcc act cag atg gcc     1555
Ala Glu Ala Gly Asp Ile Gly Arg Val Thr Val Ser Thr Gln Met Ala
470                 475                 480                 485
```

|  |  |
|---|---:|
| ggc cgc ggt acc gat att cgc ctc ggt ggc gcc gat gaa gcc gac tac<br>Gly Arg Gly Thr Asp Ile Arg Leu Gly Gly Ala Asp Glu Ala Asp Tyr<br>                490                        495                  500 | 1603 |
| gat gaa gtg gtg aaa ctc ggt gga ctc gcc gtt atc ggc acc gcc cgc<br>Asp Glu Val Val Lys Leu Gly Gly Leu Ala Val Ile Gly Thr Ala Arg<br>          505                       510                    515 | 1651 |
| cac cgt tct cag cgc ctg gac aac cag ctg cgc gga cgt gcg gga cga<br>His Arg Ser Gln Arg Leu Asp Asn Gln Leu Arg Gly Arg Ala Gly Arg<br>        520                       525                    530 | 1699 |
| caa gga gat cca ggc ctg agc ctt ttc ttt gtc tcc ctc gat gat gat<br>Gln Gly Asp Pro Gly Leu Ser Leu Phe Phe Val Ser Leu Asp Asp Asp<br>535                      540                    545 | 1747 |
| gtg gtg gtc tca ggc ggg tca agg gag agc gtg agc gcg caa ccc gat<br>Val Val Val Ser Gly Gly Ser Arg Glu Ser Val Ser Ala Gln Pro Asp<br>550                      555                    560                  565 | 1795 |
| gcc acc ggg ctg att gac tca gat cgc atc cgc gat tgg gtc gga cac<br>Ala Thr Gly Leu Ile Asp Ser Asp Arg Ile Arg Asp Trp Val Gly His<br>                570                       575                  580 | 1843 |
| tgc cag cgc gtc acc gaa gga cag ctg ctg gaa atc cac tcc cag agc<br>Cys Gln Arg Val Thr Glu Gly Gln Leu Leu Glu Ile His Ser Gln Ser<br>          585                       590                    595 | 1891 |
| tgg aat tac aac aag ctc ctt gcc gat caa cgc gtg atc att gac gag<br>Trp Asn Tyr Asn Lys Leu Leu Ala Asp Gln Arg Val Ile Ile Asp Glu<br>        600                       605                    610 | 1939 |
| cgc cgc gaa cgc ctc ctc gac acc gcc tta gcg tgg gag gaa ctg gca<br>Arg Arg Glu Arg Leu Leu Asp Thr Ala Leu Ala Trp Glu Glu Leu Ala<br>          615                       620                  625 | 1987 |
| cag cat gca cca gcg cgg gct gca gag ctt gaa gac ctt gat cag tcc<br>Gln His Ala Pro Ala Arg Ala Ala Glu Leu Glu Asp Leu Asp Gln Ser<br>630                      635                    640                  645 | 2035 |
| gtg agg gaa cag gca gca cga gac atc atg ctg tac cac ctc gat tac<br>Val Arg Glu Gln Ala Ala Arg Asp Ile Met Leu Tyr His Leu Asp Tyr<br>                650                       655                  660 | 2083 |
| aac tgg tca gag cac ctc gcg ttg atg gat gat gtc cgc gaa tcc att<br>Asn Trp Ser Glu His Leu Ala Leu Met Asp Asp Val Arg Glu Ser Ile<br>          665                       670                  675 | 2131 |
| cac ctg cgc gcc atc gcc agg gaa acc ccc ctt gat gaa tac cac cgc<br>His Leu Arg Ala Ile Ala Arg Glu Thr Pro Leu Asp Glu Tyr His Arg<br>        680                       685                    690 | 2179 |
| atc gct gtg cgt gaa ttc aag gat ttg gca caa cgc gct gtc gat gat<br>Ile Ala Val Arg Glu Phe Lys Asp Leu Ala Gln Arg Ala Val Asp Asp<br>695                      700                    705 | 2227 |
| gcg gtg tcc acg ttc aag tct gtg acc atc gat cac gag ggt gcc cat<br>Ala Val Ser Thr Phe Lys Ser Val Thr Ile Asp His Glu Gly Ala His<br>710                      715                    720                  725 | 2275 |
| ttg gat gat gag ggc ttg gcg cgt cca tca gca acg tgg acc tac atg<br>Leu Asp Asp Glu Gly Leu Ala Arg Pro Ser Ala Thr Trp Thr Tyr Met<br>                730                       735                  740 | 2323 |
| gtc tct gac aac cca ctt gcg ggt agt ggt aac tca gtg atc agt ggc<br>Val Ser Asp Asn Pro Leu Ala Gly Ser Gly Asn Ser Val Ile Ser Gly<br>                   745                    750                  755 | 2371 |
| ata gga aat atc ttt aga taacctgaga actatgaaat tccagctcac<br>Ile Gly Asn Ile Phe Arg<br>            760 | 2419 |

<210> SEQ ID NO 68
<211> LENGTH: 763
<212> TYPE: PRT
<213> ORGANISM: Corynebacterium glutamicum
<400> SEQUENCE: 68

```
Val Ala Gly Phe Asp Trp Phe Trp Lys Ala Leu Gly Gly Lys Ser Gly
  1               5                  10                  15

Arg Asn Gln Lys Arg Ser Val Ala Ile Val Asn Gln Val Glu Asn His
             20                  25                  30

Ala Ala Glu Leu Asp Ala Leu Asp Val Ala Leu Ala Gln Arg Ala
         35                  40                  45

Lys Asp Leu Ala Ser Gly Gly Arg Ile Asp Asn His Ala Glu Phe Leu
 50                  55                  60

Ala Ile Leu Gly Val Ala Ser Gln Arg Thr Leu Gly Leu Lys Pro Tyr
 65                  70                  75                  80

Pro Val Gln Ser Gln Ala Val Leu Arg Leu Ile Glu Gly Asp Val Val
                 85                  90                  95

His Met Ala Thr Gly Glu Gly Lys Thr Leu Val Gly Ala Met Ala Ala
                100                 105                 110

Thr Gly Leu Gly Leu Met Gly Lys Arg Val His Ser Ile Thr Val Asn
            115                 120                 125

Asp Tyr Leu Ala Val Arg Asp Ala Glu Trp Met Arg Pro Leu Val Glu
130                 135                 140

Phe Phe Gly Leu Ser Val Ala Ser Ile Ser Glu Lys Met Asp Ala Gly
145                 150                 155                 160

Glu Arg Arg Gln Ala Tyr Lys Ala Ala Ile Val Tyr Gly Pro Val Asn
                165                 170                 175

Glu Ile Gly Phe Asp Val Leu Arg Asp Gln Leu Ile Thr Arg Arg Glu
            180                 185                 190

Asp Ala Val Gln His Gly Ala Asp Val Ala Ile Ile Asp Glu Ala Asp
        195                 200                 205

Ser Val Leu Val Asp Glu Ala Leu Val Pro Leu Val Leu Ala Gly Asn
    210                 215                 220

Gln Pro Gly His Ala Pro Arg Gly Lys Ile Thr Asp Val Val Arg Ser
225                 230                 235                 240

Leu Lys Glu Asn Asp Asp Tyr Thr Ile Asp Asp Arg Arg Asn Val
                245                 250                 255

Phe Leu Thr Asp Lys Gly Ala Ala Lys Leu Glu Gln Gln Leu Gly Ile
            260                 265                 270

Ser Ser Leu Tyr Asp Asp Glu His Val Gly Ser Thr Leu Val Gln Val
    275                 280                 285

Asn Leu Ala Leu His Ala Gln Ala Leu Leu Ile Arg Asp Ile His Tyr
290                 295                 300

Ile Val Arg Asp Ser Lys Val Leu Leu Ile Asp Ala Ser Arg Gly Arg
305                 310                 315                 320

Val Ala Asp Leu Gln Arg Trp Pro Asp Gly Leu Gln Ala Ala Val Glu
                325                 330                 335

Ala Lys Glu Gly Leu Ala Val Ser Glu Gly Lys Ile Leu Asp Thr
            340                 345                 350

Ile Thr Leu Gln Ala Leu Ile Gly Arg Tyr Pro Met Ala Cys Gly Met
        355                 360                 365

Thr Gly Thr Ala Val Glu Ala Thr Asp Gln Leu Arg Thr Phe Tyr Asp
    370                 375                 380

Leu His Val Ser Val Ile Glu Arg Asn His Pro Leu Lys Arg Phe Asp
385                 390                 395                 400

Glu Ala Asp Arg Ile Tyr Ala Thr Met Ala Glu Lys Asn Arg Ala Ile
                405                 410                 415
```

Ile Asp Glu Ile Ala Leu Leu His Ser Thr Gly Gln Pro Val Leu Val
            420                 425                 430
Gly Thr His Asp Val Ala Glu Ser Glu Leu Ala Thr Ala Leu Arg
            435                 440                 445
Glu Leu Asn Ile Glu Val Ser Val Leu Asn Ala Lys Asn Asp Ala Glu
        450                 455                 460
Glu Ala Gln Ile Ile Ala Glu Ala Gly Asp Ile Gly Arg Val Thr Val
465                 470                 475                 480
Ser Thr Gln Met Ala Gly Arg Gly Thr Asp Ile Arg Leu Gly Gly Ala
                485                 490                 495
Asp Glu Ala Asp Tyr Asp Glu Val Val Lys Leu Gly Gly Leu Ala Val
                500                 505                 510
Ile Gly Thr Ala Arg His Arg Ser Gln Arg Leu Asp Asn Gln Leu Arg
        515                 520                 525
Gly Arg Ala Gly Arg Gln Gly Asp Pro Gly Leu Ser Leu Phe Phe Val
    530                 535                 540
Ser Leu Asp Asp Asp Val Val Ser Gly Gly Ser Arg Glu Ser Val
545                 550                 555                 560
Ser Ala Gln Pro Asp Ala Thr Gly Leu Ile Asp Ser Asp Arg Ile Arg
                565                 570                 575
Asp Trp Val Gly His Cys Gln Arg Val Thr Glu Gly Gln Leu Leu Glu
                580                 585                 590
Ile His Ser Gln Ser Trp Asn Tyr Asn Lys Leu Leu Ala Asp Gln Arg
        595                 600                 605
Val Ile Ile Asp Glu Arg Arg Glu Arg Leu Leu Asp Thr Ala Leu Ala
    610                 615                 620
Trp Glu Glu Leu Ala Gln His Ala Pro Ala Arg Ala Ala Glu Leu Glu
625                 630                 635                 640
Asp Leu Asp Gln Ser Val Arg Glu Gln Ala Ala Arg Asp Ile Met Leu
                645                 650                 655
Tyr His Leu Asp Tyr Asn Trp Ser Glu His Leu Ala Leu Met Asp Asp
                660                 665                 670
Val Arg Glu Ser Ile His Leu Arg Ala Ile Ala Arg Glu Thr Pro Leu
        675                 680                 685
Asp Glu Tyr His Arg Ile Ala Val Arg Glu Phe Lys Asp Leu Ala Gln
    690                 695                 700
Arg Ala Val Asp Asp Ala Val Ser Thr Phe Lys Ser Val Thr Ile Asp
705                 710                 715                 720
His Glu Gly Ala His Leu Asp Asp Glu Gly Leu Ala Arg Pro Ser Ala
                725                 730                 735
Thr Trp Thr Tyr Met Val Ser Asp Asn Pro Leu Ala Gly Ser Gly Asn
                740                 745                 750
Ser Val Ile Ser Gly Ile Gly Asn Ile Phe Arg
        755                 760

<210> SEQ ID NO 69
<211> LENGTH: 1582
<212> TYPE: DNA
<213> ORGANISM: Corynebacterium glutamicum
<220> FEATURE:
<221> NAME/KEY: CDS
<222> LOCATION: (101)..(1552)
<223> OTHER INFORMATION: RXA02431

<400> SEQUENCE: 69

```
                                                       -continued ggtggctgag cttgtcggca ttgtgctggt tgtcatcgca gttgctttgc gacgcccctc        60
ctagcggttt cccacaccgc cagtcttctc aaactaatcg ttg acc tgt tcg att        115
                                                 Leu Thr Cys Ser Ile
                                                  1               5 aac cta att ttc ggc tgg tca act acc ata aaa agc atg caa cgc tgg        163
Asn Leu Ile Phe Gly Trp Ser Thr Thr Ile Lys Ser Met Gln Arg Trp
             10                  15                  20 gtg ctt cac atc gat atg gat gcc ttc ttc gca tcc tgc gaa caa ctg        211
Val Leu His Ile Asp Met Asp Ala Phe Phe Ala Ser Cys Glu Gln Leu
         25                  30                  35 acc cgg ccc act tta aga ggc cgc ccc gtc ttg gtc ggt gga gtc tcc        259
Thr Arg Pro Thr Leu Arg Gly Arg Pro Val Leu Val Gly Gly Val Ser
     40                  45                  50 ggt agg gga gtt gtc gcc gga gca tcc tat gaa gcc aga aaa ttt ggc        307
Gly Arg Gly Val Val Ala Gly Ala Ser Tyr Glu Ala Arg Lys Phe Gly
 55                  60                  65 gcc cgc tca gcg atg ccc atg cac caa gcc aaa gcc cga gta ggt ttt        355
Ala Arg Ser Ala Met Pro Met His Gln Ala Lys Ala Arg Val Gly Phe
 70                  75                  80                  85 ggg gca gtg gtg gtg aca ccc cgt cat atc gtt tac tcc gca gcc tcg        403
Gly Ala Val Val Val Thr Pro Arg His Ile Val Tyr Ser Ala Ala Ser
                 90                  95                 100 cgc cgg gtg ttc caa atc gtg gaa aaa cgc gcc gga att gtc gaa cgc        451
Arg Arg Val Phe Gln Ile Val Glu Lys Arg Ala Gly Ile Val Glu Arg
             105                 110                 115 ctc agc atc gat gaa ggc ttc atg gaa cca gag gct ctc gtt gga gcc        499
Leu Ser Ile Asp Glu Gly Phe Met Glu Pro Glu Ala Leu Val Gly Ala
         120                 125                 130 acc cca gaa gag gtg aaa cag tgg gcg gaa gaa tta cgc gcg gaa att        547
Thr Pro Glu Glu Val Lys Gln Trp Ala Glu Glu Leu Arg Ala Glu Ile
     135                 140                 145 aaa gaa gtt act ggc tta ccc tcc tcg gtt ggt gct ggc tcc ggt aag        595
Lys Glu Val Thr Gly Leu Pro Ser Ser Val Gly Ala Gly Ser Gly Lys
150                 155                 160                 165 cag atc gcc aaa att ggt tca ggc gaa gca aag cca gat ggt gtg ttt        643
Gln Ile Ala Lys Ile Gly Ser Gly Glu Ala Lys Pro Asp Gly Val Phe
                 170                 175                 180 gtc gtg cca gta gac aag caa cat gac ttg ctt gat cca ctt cct gtg        691
Val Val Pro Val Asp Lys Gln His Asp Leu Leu Asp Pro Leu Pro Val
             185                 190                 195 ggc gca ctt tgg gga gtg ggt cct gtg aca ggc tcc aag ctt gcc tca        739
Gly Ala Leu Trp Gly Val Gly Pro Val Thr Gly Ser Lys Leu Ala Ser
         200                 205                 210 atg ggg gtg gaa aca att ggt gat cta gca gcg cta acc caa aaa gaa        787
Met Gly Val Glu Thr Ile Gly Asp Leu Ala Ala Leu Thr Gln Lys Glu
     215                 220                 225 gta gaa atc agc ctc ggt gca acc atc gga ata tca ctg tgg aac ctt        835
Val Glu Ile Ser Leu Gly Ala Thr Ile Gly Ile Ser Leu Trp Asn Leu
230                 235                 240                 245 gcc cga gga atc gac gac cgc cct gtg gaa ccc cgc gcc gaa gca aaa        883
Ala Arg Gly Ile Asp Asp Arg Pro Val Glu Pro Arg Ala Glu Ala Lys
                 250                 255                 260 cag atc tcc caa gag cac acc tat gaa aaa gac ctc ctc acc agg caa        931
Gln Ile Ser Gln Glu His Thr Tyr Glu Lys Asp Leu Leu Thr Arg Gln
             265                 270                 275 caa gta gat gct gcc atc att cga tca gcc gaa ggc gca cac cga cgg        979
Gln Val Asp Ala Ala Ile Ile Arg Ser Ala Glu Gly Ala His Arg Arg
         280                 285                 290 ctc ctc aaa gac gga cgc ggt gcc aga act gtc agc gtg aaa ctg cgg       1027
```

-continued

```
Leu Leu Lys Asp Gly Arg Gly Ala Arg Thr Val Ser Val Lys Leu Arg
    295                 300                 305 atg gcc gac ttt cgt att gag tct cgt tcc tac acc ttg tcc tat gcc      1075
Met Ala Asp Phe Arg Ile Glu Ser Arg Ser Tyr Thr Leu Ser Tyr Ala
310                 315                 320                 325 acc gat gat tac gca act ctt gag gca aca gca ttc cga ctt gcc cgc      1123
Thr Asp Asp Tyr Ala Thr Leu Glu Ala Thr Ala Phe Arg Leu Ala Arg
                330                 335                 340 tac ccc gga gaa gta ggc ccc atc cgc ctt gtc gga gta agt ttt tct      1171
Tyr Pro Gly Glu Val Gly Pro Ile Arg Leu Val Gly Val Ser Phe Ser
            345                 350                 355 ggt ttg gaa gaa tcc cgc caa gac atc ctc ttc ccg gaa ctt gac caa      1219
Gly Leu Glu Glu Ser Arg Gln Asp Ile Leu Phe Pro Glu Leu Asp Gln
        360                 365                 370 caa atc atc gta cca cca gca ccc gac acc gat tat gag gta ggc gtg      1267
Gln Ile Ile Val Pro Pro Ala Pro Asp Thr Asp Tyr Glu Val Gly Val
    375                 380                 385 caa tcc tct tct agt tcc gaa agt act caa gtt gaa gcg ccg caa gat      1315
Gln Ser Ser Ser Ser Ser Glu Ser Thr Gln Val Glu Ala Pro Gln Asp
390                 395                 400                 405 gtc gcg ttg agt atg tgg tgc gca acg caa gat gtc tac cac cca gaa      1363
Val Ala Leu Ser Met Trp Cys Ala Thr Gln Asp Val Tyr His Pro Glu
                410                 415                 420 tat ggc cac ggt tgg gta caa ggt gcc ggt cac ggt gtt gta tca gta      1411
Tyr Gly His Gly Trp Val Gln Gly Ala Gly His Gly Val Val Ser Val
                425                 430                 435 cgt ttt gaa acc cgc agc acc aca aaa ggg cga act aaa agt ttt tcc      1459
Arg Phe Glu Thr Arg Ser Thr Thr Lys Gly Arg Thr Lys Ser Phe Ser
        440                 445                 450 atg gat gac ccg gac ctc acc ccg gca gac cct cta gat agt ttg gat      1507
Met Asp Asp Pro Asp Leu Thr Pro Ala Asp Pro Leu Asp Ser Leu Asp
    455                 460                 465 tgg gct gac tgg ttt gct gaa aat ggt gaa acg ggg gat gac gaa          1552
Trp Ala Asp Trp Phe Ala Glu Asn Gly Glu Thr Gly Asp Asp Glu
470                 475                 480 tagggtttca tcgggtttcg gggtgctttt                                      1582
```

<210> SEQ ID NO 70
<211> LENGTH: 484
<212> TYPE: PRT
<213> ORGANISM: Corynebacterium glutamicum

<400> SEQUENCE: 70

```
Leu Thr Cys Ser Ile Asn Leu Ile Phe Gly Trp Ser Thr Thr Ile Lys
  1               5                  10                  15

Ser Met Gln Arg Trp Val Leu His Ile Asp Met Asp Ala Phe Phe Ala
                20                  25                  30

Ser Cys Glu Gln Leu Thr Arg Pro Thr Leu Arg Gly Arg Pro Val Leu
            35                  40                  45

Val Gly Val Ser Gly Arg Gly Val Val Ala Gly Ser Tyr Glu
        50                  55                  60

Ala Arg Lys Phe Gly Ala Arg Ser Ala Met Pro Met His Gln Ala Lys
 65                  70                  75                  80

Ala Arg Val Gly Phe Gly Ala Val Val Thr Pro Arg His Ile Val
                85                  90                  95

Tyr Ser Ala Ala Ser Arg Arg Val Phe Gln Ile Val Glu Lys Arg Ala
            100                 105                 110

Gly Ile Val Glu Arg Leu Ser Ile Asp Glu Gly Phe Met Glu Pro Glu
```

```
                115                 120                 125
Ala Leu Val Gly Ala Thr Pro Glu Glu Val Lys Gln Trp Ala Glu Glu
    130                 135                 140

Leu Arg Ala Glu Ile Lys Glu Val Thr Gly Leu Pro Ser Ser Val Gly
145                 150                 155                 160

Ala Gly Ser Gly Lys Gln Ile Ala Lys Ile Gly Ser Gly Glu Ala Lys
                165                 170                 175

Pro Asp Gly Val Phe Val Pro Val Asp Lys Gln His Asp Leu Leu
                180                 185                 190

Asp Pro Leu Pro Val Gly Ala Leu Trp Gly Val Gly Pro Val Thr Gly
                195                 200                 205

Ser Lys Leu Ala Ser Met Gly Val Glu Thr Ile Gly Asp Leu Ala Ala
    210                 215                 220

Leu Thr Gln Lys Glu Val Glu Ile Ser Leu Gly Ala Thr Ile Gly Ile
225                 230                 235                 240

Ser Leu Trp Asn Leu Ala Arg Gly Ile Asp Asp Arg Pro Val Glu Pro
                245                 250                 255

Arg Ala Glu Ala Lys Gln Ile Ser Gln Glu His Thr Tyr Glu Lys Asp
                260                 265                 270

Leu Leu Thr Arg Gln Gln Val Asp Ala Ala Ile Ile Arg Ser Ala Glu
        275                 280                 285

Gly Ala His Arg Arg Leu Leu Lys Asp Gly Arg Gly Ala Arg Thr Val
    290                 295                 300

Ser Val Lys Leu Arg Met Ala Asp Phe Arg Ile Glu Ser Arg Ser Tyr
305                 310                 315                 320

Thr Leu Ser Tyr Ala Thr Asp Asp Tyr Ala Thr Leu Glu Ala Thr Ala
                325                 330                 335

Phe Arg Leu Ala Arg Tyr Pro Gly Glu Val Gly Pro Ile Arg Leu Val
            340                 345                 350

Gly Val Ser Phe Ser Gly Leu Glu Glu Ser Arg Gln Asp Ile Leu Phe
        355                 360                 365

Pro Glu Leu Asp Gln Gln Ile Ile Val Pro Ala Pro Asp Thr Asp
    370                 375                 380

Tyr Glu Val Gly Val Gln Ser Ser Ser Ser Glu Ser Thr Gln Val
385                 390                 395                 400

Glu Ala Pro Gln Asp Val Ala Leu Ser Met Trp Cys Ala Thr Gln Asp
                405                 410                 415

Val Tyr His Pro Glu Tyr Gly His Gly Trp Val Gln Gly Ala Gly His
            420                 425                 430

Gly Val Val Ser Val Arg Phe Glu Thr Arg Ser Thr Thr Lys Gly Arg
        435                 440                 445

Thr Lys Ser Phe Ser Met Asp Asp Pro Asp Leu Thr Pro Ala Asp Pro
    450                 455                 460

Leu Asp Ser Leu Asp Trp Ala Asp Trp Phe Ala Glu Asn Gly Glu Thr
465                 470                 475                 480

Gly Asp Asp Glu

<210> SEQ ID NO 71
<211> LENGTH: 1819
<212> TYPE: DNA
<213> ORGANISM: Corynebacterium glutamicum
<220> FEATURE:
<221> NAME/KEY: CDS
<222> LOCATION: (101)..(1789)
<223> OTHER INFORMATION: RXA02445
```

<400> SEQUENCE: 71

```
tgtataaagt gacgctctca gtgtagaaac tgagggtctc agtgaagtag actgacaggg       60
atacctaata cgtttaatag attgtggggc actcgccacc gtg gaa cca ttc gaa       115
                                              Val Glu Pro Phe Glu
                                                1               5 tta gag aaa gac ctt gag cgt ctt agg aaa aac gga aaa gac gat gaa        163
Leu Glu Lys Asp Leu Glu Arg Leu Arg Lys Asn Gly Lys Asp Asp Glu
         10                  15                  20 acc gta gaa gtg aaa tct tgg ggt cgg tta cct tta agc aaa gga tca        211
Thr Val Glu Val Lys Ser Trp Gly Arg Leu Pro Leu Ser Lys Gly Ser
             25                  30                  35 aaa agc ttc tgg gaa tca tta agc gca ttc gca aac acc aac ggt gga        259
Lys Ser Phe Trp Glu Ser Leu Ser Ala Phe Ala Asn Thr Asn Gly Gly
         40                  45                  50 tac atc cta ttg ggg cta agc gaa cca gat ttc act cca gtt gaa gga        307
Tyr Ile Leu Leu Gly Leu Ser Glu Pro Asp Phe Thr Pro Val Glu Gly
     55                  60                  65 ttt gat tca cag gcg agt atc cag ttc att cgt gca ggt tta aat cca        355
Phe Asp Ser Gln Ala Ser Ile Gln Phe Ile Arg Ala Gly Leu Asn Pro
 70                  75                  80                  85 caa gat cgc gac gcc caa aaa gtg gaa cca gtg ccc cat cat gaa att        403
Gln Asp Arg Asp Ala Gln Lys Val Glu Pro Val Pro His His Glu Ile
                 90                  95                 100 cat gaa atg act gtt gat ggt gct gaa gtt gtt tta gtt tca gtc tca        451
His Glu Met Thr Val Asp Gly Ala Glu Val Val Leu Val Ser Val Ser
            105                 110                 115 ccg ttg tca gtg aac ggg ccc tgt tat tat ctt ccc gtc gga atc act        499
Pro Leu Ser Val Asn Gly Pro Cys Tyr Tyr Leu Pro Val Gly Ile Thr
        120                 125                 130 aat ggc agc ttc aaa cgc gtt ggc gat gaa gac cgg aag ctc agt cat        547
Asn Gly Ser Phe Lys Arg Val Gly Asp Glu Asp Arg Lys Leu Ser His
    135                 140                 145 ctt gaa att tac gag ctc caa aat agg ttt gtt caa acc aaa aca gat        595
Leu Glu Ile Tyr Glu Leu Gln Asn Arg Phe Val Gln Thr Lys Thr Asp
150                 155                 160                 165 aga aat cca gtt cca gat tca agc atc gat gat ctc aac aat cag ctc        643
Arg Asn Pro Val Pro Asp Ser Ser Ile Asp Asp Leu Asn Asn Gln Leu
                170                 175                 180 gcg gcg tca ttt aag cag cgc cta att gag tca aat agt cgc tcc ctt        691
Ala Ala Ser Phe Lys Gln Arg Leu Ile Glu Ser Asn Ser Arg Ser Leu
            185                 190                 195 gga aca gac gat aac tgg tta ctg cgc aaa aat atc act aca tca aag        739
Gly Thr Asp Asp Asn Trp Leu Leu Arg Lys Asn Ile Thr Thr Ser Lys
        200                 205                 210 gga gaa ctg acg att gct ggc tta ctg gct ctc gga agc tat cct caa        787
Gly Glu Leu Thr Ile Ala Gly Leu Leu Ala Leu Gly Ser Tyr Pro Gln
    215                 220                 225 cag ttt ttc ccc cga gtg atc att gat gtt gcc gta cat cca ggt ctg        835
Gln Phe Phe Pro Arg Val Ile Ile Asp Val Ala Val His Pro Gly Leu
230                 235                 240                 245 cat aag tca cca atc ggt acc tca att cgt ttt gaa gac cga aaa atc        883
His Lys Ser Pro Ile Gly Thr Ser Ile Arg Phe Glu Asp Arg Lys Ile
                250                 255                 260 tgc gag gga aat ctt ctc gag atg gtt caa gag gct atg tct gcc atc        931
Cys Glu Gly Asn Leu Leu Glu Met Val Gln Glu Ala Met Ser Ala Ile
            265                 270                 275 aaa cga aac cta cgt gta cgc cgc gtc gtt gaa gga ctc tca ggt aaa        979
Lys Arg Asn Leu Arg Val Arg Arg Val Val Glu Gly Leu Ser Gly Lys
```

-continued

```
                280                 285                 290
gat gtt cta gaa atc cca gaa gaa gtt ttg aga gag gct cta gca aac      1027
Asp Val Leu Glu Ile Pro Glu Glu Val Leu Arg Glu Ala Leu Ala Asn
    295                 300                 305 gcc gta ctt cac cgt gat tat tct gag cta gct caa aat gaa gca att      1075
Ala Val Leu His Arg Asp Tyr Ser Glu Leu Ala Gln Asn Glu Ala Ile
310                 315                 320                 325 cat gta gac atc tat aag gat cga gtt gag atc acg agt cca ggt gga      1123
His Val Asp Ile Tyr Lys Asp Arg Val Glu Ile Thr Ser Pro Gly Gly
                330                 335                 340 tta ccc aat ggt aaa cgc cca gag tca ata ctg gac gga tac tct gaa      1171
Leu Pro Asn Gly Lys Arg Pro Glu Ser Ile Leu Asp Gly Tyr Ser Glu
            345                 350                 355 cca aga aat cgt gtg ctt tca aga atc cta atg gat att cca tgg aca      1219
Pro Arg Asn Arg Val Leu Ser Arg Ile Leu Met Asp Ile Pro Trp Thr
        360                 365                 370 cat gaa gta caa gga gta ctt gct gaa agc aac ggt act ggc gtt ccc      1267
His Glu Val Gln Gly Val Leu Ala Glu Ser Asn Gly Thr Gly Val Pro
    375                 380                 385 cga atg ttc aat ttg atg cgt gaa gcg gga ctt ccg gta ccg aat ttt      1315
Arg Met Phe Asn Leu Met Arg Glu Ala Gly Leu Pro Val Pro Asn Phe
390                 395                 400                 405 aag att gat att tct agc gtc act gtc gaa ctc agc cgt cac ggt ctt      1363
Lys Ile Asp Ile Ser Ser Val Thr Val Glu Leu Ser Arg His Gly Leu
                410                 415                 420 cta gat gcc caa aca agt gaa tgg ctt gta gaa aaa ctc gga tca gat      1411
Leu Asp Ala Gln Thr Ser Glu Trp Leu Val Glu Lys Leu Gly Ser Asp
            425                 430                 435 ttt tct aac aca caa ggc att gct ctt gtt ctc gca aaa gaa ctt gga      1459
Phe Ser Asn Thr Gln Gly Ile Ala Leu Val Leu Ala Lys Glu Leu Gly
        440                 445                 450 gcg gta acg tct cga gat ctc cgc aat caa act ggt cat gat tca gaa      1507
Ala Val Thr Ser Arg Asp Leu Arg Asn Gln Thr Gly His Asp Ser Glu
    455                 460                 465 gac atg cgc agc tta ctt gac gct ttg gtt gat cgg ggc gtt cta aac      1555
Asp Met Arg Ser Leu Leu Asp Ala Leu Val Asp Arg Gly Val Leu Asn
470                 475                 480                 485 caa aac tta cag aac caa tat cag ctt gcg aca tcg tct gtg aat gta      1603
Gln Asn Leu Gln Asn Gln Tyr Gln Leu Ala Thr Ser Ser Val Asn Val
                490                 495                 500 act caa agc gaa caa gaa gtc tta gat gca atc aat aaa aca act cct      1651
Thr Gln Ser Glu Gln Glu Val Leu Asp Ala Ile Asn Lys Thr Thr Pro
            505                 510                 515 gtc aca att cga gaa att gcc aca aaa aca ggg aaa act gca tcg tct      1699
Val Thr Ile Arg Glu Ile Ala Thr Lys Thr Gly Lys Thr Ala Ser Ser
        520                 525                 530 ctt cgg ccg ctg ctt cgt ggc ctt gtt gaa gca ggt ctt gtg gtt gca      1747
Leu Arg Pro Leu Leu Arg Gly Leu Val Glu Ala Gly Leu Val Val Ala
    535                 540                 545 act gct cca cca tca agc cgc aac cga gcg tac ttg aag gct              1789
Thr Ala Pro Pro Ser Ser Arg Asn Arg Ala Tyr Leu Lys Ala
550                 555                 560 tgacccacca acgaactcac cggtgtcagc                                     1819

<210> SEQ ID NO 72
<211> LENGTH: 563
<212> TYPE: PRT
<213> ORGANISM: Corynebacterium glutamicum

<400> SEQUENCE: 72
```

```
Val Glu Pro Phe Glu Leu Glu Lys Asp Leu Glu Arg Leu Arg Lys Asn
  1               5                  10                  15

Gly Lys Asp Asp Glu Thr Val Glu Val Lys Ser Trp Gly Arg Leu Pro
             20                  25                  30

Leu Ser Lys Gly Ser Lys Ser Phe Trp Glu Ser Leu Ser Ala Phe Ala
         35                  40                  45

Asn Thr Asn Gly Gly Tyr Ile Leu Leu Gly Leu Ser Glu Pro Asp Phe
     50                  55                  60

Thr Pro Val Glu Gly Phe Asp Ser Gln Ala Ser Ile Gln Phe Ile Arg
 65              70                  75                  80

Ala Gly Leu Asn Pro Gln Asp Arg Asp Ala Gln Lys Val Glu Pro Val
                 85                  90                  95

Pro His His Glu Ile His Glu Met Thr Val Asp Gly Ala Glu Val Val
             100                 105                 110

Leu Val Ser Val Ser Pro Leu Ser Val Asn Gly Pro Cys Tyr Tyr Leu
             115                 120                 125

Pro Val Gly Ile Thr Asn Gly Ser Phe Lys Arg Val Gly Asp Glu Asp
130              135                 140

Arg Lys Leu Ser His Leu Glu Ile Tyr Glu Leu Gln Asn Arg Phe Val
145              150                 155                 160

Gln Thr Lys Thr Asp Arg Asn Pro Val Pro Asp Ser Ser Ile Asp Asp
                 165                 170                 175

Leu Asn Asn Gln Leu Ala Ala Ser Phe Lys Gln Arg Leu Ile Glu Ser
             180                 185                 190

Asn Ser Arg Ser Leu Gly Thr Asp Asp Asn Trp Leu Leu Arg Lys Asn
         195                 200                 205

Ile Thr Thr Ser Lys Gly Glu Leu Thr Ile Ala Gly Leu Leu Ala Leu
     210                 215                 220

Gly Ser Tyr Pro Gln Gln Phe Phe Pro Arg Val Ile Asp Val Ala
225              230                 235                 240

Val His Pro Gly Leu His Lys Ser Pro Ile Gly Thr Ser Ile Arg Phe
                 245                 250                 255

Glu Asp Arg Lys Ile Cys Glu Gly Asn Leu Leu Glu Met Val Gln Glu
             260                 265                 270

Ala Met Ser Ala Ile Lys Arg Asn Leu Arg Val Arg Val Val Glu
         275                 280                 285

Gly Leu Ser Gly Lys Asp Val Leu Glu Ile Pro Glu Glu Val Leu Arg
     290                 295                 300

Glu Ala Leu Ala Asn Ala Val Leu His Arg Asp Tyr Ser Glu Leu Ala
305              310                 315                 320

Gln Asn Glu Ala Ile His Val Asp Ile Tyr Lys Asp Arg Val Glu Ile
                 325                 330                 335

Thr Ser Pro Gly Gly Leu Pro Asn Gly Lys Arg Pro Glu Ser Ile Leu
             340                 345                 350

Asp Gly Tyr Ser Glu Pro Arg Asn Arg Val Leu Ser Arg Ile Leu Met
         355                 360                 365

Asp Ile Pro Trp Thr His Glu Val Gln Gly Val Leu Ala Glu Ser Asn
     370                 375                 380

Gly Thr Gly Val Pro Arg Met Phe Asn Leu Met Arg Glu Ala Gly Leu
385              390                 395                 400

Pro Val Pro Asn Phe Lys Ile Asp Ile Ser Ser Val Thr Val Glu Leu
                 405                 410                 415
```

```
Ser Arg His Gly Leu Leu Asp Ala Gln Thr Ser Glu Trp Leu Val Glu
        420                 425                 430

Lys Leu Gly Ser Asp Phe Ser Asn Thr Gln Gly Ile Ala Leu Val Leu
            435                 440                 445

Ala Lys Glu Leu Gly Ala Val Thr Ser Arg Asp Leu Arg Asn Gln Thr
    450                 455                 460

Gly His Asp Ser Glu Asp Met Arg Ser Leu Leu Asp Ala Leu Val Asp
465                 470                 475                 480

Arg Gly Val Leu Asn Gln Asn Leu Gln Asn Gln Tyr Gln Leu Ala Thr
            485                 490                 495

Ser Ser Val Asn Val Thr Gln Ser Glu Gln Glu Val Leu Asp Ala Ile
                500                 505                 510

Asn Lys Thr Thr Pro Val Thr Ile Arg Glu Ile Ala Thr Lys Thr Gly
            515                 520                 525

Lys Thr Ala Ser Ser Leu Arg Pro Leu Leu Arg Gly Leu Val Glu Ala
    530                 535                 540

Gly Leu Val Val Ala Thr Ala Pro Pro Ser Ser Arg Asn Arg Ala Tyr
545                 550                 555                 560

Leu Lys Ala
```

<210> SEQ ID NO 73
<211> LENGTH: 1009
<212> TYPE: DNA
<213> ORGANISM: Corynebacterium glutamicum
<220> FEATURE:
<221> NAME/KEY: CDS
<222> LOCATION: (101)..(979)
<223> OTHER INFORMATION: RXA02476

<400> SEQUENCE: 73

```
cgggcggagt tctatcaaca ttacgcaaag gcataagctt tattattcca ctcggtgtga      60
catatgacct aaagtgccag tcagtacaat catttaggtc atg tca ttt aca gct     115
                                              Met Ser Phe Thr Ala
                                                1               5 ttt caa aca gcc ctg ctc gtg tgg ttt aga gca aat gcc cgc gat ctt     163
Phe Gln Thr Ala Leu Leu Val Trp Phe Arg Ala Asn Ala Arg Asp Leu
             10                  15                  20 gcg tgg cgt gat ccc aat act tca gca tgg gga att ctc ctt tca gag     211
Ala Trp Arg Asp Pro Asn Thr Ser Ala Trp Gly Ile Leu Leu Ser Glu
         25                  30                  35 gtg atg agc caa caa act ccc gtc gcg cga gtc gag ccg att tgg cgt     259
Val Met Ser Gln Gln Thr Pro Val Ala Arg Val Glu Pro Ile Trp Arg
     40                  45                  50 gag tgg atg gaa aaa tgg ccc act ccg gaa gat ttc gcg aat gcg agc     307
Glu Trp Met Glu Lys Trp Pro Thr Pro Glu Asp Phe Ala Asn Ala Ser
 55                  60                  65 acc gat gag att ttg cgg tcg tgg ggc aag ttg ggc tat cca cgt agg     355
Thr Asp Glu Ile Leu Arg Ser Trp Gly Lys Leu Gly Tyr Pro Arg Arg
 70                  75                  80                  85 gcg ctg agg ttg aag gaa tgt gcg gag gtg atc gtc gaa aag cat gcc     403
Ala Leu Arg Leu Lys Glu Cys Ala Glu Val Ile Val Glu Lys His Ala
                 90                  95                 100 ggc gag gtg ccg gat acg gtg gag gcg ctg ctc gcg ttg ccg ggg atc     451
Gly Glu Val Pro Asp Thr Val Glu Ala Leu Leu Ala Leu Pro Gly Ile
            105                 110                 115 ggt gat tac acg gcg cgc gcg gtc gcg gcg ttt cat ttt ggg cag cgc     499
Gly Asp Tyr Thr Ala Arg Ala Val Ala Ala Phe His Phe Gly Gln Arg
        120                 125                 130
```

-continued

| | | |
|---|---|---|
| gtg ccg gtg gtc gat acg aac gtg cgt cgc gtg tac cag cgc gcg gta<br>Val Pro Val Val Asp Thr Asn Val Arg Arg Val Tyr Gln Arg Ala Val<br>135                    140                    145 | 547 |
| gcc gga cgt tac ctt gcg ggg cct gcg aaa aag caa gag ctt atc gac<br>Ala Gly Arg Tyr Leu Ala Gly Pro Ala Lys Lys Gln Glu Leu Ile Asp<br>150                  155                    160                  165 | 595 |
| gtc tcc ctt ctc ctt ccc aac act cac gcc cca gaa ttc tct gcc gca<br>Val Ser Leu Leu Leu Pro Asn Thr His Ala Pro Glu Phe Ser Ala Ala<br>                170                    175                    180 | 643 |
| ata atg gag ttg ggt gct ctt atc tgc acg gcc act tcc cca aag tgt<br>Ile Met Glu Leu Gly Ala Leu Ile Cys Thr Ala Thr Ser Pro Lys Cys<br>                    185                    190                    195 | 691 |
| gac acc tgc cca ctg ctt gac cag tgt caa tgg caa aaa ctt ggc tgt<br>Asp Thr Cys Pro Leu Leu Asp Gln Cys Gln Trp Gln Lys Leu Gly Cys<br>                200                    205                    210 | 739 |
| ccc tcc ccg agt gaa gag gag ctg gct tca gcg aaa aag cgt gtg cag<br>Pro Ser Pro Ser Glu Glu Glu Leu Ala Ser Ala Lys Lys Arg Val Gln<br>215                    220                    225 | 787 |
| aaa ttt gtg gga acc gac cga caa gtc cgt ggc cta atc atg gac gta<br>Lys Phe Val Gly Thr Asp Arg Gln Val Arg Gly Leu Ile Met Asp Val<br>230                    235                    240                  245 | 835 |
| ctg cgc aat gcc acc gca cct gtg cca cta tcc gcg att gat gtc gtg<br>Leu Arg Asn Ala Thr Ala Pro Val Pro Leu Ser Ala Ile Asp Val Val<br>                250                    255                    260 | 883 |
| tgg cct gac gat gcc caa cgc tcc cgg gcg ctg ttt tcg ctc att gag<br>Trp Pro Asp Asp Ala Gln Arg Ser Arg Ala Leu Phe Ser Leu Ile Glu<br>                  265                    270                    275 | 931 |
| gac gga ctc gcg gaa caa aat gag gcg ggt tat ttc cac ctg cca cgg<br>Asp Gly Leu Ala Glu Gln Asn Glu Ala Gly Tyr Phe His Leu Pro Arg<br>            280                    285                    290 | 979 |
| taaaccactg cgcgcctgca aaaaacagta | 1009 |

<210> SEQ ID NO 74
<211> LENGTH: 293
<212> TYPE: PRT
<213> ORGANISM: Corynebacterium glutamicum

<400> SEQUENCE: 74

Met Ser Phe Thr Ala Phe Gln Thr Ala Leu Leu Val Trp Phe Arg Ala
1               5                        10                      15

Asn Ala Arg Asp Leu Ala Trp Arg Asp Pro Asn Thr Ser Ala Trp Gly
                    20                        25                        30

Ile Leu Leu Ser Glu Val Met Ser Gln Gln Thr Pro Val Ala Arg Val
                35                        40                        45

Glu Pro Ile Trp Arg Glu Trp Met Glu Lys Trp Pro Thr Pro Glu Asp
50                      55                        60

Phe Ala Asn Ala Ser Thr Asp Glu Ile Leu Arg Ser Trp Gly Lys Leu
65               70                        75                      80

Gly Tyr Pro Arg Arg Ala Leu Arg Leu Lys Glu Cys Ala Glu Val Ile
                    85                        90                        95

Val Glu Lys His Ala Gly Glu Val Pro Asp Thr Val Glu Ala Leu Leu
                    100                      105                    110

Ala Leu Pro Gly Ile Gly Asp Tyr Thr Ala Arg Ala Val Ala Ala Phe
                115                      120                      125

His Phe Gly Gln Arg Val Pro Val Val Asp Thr Asn Val Arg Arg Val
            130                      135                      140

Tyr Gln Arg Ala Val Ala Gly Arg Tyr Leu Ala Gly Pro Ala Lys Lys
145                    150                      155                    160

```
Gln Glu Leu Ile Asp Val Ser Leu Leu Pro Asn Thr His Ala Pro
            165                 170                 175

Glu Phe Ser Ala Ala Ile Met Glu Leu Gly Ala Leu Ile Cys Thr Ala
        180                 185                 190

Thr Ser Pro Lys Cys Asp Thr Cys Pro Leu Leu Asp Gln Cys Gln Trp
        195                 200                 205

Gln Lys Leu Gly Cys Pro Ser Pro Ser Glu Glu Leu Ala Ser Ala
    210                 215                 220

Lys Lys Arg Val Gln Lys Phe Val Gly Thr Asp Arg Gln Val Arg Gly
225                 230                 235                 240

Leu Ile Met Asp Val Leu Arg Asn Ala Thr Ala Pro Val Pro Leu Ser
                245                 250                 255

Ala Ile Asp Val Val Trp Pro Asp Ala Gln Arg Ser Arg Ala Leu
            260                 265                 270

Phe Ser Leu Ile Glu Asp Gly Leu Ala Glu Gln Asn Glu Ala Gly Tyr
        275                 280                 285

Phe His Leu Pro Arg
    290

<210> SEQ ID NO 75
<211> LENGTH: 3319
<212> TYPE: DNA
<213> ORGANISM: Corynebacterium glutamicum
<220> FEATURE:
<221> NAME/KEY: CDS
<222> LOCATION: (101)..(3289)
<223> OTHER INFORMATION: RXA02726

<400> SEQUENCE: 75
```

| | |
|---|---|
| ttgtgtcaac gaagtggagc tagttaattt agctcaagct gggtggtacc gcgtccgttt | 60 |

```
tttagggcgt ccccgcaggt agaacgataa ttattgttac ttg cgt gaa gga tgg       115
                                            Leu Arg Glu Gly Trp
                                              1               5 gac cga aca cac atg tct gaa gcc gtt ggc gga gtt tac cca cag gtt       163
Asp Arg Thr His Met Ser Glu Ala Val Gly Gly Val Tyr Pro Gln Val
            10                  15                  20 gat tta tct ggt ggg tca tcc aga ttt cca gag atg gaa gag aat gta       211
Asp Leu Ser Gly Gly Ser Ser Arg Phe Pro Glu Met Glu Glu Asn Val
        25                  30                  35 ctg agc tac tgg aag aag gat gac acc ttc cag gcc agc atc gat cag       259
Leu Ser Tyr Trp Lys Lys Asp Asp Thr Phe Gln Ala Ser Ile Asp Gln
    40                  45                  50 cgc gat ggt gct gaa gac tac gtc ttt tac gat ggc cct cct ttt gca       307
Arg Asp Gly Ala Glu Asp Tyr Val Phe Tyr Asp Gly Pro Pro Phe Ala
55                  60                  65 aac ggt ctg cca cac tac ggc cac cta ctg act ggt tac gtc aag gac       355
Asn Gly Leu Pro His Tyr Gly His Leu Leu Thr Gly Tyr Val Lys Asp
70                  75                  80                  85 att gtt cct cgc tac cag acc atg cgt ggc tac cgc gtt cct cgt gtc       403
Ile Val Pro Arg Tyr Gln Thr Met Arg Gly Tyr Arg Val Pro Arg Val
                90                  95                 100 ttc ggt tgg gat acc cac ggt ctg cca gct gaa ctt gag gct gaa aag       451
Phe Gly Trp Asp Thr His Gly Leu Pro Ala Glu Leu Glu Ala Glu Lys
            105                 110                 115 cag ctc ggc atc aag gac aag ggc gag atc gag gcc atg ggt ctt gcc       499
Gln Leu Gly Ile Lys Asp Lys Gly Glu Ile Glu Ala Met Gly Leu Ala
        120                 125                 130 aag ttc aac gag tac tgt gca acc tcc gtg ttg cag tac acc aag gaa       547
```

-continued

```
                Lys Phe Asn Glu Tyr Cys Ala Thr Ser Val Leu Gln Tyr Thr Lys Glu
                    135                 140                 145 tgg gaa gag tac gtc acc cgc cag gct cgt tgg gtg gac ttt gaa aac        595
Trp Glu Glu Tyr Val Thr Arg Gln Ala Arg Trp Val Asp Phe Glu Asn
150                 155                 160                 165 ggc tac aag acc atg gac ctt tct ttc atg gag tcc gtg atc tgg gcg        643
Gly Tyr Lys Thr Met Asp Leu Ser Phe Met Glu Ser Val Ile Trp Ala
                170                 175                 180 ttc aag gaa ctc tac gac aag ggc ctg atc tac cag ggt ttc cgc gtt        691
Phe Lys Glu Leu Tyr Asp Lys Gly Leu Ile Tyr Gln Gly Phe Arg Val
            185                 190                 195 ctt cct tac tcc tgg gca gag cac acc cca ctg tcc aac cag gaa acc        739
Leu Pro Tyr Ser Trp Ala Glu His Thr Pro Leu Ser Asn Gln Glu Thr
        200                 205                 210 cga ctg gat gac tcc tac aag ctg cgc cag gat cca acc ctg acc gtc        787
Arg Leu Asp Asp Ser Tyr Lys Leu Arg Gln Asp Pro Thr Leu Thr Val
    215                 220                 225 acg ttc cca gtc acc ggt gtc gtc gaa ggt tct tct gca aac gct ggc        835
Thr Phe Pro Val Thr Gly Val Val Glu Gly Ser Ser Ala Asn Ala Gly
230                 235                 240                 245 ctg gtg gga gcg ttg gct ctt gcg tgg acg act acc ccg tgg acc ctt        883
Leu Val Gly Ala Leu Ala Leu Ala Trp Thr Thr Thr Pro Trp Thr Leu
                250                 255                 260 cca tcc aac ctt gcg ttg gct gtg aac cca gcg gtg acc tac gca ttg        931
Pro Ser Asn Leu Ala Leu Ala Val Asn Pro Ala Val Thr Tyr Ala Leu
                265                 270                 275 gtt gag gtt gct gaa gac ggt gag gca gaa ttc gtc ggc aag cgt gtg        979
Val Glu Val Ala Glu Asp Gly Glu Ala Glu Phe Val Gly Lys Arg Val
            280                 285                 290 ctt ttg gct aag gac ctc gtt ggt tcc tac gcc aag gaa ctc ggt gct       1027
Leu Leu Ala Lys Asp Leu Val Gly Ser Tyr Ala Lys Glu Leu Gly Ala
        295                 300                 305 gag gct gtt atc gtt tct gag cac cca ggc tct gaa ctg gtc gga ctg       1075
Glu Ala Val Ile Val Ser Glu His Pro Gly Ser Glu Leu Val Gly Leu
    310                 315                 320                 325 acc tac gag cca atc ttt gga tat ttc cgc gat cac gcg aac gga ttc       1123
Thr Tyr Glu Pro Ile Phe Gly Tyr Phe Arg Asp His Ala Asn Gly Phe
                330                 335                 340 cag atc ctc ggt gca gag tac gtc acc acc gaa gac ggc acc ggt atc       1171
Gln Ile Leu Gly Ala Glu Tyr Val Thr Thr Glu Asp Gly Thr Gly Ile
            345                 350                 355 gtc cac cag gca cca gct ttc ggt gaa gac gat atg aac acc tgt aac       1219
Val His Gln Ala Pro Ala Phe Gly Glu Asp Asp Met Asn Thr Cys Asn
        360                 365                 370 gct gcc ggc att gag cca gtc atc cca gtg gac atc gac ggc aag ttc       1267
Ala Ala Gly Ile Glu Pro Val Ile Pro Val Asp Ile Asp Gly Lys Phe
    375                 380                 385 acc ggt ttg gtt cct gaa tac caa ggt cag ctt gtt ttc gat gcc aac       1315
Thr Gly Leu Val Pro Glu Tyr Gln Gly Gln Leu Val Phe Asp Ala Asn
390                 395                 400                 405 aag gac atc atc aag gac ttg aag gct gca ggt cgc gtg gtt cgc cac       1363
Lys Asp Ile Ile Lys Asp Leu Lys Ala Ala Gly Arg Val Val Arg His
                410                 415                 420 cag acc atc gaa cac tcc tac cca cac tct tgg cgt tcc ggt gag cca       1411
Gln Thr Ile Glu His Ser Tyr Pro His Ser Trp Arg Ser Gly Glu Pro
                425                 430                 435 ctg atc tac atg gct ctg cca tct tgg ttt gtg aat gtc acc gaa atc       1459
Leu Ile Tyr Met Ala Leu Pro Ser Trp Phe Val Asn Val Thr Glu Ile
            440                 445                 450
```

```
cgc gac cgc atg gtt gag gtc aac cag gac atc gag tgg atg cca gcg      1507
Arg Asp Arg Met Val Glu Val Asn Gln Asp Ile Glu Trp Met Pro Ala
455                 460                 465 cac atc cgc gac ggc cag ttc ggc aag tgg cta gaa ggt gcc cgc gac      1555
His Ile Arg Asp Gly Gln Phe Gly Lys Trp Leu Glu Gly Ala Arg Asp
470                 475                 480                 485 tgg aac atc tcc cgt tcc cgt tac tgg ggt tca cca att cca gca tgg      1603
Trp Asn Ile Ser Arg Ser Arg Tyr Trp Gly Ser Pro Ile Pro Ala Trp
                490                 495                 500 gtc tcc gac aac gac gaa tac cca cgc gtt gat gtt tat ggt tcc ctc      1651
Val Ser Asp Asn Asp Glu Tyr Pro Arg Val Asp Val Tyr Gly Ser Leu
                505                 510                 515 gat gag ctt gag gct gac ttt ggc gtg cgt cca aag tcc ctg cac cgt      1699
Asp Glu Leu Glu Ala Asp Phe Gly Val Arg Pro Lys Ser Leu His Arg
520                 525                 530 cca gac atc gat gaa cta act cgt cca aac cca gac gat cca acc ggc      1747
Pro Asp Ile Asp Glu Leu Thr Arg Pro Asn Pro Asp Asp Pro Thr Gly
535                 540                 545 aag tcc acc atg cga cgc gtc acc gat gtt ttg gac gtg tgg ttc gac      1795
Lys Ser Thr Met Arg Arg Val Thr Asp Val Leu Asp Val Trp Phe Asp
550                 555                 560                 565 tcc ggt tcc atg ccg ttt gcc cag gtg cac tac cca ttc gag aac aaa      1843
Ser Gly Ser Met Pro Phe Ala Gln Val His Tyr Pro Phe Glu Asn Lys
                570                 575                 580 gaa tgg ttt gat acc cac gca cca gca gac ttc atc gtg gag tac atc      1891
Glu Trp Phe Asp Thr His Ala Pro Ala Asp Phe Ile Val Glu Tyr Ile
                585                 590                 595 ggt cag acc cgc ggt tgg ttc tac ctg ctg cac gtg ctg tcc acc gca      1939
Gly Gln Thr Arg Gly Trp Phe Tyr Leu Leu His Val Leu Ser Thr Ala
                600                 605                 610 ctg ttt gac cgc cca gct ttc aag aag gtt gtc gca cac ggc atc gtc      1987
Leu Phe Asp Arg Pro Ala Phe Lys Lys Val Val Ala His Gly Ile Val
615                 620                 625 ttg ggt gat gac gga ctg aag atg tcc aag tcc aag ggc aac tac ccg      2035
Leu Gly Asp Asp Gly Leu Lys Met Ser Lys Ser Lys Gly Asn Tyr Pro
630                 635                 640                 645 aac gtc aac gag gtc ttc gac cgc gac ggt tcc gac gcc atg cgt tgg      2083
Asn Val Asn Glu Val Phe Asp Arg Asp Gly Ser Asp Ala Met Arg Trp
                650                 655                 660 ttc ctc atg agt tcc cca atc ctg cgc ggc ggc aac ttg att gtc acc      2131
Phe Leu Met Ser Ser Pro Ile Leu Arg Gly Gly Asn Leu Ile Val Thr
                665                 670                 675 gaa aag ggc atc cgc gaa ggt gtg cgc caa gca cag ctt cca atg tgg      2179
Glu Lys Gly Ile Arg Glu Gly Val Arg Gln Ala Gln Leu Pro Met Trp
                680                 685                 690 aac gca tac tcc ttc ctg cag ctg tac acc tcc aag aac gca acc tgg      2227
Asn Ala Tyr Ser Phe Leu Gln Leu Tyr Thr Ser Lys Asn Ala Thr Trp
695                 700                 705 tca gtc gac tcc act gac gtg ctg gac cgc tac atc ctg gcg aag ctg      2275
Ser Val Asp Ser Thr Asp Val Leu Asp Arg Tyr Ile Leu Ala Lys Leu
710                 715                 720                 725 cac gat ttg gtg gca gag acc cag gcg gca ctc gac ggc act gac att      2323
His Asp Leu Val Ala Glu Thr Gln Ala Ala Leu Asp Gly Thr Asp Ile
                730                 735                 740 gca aag gct tgc gac ttg gtt cgt aac ttc tgt gat gcg ttg acc aac      2371
Ala Lys Ala Cys Asp Leu Val Arg Asn Phe Cys Asp Ala Leu Thr Asn
                745                 750                 755 tgg tac gtg cgt cgt tcc cgc gac cgt ttc tgg gct ggt gat gaa gca      2419
Trp Tyr Val Arg Arg Ser Arg Asp Arg Phe Trp Ala Gly Asp Glu Ala
                760                 765                 770
```

-continued

```
cac cca gag gct ttc aac acc ttg tac acc gtg ctg gaa acc ctc acc       2467
His Pro Glu Ala Phe Asn Thr Leu Tyr Thr Val Leu Glu Thr Leu Thr
775                 780                 785 cgc gtg gca gct cca ctg ctg cca atg acc acc gaa gtg atc tgg cgt       2515
Arg Val Ala Ala Pro Leu Leu Pro Met Thr Thr Glu Val Ile Trp Arg
790                 795                 800                 805 gga ctg acc ggc gag cgt tct gtg cac ctg act gat ttc cca tcc gct       2563
Gly Leu Thr Gly Glu Arg Ser Val His Leu Thr Asp Phe Pro Ser Ala
            810                 815                 820 gag tct ttc cca gca gat gct gat ttg gtt cgc acc atg gat gag atc       2611
Glu Ser Phe Pro Ala Asp Ala Asp Leu Val Arg Thr Met Asp Glu Ile
        825                 830                 835 cgt ggc gtg tgc tct gcg gct tcc tct gtt cgt aag gct cac aag ctg       2659
Arg Gly Val Cys Ser Ala Ala Ser Ser Val Arg Lys Ala His Lys Leu
    840                 845                 850 cgt aac cgt ctg cca ctt cca ggc ctg act gtt gct ctt cca gac tct       2707
Arg Asn Arg Leu Pro Leu Pro Gly Leu Thr Val Ala Leu Pro Asp Ser
855                 860                 865 gct cgc ctg gca gac ttc gct tcg atc atc cgc gat gag gtc aac gtg       2755
Ala Arg Leu Ala Asp Phe Ala Ser Ile Ile Arg Asp Glu Val Asn Val
870                 875                 880                 885 aag aac gtg gat ctg acc tct gac gtg gat tcc gtg gga acc ttc gag       2803
Lys Asn Val Asp Leu Thr Ser Asp Val Asp Ser Val Gly Thr Phe Glu
            890                 895                 900 gtt gtt gtt aac gct aag gtt gca ggt cct cgc ttg ggc aag gac gtc       2851
Val Val Val Asn Ala Lys Val Ala Gly Pro Arg Leu Gly Lys Asp Val
        905                 910                 915 cag cgc gtg atc aag gct gtg aag gct ggc aac tac acc cgc gaa ggc       2899
Gln Arg Val Ile Lys Ala Val Lys Ala Gly Asn Tyr Thr Arg Glu Gly
    920                 925                 930 gac gtc gtt gtt gcc gat ggc atc gag ctc aac gag ggt gaa ttc acc       2947
Asp Val Val Val Ala Asp Gly Ile Glu Leu Asn Glu Gly Glu Phe Thr
935                 940                 945 gag cgt ctc gta gca gca aac cct gat tcc acc gcg cag atc gac ggc       2995
Glu Arg Leu Val Ala Ala Asn Pro Asp Ser Thr Ala Gln Ile Asp Gly
950                 955                 960                 965 gtg gat gga ctc gtg gtt ctg gac atg gaa gtc acg gaa gaa ctt gaa       3043
Val Asp Gly Leu Val Val Leu Asp Met Glu Val Thr Glu Glu Leu Glu
            970                 975                 980 gca gaa ggc tgg gca gcg gac gcg atc cgt ggc ctg cag gat gct cga       3091
Ala Glu Gly Trp Ala Ala Asp Ala Ile Arg Gly Leu Gln Asp Ala Arg
        985                 990                 995 aag aac tcc ggc ttt gag gtt tct gac cgc att tct gtt gtc gtc agc       3139
Lys Asn Ser Gly Phe Glu Val Ser Asp Arg Ile Ser Val Val Val Ser
    1000                1005                1010 gtt cct gag gac aag aag gaa tgg atc acc act cac gct gat cac atc       3187
Val Pro Glu Asp Lys Lys Glu Trp Ile Thr Thr His Ala Asp His Ile
1015                1020                1025 gca gcg gaa gtt ttg gca acc tcc ttt gag atc gtc act gat gcc ctc       3235
Ala Ala Glu Val Leu Ala Thr Ser Phe Glu Ile Val Thr Asp Ala Leu
1030                1035                1040                1045 gac ggc gaa acc cac gac att gtc gct ggt gtg acc gcg aag gtt act       3283
Asp Gly Glu Thr His Asp Ile Val Ala Gly Val Thr Ala Lys Val Thr
            1050                1055                1060 aag aac taagagttgt tttgttgaga aagcccgctg                              3319
Lys Asn
```

<210> SEQ ID NO 76
<211> LENGTH: 1063

```
<212> TYPE: PRT
<213> ORGANISM: Corynebacterium glutamicum

<400> SEQUENCE: 76

Leu Arg Glu Gly Trp Asp Arg Thr His Met Ser Glu Ala Val Gly Gly
  1               5                  10                  15

Val Tyr Pro Gln Val Asp Leu Ser Gly Gly Ser Ser Arg Phe Pro Glu
             20                  25                  30

Met Glu Glu Asn Val Leu Ser Tyr Trp Lys Lys Asp Thr Phe Gln
         35                  40                  45

Ala Ser Ile Asp Gln Arg Asp Gly Ala Glu Asp Tyr Val Phe Tyr Asp
     50                  55                  60

Gly Pro Pro Phe Ala Asn Gly Leu Pro His Tyr Gly His Leu Leu Thr
 65                  70                  75                  80

Gly Tyr Val Lys Asp Ile Val Pro Arg Tyr Gln Thr Met Arg Gly Tyr
                 85                  90                  95

Arg Val Pro Arg Val Phe Gly Trp Asp Thr His Gly Leu Pro Ala Glu
            100                 105                 110

Leu Glu Ala Glu Lys Gln Leu Gly Ile Lys Asp Lys Gly Glu Ile Glu
        115                 120                 125

Ala Met Gly Leu Ala Lys Phe Asn Glu Tyr Cys Ala Thr Ser Val Leu
130                 135                 140

Gln Tyr Thr Lys Glu Trp Glu Glu Tyr Val Thr Arg Gln Ala Arg Trp
145                 150                 155                 160

Val Asp Phe Glu Asn Gly Tyr Lys Thr Met Asp Leu Ser Phe Met Glu
                165                 170                 175

Ser Val Ile Trp Ala Phe Lys Glu Leu Tyr Asp Lys Gly Leu Ile Tyr
            180                 185                 190

Gln Gly Phe Arg Val Leu Pro Tyr Ser Trp Ala Glu His Thr Pro Leu
        195                 200                 205

Ser Asn Gln Glu Thr Arg Leu Asp Asp Ser Tyr Lys Leu Arg Gln Asp
    210                 215                 220

Pro Thr Leu Thr Val Thr Phe Pro Val Thr Gly Val Val Glu Gly Ser
225                 230                 235                 240

Ser Ala Asn Ala Gly Leu Val Gly Ala Leu Ala Leu Trp Thr Thr
                245                 250                 255

Thr Pro Trp Thr Leu Pro Ser Asn Leu Ala Leu Ala Val Asn Pro Ala
            260                 265                 270

Val Thr Tyr Ala Leu Val Glu Val Ala Glu Asp Gly Glu Ala Glu Phe
        275                 280                 285

Val Gly Lys Arg Val Leu Leu Ala Lys Asp Leu Val Gly Ser Tyr Ala
    290                 295                 300

Lys Glu Leu Gly Ala Glu Ala Val Ile Val Ser Glu His Pro Gly Ser
305                 310                 315                 320

Glu Leu Val Gly Leu Thr Tyr Glu Pro Ile Phe Gly Tyr Phe Arg Asp
                325                 330                 335

His Ala Asn Gly Phe Gln Ile Leu Gly Ala Glu Tyr Val Thr Thr Glu
            340                 345                 350

Asp Gly Thr Gly Ile Val His Gln Ala Pro Ala Phe Gly Glu Asp Asp
        355                 360                 365

Met Asn Thr Cys Asn Ala Ala Gly Ile Glu Pro Val Ile Pro Val Asp
    370                 375                 380

Ile Asp Gly Lys Phe Thr Gly Leu Val Pro Glu Tyr Gln Gly Gln Leu
385                 390                 395                 400
```

-continued

Val Phe Asp Ala Asn Lys Asp Ile Ile Lys Asp Leu Lys Ala Ala Gly
                405                 410                 415
Arg Val Val Arg His Gln Thr Ile Glu His Ser Tyr Pro His Ser Trp
            420                 425                 430
Arg Ser Gly Glu Pro Leu Ile Tyr Met Ala Leu Pro Ser Trp Phe Val
        435                 440                 445
Asn Val Thr Glu Ile Arg Asp Arg Met Val Glu Val Asn Gln Asp Ile
    450                 455                 460
Glu Trp Met Pro Ala His Ile Arg Asp Gly Gln Phe Gly Lys Trp Leu
465                 470                 475                 480
Glu Gly Ala Arg Asp Trp Asn Ile Ser Arg Ser Arg Tyr Trp Gly Ser
                485                 490                 495
Pro Ile Pro Ala Trp Val Ser Asp Asn Asp Glu Tyr Pro Arg Val Asp
            500                 505                 510
Val Tyr Gly Ser Leu Asp Glu Leu Glu Ala Asp Phe Gly Val Arg Pro
        515                 520                 525
Lys Ser Leu His Arg Pro Asp Ile Asp Glu Leu Thr Arg Pro Asn Pro
    530                 535                 540
Asp Asp Pro Thr Gly Lys Ser Thr Met Arg Arg Val Thr Asp Val Leu
545                 550                 555                 560
Asp Val Trp Phe Asp Ser Gly Ser Met Pro Phe Ala Gln Val His Tyr
                565                 570                 575
Pro Phe Glu Asn Lys Glu Trp Phe Asp Thr His Ala Pro Ala Asp Phe
            580                 585                 590
Ile Val Glu Tyr Ile Gly Gln Thr Arg Gly Trp Phe Tyr Leu Leu His
        595                 600                 605
Val Leu Ser Thr Ala Leu Phe Asp Arg Pro Ala Phe Lys Lys Val Val
    610                 615                 620
Ala His Gly Ile Val Leu Gly Asp Asp Gly Leu Lys Met Ser Lys Ser
625                 630                 635                 640
Lys Gly Asn Tyr Pro Asn Val Asn Glu Val Phe Asp Arg Asp Gly Ser
                645                 650                 655
Asp Ala Met Arg Trp Phe Leu Met Ser Ser Pro Ile Leu Arg Gly Gly
            660                 665                 670
Asn Leu Ile Val Thr Glu Lys Gly Ile Arg Glu Gly Val Arg Gln Ala
        675                 680                 685
Gln Leu Pro Met Trp Asn Ala Tyr Ser Phe Leu Gln Leu Tyr Thr Ser
    690                 695                 700
Lys Asn Ala Thr Trp Ser Val Asp Ser Thr Asp Val Leu Asp Arg Tyr
705                 710                 715                 720
Ile Leu Ala Lys Leu His Asp Leu Val Ala Glu Thr Gln Ala Ala Leu
                725                 730                 735
Asp Gly Thr Asp Ile Ala Lys Ala Cys Asp Leu Val Arg Asn Phe Cys
            740                 745                 750
Asp Ala Leu Thr Asn Trp Tyr Val Arg Arg Ser Arg Asp Arg Phe Trp
        755                 760                 765
Ala Gly Asp Glu Ala His Pro Glu Ala Phe Asn Thr Leu Tyr Thr Val
    770                 775                 780
Leu Glu Thr Leu Thr Arg Val Ala Ala Pro Leu Pro Met Thr Thr
785                 790                 795                 800
Glu Val Ile Trp Arg Gly Leu Thr Gly Glu Arg Ser Val His Leu Thr
                805                 810                 815

-continued

```
Asp Phe Pro Ser Ala Glu Ser Phe Pro Ala Asp Ala Asp Leu Val Arg
        820                 825                 830

Thr Met Asp Glu Ile Arg Gly Val Cys Ser Ala Ala Ser Ser Val Arg
        835                 840                 845

Lys Ala His Lys Leu Arg Asn Arg Leu Pro Leu Pro Gly Leu Thr Val
        850                 855                 860

Ala Leu Pro Asp Ser Ala Arg Leu Ala Asp Phe Ala Ser Ile Ile Arg
865                 870                 875                 880

Asp Glu Val Asn Val Lys Asn Val Asp Leu Thr Ser Asp Val Asp Ser
                    885                 890                 895

Val Gly Thr Phe Glu Val Val Asn Ala Lys Val Ala Gly Pro Arg
            900                 905                 910

Leu Gly Lys Asp Val Gln Arg Val Ile Lys Ala Val Lys Ala Gly Asn
            915                 920                 925

Tyr Thr Arg Glu Gly Asp Val Val Ala Asp Gly Ile Glu Leu Asn
            930                 935                 940

Glu Gly Glu Phe Thr Glu Arg Leu Val Ala Ala Asn Pro Asp Ser Thr
945                 950                 955                 960

Ala Gln Ile Asp Gly Val Asp Gly Leu Val Leu Asp Met Glu Val
            965                 970                 975

Thr Glu Glu Leu Glu Ala Glu Gly Trp Ala Ala Asp Ala Ile Arg Gly
            980                 985                 990

Leu Gln Asp Ala Arg Lys Asn Ser Gly Phe Glu Val Ser Asp Arg Ile
            995                1000                1005

Ser Val Val Ser Val Pro Glu Asp Lys Lys Glu Trp Ile Thr Thr
    1010                1015                1020

His Ala Asp His Ile Ala Ala Glu Val Leu Ala Thr Ser Phe Glu Ile
1025                1030                1035                1040

Val Thr Asp Ala Leu Asp Gly Glu Thr His Asp Ile Val Ala Gly Val
                1045                1050                1055

Thr Ala Lys Val Thr Lys Asn
        1060
```

```
<210> SEQ ID NO 77
<211> LENGTH: 2290
<212> TYPE: DNA
<213> ORGANISM: Corynebacterium glutamicum
<220> FEATURE:
<221> NAME/KEY: CDS
<222> LOCATION: (101)..(2260)
<223> OTHER INFORMATION: RXA02731

<400> SEQUENCE: 77
```

| | | |
|---|---|---:|
| gttgcatcga gtccgcgggt ttcgcacgct tgatctaaat tcttgagggt tttccggccg | | 60 |
| ttgtttgcgc taaacgtagg ggtcaagcgt cgaaaagcgc ttg ctt gca cgc tgt<br>                                                                                      Leu Leu Ala Arg Cys<br>                                                                                       1                 5 | | 115 |
| ttt gct gcg ggc cgc aac gtg tcc acc ctg tgg cgt atc cta gaa tgc<br>Phe Ala Ala Gly Arg Asn Val Ser Thr Leu Trp Arg Ile Leu Glu Cys<br>          10                    15                        20 | | 163 |
| atg gct ttt gct gct gaa cat cct gtc ctg tcc cac tct gag cac cgc<br>Met Ala Phe Ala Ala Glu His Pro Val Leu Ser His Ser Glu His Arg<br>              25                    30                        35 | | 211 |
| ccg gtt ggt gaa atc gag cgt agc gat gac aaa ttt gtt gtc gtt agt<br>Pro Val Gly Glu Ile Glu Arg Ser Asp Asp Lys Phe Val Val Val Ser<br>    40                    45                    50 | | 259 |
| gaa ttt gag cct gcg ggt gac cag cct gcg gct att aaa gag ctc gat | | 307 |

|   |   |
|---|---|
| Glu Phe Glu Pro Ala Gly Asp Gln Pro Ala Ala Ile Lys Glu Leu Asp<br>55 60 65 |   |
| gag cgc ttg gat cgc ggt gag cgg gac gtc gtt ttg atg ggt gct act<br>Glu Arg Leu Asp Arg Gly Glu Arg Asp Val Val Leu Met Gly Ala Thr<br>70 75 80 85 | 355 |
| ggt acg ggt aag tcc gcg act gcg gcg tgg ttg atc gaa aag cag cag<br>Gly Thr Gly Lys Ser Ala Thr Ala Ala Trp Leu Ile Glu Lys Gln Gln<br>90 95 100 | 403 |
| cgc ccc gct ttg gtg atg gcg ccg aat aag acg ctg gct gcg cag ttg<br>Arg Pro Ala Leu Val Met Ala Pro Asn Lys Thr Leu Ala Ala Gln Leu<br>105 110 115 | 451 |
| gct aat gaa ttg cgg cag ctg ttg ccc aat aac gcg gtg gag tat ttc<br>Ala Asn Glu Leu Arg Gln Leu Leu Pro Asn Asn Ala Val Glu Tyr Phe<br>120 125 130 | 499 |
| gtg tct tat tac gat tac tac cag cca gaa gcg tat atc gcg cag act<br>Val Ser Tyr Tyr Asp Tyr Tyr Gln Pro Glu Ala Tyr Ile Ala Gln Thr<br>135 140 145 | 547 |
| gat acc tat att gaa aag gac tcc tcg att aat gag gat gtg gag cgt<br>Asp Thr Tyr Ile Glu Lys Asp Ser Ser Ile Asn Glu Asp Val Glu Arg<br>150 155 160 165 | 595 |
| ctg cgt cac tcg gcg acg tcg tct ttg ctg agt agg cga gac gtc gtg<br>Leu Arg His Ser Ala Thr Ser Ser Leu Leu Ser Arg Arg Asp Val Val<br>170 175 180 | 643 |
| gtt gtt agt tcg gtg tcg tgt att tat ggc ttg ggc act cca cag tct<br>Val Val Ser Ser Val Ser Cys Ile Tyr Gly Leu Gly Thr Pro Gln Ser<br>185 190 195 | 691 |
| tat ctt gac cgt tcc gtt gtg ttg aac gtg ggg gag gag atc gac cgc<br>Tyr Leu Asp Arg Ser Val Val Leu Asn Val Gly Glu Glu Ile Asp Arg<br>200 205 210 | 739 |
| gat cgc ttt ttg cgc cta ttg gta gat att caa tac gaa cgc aat gat<br>Asp Arg Phe Leu Arg Leu Leu Val Asp Ile Gln Tyr Glu Arg Asn Asp<br>215 220 225 | 787 |
| gtg ggc ttt act cgt ggt gct ttc cgc gtg aag ggc gat acc gtg gac<br>Val Gly Phe Thr Arg Gly Ala Phe Arg Val Lys Gly Asp Thr Val Asp<br>230 235 240 245 | 835 |
| atc atc ccg gcc tat gag gaa ttg gcg gtg cgc att gag ttt ttc ggt<br>Ile Ile Pro Ala Tyr Glu Glu Leu Ala Val Arg Ile Glu Phe Phe Gly<br>250 255 260 | 883 |
| gat gaa att gat gcg ttg tac tac atc cat ccc ctg act ggt gac acc<br>Asp Glu Ile Asp Ala Leu Tyr Tyr Ile His Pro Leu Thr Gly Asp Thr<br>265 270 275 | 931 |
| atc cgg cag gtg aat gag atc cgt att ttc cca gct acg cac tat gtt<br>Ile Arg Gln Val Asn Glu Ile Arg Ile Phe Pro Ala Thr His Tyr Val<br>280 285 290 | 979 |
| gcg gga cct gag cgg atg gaa aag gca gtc gct gat att aag gcg gag<br>Ala Gly Pro Glu Arg Met Glu Lys Ala Val Ala Asp Ile Lys Ala Glu<br>295 300 305 | 1027 |
| ttg gaa gtg cgc ctg gct gat ttg gag aac cgt ggc aag tta ttg gaa<br>Leu Glu Val Arg Leu Ala Asp Leu Glu Asn Arg Gly Lys Leu Leu Glu<br>310 315 320 325 | 1075 |
| gcg cag cgt ctt agg atg cgt act gaa tat gac tta gaa atg atc gag<br>Ala Gln Arg Leu Arg Met Arg Thr Glu Tyr Asp Leu Glu Met Ile Glu<br>330 335 340 | 1123 |
| cag gtt ggt ttc tgt tcg ggc att gag aac tat tct cgc cac att gat<br>Gln Val Gly Phe Cys Ser Gly Ile Glu Asn Tyr Ser Arg His Ile Asp<br>345 350 355 | 1171 |
| gga cgt ggg gag gga acc gca ccg gcc acg ctg att gac tat ttc cca<br>Gly Arg Gly Glu Gly Thr Ala Pro Ala Thr Leu Ile Asp Tyr Phe Pro<br>360 365 370 | 1219 |

-continued

```
gag gat ttc ctc acc atc atc gat gag tct cac gtg aca gtc ccg cag      1267
Glu Asp Phe Leu Thr Ile Ile Asp Glu Ser His Val Thr Val Pro Gln
375                 380                 385 atc ggc ggc atg ttt gag ggc gat atg tcc cgt aaa cgt aac ctc gta      1315
Ile Gly Gly Met Phe Glu Gly Asp Met Ser Arg Lys Arg Asn Leu Val
390                 395                 400                 405 gaa ttc ggt ttc cgc ctg cca tcc gcg atg gat aac cgc cca ttg acc      1363
Glu Phe Gly Phe Arg Leu Pro Ser Ala Met Asp Asn Arg Pro Leu Thr
            410                 415                 420 tgg gag gag ttc gat gaa cgc cgt ggc caa acg gtg ttc atg tct gca      1411
Trp Glu Glu Phe Asp Glu Arg Arg Gly Gln Thr Val Phe Met Ser Ala
        425                 430                 435 act cca ggc aag ttt gag atc gct gct gct gat ggt gag ttt gtg gag      1459
Thr Pro Gly Lys Phe Glu Ile Ala Ala Ala Asp Gly Glu Phe Val Glu
    440                 445                 450 cag gtc att cgc cca aca ggt ctg gtg gat cca aag gtc acc gtc aag      1507
Gln Val Ile Arg Pro Thr Gly Leu Val Asp Pro Lys Val Thr Val Lys
455                 460                 465 cca acg aag ggg cag att gat gat ctg atc cat gaa att cgc caa cgc      1555
Pro Thr Lys Gly Gln Ile Asp Asp Leu Ile His Glu Ile Arg Gln Arg
470                 475                 480                 485 acc gat aaa gat gag cgc gtt ttg gtc acc aca ttg acc aag aaa atg      1603
Thr Asp Lys Asp Glu Arg Val Leu Val Thr Thr Leu Thr Lys Lys Met
            490                 495                 500 gct gag gat ctt act gat tac ctg ctg gaa aac ggc atc cgc gtg cgc      1651
Ala Glu Asp Leu Thr Asp Tyr Leu Leu Glu Asn Gly Ile Arg Val Arg
        505                 510                 515 tac ctg cac tca gat att gat acc ttg cag cgt gtg gaa ttg ctg cgt      1699
Tyr Leu His Ser Asp Ile Asp Thr Leu Gln Arg Val Glu Leu Leu Arg
    520                 525                 530 cag ctt cgc ctg ggc gaa tac gat gtg ttg gta ggt att aac ctg ctg      1747
Gln Leu Arg Leu Gly Glu Tyr Asp Val Leu Val Gly Ile Asn Leu Leu
535                 540                 545 cgt gag ggc ctt gac ctg cca gaa gtc tct ctg gtt gcg att ctc gac      1795
Arg Glu Gly Leu Asp Leu Pro Glu Val Ser Leu Val Ala Ile Leu Asp
550                 555                 560                 565 gcc gac aag gaa ggc ttc ctg cgc tcc acc acc tca ctg att cag acc      1843
Ala Asp Lys Glu Gly Phe Leu Arg Ser Thr Thr Ser Leu Ile Gln Thr
            570                 575                 580 att ggc cgc gcc gcc cga aat gtg tcc ggc gag gtc atc atg tac gcc      1891
Ile Gly Arg Ala Ala Arg Asn Val Ser Gly Glu Val Ile Met Tyr Ala
        585                 590                 595 gac aag atc act gat tcg atg cag tat gcc atc gag gaa acc gat cga      1939
Asp Lys Ile Thr Asp Ser Met Gln Tyr Ala Ile Glu Glu Thr Asp Arg
    600                 605                 610 cgc cgt gaa aag cag gtc gct tat aac aag gaa cac ggc atc gat ccg      1987
Arg Arg Glu Lys Gln Val Ala Tyr Asn Lys Glu His Gly Ile Asp Pro
615                 620                 625 cag ccg ctt cga aag aaa atc gcg gac atc ctc gac cag gtc tat gac      2035
Gln Pro Leu Arg Lys Lys Ile Ala Asp Ile Leu Asp Gln Val Tyr Asp
630                 635                 640                 645 aat tcc gct gat gga gca gga cct tct gcc tct ggc gat gcg gca gtc      2083
Asn Ser Ala Asp Gly Ala Gly Pro Ser Ala Ser Gly Asp Ala Ala Val
            650                 655                 660 gtg gct aaa cct gac gtg tct agc atg ccc gcc aaa gaa gtg caa aag      2131
Val Ala Lys Pro Asp Val Ser Ser Met Pro Ala Lys Glu Val Gln Lys
        665                 670                 675 ctt atc gac gac ctc agc gct cag atg gct gcg gcc gcg cgg gag ctc      2179
Leu Ile Asp Asp Leu Ser Ala Gln Met Ala Ala Ala Arg Glu Leu
    680                 685                 690
```

```
aag ttc gag ctg gca ggg cgt ctg cga gat gag atc ttc gag ctc aag      2227
Lys Phe Glu Leu Ala Gly Arg Leu Arg Asp Glu Ile Phe Glu Leu Lys
    695                 700                 705 aag gaa ctg aga ggt atc aag gat gcc ggc atc taagtcagct tgctcactta    2280
Lys Glu Leu Arg Gly Ile Lys Asp Ala Gly Ile
710                 715                 720 aagcttcgaa                                                            2290

<210> SEQ ID NO 78
<211> LENGTH: 720
<212> TYPE: PRT
<213> ORGANISM: Corynebacterium glutamicum

<400> SEQUENCE: 78

Leu Leu Ala Arg Cys Phe Ala Ala Gly Arg Asn Val Ser Thr Leu Trp
 1               5                  10                  15

Arg Ile Leu Glu Cys Met Ala Phe Ala Ala Glu His Pro Val Leu Ser
            20                  25                  30

His Ser Glu His Arg Pro Val Gly Glu Ile Glu Arg Ser Asp Asp Lys
        35                  40                  45

Phe Val Val Ser Glu Phe Glu Pro Ala Gly Asp Gln Pro Ala Ala
    50                  55                  60

Ile Lys Glu Leu Asp Glu Arg Leu Asp Arg Gly Glu Arg Asp Val Val
 65                  70                  75                  80

Leu Met Gly Ala Thr Gly Thr Gly Lys Ser Ala Thr Ala Ala Trp Leu
                85                  90                  95

Ile Glu Lys Gln Gln Arg Pro Ala Leu Val Met Ala Pro Asn Lys Thr
            100                 105                 110

Leu Ala Ala Gln Leu Ala Asn Glu Leu Arg Gln Leu Leu Pro Asn Asn
        115                 120                 125

Ala Val Glu Tyr Phe Val Ser Tyr Tyr Asp Tyr Tyr Gln Pro Glu Ala
    130                 135                 140

Tyr Ile Ala Gln Thr Asp Thr Tyr Ile Glu Lys Asp Ser Ser Ile Asn
145                 150                 155                 160

Glu Asp Val Glu Arg Leu Arg His Ser Ala Thr Ser Ser Leu Leu Ser
                165                 170                 175

Arg Arg Asp Val Val Val Ser Ser Val Ser Cys Ile Tyr Gly Leu
            180                 185                 190

Gly Thr Pro Gln Ser Tyr Leu Asp Arg Ser Val Val Leu Asn Val Gly
        195                 200                 205

Glu Glu Ile Asp Arg Asp Arg Phe Leu Arg Leu Leu Val Asp Ile Gln
    210                 215                 220

Tyr Glu Arg Asn Asp Val Gly Phe Thr Arg Gly Ala Phe Arg Val Lys
225                 230                 235                 240

Gly Asp Thr Val Asp Ile Pro Ala Tyr Glu Glu Leu Ala Val Arg
                245                 250                 255

Ile Glu Phe Phe Gly Asp Glu Ile Asp Ala Leu Tyr Tyr Ile His Pro
            260                 265                 270

Leu Thr Gly Asp Thr Ile Arg Gln Val Asn Glu Ile Arg Ile Phe Pro
        275                 280                 285

Ala Thr His Tyr Val Ala Gly Pro Glu Arg Met Glu Lys Ala Val Ala
    290                 295                 300

Asp Ile Lys Ala Glu Leu Glu Val Arg Leu Ala Asp Leu Glu Asn Arg
305                 310                 315                 320
```

-continued

```
Gly Lys Leu Leu Glu Ala Gln Arg Leu Arg Met Arg Thr Glu Tyr Asp
            325                 330                 335
Leu Glu Met Ile Glu Gln Val Gly Phe Cys Ser Gly Ile Glu Asn Tyr
            340                 345                 350
Ser Arg His Ile Asp Gly Arg Gly Glu Gly Thr Ala Pro Ala Thr Leu
            355                 360                 365
Ile Asp Tyr Phe Pro Glu Asp Phe Leu Thr Ile Ile Asp Glu Ser His
370                 375                 380
Val Thr Val Pro Gln Ile Gly Gly Met Phe Glu Gly Asp Met Ser Arg
385                 390                 395                 400
Lys Arg Asn Leu Val Glu Phe Gly Phe Arg Leu Pro Ser Ala Met Asp
                405                 410                 415
Asn Arg Pro Leu Thr Trp Glu Glu Phe Asp Glu Arg Arg Gly Gln Thr
            420                 425                 430
Val Phe Met Ser Ala Thr Pro Gly Lys Phe Glu Ile Ala Ala Ala Asp
            435                 440                 445
Gly Glu Phe Val Glu Gln Val Ile Arg Pro Thr Gly Leu Val Asp Pro
    450                 455                 460
Lys Val Thr Val Lys Pro Thr Lys Gly Gln Ile Asp Asp Leu Ile His
465                 470                 475                 480
Glu Ile Arg Gln Arg Thr Asp Lys Asp Glu Arg Val Leu Val Thr Thr
                485                 490                 495
Leu Thr Lys Lys Met Ala Glu Asp Leu Thr Asp Tyr Leu Leu Glu Asn
            500                 505                 510
Gly Ile Arg Val Arg Tyr Leu His Ser Asp Ile Asp Thr Leu Gln Arg
            515                 520                 525
Val Glu Leu Leu Arg Gln Leu Arg Leu Gly Tyr Asp Val Leu Val
            530                 535                 540
Gly Ile Asn Leu Leu Arg Glu Gly Leu Asp Leu Pro Glu Val Ser Leu
545                 550                 555                 560
Val Ala Ile Leu Asp Ala Asp Lys Glu Gly Phe Leu Arg Ser Thr Thr
                565                 570                 575
Ser Leu Ile Gln Thr Ile Gly Arg Ala Ala Arg Asn Val Ser Gly Glu
            580                 585                 590
Val Ile Met Tyr Ala Asp Lys Ile Thr Asp Ser Met Gln Tyr Ala Ile
            595                 600                 605
Glu Glu Thr Asp Arg Arg Glu Lys Gln Val Ala Tyr Asn Lys Glu
    610                 615                 620
His Gly Ile Asp Pro Gln Pro Leu Arg Lys Lys Ile Ala Asp Ile Leu
625                 630                 635                 640
Asp Gln Val Tyr Asp Asn Ser Ala Asp Gly Ala Gly Pro Ser Ala Ser
                645                 650                 655
Gly Asp Ala Ala Val Val Ala Lys Pro Asp Val Ser Ser Met Pro Ala
            660                 665                 670
Lys Glu Val Gln Lys Leu Ile Asp Asp Leu Ser Ala Gln Met Ala Ala
            675                 680                 685
Ala Ala Arg Glu Leu Lys Phe Glu Leu Ala Gly Arg Leu Arg Asp Glu
    690                 695                 700
Ile Phe Glu Leu Lys Lys Glu Leu Arg Gly Ile Lys Asp Ala Gly Ile
705                 710                 715                 720
```

<210> SEQ ID NO 79
<211> LENGTH: 1087
<212> TYPE: DNA

<213> ORGANISM: Corynebacterium glutamicum
<220> FEATURE:
<221> NAME/KEY: CDS
<222> LOCATION: (101)..(1057)
<223> OTHER INFORMATION: RXA02736

<400> SEQUENCE: 79

```
cagaggatta cccagcgggt acgtggggtc caaagagcgc tgatgaaatg ctttcccgca      60
acggtcacac ctggcgcagg ccataattta ggggcaaaaa atg atc ttt gaa ctt      115
                                              Met Ile Phe Glu Leu
                                                1               5 ccg gat acc acc acc cag caa att tcc aag acc cta act cga ctg cgt      163
Pro Asp Thr Thr Thr Gln Gln Ile Ser Lys Thr Leu Thr Arg Leu Arg
                10                  15                  20 gaa tcg ggc acc cag gtc acc acc ggc cga gtg ctc acc ctc atc gtg      211
Glu Ser Gly Thr Gln Val Thr Thr Gly Arg Val Leu Thr Leu Ile Val
            25                  30                  35 gtc act gac tcc gaa agc gat gtc gct gca gtt acc gag tcc acc aat      259
Val Thr Asp Ser Glu Ser Asp Val Ala Ala Val Thr Glu Ser Thr Asn
        40                  45                  50 gaa gcc tcg cgc gag cac cca tct cgc gtg atc att ttg gtg gtt ggc      307
Glu Ala Ser Arg Glu His Pro Ser Arg Val Ile Ile Leu Val Val Gly
    55                  60                  65 gat aaa act gca gaa aac aaa gtt gac gca gaa gtc cgt atc ggt ggc      355
Asp Lys Thr Ala Glu Asn Lys Val Asp Ala Glu Val Arg Ile Gly Gly
 70                  75                  80                  85 gac gct ggt gct tcc gag atg atc atc atg cat ctc aac gga cct gtc      403
Asp Ala Gly Ala Ser Glu Met Ile Ile Met His Leu Asn Gly Pro Val
                90                  95                 100 gct gac aag ctc cag tat gtc gtc aca cca ctg ttg ctt cct gac acc      451
Ala Asp Lys Leu Gln Tyr Val Val Thr Pro Leu Leu Leu Pro Asp Thr
            105                 110                 115 ccc atc gtt gct tgg tgg cca ggt gaa tca cca aag aat cct tcc cag      499
Pro Ile Val Ala Trp Trp Pro Gly Glu Ser Pro Lys Asn Pro Ser Gln
        120                 125                 130 gac cca att gga cgc atc gca caa cga cgc atc act gat gct ttg tac      547
Asp Pro Ile Gly Arg Ile Ala Gln Arg Arg Ile Thr Asp Ala Leu Tyr
    135                 140                 145 gac cgt gat gac gca cta gaa gat cgt gtt gag aac tat cac cca ggt      595
Asp Arg Asp Asp Ala Leu Glu Asp Arg Val Glu Asn Tyr His Pro Gly
150                 155                 160                 165 gat acc gac atg acg tgg gcg cgc ctt acc cag tgg cgg gga ctt gtt      643
Asp Thr Asp Met Thr Trp Ala Arg Leu Thr Gln Trp Arg Gly Leu Val
                170                 175                 180 gcc tcc tca ttg gat cac cca cca cac agc gaa atc act tcc gtg agg      691
Ala Ser Ser Leu Asp His Pro Pro His Ser Glu Ile Thr Ser Val Arg
            185                 190                 195 ctg acc ggt gca agc ggc agt acc tcg gtg gat ttg gct gca ggc tgg      739
Leu Thr Gly Ala Ser Gly Ser Thr Ser Val Asp Leu Ala Ala Gly Trp
        200                 205                 210 ttg gcg cgg agg ctg aaa gtg cct gtg atc cgc gag gtg aca gat gct      787
Leu Ala Arg Arg Leu Lys Val Pro Val Ile Arg Glu Val Thr Asp Ala
    215                 220                 225 ccc acc gtg cca acc gat gag ttt ggt act cca ctg ctg gct atc cag      835
Pro Thr Val Pro Thr Asp Glu Phe Gly Thr Pro Leu Leu Ala Ile Gln
230                 235                 240                 245 cgc ctg gag atc gtt cgc acc acc ggc tcg atc atc atc acc atc tat      883
Arg Leu Glu Ile Val Arg Thr Thr Gly Ser Ile Ile Ile Thr Ile Tyr
                250                 255                 260 gac gct cat acc ctt cag gta gag atg ccg gaa tcc ggc aat gcc cca      931
```

```
Asp Ala His Thr Leu Gln Val Glu Met Pro Glu Ser Gly Asn Ala Pro
            265                 270                 275 tcg ctg gtg gct att ggt cgt cga agt gag tcc gac tgc ttg tct gag      979
Ser Leu Val Ala Ile Gly Arg Arg Ser Glu Ser Asp Cys Leu Ser Glu
        280                 285                 290 gag ctt cgc cac atg gat cca gat ttg ggc tac cag cac gca cta tcc     1027
Glu Leu Arg His Met Asp Pro Asp Leu Gly Tyr Gln His Ala Leu Ser
    295                 300                 305 ggc ttg tcc agc gtc aag ctg gaa acc gtc taaggagaaa tacaacacta       1077
Gly Leu Ser Ser Val Lys Leu Glu Thr Val
310             315 tggttgatgt                                                           1087

<210> SEQ ID NO 80
<211> LENGTH: 319
<212> TYPE: PRT
<213> ORGANISM: Corynebacterium glutamicum

<400> SEQUENCE: 80
```

Met Ile Phe Glu Leu Pro Asp Thr Thr Thr Gln Gln Ile Ser Lys Thr
1               5                   10                  15

Leu Thr Arg Leu Arg Glu Ser Gly Thr Gln Val Thr Thr Gly Arg Val
            20                  25                  30

Leu Thr Leu Ile Val Val Thr Asp Ser Glu Ser Asp Val Ala Ala Val
        35                  40                  45

Thr Glu Ser Thr Asn Glu Ala Ser Arg Glu His Pro Ser Arg Val Ile
    50                  55                  60

Ile Leu Val Val Gly Asp Lys Thr Ala Glu Asn Lys Val Asp Ala Glu
65                  70                  75                  80

Val Arg Ile Gly Gly Asp Ala Gly Ala Ser Glu Met Ile Ile Met His
                85                  90                  95

Leu Asn Gly Pro Val Ala Asp Lys Leu Gln Tyr Val Val Thr Pro Leu
            100                 105                 110

Leu Leu Pro Asp Thr Pro Ile Val Ala Trp Trp Pro Gly Glu Ser Pro
        115                 120                 125

Lys Asn Pro Ser Gln Asp Pro Ile Gly Arg Ile Ala Gln Arg Arg Ile
    130                 135                 140

Thr Asp Ala Leu Tyr Asp Arg Asp Ala Leu Glu Asp Arg Val Glu
145                 150                 155                 160

Asn Tyr His Pro Gly Asp Thr Asp Met Thr Trp Ala Arg Leu Thr Gln
                165                 170                 175

Trp Arg Gly Leu Val Ala Ser Ser Leu Asp His Pro His Ser Glu
            180                 185                 190

Ile Thr Ser Val Arg Leu Thr Gly Ala Ser Gly Ser Thr Ser Val Asp
        195                 200                 205

Leu Ala Ala Gly Trp Leu Ala Arg Arg Leu Lys Val Pro Val Ile Arg
    210                 215                 220

Glu Val Thr Asp Ala Pro Thr Val Pro Thr Asp Glu Phe Gly Thr Pro
225                 230                 235                 240

Leu Leu Ala Ile Gln Arg Leu Glu Ile Val Arg Thr Thr Gly Ser Ile
                245                 250                 255

Ile Ile Thr Ile Tyr Asp Ala His Thr Leu Gln Val Glu Met Pro Glu
            260                 265                 270

Ser Gly Asn Ala Pro Ser Leu Val Ala Ile Gly Arg Arg Ser Glu Ser
        275                 280                 285

```
Asp Cys Leu Ser Glu Glu Leu Arg His Met Asp Pro Asp Leu Gly Tyr
    290                 295                 300

Gln His Ala Leu Ser Gly Leu Ser Ser Val Lys Leu Glu Thr Val
305                 310                 315

<210> SEQ ID NO 81
<211> LENGTH: 2479
<212> TYPE: DNA
<213> ORGANISM: Corynebacterium glutamicum
<220> FEATURE:
<221> NAME/KEY: CDS
<222> LOCATION: (101)..(2449)
<223> OTHER INFORMATION: RXA02742

<400> SEQUENCE: 81
gtatcggtaa aaggcccaat caaggattct tggttgggtc tttttccatg cttttcatgc      60
ttcgaacagt ccagaatagc cctgacctag acttagagct atg tcc gaa caa aga     115
                                             Met Ser Glu Gln Arg
                                               1               5 ctc gat cag ctt gag cga cgg ctt tct gaa ctg gaa cgg gag atc gcc     163
Leu Asp Gln Leu Glu Arg Arg Leu Ser Glu Leu Glu Arg Glu Ile Ala
                10                  15                  20 gcg att cgt cag gag atc cgc cag gaa cgc cta gtg ctt ccg gaa ccg     211
Ala Ile Arg Gln Glu Ile Arg Gln Glu Arg Leu Val Leu Pro Glu Pro
             25                  30                  35 gaa cct gtg aaa gtt gat aca gtc atc gcc acc gaa gcg acc gga gtc     259
Glu Pro Val Lys Val Asp Thr Val Ile Ala Thr Glu Ala Thr Gly Val
         40                  45                  50 aat gca tcg tcg ggt ccg gag gcg aag atc gct ttg ttc atg gag agg     307
Asn Ala Ser Ser Gly Pro Glu Ala Lys Ile Ala Leu Phe Met Glu Arg
     55                  60                  65 ttt agt ggt cgc cac gat gtg tat gcg cgg cgc tgg acc agc aga aaa     355
Phe Ser Gly Arg His Asp Val Tyr Ala Arg Arg Trp Thr Ser Arg Lys
 70                  75                  80                  85 acg ggc aaa agt gga tgg tcg ccg gct act cgc cag ggt ttt tac tca     403
Thr Gly Lys Ser Gly Trp Ser Pro Ala Thr Arg Gln Gly Phe Tyr Ser
                 90                  95                 100 aaa gac acc aca ccg aag gac tat ctc ccc ttc acc gtt gac acc gtc     451
Lys Asp Thr Thr Pro Lys Asp Tyr Leu Pro Phe Thr Val Asp Thr Val
            105                 110                 115 aat gcg cat ctg cgc cgg ggc ggc gac cat atc ggt ctc tat gtg atg     499
Asn Ala His Leu Arg Arg Gly Gly Asp His Ile Gly Leu Tyr Val Met
        120                 125                 130 gtc ccc atc gac acg tgc aaa ctt ctc gcc tgc gat ttc gac gat ggc     547
Val Pro Ile Asp Thr Cys Lys Leu Leu Ala Cys Asp Phe Asp Asp Gly
    135                 140                 145 acc tgg aag caa gat gcg gcc gct ttc gtg tca gcc tgc acc gac cac     595
Thr Trp Lys Gln Asp Ala Ala Ala Phe Val Ser Ala Cys Thr Asp His
150                 155                 160                 165 gga atc gat gcg ttg gct gaa att tct cga tcc gac gac ggc gcc ccc     643
Gly Ile Asp Ala Leu Ala Glu Ile Ser Arg Ser Asp Asp Gly Ala Pro
                170                 175                 180 gtg tgg ata ttt ttc gat acc cca atc tcc gcg atg ctg gct cgg cgc     691
Val Trp Ile Phe Phe Asp Thr Pro Ile Ser Ala Met Leu Ala Arg Arg
            185                 190                 195 cta ggt ttt gcc atg ctc cgc caa gcc atg aac tcc cgc cct gac atg     739
Leu Gly Phe Ala Met Leu Arg Gln Ala Met Asn Ser Arg Pro Asp Met
        200                 205                 210 gat atg tct tct tat gat cgc ttc ttc cct gct caa gac acc atc gca     787
Asp Met Ser Ser Tyr Asp Arg Phe Phe Pro Ala Gln Asp Thr Ile Ala
    215                 220                 225
```

-continued acg cgc gca aac gga agc gca cgg ctg gga aat ttg atc gcg ctg ccc        835
Thr Arg Ala Asn Gly Ser Ala Arg Leu Gly Asn Leu Ile Ala Leu Pro
230                 235                 240                 245 ctc aac ggc gac tgt cga gcc cgc aac acc gcc gtc ttc gcc gat tcg        883
Leu Asn Gly Asp Cys Arg Ala Arg Asn Thr Ala Val Phe Ala Asp Ser
            250                 255                 260 gaa acg tgg gtt ccc ttc gaa gat cct ttc gca gcg ctc gcg gcc atc        931
Glu Thr Trp Val Pro Phe Glu Asp Pro Phe Ala Ala Leu Ala Ala Ile
        265                 270                 275 acg cca cta gcc acc gaa aaa atc gag cag atc ctt gcc acc acg cag        979
Thr Pro Leu Ala Thr Glu Lys Ile Glu Gln Ile Leu Ala Thr Thr Gln
    280                 285                 290 gaa aaa ttt ggc ccc gaa ccc gaa cac atc aaa cgc ccc acc cgc gcc       1027
Glu Lys Phe Gly Pro Glu Pro Glu His Ile Lys Arg Pro Thr Arg Ala
295                 300                 305 gaa ctc aaa cag gtt aaa gcc aac ggc gaa acc atc aaa ctc acc atc       1075
Glu Leu Lys Gln Val Lys Ala Asn Gly Glu Thr Ile Lys Leu Thr Ile
310                 315                 320                 325 acc aac gag ctg agc gtc ccc acc gaa agg tta ccc gcg gcc gtc atc       1123
Thr Asn Glu Leu Ser Val Pro Thr Glu Arg Leu Pro Ala Ala Val Ile
            330                 335                 340 gcg gag att aaa cac cgg gcg gta atc cca aac cct gag ttt tat cgt       1171
Ala Glu Ile Lys His Arg Ala Val Ile Pro Asn Pro Glu Phe Tyr Arg
        345                 350                 355 cga caa gcg caa aga ttt tcg acc ttc ggc gtg ccg cgc atc gtc atc       1219
Arg Gln Ala Gln Arg Phe Ser Thr Phe Gly Val Pro Arg Ile Val Ile
    360                 365                 370 cgc ttc gcc cag gcc gag cag cgc ttg ctg ctc cca cgc ggg ctt gtc       1267
Arg Phe Ala Gln Ala Glu Gln Arg Leu Leu Leu Pro Arg Gly Leu Val
375                 380                 385 gac gac acc ctc cgg atc ctc acc ctc gcc ggg tac aaa gtc agc gtc       1315
Asp Asp Thr Leu Arg Ile Leu Thr Leu Ala Gly Tyr Lys Val Ser Val
390                 395                 400                 405 atc tgg cct cgg caa act cgg aaa acc atc gac gcg tct ttc gag ggc       1363
Ile Trp Pro Arg Gln Thr Arg Lys Thr Ile Asp Ala Ser Phe Glu Gly
            410                 415                 420 gaa ttg cga tcc atg caa caa gag gga atc gac tcg ctc aaa ggc caa       1411
Glu Leu Arg Ser Met Gln Gln Glu Gly Ile Asp Ser Leu Lys Gly Gln
        425                 430                 435 cgc acc ggc gta ttg gta gca ccg ccg ggc gct gga aaa aca gtg atg       1459
Arg Thr Gly Val Leu Val Ala Pro Pro Gly Ala Gly Lys Thr Val Met
    440                 445                 450 gcc tgt gca ctc atc gcg aac aga aaa atc ccc acc gca gtg ata gtc       1507
Ala Cys Ala Leu Ile Ala Asn Arg Lys Ile Pro Thr Ala Val Ile Val
455                 460                 465 aac cgt gca gaa ttg att tcc caa tgg cgg gat cgt ctc gcg caa tac       1555
Asn Arg Ala Glu Leu Ile Ser Gln Trp Arg Asp Arg Leu Ala Gln Tyr
470                 475                 480                 485 ctg agc atc gac gca gac tcc atc gga cag atc ggc gcg ggc cga cgc       1603
Leu Ser Ile Asp Ala Asp Ser Ile Gly Gln Ile Gly Ala Gly Arg Arg
            490                 495                 500 aaa acc acc gga att atc gat ctc atc acc gtc caa tcc ttg agc cgt       1651
Lys Thr Thr Gly Ile Ile Asp Leu Ile Thr Val Gln Ser Leu Ser Arg
        505                 510                 515 aaa gat tcc gat ccg aaa att ttg gaa caa tac ggc caa atc atc gtc       1699
Lys Asp Ser Asp Pro Lys Ile Leu Glu Gln Tyr Gly Gln Ile Ile Val
    520                 525                 530 gac gag tgc cac aac atc gca gcc cca ggc gcc gaa gcc gca ttg aac       1747
Asp Glu Cys His Asn Ile Ala Ala Pro Gly Ala Glu Ala Ala Leu Asn -continued

```
            535                 540                 545
cag gtc aag gcc ccc tac tgg ctg ggt cta acc gcc acg ccg ttt cgt    1795
Gln Val Lys Ala Pro Tyr Trp Leu Gly Leu Thr Ala Thr Pro Phe Arg
550                 555                 560                 565 tca gac cac atg gat gaa atc atc acc atg cag tgc ggt cct gtg cgc    1843
Ser Asp His Met Asp Glu Ile Ile Thr Met Gln Cys Gly Pro Val Arg
                570                 575                 580 cac cgc atg gaa gtg gca aca gac aat gaa cag cgc ttg att cac atc    1891
His Arg Met Glu Val Ala Thr Asp Asn Glu Gln Arg Leu Ile His Ile
            585                 590                 595 cac gaa acc tct ttc gac tct gag gaa acc acc gaa atc cag gat ctc    1939
His Glu Thr Ser Phe Asp Ser Glu Glu Thr Thr Glu Ile Gln Asp Leu
        600                 605                 610 tac aat gag ctc gcg gtc gat tct gcc cga aat gcg caa atc act gcc    1987
Tyr Asn Glu Leu Ala Val Asp Ser Ala Arg Asn Ala Gln Ile Thr Ala
    615                 620                 625 gaa gtg cac aaa gcg ctt gaa gct ggc gac cga tgt cta gtt ttg gtc    2035
Glu Val His Lys Ala Leu Glu Ala Gly Asp Arg Cys Leu Val Leu Val
630                 635                 640                 645 aac cga att gca gcc ctt gaa gca ctg acc agc agt att acc gaa tct    2083
Asn Arg Ile Ala Ala Leu Glu Ala Leu Thr Ser Ser Ile Thr Glu Ser
                650                 655                 660 ggc gat cac act gtc tta gtg atg cat ggc cgc caa acc caa gag gag    2131
Gly Asp His Thr Val Leu Val Met His Gly Arg Gln Thr Gln Glu Glu
            665                 670                 675 cga gtt cac ctt cgt gcg caa ctt gcc tca ttg agt gaa aag cag gat    2179
Arg Val His Leu Arg Ala Gln Leu Ala Ser Leu Ser Glu Lys Gln Asp
        680                 685                 690 ccg ttt gta ctg gtc gcg atg aat aaa gtc gcc ggc gaa ggc ctt gac    2227
Pro Phe Val Leu Val Ala Met Asn Lys Val Ala Gly Glu Gly Leu Asp
    695                 700                 705 atc ccc agc ctc aac acg ctg ttt ttg gca gcg ccg gtg tcc ttc aag    2275
Ile Pro Ser Leu Asn Thr Leu Phe Leu Ala Ala Pro Val Ser Phe Lys
710                 715                 720                 725 ggg ctg gtg att cag caa atc ggc cga gtt act cgc gca acc ggt gat    2323
Gly Leu Val Ile Gln Gln Ile Gly Arg Val Thr Arg Ala Thr Gly Asp
                730                 735                 740 caa aac gct cct ccg gtg act gcc acg gtc cat gat ttt gtt gat tcc    2371
Gln Asn Ala Pro Pro Val Thr Ala Thr Val His Asp Phe Val Asp Ser
            745                 750                 755 aag att ccg aca ctc aaa cgc atg cac ggt cgc cga ttg cgg gct atg    2419
Lys Ile Pro Thr Leu Lys Arg Met His Gly Arg Arg Leu Arg Ala Met
        760                 765                 770 caa aag gaa gga ttc gct gtt tcg gag cct tgaggaggac cagaccaaac      2469
Gln Lys Glu Gly Phe Ala Val Ser Glu Pro
    775                 780 cagcgtgccc                                                          2479
```

<210> SEQ ID NO 82
<211> LENGTH: 783
<212> TYPE: PRT
<213> ORGANISM: Corynebacterium glutamicum

<400> SEQUENCE: 82

```
Met Ser Glu Gln Arg Leu Asp Gln Leu Glu Arg Arg Leu Ser Glu Leu
 1               5                  10                  15

Glu Arg Glu Ile Ala Ala Ile Arg Gln Glu Ile Arg Gln Glu Arg Leu
            20                  25                  30

Val Leu Pro Glu Pro Glu Pro Val Lys Val Asp Thr Val Ile Ala Thr
```

-continued

```
                35                  40                  45
Glu Ala Thr Gly Val Asn Ala Ser Ser Gly Pro Glu Ala Lys Ile Ala
 50                  55                  60
Leu Phe Met Glu Arg Phe Ser Gly Arg His Asp Val Tyr Ala Arg Arg
 65                  70                  75                  80
Trp Thr Ser Arg Lys Thr Gly Lys Ser Gly Trp Ser Pro Ala Thr Arg
                 85                  90                  95
Gln Gly Phe Tyr Ser Lys Asp Thr Thr Pro Lys Asp Tyr Leu Pro Phe
                100                 105                 110
Thr Val Asp Thr Val Asn Ala His Leu Arg Arg Gly Gly Asp His Ile
                115                 120                 125
Gly Leu Tyr Val Met Val Pro Ile Asp Thr Cys Lys Leu Leu Ala Cys
130                 135                 140
Asp Phe Asp Asp Gly Thr Trp Lys Gln Asp Ala Ala Phe Val Ser
145                 150                 155                 160
Ala Cys Thr Asp His Gly Ile Asp Ala Leu Ala Glu Ile Ser Arg Ser
                165                 170                 175
Asp Asp Gly Ala Pro Val Trp Ile Phe Phe Asp Thr Pro Ile Ser Ala
                180                 185                 190
Met Leu Ala Arg Arg Leu Gly Phe Ala Met Leu Arg Gln Ala Met Asn
                195                 200                 205
Ser Arg Pro Asp Met Asp Met Ser Ser Tyr Asp Arg Phe Phe Pro Ala
                210                 215                 220
Gln Asp Thr Ile Ala Thr Arg Ala Asn Gly Ser Ala Arg Leu Gly Asn
225                 230                 235                 240
Leu Ile Ala Leu Pro Leu Asn Gly Asp Cys Arg Ala Arg Asn Thr Ala
                245                 250                 255
Val Phe Ala Asp Ser Glu Thr Trp Val Pro Phe Glu Asp Pro Phe Ala
                260                 265                 270
Ala Leu Ala Ala Ile Thr Pro Leu Ala Thr Glu Lys Ile Glu Gln Ile
                275                 280                 285
Leu Ala Thr Thr Gln Glu Lys Phe Gly Pro Glu Pro Glu His Ile Lys
                290                 295                 300
Arg Pro Thr Arg Ala Glu Leu Lys Gln Val Lys Ala Asn Gly Glu Thr
305                 310                 315                 320
Ile Lys Leu Thr Ile Thr Asn Glu Leu Ser Val Pro Thr Glu Arg Leu
                325                 330                 335
Pro Ala Ala Val Ile Ala Glu Ile Lys His Arg Ala Val Ile Pro Asn
                340                 345                 350
Pro Glu Phe Tyr Arg Arg Gln Ala Gln Arg Phe Ser Thr Phe Gly Val
                355                 360                 365
Pro Arg Ile Val Ile Arg Phe Ala Gln Ala Glu Gln Arg Leu Leu Leu
                370                 375                 380
Pro Arg Gly Leu Val Asp Asp Thr Leu Arg Ile Leu Thr Leu Ala Gly
385                 390                 395                 400
Tyr Lys Val Ser Val Ile Trp Pro Arg Gln Thr Arg Lys Thr Ile Asp
                405                 410                 415
Ala Ser Phe Glu Gly Glu Leu Arg Ser Met Gln Gln Glu Gly Ile Asp
                420                 425                 430
Ser Leu Lys Gly Gln Arg Thr Gly Val Leu Val Ala Pro Pro Gly Ala
                435                 440                 445
Gly Lys Thr Val Met Ala Cys Ala Leu Ile Ala Asn Arg Lys Ile Pro
450                 455                 460
```

```
Thr Ala Val Ile Val Asn Arg Ala Glu Leu Ile Ser Gln Trp Arg Asp
465                 470                 475                 480

Arg Leu Ala Gln Tyr Leu Ser Ile Asp Ala Asp Ser Ile Gly Gln Ile
                485                 490                 495

Gly Ala Gly Arg Arg Lys Thr Thr Gly Ile Ile Asp Leu Ile Thr Val
                500                 505                 510

Gln Ser Leu Ser Arg Lys Asp Ser Asp Pro Lys Ile Leu Glu Gln Tyr
            515                 520                 525

Gly Gln Ile Ile Val Asp Glu Cys His Asn Ile Ala Ala Pro Gly Ala
        530                 535                 540

Glu Ala Ala Leu Asn Gln Val Lys Ala Pro Tyr Trp Leu Gly Leu Thr
545                 550                 555                 560

Ala Thr Pro Phe Arg Ser Asp His Met Asp Glu Ile Ile Thr Met Gln
                565                 570                 575

Cys Gly Pro Val Arg His Arg Met Glu Val Ala Thr Asp Asn Glu Gln
                580                 585                 590

Arg Leu Ile His Ile His Glu Thr Ser Phe Asp Ser Glu Glu Thr Thr
            595                 600                 605

Glu Ile Gln Asp Leu Tyr Asn Glu Leu Ala Val Asp Ser Ala Arg Asn
        610                 615                 620

Ala Gln Ile Thr Ala Glu Val His Lys Ala Leu Glu Ala Gly Asp Arg
625                 630                 635                 640

Cys Leu Val Leu Val Asn Arg Ile Ala Ala Leu Glu Ala Leu Thr Ser
                645                 650                 655

Ser Ile Thr Glu Ser Gly Asp His Thr Val Leu Val Met His Gly Arg
                660                 665                 670

Gln Thr Gln Glu Glu Arg Val His Leu Arg Ala Gln Leu Ala Ser Leu
            675                 680                 685

Ser Glu Lys Gln Asp Pro Phe Val Leu Val Ala Met Asn Lys Val Ala
        690                 695                 700

Gly Glu Gly Leu Asp Ile Pro Ser Leu Asn Thr Leu Phe Leu Ala Ala
705                 710                 715                 720

Pro Val Ser Phe Lys Gly Leu Val Ile Gln Gln Ile Gly Arg Val Thr
                725                 730                 735

Arg Ala Thr Gly Asp Gln Asn Ala Pro Pro Val Thr Ala Thr Val His
                740                 745                 750

Asp Phe Val Asp Ser Lys Ile Pro Thr Leu Lys Arg Met His Gly Arg
                755                 760                 765

Arg Leu Arg Ala Met Gln Lys Glu Gly Phe Ala Val Ser Glu Pro
    770                 775                 780

<210> SEQ ID NO 83
<211> LENGTH: 1771
<212> TYPE: DNA
<213> ORGANISM: Corynebacterium glutamicum
<220> FEATURE:
<221> NAME/KEY: CDS
<222> LOCATION: (101)..(1741)
<223> OTHER INFORMATION: RXA02748

<400> SEQUENCE: 83
caggtcgttg gcaggtagct gacgtgacct gagcggggc aaccggctaa catgtaggga      60
ttagcaaccc cgcactctag aacctactgg gagttcattc gtg ttt gag tca ctg     115
                                            Val Phe Glu Ser Leu
                                              1               5
```

-continued

| | | |
|---|---|---|
| tcc gat cgg ttg aat agc gcg ctt tcc ggc ctg cgc ggc aaa gga aag<br>Ser Asp Arg Leu Asn Ser Ala Leu Ser Gly Leu Arg Gly Lys Gly Lys<br>            10                      15                    20 | 163 |
| ctc acc gag gca gac atc aat gca acc aca cgc gag atc cgt ctc gcg<br>Leu Thr Glu Ala Asp Ile Asn Ala Thr Thr Arg Glu Ile Arg Leu Ala<br>            25                      30                    35 | 211 |
| ctg ctg gaa gct gac gtt tca tta acg gtt gtt cgt gcc ttc att aac<br>Leu Leu Glu Ala Asp Val Ser Leu Thr Val Val Arg Ala Phe Ile Asn<br>            40                      45                    50 | 259 |
| cga atc aag gaa cgc gcc gct ggt gca gaa gtt tct cag gca ctc aac<br>Arg Ile Lys Glu Arg Ala Ala Gly Ala Glu Val Ser Gln Ala Leu Asn<br> 55                      60                      65 | 307 |
| ccc gcg cag caa gtc atc aag atc gtc aac gag gaa ctg gtt cag atc<br>Pro Ala Gln Gln Val Ile Lys Ile Val Asn Glu Glu Leu Val Gln Ile<br> 70                      75                      80                    85 | 355 |
| ctc ggt ggc gaa acc cgc cga ctg tca ctg gcc aaa aac cca ccg acc<br>Leu Gly Gly Glu Thr Arg Arg Leu Ser Leu Ala Lys Asn Pro Pro Thr<br>            90                      95                    100 | 403 |
| gtc atc atg ctg gca ggt ctg cag ggt gca ggt aag acc acc ctc gca<br>Val Ile Met Leu Ala Gly Leu Gln Gly Ala Gly Lys Thr Thr Leu Ala<br>            105                     110                     115 | 451 |
| ggt aaa ctg tcc aag cac ctg gtc aag cag ggt cac act cct atg ctt<br>Gly Lys Leu Ser Lys His Leu Val Lys Gln Gly His Thr Pro Met Leu<br>           120                     125                     130 | 499 |
| gtt gcc tgt gac ctt cag cgt cca ggc gca gtt cag cag ctg caa att<br>Val Ala Cys Asp Leu Gln Arg Pro Gly Ala Val Gln Gln Leu Gln Ile<br>135                      140                      145 | 547 |
| gtg ggt gaa cgc gca ggc gtt acc act ttc gca ccg gat cca ggc acc<br>Val Gly Glu Arg Ala Gly Val Thr Thr Phe Ala Pro Asp Pro Gly Thr<br>150                      155                      160                    165 | 595 |
| agc atc gac tcc ctc gag cac gaa atg ggc acc tcc cac ggt gat cca<br>Ser Ile Asp Ser Leu Glu His Glu Met Gly Thr Ser His Gly Asp Pro<br>           170                     175                     180 | 643 |
| gtc gag gta gcg cgc gca ggt atc gaa gaa gcc aag cgc acc cag cac<br>Val Glu Val Ala Arg Ala Gly Ile Glu Glu Ala Lys Arg Thr Gln His<br>                185                     190                     195 | 691 |
| gac atc gtg atc gtg gat acc gca ggt cgc ctc ggt atc gat gaa acc<br>Asp Ile Val Ile Val Asp Thr Ala Gly Arg Leu Gly Ile Asp Glu Thr<br>           200                     205                     210 | 739 |
| ctg atg act cag gca cgc aac atc cgc gaa gcc atc aac cct gat gaa<br>Leu Met Thr Gln Ala Arg Asn Ile Arg Glu Ala Ile Asn Pro Asp Glu<br>           215                     220                     225 | 787 |
| gtg ctc ttt gtc att gac tcc atg att ggt caa gac gcc gta gac acc<br>Val Leu Phe Val Ile Asp Ser Met Ile Gly Gln Asp Ala Val Asp Thr<br>230                      235                      240                    245 | 835 |
| gcc gaa gca ttc cgc gac ggc gtc gac ttc acc ggt gtt gtc ctg acc<br>Ala Glu Ala Phe Arg Asp Gly Val Asp Phe Thr Gly Val Val Leu Thr<br>               250                     255                     260 | 883 |
| aag ctt gat ggc gac gcc cgc ggt ggt gct gca cta tcc atc cgt gaa<br>Lys Leu Asp Gly Asp Ala Arg Gly Gly Ala Ala Leu Ser Ile Arg Glu<br>           265                     270                     275 | 931 |
| gtc acc ggc aag ccc atc atg ttt gcc tcc act ggt gaa aaa ctc gac<br>Val Thr Gly Lys Pro Ile Met Phe Ala Ser Thr Gly Glu Lys Leu Asp<br>           280                     285                     290 | 979 |
| gac ttc gac gtc ttc cac cca gag cgc atg gcc agc cga atc ctg ggc<br>Asp Phe Asp Val Phe His Pro Glu Arg Met Ala Ser Arg Ile Leu Gly<br>               295                     300                     305 | 1027 |
| atg ggt gac gta ctg tca ctc atc gag cag gcc gaa gca gtc atg gat<br>Met Gly Asp Val Leu Ser Leu Ile Glu Gln Ala Glu Ala Val Met Asp<br>310                      315                      320                    325 | 1075 |

-continued

```
cag gaa aag gca gag gtc gct gcc cag aag ttg ggc tcc ggc gag ctc      1123
Gln Glu Lys Ala Glu Val Ala Ala Gln Lys Leu Gly Ser Gly Glu Leu
                330                 335                 340 acc ctg gaa gac ttc ctt gac caa atg ctg atg atc cgc cgc atg gga      1171
Thr Leu Glu Asp Phe Leu Asp Gln Met Leu Met Ile Arg Arg Met Gly
            345                 350                 355 cca atc ggc aac atc ctc aag atg ctg cct ggt ggc aag cag atg tcc      1219
Pro Ile Gly Asn Ile Leu Lys Met Leu Pro Gly Gly Lys Gln Met Ser
        360                 365                 370 caa atg gcg gac atg gtt gat gag aag caa ctc gac cgc atc cag gcg      1267
Gln Met Ala Asp Met Val Asp Glu Lys Gln Leu Asp Arg Ile Gln Ala
    375                 380                 385 att atc cgc ggt atg acc ccg gcc gag cgc gat aat cca aag atc ctc      1315
Ile Ile Arg Gly Met Thr Pro Ala Glu Arg Asp Asn Pro Lys Ile Leu
390                 395                 400                 405 aac gct tcc agg cgc aag cgc atc gcc aac ggt tcc ggt gtg acc gtg      1363
Asn Ala Ser Arg Arg Lys Arg Ile Ala Asn Gly Ser Gly Val Thr Val
                410                 415                 420 tcc gaa gta aac aaa ctt gtt gaa cgc ttc ttc gag gct cgc aag atg      1411
Ser Glu Val Asn Lys Leu Val Glu Arg Phe Phe Glu Ala Arg Lys Met
            425                 430                 435 atg ggt caa atg gct ggc cag ttt ggc atg ggt cct gga tcc cgc agt      1459
Met Gly Gln Met Ala Gly Gln Phe Gly Met Gly Pro Gly Ser Arg Ser
        440                 445                 450 gca acc aag aag caa gcc aag ggc cgc aag ggt aag aac ggc aag cgt      1507
Ala Thr Lys Lys Gln Ala Lys Gly Arg Lys Gly Lys Asn Gly Lys Arg
    455                 460                 465 aaa cca gcc aag aag ggc cca acc cag cca aag atg cca atg ggc ggt      1555
Lys Pro Ala Lys Lys Gly Pro Thr Gln Pro Lys Met Pro Met Gly Gly
470                 475                 480                 485 atg cca gga atg cct ggg atg ccg ggt atg ggt gga gcc gga atg cct      1603
Met Pro Gly Met Pro Gly Met Pro Gly Met Gly Gly Ala Gly Met Pro
                490                 495                 500 gac ctt gct gaa cta cag aag cag ctt ggt gga gca ggt ggc ggt atg      1651
Asp Leu Ala Glu Leu Gln Lys Gln Leu Gly Gly Ala Gly Gly Gly Met
            505                 510                 515 gga ggc ctt ggt ggc gga ctc ccg ggc atg cca aag ccg cct aaa ggc      1699
Gly Gly Leu Gly Gly Gly Leu Pro Gly Met Pro Lys Pro Pro Lys Gly
        520                 525                 530 atg gag aac ata gat ctc aac aac cta gac ttc ggt aag aag              1741
Met Glu Asn Ile Asp Leu Asn Asn Leu Asp Phe Gly Lys Lys
    535                 540                 545 taactttgct ttagttggtc ggcgcatcac                                     1771

<210> SEQ ID NO 84
<211> LENGTH: 547
<212> TYPE: PRT
<213> ORGANISM: Corynebacterium glutamicum

<400> SEQUENCE: 84

Val Phe Glu Ser Leu Ser Asp Arg Leu Asn Ser Ala Leu Ser Gly Leu
 1               5                  10                  15

Arg Gly Lys Gly Lys Leu Thr Glu Ala Asp Ile Asn Ala Thr Thr Arg
            20                  25                  30

Glu Ile Arg Leu Ala Leu Leu Glu Ala Asp Val Ser Leu Thr Val Val
        35                  40                  45

Arg Ala Phe Ile Asn Arg Ile Lys Glu Arg Ala Ala Gly Ala Glu Val
    50                  55                  60
```

-continued

```
Ser Gln Ala Leu Asn Pro Ala Gln Gln Val Ile Lys Ile Val Asn Glu
 65                  70                  75                  80

Glu Leu Val Gln Ile Leu Gly Gly Glu Thr Arg Arg Leu Ser Leu Ala
                 85                  90                  95

Lys Asn Pro Pro Thr Val Ile Met Leu Ala Gly Leu Gln Gly Ala Gly
            100                 105                 110

Lys Thr Thr Leu Ala Gly Lys Leu Ser Lys His Leu Val Lys Gln Gly
        115                 120                 125

His Thr Pro Met Leu Val Ala Cys Asp Leu Gln Arg Pro Gly Ala Val
    130                 135                 140

Gln Gln Leu Gln Ile Val Gly Glu Arg Ala Gly Val Thr Thr Phe Ala
145                 150                 155                 160

Pro Asp Pro Gly Thr Ser Ile Asp Ser Leu Glu His Glu Met Gly Thr
                165                 170                 175

Ser His Gly Asp Pro Val Glu Val Ala Arg Ala Gly Ile Glu Glu Ala
            180                 185                 190

Lys Arg Thr Gln His Asp Ile Val Ile Val Asp Thr Ala Gly Arg Leu
        195                 200                 205

Gly Ile Asp Glu Thr Leu Met Thr Gln Ala Arg Asn Ile Arg Glu Ala
210                 215                 220

Ile Asn Pro Asp Glu Val Leu Phe Val Ile Asp Ser Met Ile Gly Gln
225                 230                 235                 240

Asp Ala Val Asp Thr Ala Glu Ala Phe Arg Asp Gly Val Asp Phe Thr
                245                 250                 255

Gly Val Val Leu Thr Lys Leu Asp Gly Asp Ala Arg Gly Gly Ala Ala
            260                 265                 270

Leu Ser Ile Arg Glu Val Thr Gly Lys Pro Ile Met Phe Ala Ser Thr
        275                 280                 285

Gly Glu Lys Leu Asp Asp Phe Asp Val Phe His Pro Glu Arg Met Ala
290                 295                 300

Ser Arg Ile Leu Gly Met Gly Asp Val Leu Ser Leu Ile Glu Gln Ala
305                 310                 315                 320

Glu Ala Val Met Asp Gln Glu Lys Ala Glu Val Ala Ala Gln Lys Leu
                325                 330                 335

Gly Ser Gly Glu Leu Thr Leu Glu Asp Phe Leu Asp Gln Met Leu Met
            340                 345                 350

Ile Arg Arg Met Gly Pro Ile Gly Asn Ile Leu Lys Met Leu Pro Gly
        355                 360                 365

Gly Lys Gln Met Ser Gln Met Ala Asp Met Val Asp Glu Lys Gln Leu
370                 375                 380

Asp Arg Ile Gln Ala Ile Ile Arg Gly Met Thr Pro Ala Glu Arg Asp
385                 390                 395                 400

Asn Pro Lys Ile Leu Asn Ala Ser Arg Lys Arg Ile Ala Asn Gly
                405                 410                 415

Ser Gly Val Thr Val Ser Glu Val Asn Lys Leu Val Glu Arg Phe Phe
            420                 425                 430

Glu Ala Arg Lys Met Met Gly Gln Met Ala Gly Gln Phe Gly Met Gly
        435                 440                 445

Pro Gly Ser Arg Ser Ala Thr Lys Lys Gln Ala Lys Gly Arg Lys Gly
    450                 455                 460

Lys Asn Gly Lys Arg Lys Pro Ala Lys Lys Gly Pro Thr Gln Pro Lys
465                 470                 475                 480

Met Pro Met Gly Gly Met Pro Gly Met Pro Gly Met Pro Gly Met Gly
```

-continued

```
                   485                 490                 495
Gly Ala Gly Met Pro Asp Leu Ala Glu Leu Gln Lys Gln Leu Gly Gly
                500                 505                 510

Ala Gly Gly Met Gly Gly Leu Gly Gly Leu Pro Gly Met Pro
        515                 520                 525

Lys Pro Pro Lys Gly Met Glu Asn Ile Asp Leu Asn Asn Leu Asp Phe
        530                 535                 540

Gly Lys Lys
545

<210> SEQ ID NO 85
<211> LENGTH: 958
<212> TYPE: DNA
<213> ORGANISM: Corynebacterium glutamicum
<220> FEATURE:
<221> NAME/KEY: CDS
<222> LOCATION: (101)..(928)
<223> OTHER INFORMATION: RXA03070

<400> SEQUENCE: 85
gtggataaaa gggaaaacat aggggtcatg aaatagaaca agcacgaggc ctggtaaata        60
cgaattcgac caagaaaacg taaacacccc aggagtactc gtg cct gcc ctt cca        115
                                              Val Pro Ala Leu Pro
                                                1               5 tca tct atc atc gac ccc ctc tgg cgc cag ttc tcc gcc tta atc cca        163
Ser Ser Ile Ile Asp Pro Leu Trp Arg Gln Phe Ser Ala Leu Ile Pro
              10                  15                  20 ccg gtt atc atc acc cac cca cta ggg tgc cac cgt gca cgc att gct        211
Pro Val Ile Ile Thr His Pro Leu Gly Cys His Arg Ala Arg Ile Ala
          25                  30                  35 gac cgg atc atc gtc gac aaa ctc atc gca gtg ctt gtc ctc ggt gtc        259
Asp Arg Ile Ile Val Asp Lys Leu Ile Ala Val Leu Val Leu Gly Val
      40                  45                  50 tcc tat atc aag att tcc gat tcc acc tgc tca gcc acc acg ata cgc        307
Ser Tyr Ile Lys Ile Ser Asp Ser Thr Cys Ser Ala Thr Thr Ile Arg
  55                  60                  65 acc cgc cga gac gag tgg atc act gcc ggg att ttc aag aat tta gaa        355
Thr Arg Arg Asp Glu Trp Ile Thr Ala Gly Ile Phe Lys Asn Leu Glu
 70                  75                  80                  85 cag atc tgt ctg gag tcc tac gac cgt ttc atc ggg tta gac cta gaa        403
Gln Ile Cys Leu Glu Ser Tyr Asp Arg Phe Ile Gly Leu Asp Leu Glu
                 90                  95                 100 aac tta aat gtt gat ggc tgc att gtt aaa gct ccc tgc ggc gga gag        451
Asn Leu Asn Val Asp Gly Cys Ile Val Lys Ala Pro Cys Gly Gly Glu
             105                 110                 115 gta gcc ggc aga ttc ccg gtt gac cgg gaa aaa ggc acc aaa cgc tcg        499
Val Ala Gly Arg Phe Pro Val Asp Arg Glu Lys Gly Thr Lys Arg Ser
         120                 125                 130 tta atg gtc gat gga cat gga atc ccg atc ggg tgc gtg gtc gcc gga        547
Leu Met Val Asp Gly His Gly Ile Pro Ile Gly Cys Val Val Ala Gly
    135                 140                 145 gcc aat cgg cat gat tta ccg ttg tta gct gca acc ttg gac acg ctc        595
Ala Asn Arg His Asp Leu Pro Leu Leu Ala Ala Thr Leu Asp Thr Leu
150                 155                 160                 165 ggc cgg ttt ggg ggc tct ctt ccc gat cag atc acg gtg cat ctc gat        643
Gly Arg Phe Gly Gly Ser Leu Pro Asp Gln Ile Thr Val His Leu Asp
                170                 175                 180 gct ggg tat gac tcg aag aaa acc cgc agg cta ctc agc gaa ttt ggt        691
Ala Gly Tyr Asp Ser Lys Lys Thr Arg Arg Leu Leu Ser Glu Phe Gly
            185                 190                 195
```

```
                                                          -continued tat agc tgg gtg atc agc att aaa ggt gag ccg ctg cag gct ggg act       739
Tyr Ser Trp Val Ile Ser Ile Lys Gly Glu Pro Leu Gln Ala Gly Thr
        200                 205                 210 cgg tgg gtg gtg gag cgt act aac tct tgg cat aac cgg ggt ttt aag       787
Arg Trp Val Val Glu Arg Thr Asn Ser Trp His Asn Arg Gly Phe Lys
215                 220                 225 aaa ctt agt atc tgc acc gaa cgt tgt acc cgg gtt gtg gaa gcg ttt       835
Lys Leu Ser Ile Cys Thr Glu Arg Cys Thr Arg Val Val Glu Ala Phe
230                 235                 240                 245 atc gct tta gcc aac gcg gtg att att ctg cgt cgg ctt atc aaa cag       883
Ile Ala Leu Ala Asn Ala Val Ile Ile Leu Arg Arg Leu Ile Lys Gln
            250                 255                 260 gcc tgg act agt tac cgc tgg gac acc cga ccg ggc cac aga cct           928
Ala Trp Thr Ser Tyr Arg Trp Asp Thr Arg Pro Gly His Arg Pro
                265                 270                 275 taatctatcc gcgcaatctc taaggagaaa                                      958

<210> SEQ ID NO 86
<211> LENGTH: 276
<212> TYPE: PRT
<213> ORGANISM: Corynebacterium glutamicum

<400> SEQUENCE: 86

Val Pro Ala Leu Pro Ser Ser Ile Ile Asp Pro Leu Trp Arg Gln Phe
 1               5                  10                  15

Ser Ala Leu Ile Pro Val Ile Ile Thr His Pro Leu Gly Cys His
             20                  25                  30

Arg Ala Arg Ile Ala Asp Arg Ile Ile Val Asp Lys Leu Ile Ala Val
         35                  40                  45

Leu Val Leu Gly Val Ser Tyr Ile Lys Ile Ser Asp Ser Thr Cys Ser
     50                  55                  60

Ala Thr Thr Ile Arg Thr Arg Arg Asp Glu Trp Ile Thr Ala Gly Ile
 65                  70                  75                  80

Phe Lys Asn Leu Glu Gln Ile Cys Leu Glu Ser Tyr Asp Arg Phe Ile
                 85                  90                  95

Gly Leu Asp Leu Glu Asn Leu Asn Val Asp Gly Cys Ile Val Lys Ala
            100                 105                 110

Pro Cys Gly Gly Glu Val Ala Gly Arg Phe Pro Val Asp Arg Glu Lys
        115                 120                 125

Gly Thr Lys Arg Ser Leu Met Val Asp Gly His Gly Ile Pro Ile Gly
    130                 135                 140

Cys Val Val Ala Gly Ala Asn Arg His Asp Leu Pro Leu Leu Ala Ala
145                 150                 155                 160

Thr Leu Asp Thr Leu Gly Arg Phe Gly Gly Ser Leu Pro Asp Gln Ile
                165                 170                 175

Thr Val His Leu Asp Ala Gly Tyr Asp Ser Lys Lys Thr Arg Arg Leu
            180                 185                 190

Leu Ser Glu Phe Gly Tyr Ser Trp Val Ile Ser Ile Lys Gly Glu Pro
        195                 200                 205

Leu Gln Ala Gly Thr Arg Trp Val Glu Arg Thr Asn Ser Trp His
    210                 215                 220

Asn Arg Gly Phe Lys Lys Leu Ser Ile Cys Thr Glu Arg Cys Thr Arg
225                 230                 235                 240

Val Val Glu Ala Phe Ile Ala Leu Ala Asn Ala Val Ile Ile Leu Arg
                245                 250                 255
```

```
Arg Leu Ile Lys Gln Ala Trp Thr Ser Tyr Arg Trp Asp Thr Arg Pro
        260                 265                 270

Gly His Arg Pro
        275

<210> SEQ ID NO 87
<211> LENGTH: 754
<212> TYPE: DNA
<213> ORGANISM: Corynebacterium glutamicum
<220> FEATURE:
<221> NAME/KEY: CDS
<222> LOCATION: (101)..(724)
<223> OTHER INFORMATION: RXA03098

<400> SEQUENCE: 87
gaccgttttg tcgatcgcac cgctgctggc tcgcaccatc aacgagatct tcgaaaacgg      60
ttccgtcacc accctcttcg agggcgaggc ctaaacaccc atg ccc acc acg gac     115
                                             Met Pro Thr Thr Asp
                                               1               5 gtc ttc aac cgc gtc cgg ttg gca ttg gaa cct cta gct gat ccc gca     163
Val Phe Asn Arg Val Arg Leu Ala Leu Glu Pro Leu Ala Asp Pro Ala
                 10                  15                  20 cgt gcc acc gga atg gca agc tac atg cgg gat cag ttt tct ttt ctc     211
Arg Ala Thr Gly Met Ala Ser Tyr Met Arg Asp Gln Phe Ser Phe Leu
             25                  30                  35 ggc atc cca tcc acc ccc aga aaa gaa gcc tgc aaa ccc gtg ctg tcc     259
Gly Ile Pro Ser Thr Pro Arg Lys Glu Ala Cys Lys Pro Val Leu Ser
         40                  45                  50 gcg cta aaa gag ttg gac act gac ttt gtc tca gac tgc ttt ggc gca     307
Ala Leu Lys Glu Leu Asp Thr Asp Phe Val Ser Asp Cys Phe Gly Ala
     55                  60                  65 gct gaa cgg gaa tac cag tat gtc gcc tgc gat cac atc aat cgc gtc     355
Ala Glu Arg Glu Tyr Gln Tyr Val Ala Cys Asp His Ile Asn Arg Val
 70                  75                  80                  85 ggc atc acc gat cta ggt ttt gcc aaa gca tta gtg cag acc aaa tcc     403
Gly Ile Thr Asp Leu Gly Phe Ala Lys Ala Leu Val Gln Thr Lys Ser
                 90                  95                 100 tgg tgg gac acc gtc gat tcc cta gca aaa ccg atc ggc gcc aaa cac     451
Trp Trp Asp Thr Val Asp Ser Leu Ala Lys Pro Ile Gly Ala Lys His
            105                 110                 115 gat gat gat ctg atg aaa acg tgg gcg ctt gat gag gac ttc tgg gtg     499
Asp Asp Asp Leu Met Lys Thr Trp Ala Leu Asp Glu Asp Phe Trp Val
        120                 125                 130 cgc cgc atc gcg atc atc cac caa ctg ggc cgc aag aaa aac acc gac     547
Arg Arg Ile Ala Ile Ile His Gln Leu Gly Arg Lys Lys Asn Thr Asp
    135                 140                 145 gct gcc ctg ctg gcc tgg atc atc gag cag aac ctc ggc tcc agc gag     595
Ala Ala Leu Leu Ala Trp Ile Ile Glu Gln Asn Leu Gly Ser Ser Glu
150                 155                 160                 165 ttc ttc atc aac aaa gcg atc ggc tgg gca ctg cgg gat ttc gcc cgc     643
Phe Phe Ile Asn Lys Ala Ile Gly Trp Ala Leu Arg Asp Phe Ala Arg
                170                 175                 180 cac gac ccc agc tgg gtc cgg gct ttt gtc gac gcc acg gac ctt tcc     691
His Asp Pro Ser Trp Val Arg Ala Phe Val Asp Ala Thr Asp Leu Ser
            185                 190                 195 cca ctg agc cgg cga gaa gcc ctg aag aat att tagccctcag gcatcatctg    744
Pro Leu Ser Arg Arg Glu Ala Leu Lys Asn Ile
        200                 205 agcgagtgcc                                                           754
```

-continued

<210> SEQ ID NO 88
<211> LENGTH: 208
<212> TYPE: PRT
<213> ORGANISM: Corynebacterium glutamicum

<400> SEQUENCE: 88

Met Pro Thr Thr Asp Val Phe Asn Arg Val Arg Leu Ala Leu Glu Pro
1               5                   10                  15

Leu Ala Asp Pro Ala Arg Ala Thr Gly Met Ala Ser Tyr Met Arg Asp
                20                  25                  30

Gln Phe Ser Phe Leu Gly Ile Pro Ser Thr Pro Arg Lys Glu Ala Cys
            35                  40                  45

Lys Pro Val Leu Ser Ala Leu Lys Glu Leu Asp Thr Asp Phe Val Ser
    50                  55                  60

Asp Cys Phe Gly Ala Ala Glu Arg Glu Tyr Gln Tyr Val Ala Cys Asp
65                  70                  75                  80

His Ile Asn Arg Val Gly Ile Thr Asp Leu Gly Phe Ala Lys Ala Leu
                85                  90                  95

Val Gln Thr Lys Ser Trp Trp Asp Thr Val Asp Ser Leu Ala Lys Pro
            100                 105                 110

Ile Gly Ala Lys His Asp Asp Leu Met Lys Thr Trp Ala Leu Asp
        115                 120                 125

Glu Asp Phe Trp Val Arg Arg Ile Ala Ile His Gln Leu Gly Arg
    130                 135                 140

Lys Lys Asn Thr Asp Ala Ala Leu Leu Ala Trp Ile Ile Glu Gln Asn
145                 150                 155                 160

Leu Gly Ser Ser Glu Phe Phe Ile Asn Lys Ala Ile Gly Trp Ala Leu
                165                 170                 175

Arg Asp Phe Ala Arg His Asp Pro Ser Trp Val Arg Ala Phe Val Asp
            180                 185                 190

Ala Thr Asp Leu Ser Pro Leu Ser Arg Arg Glu Ala Leu Lys Asn Ile
        195                 200                 205

<210> SEQ ID NO 89
<211> LENGTH: 562
<212> TYPE: DNA
<213> ORGANISM: Corynebacterium glutamicum
<220> FEATURE:
<221> NAME/KEY: CDS
<222> LOCATION: (101)..(532)
<223> OTHER INFORMATION: RXA03206

<400> SEQUENCE: 89
gaatccctgc acaacggcgc cattgcggcg ttggtggatc tcatccgcca cggattggtg      60
ttgcccgctg atcttctcga ttcttaaata aggactgatt gtg aaa gcc gtt tta     115
                                            Val Lys Ala Val Leu
                                            1               5 acc cgt gtg agt tcc gcc agc gtc agc gtg gat gat gaa att gtt gga      163
Thr Arg Val Ser Ser Ala Ser Val Ser Val Asp Asp Glu Ile Val Gly
                10                  15                  20 gcc atc gat tgc ccc gac acc gga ggc att ttg gcg ctg gtt gga gtc      211
Ala Ile Asp Cys Pro Asp Thr Gly Gly Ile Leu Ala Leu Val Gly Val
            25                  30                  35 ggc gct gct gat agc gac gac gcc tgg gaa acc atg gtg cga aaa att      259
Gly Ala Ala Asp Ser Asp Asp Ala Trp Glu Thr Met Val Arg Lys Ile
        40                  45                  50 gct gag ctg cgc atc ttg gat ggc gaa caa tcc gtc agt gat gtc aat      307
Ala Glu Leu Arg Ile Leu Asp Gly Glu Gln Ser Val Ser Asp Val Asn
    55                  60                  65

```
gct ccc gta ctg ctt gtt agc caa ttc acc ctg cat ggt cgc acc gca    355
Ala Pro Val Leu Leu Val Ser Gln Phe Thr Leu His Gly Arg Thr Ala
 70                  75                  80                  85 aaa ggc cgg cgc cca tcg tgg tct gat gca gca cct ggt gag gtg gct    403
Lys Gly Arg Arg Pro Ser Trp Ser Asp Ala Ala Pro Gly Glu Val Ala
                 90                  95                 100 gag ccg gtg att gaa aag att gca caa ggt tta cgt gag cgc gga atc    451
Glu Pro Val Ile Glu Lys Ile Ala Gln Gly Leu Arg Glu Arg Gly Ile
            105                 110                 115 acc gtg gaa caa gga cga ttc ggc gca atg atg aag gtc aca tcg gtt    499
Thr Val Glu Gln Gly Arg Phe Gly Ala Met Met Lys Val Thr Ser Val
        120                 125                 130 aac gaa ggc ccc ttc acc gtt ttg gtc gag tgc tagccagtca atcctaagag  552
Asn Glu Gly Pro Phe Thr Val Leu Val Glu Cys
    135                 140 cttgaaacgc                                                         562

<210> SEQ ID NO 90
<211> LENGTH: 144
<212> TYPE: PRT
<213> ORGANISM: Corynebacterium glutamicum

<400> SEQUENCE: 90

Val Lys Ala Val Leu Thr Arg Val Ser Ser Ala Ser Val Ser Val Asp
  1               5                  10                  15

Asp Glu Ile Val Gly Ala Ile Asp Cys Pro Asp Thr Gly Gly Ile Leu
                 20                  25                  30

Ala Leu Val Gly Val Gly Ala Ala Asp Ser Asp Asp Ala Trp Glu Thr
             35                  40                  45

Met Val Arg Lys Ile Ala Glu Leu Arg Ile Leu Asp Gly Glu Gln Ser
 50                  55                  60

Val Ser Asp Val Asn Ala Pro Val Leu Val Ser Gln Phe Thr Leu
 65                  70                  75                  80

His Gly Arg Thr Ala Lys Gly Arg Arg Pro Ser Trp Ser Asp Ala Ala
                 85                  90                  95

Pro Gly Glu Val Ala Glu Pro Val Ile Glu Lys Ile Ala Gln Gly Leu
                100                 105                 110

Arg Glu Arg Gly Ile Thr Val Glu Gln Gly Arg Phe Gly Ala Met Met
            115                 120                 125

Lys Val Thr Ser Val Asn Glu Gly Pro Phe Thr Val Leu Val Glu Cys
        130                 135                 140

<210> SEQ ID NO 91
<211> LENGTH: 607
<212> TYPE: DNA
<213> ORGANISM: Corynebacterium glutamicum
<220> FEATURE:
<221> NAME/KEY: CDS
<222> LOCATION: (101)..(577)
<223> OTHER INFORMATION: RXA03260

<400> SEQUENCE: 91
cagatggctg gcaggatca gctgaccacg ttgctcaacc agcgtggtgt caaagtttct    60
actgggactg tgggatcaat tatgaacgaa tgaggagtgc gtg tca gac gaa tgc    115
                                              Val Ser Asp Glu Cys
                                                1               5 ggg cct gga aga aca cca cgg tca gtg acc ctt tct gcc cgg acc gag    163
Gly Pro Gly Arg Thr Pro Arg Ser Val Thr Leu Ser Ala Arg Thr Glu
             10                  15                  20
```

```
cat att aaa aat cat atg ctc gat agc cac ggg aaa cga gac ttt acc         211
His Ile Lys Asn His Met Leu Asp Ser His Gly Lys Arg Asp Phe Thr
             25                  30                  35 gct acc gtg cct ggg acc agg ctc gtt ggt gac att acg tac tta aag         259
Ala Thr Val Pro Gly Thr Arg Leu Val Gly Asp Ile Thr Tyr Leu Lys
         40                  45                  50 acg ggt tcc ggg tgg ctg tat gtg gct acc gtg atc gat ttg gct acg         307
Thr Gly Ser Gly Trp Leu Tyr Val Ala Thr Val Ile Asp Leu Ala Thr
 55                  60                  65 cgg atg gtg gtg ggg tgg tct atg gat tct aat atg cgc aca ccg ttg         355
Arg Met Val Val Gly Trp Ser Met Asp Ser Asn Met Arg Thr Pro Leu
 70                  75                  80                  85 gtg atc aat gcg ctg gct atg gcg cgt gat cat ggg tgt ctt cat cct         403
Val Ile Asn Ala Leu Ala Met Ala Arg Asp His Gly Cys Leu His Pro
         90                  95                 100 gaa ggc gca att ttt cac tcc gat aga gga tcg caa tac acc tcc gag         451
Glu Gly Ala Ile Phe His Ser Asp Arg Gly Ser Gln Tyr Thr Ser Glu
             105                 110                 115 cag ttc cag aca tgg tgc gcc ggc aac aag atc acc caa tcc atg gga         499
Gln Phe Gln Thr Trp Cys Ala Gly Asn Lys Ile Thr Gln Ser Met Gly
         120                 125                 130 ttg acc ggg gtg tgt tgg gat aac gga agt cgc gga gaa ttt ttt ctc         547
Leu Thr Gly Val Cys Trp Asp Asn Gly Ser Arg Gly Glu Phe Phe Leu
135                 140                 145 aca ttt gaa gac cga aat gta tca cca cta tgatttgag aatcacctgt            597
Thr Phe Glu Asp Arg Asn Val Ser Pro Leu
150                 155 cggaccgaac                                                              607
```

<210> SEQ ID NO 92
<211> LENGTH: 159
<212> TYPE: PRT
<213> ORGANISM: Corynebacterium glutamicum

<400> SEQUENCE: 92

Val Ser Asp Glu Cys Gly Pro Gly Arg Thr Pro Arg Ser Val Thr Leu
 1               5                  10                  15

Ser Ala Arg Thr Glu His Ile Lys Asn His Met Leu Asp Ser His Gly
             20                  25                  30

Lys Arg Asp Phe Thr Ala Thr Val Pro Gly Thr Arg Leu Val Gly Asp
         35                  40                  45

Ile Thr Tyr Leu Lys Thr Gly Ser Gly Trp Leu Tyr Val Ala Thr Val
     50                  55                  60

Ile Asp Leu Ala Thr Arg Met Val Val Gly Trp Ser Met Asp Ser Asn
 65                  70                  75                  80

Met Arg Thr Pro Leu Val Ile Asn Ala Leu Ala Met Ala Arg Asp His
             85                  90                  95

Gly Cys Leu His Pro Glu Gly Ala Ile Phe His Ser Asp Arg Gly Ser
         100                 105                 110

Gln Tyr Thr Ser Glu Gln Phe Gln Thr Trp Cys Ala Gly Asn Lys Ile
     115                 120                 125

Thr Gln Ser Met Gly Leu Thr Gly Val Cys Trp Asp Asn Gly Ser Arg
 130                 135                 140

Gly Glu Phe Phe Leu Thr Phe Glu Asp Arg Asn Val Ser Pro Leu
145                 150                 155

<210> SEQ ID NO 93

```
<211> LENGTH: 1969
<212> TYPE: DNA
<213> ORGANISM: Corynebacterium glutamicum
<220> FEATURE:
<221> NAME/KEY: CDS
<222> LOCATION: (101)..(1939)
<223> OTHER INFORMATION: RXA03394

<400> SEQUENCE: 93
ctgcaaagcg acgcagggag cgtaaggcga gtggcgcggg aagcgtcga taggcaattt      60 ttaacccctg atacccttt ccggccgggc ataaattaag gtg gta cgc atg acg      115
                                            Val Val Arg Met Thr
                                             1               5 aag aac gtg ctc gta tct gtt gcc tgg ccg tat gcc aac gga ccc cgt      163
Lys Asn Val Leu Val Ser Val Ala Trp Pro Tyr Ala Asn Gly Pro Arg
             10                  15                  20 cac att gga cat gtg gcg ggg ttt ggt gtc ccc tcc gat gtg ttc gca      211
His Ile Gly His Val Ala Gly Phe Gly Val Pro Ser Asp Val Phe Ala
         25                  30                  35 agg ttc cag cga atg tct ggc aac aac gtg ctc atg gtg tcc ggc acc      259
Arg Phe Gln Arg Met Ser Gly Asn Asn Val Leu Met Val Ser Gly Thr
     40                  45                  50 gat gag cac ggc acg cca ctt ctg gtt caa gca gac aaa gaa ggc gtc      307
Asp Glu His Gly Thr Pro Leu Leu Val Gln Ala Asp Lys Glu Gly Val
 55                  60                  65 acc gtt caa gac cta gcg gat aag tac aac cgc cag atc gtc gaa gac      355
Thr Val Gln Asp Leu Ala Asp Lys Tyr Asn Arg Gln Ile Val Glu Asp
 70                  75                  80                  85 ctc acc ggc ctg ggc ctg tcc tat gac ctt ttc acc cgc acc acc acc      403
Leu Thr Gly Leu Gly Leu Ser Tyr Asp Leu Phe Thr Arg Thr Thr Thr
                 90                  95                 100 tcc aac cac tac gca gta gtg cag gaa ctg ttc cgt ggt ctg tac gac      451
Ser Asn His Tyr Ala Val Val Gln Glu Leu Phe Arg Gly Leu Tyr Asp
            105                 110                 115 aac ggt tac atg atc aag gaa acc acc ctc ggt gcg att tcc cca tcc      499
Asn Gly Tyr Met Ile Lys Glu Thr Thr Leu Gly Ala Ile Ser Pro Ser
        120                 125                 130 act ggc cgt acc ctg cca gac cgc tac att gaa ggc acc tgc cca atc      547
Thr Gly Arg Thr Leu Pro Asp Arg Tyr Ile Glu Gly Thr Cys Pro Ile
135                 140                 145 tgt ggc acc gac ggc gct cgt ggc gac cag tgc gac aac tgc gga aac      595
Cys Gly Thr Asp Gly Ala Arg Gly Asp Gln Cys Asp Asn Cys Gly Asn
150                 155                 160                 165 cag ctc gat cca gcg gac ctg atc aac ccg gtg tcc aag atc aac ggc      643
Gln Leu Asp Pro Ala Asp Leu Ile Asn Pro Val Ser Lys Ile Asn Gly
                170                 175                 180 gaa acc cca gag ttc gtt gag acc gaa cac ttc ctc gac ctg cca      691
Glu Thr Pro Glu Phe Val Glu Thr Glu His Phe Leu Leu Asp Leu Pro
            185                 190                 195 gca ctg gct gaa gca cta acc gag tgg ctg aag gga cgc gaa gac tgg      739
Ala Leu Ala Glu Ala Leu Thr Glu Trp Leu Lys Gly Arg Glu Asp Trp
        200                 205                 210 cgt cca aac gtg ttg aag ttc tcg ctc aac ctg ctg gac gat atc cgc      787
Arg Pro Asn Val Leu Lys Phe Ser Leu Asn Leu Leu Asp Asp Ile Arg
    215                 220                 225 cca cgc gca atg tcg cgc gat atc gac tgg ggc atc cca atc cca gtt      835
Pro Arg Ala Met Ser Arg Asp Ile Asp Trp Gly Ile Pro Ile Pro Val
230                 235                 240                 245 gaa gga tgg caa gac aac aac gcc aag aag ctc tac gtc tgg ttc gac      883
Glu Gly Trp Gln Asp Asn Asn Ala Lys Lys Leu Tyr Val Trp Phe Asp
                250                 255                 260
```

```
gct gtc gtg ggc tac ttg tcc gca tcc atc gaa tgg gcc tac cgc tcc           931
Ala Val Val Gly Tyr Leu Ser Ala Ser Ile Glu Trp Ala Tyr Arg Ser
            265                 270                 275 ggc gac cca gaa gca tgg cgc acc ttc tgg aat gat cca gaa acc aag           979
Gly Asp Pro Glu Ala Trp Arg Thr Phe Trp Asn Asp Pro Glu Thr Lys
        280                 285                 290 tcc tac tac ttc atg ggc aaa gac aac atc acc ttc cac tcc cag atc          1027
Ser Tyr Tyr Phe Met Gly Lys Asp Asn Ile Thr Phe His Ser Gln Ile
    295                 300                 305 tgg cca gcg gag ctt ctc ggc tac gca ggc aag ggc tcc cgc ggt gga          1075
Trp Pro Ala Glu Leu Leu Gly Tyr Ala Gly Lys Gly Ser Arg Gly Gly
310                 315                 320                 325 gaa atc ggt gac ctg ggt gtt ctg aac ctg cct act gag gtt gtt tcc          1123
Glu Ile Gly Asp Leu Gly Val Leu Asn Leu Pro Thr Glu Val Val Ser
                330                 335                 340 tct gag ttc ctg act atg tct gga tcc aag ttc tcc tca tcc aag ggc          1171
Ser Glu Phe Leu Thr Met Ser Gly Ser Lys Phe Ser Ser Ser Lys Gly
            345                 350                 355 gtt gtc atc tac gtg aag gac ttc ctc aag gag ttc ggc cca gat gcg          1219
Val Val Ile Tyr Val Lys Asp Phe Leu Lys Glu Phe Gly Pro Asp Ala
        360                 365                 370 ctg cga tac ttc atc gct gtc gca ggc cca gaa aac aac gac acc gac          1267
Leu Arg Tyr Phe Ile Ala Val Ala Gly Pro Glu Asn Asn Asp Thr Asp
    375                 380                 385 ttc acc tgg gat gaa ttt gtc cgc cgc gta aat aac gag ctg gca aac          1315
Phe Thr Trp Asp Glu Phe Val Arg Arg Val Asn Asn Glu Leu Ala Asn
390                 395                 400                 405 ggc tgg ggc aac ctg gtc aac cgc act gta tcc atg gcg cac aag aac          1363
Gly Trp Gly Asn Leu Val Asn Arg Thr Val Ser Met Ala His Lys Asn
                410                 415                 420 ttc ggt gaa gta cca gta cct ggc gca ctg gaa gaa tct gac aag aag          1411
Phe Gly Glu Val Pro Val Pro Gly Ala Leu Glu Glu Ser Asp Lys Lys
            425                 430                 435 atc ctt gat ctt gct acc gct gcc ttt gaa tcc gtt gct gcg aac ctg          1459
Ile Leu Asp Leu Ala Thr Ala Ala Phe Glu Ser Val Ala Ala Asn Leu
        440                 445                 450 gat cag tcc aag ttc aag gcc ggt atc tct gaa atc atg cac gtt gtc          1507
Asp Gln Ser Lys Phe Lys Ala Gly Ile Ser Glu Ile Met His Val Val
    455                 460                 465 ggt gag gcc aac gcc tac atc gca gag caa gaa cca tgg aag ctt gcc          1555
Gly Glu Ala Asn Ala Tyr Ile Ala Glu Gln Glu Pro Trp Lys Leu Ala
470                 475                 480                 485 aag gat gac acc aag cgc gag cgt ctt gcc acc gtg ctg tgg act gcg          1603
Lys Asp Asp Thr Lys Arg Glu Arg Leu Ala Thr Val Leu Trp Thr Ala
                490                 495                 500 ctg cag gtt gtt tct gac tgc aac acc atg ctg acc cca tac ctg cca          1651
Leu Gln Val Val Ser Asp Cys Asn Thr Met Leu Thr Pro Tyr Leu Pro
            505                 510                 515 cac acc gcc caa aag gtg cat gag acc ttg ggc cgt gat gga atc tgg          1699
His Thr Ala Gln Lys Val His Glu Thr Leu Gly Arg Asp Gly Ile Trp
        520                 525                 530 gct gca aca cca cag atc gtg gaa gtc acc aac gaa tca cca cgc cag          1747
Ala Ala Thr Pro Gln Ile Val Glu Val Thr Asn Glu Ser Pro Arg Gln
    535                 540                 545 cca atc ggc gtg ggg cta cca gat cca gag cac acc tac cca gta atc          1795
Pro Ile Gly Val Gly Leu Pro Asp Pro Glu His Thr Tyr Pro Val Ile
550                 555                 560                 565 atg ggc gac tac aag acc cag ctg gct aag tgg cag cgc atc gac gtt          1843
Met Gly Asp Tyr Lys Thr Gln Leu Ala Lys Trp Gln Arg Ile Asp Val
```

-continued

```
                  570               575               580
gtg cca ggc acc acc ttg gag aag cca gca ccg ctg att gct aag ctc    1891
Val Pro Gly Thr Thr Leu Glu Lys Pro Ala Pro Leu Ile Ala Lys Leu
            585               590               595 gat cca gaa ctt ggt gaa acc ggc cca gaa tgg gca cca gtg cag aac    1939
Asp Pro Glu Leu Gly Glu Thr Gly Pro Glu Trp Ala Pro Val Gln Asn
        600               605               610 taaagcatct ttagcatgaa ccgagcaggt                                   1969
```

<210> SEQ ID NO 94
<211> LENGTH: 613
<212> TYPE: PRT
<213> ORGANISM: Corynebacterium glutamicum

<400> SEQUENCE: 94

Val Val Arg Met Thr Lys Asn Val Leu Val Ser Val Ala Trp Pro Tyr
 1               5                  10                  15

Ala Asn Gly Pro Arg His Ile Gly His Val Ala Gly Phe Gly Val Pro
                20                  25                  30

Ser Asp Val Phe Ala Arg Phe Gln Arg Met Ser Gly Asn Asn Val Leu
            35                  40                  45

Met Val Ser Gly Thr Asp Glu His Gly Thr Pro Leu Leu Val Gln Ala
        50                  55                  60

Asp Lys Glu Gly Val Thr Val Gln Asp Leu Ala Asp Lys Tyr Asn Arg
    65                  70                  75                  80

Gln Ile Val Glu Asp Leu Thr Gly Leu Gly Leu Ser Tyr Asp Leu Phe
                85                  90                  95

Thr Arg Thr Thr Thr Ser Asn His Tyr Ala Val Val Gln Glu Leu Phe
            100                 105                 110

Arg Gly Leu Tyr Asp Asn Gly Tyr Met Ile Lys Glu Thr Thr Leu Gly
        115                 120                 125

Ala Ile Ser Pro Ser Thr Gly Arg Thr Leu Pro Asp Arg Tyr Ile Glu
    130                 135                 140

Gly Thr Cys Pro Ile Cys Gly Thr Asp Gly Ala Arg Gly Asp Gln Cys
145                 150                 155                 160

Asp Asn Cys Gly Asn Gln Leu Asp Pro Ala Asp Leu Ile Asn Pro Val
                165                 170                 175

Ser Lys Ile Asn Gly Glu Thr Pro Glu Phe Val Glu Thr Glu His Phe
            180                 185                 190

Leu Leu Asp Leu Pro Ala Leu Ala Glu Ala Leu Thr Glu Trp Leu Lys
        195                 200                 205

Gly Arg Glu Asp Trp Arg Pro Asn Val Leu Lys Phe Ser Leu Asn Leu
    210                 215                 220

Leu Asp Asp Ile Arg Pro Arg Ala Met Ser Arg Asp Ile Asp Trp Gly
225                 230                 235                 240

Ile Pro Ile Pro Val Glu Gly Trp Gln Asp Asn Ala Lys Lys Leu
                245                 250                 255

Tyr Val Trp Phe Asp Ala Val Val Gly Tyr Leu Ser Ala Ser Ile Glu
            260                 265                 270

Trp Ala Tyr Arg Ser Gly Asp Pro Glu Ala Trp Arg Thr Phe Trp Asn
        275                 280                 285

Asp Pro Glu Thr Lys Ser Tyr Tyr Phe Met Gly Lys Asp Asn Ile Thr
    290                 295                 300

Phe His Ser Gln Ile Trp Pro Ala Glu Leu Leu Gly Tyr Ala Gly Lys
305                 310                 315                 320

```
Gly Ser Arg Gly Gly Glu Ile Gly Asp Leu Gly Val Leu Asn Leu Pro
                325                 330                 335

Thr Glu Val Val Ser Glu Phe Leu Thr Met Ser Gly Ser Lys Phe
            340                 345                 350

Ser Ser Ser Lys Gly Val Val Ile Tyr Val Lys Asp Phe Leu Lys Glu
        355                 360                 365

Phe Gly Pro Asp Ala Leu Arg Tyr Phe Ile Ala Val Ala Gly Pro Glu
    370                 375                 380

Asn Asn Asp Thr Asp Phe Thr Trp Asp Glu Phe Val Arg Arg Val Asn
385                 390                 395                 400

Asn Glu Leu Ala Asn Gly Trp Gly Asn Leu Val Asn Arg Thr Val Ser
                405                 410                 415

Met Ala His Lys Asn Phe Gly Glu Val Pro Val Pro Gly Ala Leu Glu
            420                 425                 430

Glu Ser Asp Lys Lys Ile Leu Asp Leu Ala Thr Ala Ala Phe Glu Ser
        435                 440                 445

Val Ala Ala Asn Leu Asp Gln Ser Lys Phe Lys Ala Gly Ile Ser Glu
    450                 455                 460

Ile Met His Val Val Gly Glu Ala Asn Ala Tyr Ile Ala Glu Gln Glu
465                 470                 475                 480

Pro Trp Lys Leu Ala Lys Asp Asp Thr Lys Arg Glu Arg Leu Ala Thr
                485                 490                 495

Val Leu Trp Thr Ala Leu Gln Val Val Ser Asp Cys Asn Thr Met Leu
            500                 505                 510

Thr Pro Tyr Leu Pro His Thr Ala Gln Lys Val His Glu Thr Leu Gly
        515                 520                 525

Arg Asp Gly Ile Trp Ala Ala Thr Pro Gln Ile Val Glu Val Thr Asn
    530                 535                 540

Glu Ser Pro Arg Gln Pro Ile Gly Val Gly Leu Pro Asp Pro Glu His
545                 550                 555                 560

Thr Tyr Pro Val Ile Met Gly Asp Tyr Lys Thr Gln Leu Ala Lys Trp
                565                 570                 575

Gln Arg Ile Asp Val Val Pro Gly Thr Thr Leu Glu Lys Pro Ala Pro
            580                 585                 590

Leu Ile Ala Lys Leu Asp Pro Glu Leu Gly Glu Thr Gly Pro Glu Trp
        595                 600                 605

Ala Pro Val Gln Asn
    610

<210> SEQ ID NO 95
<211> LENGTH: 3016
<212> TYPE: DNA
<213> ORGANISM: Corynebacterium glutamicum
<220> FEATURE:
<221> NAME/KEY: CDS
<222> LOCATION: (101)..(2986)
<223> OTHER INFORMATION: RXA03674

<400> SEQUENCE: 95
tccccgcagc ccaccaccgt gggctgcggg gtgtggcgtt tttgccacaa agtggaccgt      60
attcgcaaat actttgttaa gacgcgttaa tctttaacct atg tct gaa tca ggt     115
                                               Met Ser Glu Ser Gly
                                                 1               5 gcg cta agt tct act gac tct cta tcc ccg ggt gtc acc att gaa gtc    163
Ala Leu Ser Ser Thr Asp Ser Leu Ser Pro Gly Val Thr Ile Glu Val
         10                  15                  20
```

|  |  |
|---|---:|
| cga gat gaa att tgg ctg gtt act cac gtt act cgc tcc aca gat ggt<br>Arg Asp Glu Ile Trp Leu Val Thr His Val Thr Arg Ser Thr Asp Gly<br>               25                      30                   35 | 211 |
| ttt agg gtt aaa gct cgt ggt ctc tct gat tat gtg cgg gac cac gaa<br>Phe Arg Val Lys Ala Arg Gly Leu Ser Asp Tyr Val Arg Asp His Glu<br>     40                      45                      50 | 259 |
| gct acg ttc ttc acc gca ctt gat aaa gat ttg aag gtc att gac cct<br>Ala Thr Phe Phe Thr Ala Leu Asp Lys Asp Leu Lys Val Ile Asp Pro<br>55                      60                      65 | 307 |
| acc cag gtc acc gtc agt ctt gat gat tcc tcc aat tac cgt cgc acc<br>Thr Gln Val Thr Val Ser Leu Asp Asp Ser Ser Asn Tyr Arg Arg Thr<br>70                      75                      80                      85 | 355 |
| cgc ctg tgg ttg gag gcc acc atg cgt aaa act ccg gta ccg ctc tat<br>Arg Leu Trp Leu Glu Ala Thr Met Arg Lys Thr Pro Val Pro Leu Tyr<br>                 90                      95                     100 | 403 |
| caa gag tca ctt tcc gtg gca gat caa atg ctc gcc gat cca ctg gag<br>Gln Glu Ser Leu Ser Val Ala Asp Gln Met Leu Ala Asp Pro Leu Glu<br>               105                   110                  115 | 451 |
| tac caa tta gca gcc gtg cgc aaa acc ctc tct agt gct aac ttg cgc<br>Tyr Gln Leu Ala Ala Val Arg Lys Thr Leu Ser Ser Ala Asn Leu Arg<br>          120                   125                   130 | 499 |
| ccc cgc gtg ctt att gct gat gcc gtg gga ctt ggc aaa acc cta gaa<br>Pro Arg Val Leu Ile Ala Asp Ala Val Gly Leu Gly Lys Thr Leu Glu<br>135                    140                   145 | 547 |
| atg ggc atg atc ttg gcg gaa ctt atc cgc cgt ggc cgt ggt gag cgc<br>Met Gly Met Ile Leu Ala Glu Leu Ile Arg Arg Gly Arg Gly Glu Arg<br>150                    155                   160                   165 | 595 |
| att ttg gta gtc acc ccg cgc cac att atg gag cag ttc cag cag gaa<br>Ile Leu Val Val Thr Pro Arg His Ile Met Glu Gln Phe Gln Gln Glu<br>               170                   175                  180 | 643 |
| atg tgg acc cgt ttt gcc atc ccg ctc gtt cgt cta gat tcc gtg ggc<br>Met Trp Thr Arg Phe Ala Ile Pro Leu Val Arg Leu Asp Ser Val Gly<br>          185                   190                   195 | 691 |
| atc cag caa gtg cgc caa aaa ttg cca gca tca cgc aac cct ttt act<br>Ile Gln Gln Val Arg Gln Lys Leu Pro Ala Ser Arg Asn Pro Phe Thr<br>          200                   205                   210 | 739 |
| tat ttc ccg cgc gtg att gtc tct atg gat act ttg aaa tct ccg aag<br>Tyr Phe Pro Arg Val Ile Val Ser Met Asp Thr Leu Lys Ser Pro Lys<br>215                    220                   225 | 787 |
| tac cgc gcg caa cta gaa aag gtg cac tgg gat gcg gtg gtt ata gat<br>Tyr Arg Ala Gln Leu Glu Lys Val His Trp Asp Ala Val Val Ile Asp<br>230                    235                   240                   245 | 835 |
| gaa atc cac aat gca acc aat gct ggc acc caa aat aat gag cta gcc<br>Glu Ile His Asn Ala Thr Asn Ala Gly Thr Gln Asn Asn Glu Leu Ala<br>               250                   255                  260 | 883 |
| cgc aca ctt gcg cct act gcc gag gct ctt att ttg gcc tct gcc acc<br>Arg Thr Leu Ala Pro Thr Ala Glu Ala Leu Ile Leu Ala Ser Ala Thr<br>          265                   270                   275 | 931 |
| ccg cac aat ggt gat cca gaa tcc ttt aag gag atc ttg cgt ttg ctt<br>Pro His Asn Gly Asp Pro Glu Ser Phe Lys Glu Ile Leu Arg Leu Leu<br>280                    285                   290 | 979 |
| gat ccc acc gct gtg atg cct gat ggc acc att gat gcc gaa gct gca<br>Asp Pro Thr Ala Val Met Pro Asp Gly Thr Ile Asp Ala Glu Ala Ala<br>295                    300                   305 | 1027 |
| cag cgt ctg atc att cgt cgc cat cgc aat agc cct gag gtt tca ggt<br>Gln Arg Leu Ile Ile Arg Arg His Arg Asn Ser Pro Glu Val Ser Gly<br>310                    315                   320                   325 | 1075 |
| ttt gtg ggc gaa aaa tgg gct cca cgc aat gag cct cag aac ttc ctg<br>Phe Val Gly Glu Lys Trp Ala Pro Arg Asn Glu Pro Gln Asn Phe Leu | 1123 |

```
                            -continued
            330                 335                  340
gtc gct gcg tca aaa gaa gaa aac ggc gtt gct gca gaa ctc aac cat    1171
Val Ala Ala Ser Lys Glu Glu Asn Gly Val Ala Ala Glu Leu Asn His
            345                 350                  355 gtg tgg att tca cca ggt gcg agc aat ccg atc aag gat cgc ctc ttc    1219
Val Trp Ile Ser Pro Gly Ala Ser Asn Pro Ile Lys Asp Arg Leu Phe
            360                 365                  370 ccc tgg aca ttg gtg aag gct ttt ctc tcc tcc cct gca gcc ttg ggc    1267
Pro Trp Thr Leu Val Lys Ala Phe Leu Ser Ser Pro Ala Ala Leu Gly
    375                 380                 385 gaa aca gtg tcc aat cgc ctc aaa aag gcc tct gca cca gaa gaa aaa    1315
Glu Thr Val Ser Asn Arg Leu Lys Lys Ala Ser Ala Pro Glu Glu Lys
390                 395                 400                 405 cgc gcc cta gaa acc ctt tca caa ctt aat tct gcg atc acc ccg cag    1363
Arg Ala Leu Glu Thr Leu Ser Gln Leu Asn Ser Ala Ile Thr Pro Gln
                410                 415                 420 acc tca cag aag tac caa tct cta ctg agc tac ctc ggt gac atc gga    1411
Thr Ser Gln Lys Tyr Gln Ser Leu Leu Ser Tyr Leu Gly Asp Ile Gly
            425                 430                 435 gtg aag aag aac tcc gat acc cgc gtg gtg att ttc tct gag cgt gtc    1459
Val Lys Lys Asn Ser Asp Thr Arg Val Val Ile Phe Ser Glu Arg Val
        440                 445                 450 gct act ttg cac tgg ctg cag gaa aac ctc atc cgt gat ctc aag atg    1507
Ala Thr Leu His Trp Leu Gln Glu Asn Leu Ile Arg Asp Leu Lys Met
    455                 460                 465 cca ccc aac tct att gct gtt atg cac ggc ggt ctc ccc gac cag gag    1555
Pro Pro Asn Ser Ile Ala Val Met His Gly Gly Leu Pro Asp Gln Glu
470                 475                 480                 485 caa atg cgc ctg gtg gat gag ttt aaa aag acg gat tct ccc atc cgc    1603
Gln Met Arg Leu Val Asp Glu Phe Lys Lys Thr Asp Ser Pro Ile Arg
                490                 495                 500 atc atg atc acc ggc gat gtt gcc tca gaa ggt gtg aac ctg cat act    1651
Ile Met Ile Thr Gly Asp Val Ala Ser Glu Gly Val Asn Leu His Thr
            505                 510                 515 ctc tgc cac aac ttg gtg cac tat gac atc ccg tgg tca ctg atc cgc    1699
Leu Cys His Asn Leu Val His Tyr Asp Ile Pro Trp Ser Leu Ile Arg
        520                 525                 530 att cag cag cgc aat ggc cgt att gat cgt tat ggt caa acc cac aac    1747
Ile Gln Gln Arg Asn Gly Arg Ile Asp Arg Tyr Gly Gln Thr His Asn
    535                 540                 545 cct tcc atc gtt acc ttc ttg ctc gat ccc gcc gag gat tcc aaa gta    1795
Pro Ser Ile Val Thr Phe Leu Leu Asp Pro Ala Glu Asp Ser Lys Val
550                 555                 560                 565 ggt gaa gtc cat gtg ctg gag agg ctc atg gag cgc gaa cat gag gcg    1843
Gly Glu Val His Val Leu Glu Arg Leu Met Glu Arg Glu His Glu Ala
                570                 575                 580 cac tct ttg ctc ggt gat gcc gca tct ctc atg ggc aag cac tct gag    1891
His Ser Leu Leu Gly Asp Ala Ala Ser Leu Met Gly Lys His Ser Glu
            585                 590                 595 cgt ttg gaa gaa gaa acc atc cgc gaa gtc ctg cgc ggt gcc caa aac    1939
Arg Leu Glu Glu Glu Thr Ile Arg Glu Val Leu Arg Gly Ala Gln Asn
        600                 605                 610 ttt aat gat gca gtg gct gat cca gcg gaa gtc cta gaa aac cca gca    1987
Phe Asn Asp Ala Val Ala Asp Pro Ala Glu Val Leu Glu Asn Pro Ala
    615                 620                 625 ggc cta gat gat att gat tgg ttg cta gcc caa atc gcc caa gcc gat    2035
Gly Leu Asp Asp Ile Asp Trp Leu Leu Ala Gln Ile Ala Gln Ala Asp
630                 635                 640                 645 gcc aag gca gaa aca gaa gca gaa gca gaa aca gaa aac caa aca gca    2083
```

```
                    Ala Lys Ala Glu Thr Glu Ala Glu Ala Glu Thr Glu Asn Gln Thr Ala
                                    650                 655                 660 cca gat gca gct tcc aat agc acg cag cat gca caa cgc cgg ttg tat              2131
Pro Asp Ala Ala Ser Asn Ser Thr Gln His Ala Gln Arg Arg Leu Tyr
                665                 670                 675 gca cag gaa agc tct ttc ctc tat gac tgc ctc ctc gaa ggt ttc aat              2179
Ala Gln Glu Ser Ser Phe Leu Tyr Asp Cys Leu Leu Glu Gly Phe Asn
            680                 685                 690 aac gta ccg gag gat tcc atc aac cgc ggt ggc gtg ggg ttc aaa aaa              2227
Asn Val Pro Glu Asp Ser Ile Asn Arg Gly Gly Val Gly Phe Lys Lys
        695                 700                 705 cac gat aat gac atc gtg gag ctc acc ccc acc gat gat ctg cgc cgt              2275
His Asp Asn Asp Ile Val Glu Leu Thr Pro Thr Asp Asp Leu Arg Arg
710                 715                 720                 725 cgt cta gat ttc ctc ccg cag gat tat gtg gct gcc cgg aaa gtt aag              2323
Arg Leu Asp Phe Leu Pro Gln Asp Tyr Val Ala Ala Arg Lys Val Lys
                730                 735                 740 gaa gat ctc cta cta gct tcc aca ctg atg cgt ggc caa gaa cgc ctc              2371
Glu Asp Leu Leu Leu Ala Ser Thr Leu Met Arg Gly Gln Glu Arg Leu
                745                 750                 755 aac gct gcg cgc act ggt gaa gat ggc agt acc tgg cca agt gcc cac              2419
Asn Ala Ala Arg Thr Gly Glu Asp Gly Ser Thr Trp Pro Ser Ala His
            760                 765                 770 tat cta ggc ccc ctg cac cca gtc act tcg tgg gca gct gac cgc gcg              2467
Tyr Leu Gly Pro Leu His Pro Val Thr Ser Trp Ala Ala Asp Arg Ala
        775                 780                 785 ctg gca acc atg cca cgt tcg gaa att ccg gcg gct agt ggc aaa gtc              2515
Leu Ala Thr Met Pro Arg Ser Glu Ile Pro Ala Ala Ser Gly Lys Val
790                 795                 800                 805 aca gag cca acg gtg ctg ctt atg tcc aca ttg agc aat cgg cgt ggc              2563
Thr Glu Pro Thr Val Leu Leu Met Ser Thr Leu Ser Asn Arg Arg Gly
                810                 815                 820 caa att gtg tct cgt tct ttt gtg gct tct tct ggc ccc ttt gat act              2611
Gln Ile Val Ser Arg Ser Phe Val Ala Ser Ser Gly Pro Phe Asp Thr
                825                 830                 835 gag gtg ctg tcc gat ccc atc caa tgg tta cat tcc ata ggc ctc gat              2659
Glu Val Leu Ser Asp Pro Ile Gln Trp Leu His Ser Ile Gly Leu Asp
            840                 845                 850 gaa acc gcc att aac cca ggt acc gct gca ctc ccc gac gat att gag              2707
Glu Thr Ala Ile Asn Pro Gly Thr Ala Ala Leu Pro Asp Asp Ile Glu
        855                 860                 865 cag ctt att tcc ctt gct gtt cag gcc gcc cgc ggc gag atc cgt cca              2755
Gln Leu Ile Ser Leu Ala Val Gln Ala Ala Arg Gly Glu Ile Arg Pro
870                 875                 880                 885 tta atg atc gcc gcc cgc gct cag gct caa act cgc gtt gag cat tgg              2803
Leu Met Ile Ala Ala Arg Ala Gln Ala Gln Thr Arg Val Glu His Trp
                890                 895                 900 gct aag cga gcc gaa gcc tgg aat aac aaa cga agt ggc gca gcg tcc              2851
Ala Lys Arg Ala Glu Ala Trp Asn Asn Lys Arg Ser Gly Ala Ala Ser
                905                 910                 915 acg tcc cgt acc gcg cga act gca aaa ttg att gag gag cag cag aaa              2899
Thr Ser Arg Thr Ala Arg Thr Ala Lys Leu Ile Glu Glu Gln Gln Lys
            920                 925                 930 ttg agt aat gct ctc gag cca gac cgt gaa ctt att agg cct ttg gcc              2947
Leu Ser Asn Ala Leu Glu Pro Asp Arg Glu Leu Ile Arg Pro Leu Ala
        935                 940                 945 gtc att ctt ccg cag ccc gca act ttg aac acc gag gtt taacacaatg              2996
Val Ile Leu Pro Gln Pro Ala Thr Leu Asn Thr Glu Val
950                 955                 960
```

-continued agtgcatttg attcgatcct            3016

<210> SEQ ID NO 96
<211> LENGTH: 962
<212> TYPE: PRT
<213> ORGANISM: Corynebacterium glutamicum

<400> SEQUENCE: 96

Met Ser Glu Ser Gly Ala Leu Ser Ser Thr Asp Ser Leu Ser Pro Gly
 1               5                  10                  15

Val Thr Ile Glu Val Arg Asp Glu Ile Trp Leu Val Thr His Val Thr
                20                  25                  30

Arg Ser Thr Asp Gly Phe Arg Val Lys Ala Arg Gly Leu Ser Asp Tyr
            35                  40                  45

Val Arg Asp His Glu Ala Thr Phe Phe Thr Ala Leu Asp Lys Asp Leu
        50                  55                  60

Lys Val Ile Asp Pro Thr Gln Val Thr Val Ser Leu Asp Asp Ser Ser
 65                  70                  75                  80

Asn Tyr Arg Arg Thr Arg Leu Trp Leu Glu Ala Thr Met Arg Lys Thr
                85                  90                  95

Pro Val Pro Leu Tyr Gln Glu Ser Leu Ser Val Ala Asp Gln Met Leu
                100                 105                 110

Ala Asp Pro Leu Glu Tyr Gln Leu Ala Ala Val Arg Lys Thr Leu Ser
            115                 120                 125

Ser Ala Asn Leu Arg Pro Arg Val Leu Ile Ala Asp Ala Val Gly Leu
        130                 135                 140

Gly Lys Thr Leu Glu Met Gly Met Ile Leu Ala Glu Leu Ile Arg Arg
145                 150                 155                 160

Gly Arg Gly Glu Arg Ile Leu Val Val Thr Pro Arg His Ile Met Glu
                165                 170                 175

Gln Phe Gln Gln Glu Met Trp Thr Arg Phe Ala Ile Pro Leu Val Arg
            180                 185                 190

Leu Asp Ser Val Gly Ile Gln Gln Val Arg Gln Lys Leu Pro Ala Ser
        195                 200                 205

Arg Asn Pro Phe Thr Tyr Phe Pro Arg Val Ile Val Ser Met Asp Thr
    210                 215                 220

Leu Lys Ser Pro Lys Tyr Arg Ala Gln Leu Glu Lys Val His Trp Asp
225                 230                 235                 240

Ala Val Val Ile Asp Glu Ile His Asn Ala Thr Asn Ala Gly Thr Gln
                245                 250                 255

Asn Asn Glu Leu Ala Arg Thr Leu Ala Pro Thr Ala Glu Ala Leu Ile
            260                 265                 270

Leu Ala Ser Ala Thr Pro His Asn Gly Asp Pro Glu Ser Phe Lys Glu
        275                 280                 285

Ile Leu Arg Leu Leu Asp Pro Thr Ala Val Met Pro Asp Gly Thr Ile
    290                 295                 300

Asp Ala Glu Ala Ala Gln Arg Leu Ile Arg Arg His Arg Asn Ser
305                 310                 315                 320

Pro Glu Val Ser Gly Phe Val Gly Lys Trp Ala Pro Arg Asn Glu
                325                 330                 335

Pro Gln Asn Phe Leu Val Ala Ser Lys Glu Glu Asn Gly Val Ala
            340                 345                 350

Ala Glu Leu Asn His Val Trp Ile Ser Pro Gly Ala Ser Asn Pro Ile
        355                 360                 365

-continued

```
Lys Asp Arg Leu Phe Pro Trp Thr Leu Val Lys Ala Phe Leu Ser Ser
370                 375                 380

Pro Ala Ala Leu Gly Glu Thr Val Ser Asn Arg Leu Lys Lys Ala Ser
385                 390                 395                 400

Ala Pro Glu Glu Lys Arg Ala Leu Glu Thr Leu Ser Gln Leu Asn Ser
            405                 410                 415

Ala Ile Thr Pro Gln Thr Ser Gln Lys Tyr Gln Ser Leu Leu Ser Tyr
            420                 425                 430

Leu Gly Asp Ile Gly Val Lys Lys Asn Ser Asp Thr Arg Val Val Ile
            435                 440                 445

Phe Ser Glu Arg Val Ala Thr Leu His Trp Leu Gln Glu Asn Leu Ile
450                 455                 460

Arg Asp Leu Lys Met Pro Pro Asn Ser Ile Ala Val Met His Gly Gly
465                 470                 475                 480

Leu Pro Asp Gln Glu Gln Met Arg Leu Val Asp Glu Phe Lys Lys Thr
                485                 490                 495

Asp Ser Pro Ile Arg Ile Met Ile Thr Gly Asp Val Ala Ser Glu Gly
                500                 505                 510

Val Asn Leu His Thr Leu Cys His Asn Leu Val His Tyr Asp Ile Pro
                515                 520                 525

Trp Ser Leu Ile Arg Ile Gln Gln Arg Asn Gly Arg Ile Asp Arg Tyr
530                 535                 540

Gly Gln Thr His Asn Pro Ser Ile Val Thr Phe Leu Leu Asp Pro Ala
545                 550                 555                 560

Glu Asp Ser Lys Val Gly Glu Val His Val Leu Glu Arg Leu Met Glu
                565                 570                 575

Arg Glu His Glu Ala His Ser Leu Leu Gly Asp Ala Ala Ser Leu Met
                580                 585                 590

Gly Lys His Ser Glu Arg Leu Glu Glu Glu Thr Ile Arg Glu Val Leu
                595                 600                 605

Arg Gly Ala Gln Asn Phe Asn Asp Ala Val Ala Asp Pro Ala Glu Val
610                 615                 620

Leu Glu Asn Pro Ala Gly Leu Asp Asp Ile Asp Trp Leu Leu Ala Gln
625                 630                 635                 640

Ile Ala Gln Ala Asp Ala Lys Ala Glu Thr Glu Ala Glu Ala Glu Thr
                645                 650                 655

Glu Asn Gln Thr Ala Pro Asp Ala Ala Ser Asn Ser Thr Gln His Ala
                660                 665                 670

Gln Arg Arg Leu Tyr Ala Gln Glu Ser Ser Phe Leu Tyr Asp Cys Leu
            675                 680                 685

Leu Glu Gly Phe Asn Asn Val Pro Glu Asp Ser Ile Asn Arg Gly Gly
690                 695                 700

Val Gly Phe Lys Lys His Asp Asn Asp Ile Val Glu Leu Thr Pro Thr
705                 710                 715                 720

Asp Asp Leu Arg Arg Arg Leu Asp Phe Leu Pro Gln Asp Tyr Val Ala
                725                 730                 735

Ala Arg Lys Val Lys Glu Asp Leu Leu Leu Ala Ser Thr Leu Met Arg
                740                 745                 750

Gly Gln Glu Arg Leu Asn Ala Ala Arg Thr Gly Glu Asp Gly Ser Thr
            755                 760                 765

Trp Pro Ser Ala His Tyr Leu Gly Pro Leu His Pro Val Thr Ser Trp
770                 775                 780

Ala Ala Asp Arg Ala Leu Ala Thr Met Pro Arg Ser Glu Ile Pro Ala
```

```
                        785                 790                 795                 800
Ala Ser Gly Lys Val Thr Glu Pro Thr Val Leu Leu Met Ser Thr Leu
                805                 810                 815

Ser Asn Arg Arg Gly Gln Ile Val Ser Arg Ser Phe Val Ala Ser Ser
            820                 825                 830

Gly Pro Phe Asp Thr Glu Val Leu Ser Asp Pro Ile Gln Trp Leu His
        835                 840                 845

Ser Ile Gly Leu Asp Glu Thr Ala Ile Asn Pro Gly Thr Ala Ala Leu
    850                 855                 860

Pro Asp Asp Ile Glu Gln Leu Ile Ser Leu Ala Val Gln Ala Ala Arg
865                 870                 875                 880

Gly Glu Ile Arg Pro Leu Met Ile Ala Ala Arg Ala Gln Ala Gln Thr
                885                 890                 895

Arg Val Glu His Trp Ala Lys Arg Ala Glu Ala Trp Asn Asn Lys Arg
            900                 905                 910

Ser Gly Ala Ala Ser Thr Ser Arg Thr Ala Arg Thr Ala Lys Leu Ile
        915                 920                 925

Glu Glu Gln Gln Lys Leu Ser Asn Ala Leu Glu Pro Asp Arg Glu Leu
    930                 935                 940

Ile Arg Pro Leu Ala Val Ile Leu Pro Gln Pro Ala Thr Leu Asn Thr
945                 950                 955                 960

Glu Val

<210> SEQ ID NO 97
<211> LENGTH: 1624
<212> TYPE: DNA
<213> ORGANISM: Corynebacterium glutamicum
<220> FEATURE:
<221> NAME/KEY: CDS
<222> LOCATION: (101)..(1594)
<223> OTHER INFORMATION: RXA03793

<400> SEQUENCE: 97
atggaaagaa gctaggcgga aagggcgtta agtacttgcc atttaatcct cagcatcact      60
cggatcagtc ggagatgtcg atgaaaatgc accaggagcc gtg gag agc agc atg     115
                                              Val Glu Ser Ser Met
                                                              1   5 gta gaa aac aac gta gca aaa aag acg gtc gct aaa aag acc gca cgc     163
Val Glu Asn Asn Val Ala Lys Lys Thr Val Ala Lys Lys Thr Ala Arg
            10                  15                  20 aag acc gca cgc aaa gca gcc ccg cgc gtg gca acc cca ttg gga gtc     211
Lys Thr Ala Arg Lys Ala Ala Pro Arg Val Ala Thr Pro Leu Gly Val
        25                  30                  35 gca tct gag tct ccc att tcg gcc acc cct gcg cgc agc atc gat gga     259
Ala Ser Glu Ser Pro Ile Ser Ala Thr Pro Ala Arg Ser Ile Asp Gly
    40                  45                  50 acc tca acc cct gtt gaa gct gct gac acc ata gag acc acc gcc cct     307
Thr Ser Thr Pro Val Glu Ala Ala Asp Thr Ile Glu Thr Thr Ala Pro
55                  60                  65 gca gcg aag gct cct gcg gcc aag gct ccc gct aaa aag gtt gcc aag     355
Ala Ala Lys Ala Pro Ala Ala Lys Ala Pro Ala Lys Lys Val Ala Lys
    70                  75                  80                  85 aag aca gct cgc aag gca cct gcg aaa aag act gtc gcc aag aaa gcc     403
Lys Thr Ala Arg Lys Ala Pro Ala Lys Lys Thr Val Ala Lys Lys Ala
                90                  95                  100 aca acc gcc aag gct gca cct gca act gcc aag gac gaa aac gca cct     451
Thr Thr Ala Lys Ala Ala Pro Ala Thr Ala Lys Asp Glu Asn Ala Pro
            105                 110                 115
```

-continued

| | |
|---|---|
| gtt gac gac gac gag gag aac ctc gct cag gat gaa cag gac ttc gac<br>Val Asp Asp Asp Glu Glu Asn Leu Ala Gln Asp Glu Gln Asp Phe Asp<br>120                 125                 130 | 499 |
| ggc gat gac ttc gta gac ggc atc gaa gac gaa gaa gat gaa gac ggc<br>Gly Asp Asp Phe Val Asp Gly Ile Glu Asp Glu Glu Asp Glu Asp Gly<br>      135                 140                 145 | 547 |
| gtc gaa gcc ctc ggt gaa gaa agc gaa gac gac gaa gag gac ggc tca<br>Val Glu Ala Leu Gly Glu Glu Ser Glu Asp Asp Glu Glu Asp Gly Ser<br>150                 155                 160                 165 | 595 |
| tcc gtt tgg gat gaa gac gaa tcc gca acc ctg cgt cag gca cgt aaa<br>Ser Val Trp Asp Glu Asp Glu Ser Ala Thr Leu Arg Gln Ala Arg Lys<br>            170                 175                 180 | 643 |
| gat gcc gag ctc acc gct tcc gcc gac tct gtt cgc gct tac ctg aag<br>Asp Ala Glu Leu Thr Ala Ser Ala Asp Ser Val Arg Ala Tyr Leu Lys<br>      185                 190                 195 | 691 |
| caa atc ggt aaa gtt gcc ctg ctg aac gct gaa cag gaa gtc tcc ctg<br>Gln Ile Gly Lys Val Ala Leu Leu Asn Ala Glu Gln Glu Val Ser Leu<br>200                 205                 210 | 739 |
| gca aag cgc atc gaa gca ggc ctt tac gcc acc cac cgc atg gag gaa<br>Ala Lys Arg Ile Glu Ala Gly Leu Tyr Ala Thr His Arg Met Glu Glu<br>215                 220                 225 | 787 |
| atg gaa gaa gct ttc gca gcc ggt gac aag gac gcg aaa ctc acc cca<br>Met Glu Glu Ala Phe Ala Ala Gly Asp Lys Asp Ala Lys Leu Thr Pro<br>230                 235                 240                 245 | 835 |
| gcc gtc aag cgt gac ctc cgc gcc atc gct cgt gac ggc cgc aag gcg<br>Ala Val Lys Arg Asp Leu Arg Ala Ile Ala Arg Asp Gly Arg Lys Ala<br>            250                 255                 260 | 883 |
| aaa aac cac ctc ctg gaa gcc aac ctt cgt ctg gtt gtc tcc ctg gca<br>Lys Asn His Leu Leu Glu Ala Asn Leu Arg Leu Val Val Ser Leu Ala<br>      265                 270                 275 | 931 |
| aag cgc tac acc ggc cgt ggc atg gca ttc ctg gac ctc atc cag gaa<br>Lys Arg Tyr Thr Gly Arg Gly Met Ala Phe Leu Asp Leu Ile Gln Glu<br>280                 285                 290 | 979 |
| ggc aac ctc ggt ctg att cgt gcc gta gag aag ttc gac tac tcc aag<br>Gly Asn Leu Gly Leu Ile Arg Ala Val Glu Lys Phe Asp Tyr Ser Lys<br>295                 300                 305 | 1027 |
| ggc tac aag ttc tcc acc tac gca acc tgg tgg atc cgt cag gca atc<br>Gly Tyr Lys Phe Ser Thr Tyr Ala Thr Trp Trp Ile Arg Gln Ala Ile<br>310                 315                 320                 325 | 1075 |
| acc cgc gcc atg gcc gac caa gca cga acc atc cgt atc cca gtc cac<br>Thr Arg Ala Met Ala Asp Gln Ala Arg Thr Ile Arg Ile Pro Val His<br>            330                 335                 340 | 1123 |
| atg gtt gaa gtg atc aac aaa ctt ggt cgc atc caa cgt gaa ctc ctt<br>Met Val Glu Val Ile Asn Lys Leu Gly Arg Ile Gln Arg Glu Leu Leu<br>      345                 350                 355 | 1171 |
| cag gaa ctc ggc cgc gaa cca acc cca cag gaa ctg tcc aaa gaa atg<br>Gln Glu Leu Gly Arg Glu Pro Thr Pro Gln Glu Leu Ser Lys Glu Met<br>360                 365                 370 | 1219 |
| gac atc tcc gag gaa aag gta ctg gaa atc cag cag tac gcc cgc gaa<br>Asp Ile Ser Glu Glu Lys Val Leu Glu Ile Gln Gln Tyr Ala Arg Glu<br>375                 380                 385 | 1267 |
| cca atc tcc ctg gac caa acc atc ggc gac gaa ggc gac agc cag ctc<br>Pro Ile Ser Leu Asp Gln Thr Ile Gly Asp Glu Gly Asp Ser Gln Leu<br>390                 395                 400                 405 | 1315 |
| ggc gac ttc atc gaa gac tcc gaa gcc gtc gtc gca gtc gac gcc gtc<br>Gly Asp Phe Ile Glu Asp Ser Glu Ala Val Val Ala Val Asp Ala Val<br>            410                 415                 420 | 1363 |
| tca ttc acc ctg ctg caa gac cag cta cag gac gtc cta gag acc ctc<br>Ser Phe Thr Leu Leu Gln Asp Gln Leu Gln Asp Val Leu Glu Thr Leu | 1411 |

|  |  |  | 425 |  |  |  | 430 |  |  |  | 435 |  |  |  |  |
|---|---|---|---|---|---|---|---|---|---|---|---|---|---|---|---|
| tcc | gaa | cgt | gaa | gcc | ggc | gtg | gtt | aaa | ctc | cgc | ttc | gga | ctc | acc | gac | 1459 |
| Ser | Glu | Arg | Glu | Ala | Gly | Val | Val | Lys | Leu | Arg | Phe | Gly | Leu | Thr | Asp |
|  |  | 440 |  |  |  |  | 445 |  |  |  |  | 450 |  |  |  |
| gga | atg | cca | cgc | act | tta | gac | gaa | atc | ggc | caa | gtt | tac | ggt | gtc | acc | 1507 |
| Gly | Met | Pro | Arg | Thr | Leu | Asp | Glu | Ile | Gly | Gln | Val | Tyr | Gly | Val | Thr |
|  | 455 |  |  |  |  | 460 |  |  |  |  | 465 |  |  |  |  |
| cgt | gag | cgc | atc | cgc | cag | att | gag | tcc | aag | acc | atg | tct | aag | ctg | cgc | 1555 |
| Arg | Glu | Arg | Ile | Arg | Gln | Ile | Glu | Ser | Lys | Thr | Met | Ser | Lys | Leu | Arg |
| 470 |  |  |  |  | 475 |  |  |  |  | 480 |  |  |  |  | 485 |
| cac | cca | tca | cgc | tcc | cag | gtc | ctt | cgc | gac | tac | ctg | gac | taaaacccca |  |  | 1604 |
| His | Pro | Ser | Arg | Ser | Gln | Val | Leu | Arg | Asp | Tyr | Leu | Asp |  |  |  |
|  |  |  |  | 490 |  |  |  |  | 495 |  |  |  |  |  |  | gtcgggctca agaccgggcc                                                          1624

<210> SEQ ID NO 98
<211> LENGTH: 498
<212> TYPE: PRT
<213> ORGANISM: Corynebacterium glutamicum

<400> SEQUENCE: 98

Val Glu Ser Ser Met Val Glu Asn Asn Val Ala Lys Lys Thr Val Ala
 1               5                  10                  15

Lys Lys Thr Ala Arg Lys Thr Ala Arg Lys Ala Ala Pro Arg Val Ala
            20                  25                  30

Thr Pro Leu Gly Val Ala Ser Glu Ser Pro Ile Ser Ala Thr Pro Ala
        35                  40                  45

Arg Ser Ile Asp Gly Thr Ser Thr Pro Val Glu Ala Ala Asp Thr Ile
    50                  55                  60

Glu Thr Thr Ala Pro Ala Ala Lys Ala Pro Ala Ala Lys Ala Pro Ala
65                  70                  75                  80

Lys Lys Val Ala Lys Thr Ala Arg Lys Ala Pro Ala Lys Lys Thr
            85                  90                  95

Val Ala Lys Lys Ala Thr Thr Ala Lys Ala Ala Pro Ala Thr Ala Lys
            100                 105                 110

Asp Glu Asn Ala Pro Val Asp Asp Glu Glu Asn Leu Ala Gln Asp
            115                 120                 125

Glu Gln Asp Phe Asp Gly Asp Asp Phe Val Asp Gly Ile Glu Asp Glu
    130                 135                 140

Glu Asp Glu Asp Gly Val Glu Ala Leu Gly Glu Glu Ser Glu Asp Asp
145                 150                 155                 160

Glu Glu Asp Gly Ser Ser Val Trp Asp Glu Asp Glu Ser Ala Thr Leu
                165                 170                 175

Arg Gln Ala Arg Lys Asp Ala Glu Leu Thr Ala Ser Ala Asp Ser Val
            180                 185                 190

Arg Ala Tyr Leu Lys Gln Ile Gly Lys Val Ala Leu Leu Asn Ala Glu
        195                 200                 205

Gln Glu Val Ser Leu Ala Lys Arg Ile Glu Ala Gly Leu Tyr Ala Thr
    210                 215                 220

His Arg Met Glu Glu Met Glu Glu Ala Phe Ala Ala Gly Asp Lys Asp
225                 230                 235                 240

Ala Lys Leu Thr Pro Ala Val Lys Arg Asp Leu Arg Ala Ile Ala Arg
                245                 250                 255

Asp Gly Arg Lys Ala Lys Asn His Leu Leu Glu Ala Asn Leu Arg Leu
            260                 265                 270

```
Val Val Ser Leu Ala Lys Arg Tyr Thr Gly Arg Gly Met Ala Phe Leu
        275                 280                 285

Asp Leu Ile Gln Glu Gly Asn Leu Gly Leu Ile Arg Ala Val Glu Lys
        290                 295                 300

Phe Asp Tyr Ser Lys Gly Tyr Lys Phe Ser Thr Tyr Ala Thr Trp Trp
305                 310                 315                 320

Ile Arg Gln Ala Ile Thr Arg Ala Met Ala Asp Gln Ala Arg Thr Ile
                325                 330                 335

Arg Ile Pro Val His Met Val Glu Val Ile Asn Lys Leu Gly Arg Ile
            340                 345                 350

Gln Arg Glu Leu Leu Gln Glu Leu Gly Arg Glu Pro Thr Pro Gln Glu
        355                 360                 365

Leu Ser Lys Glu Met Asp Ile Ser Glu Glu Lys Val Leu Glu Ile Gln
    370                 375                 380

Gln Tyr Ala Arg Glu Pro Ile Ser Leu Asp Gln Thr Ile Gly Asp Glu
385                 390                 395                 400

Gly Asp Ser Gln Leu Gly Asp Phe Ile Glu Asp Ser Glu Ala Val Val
                405                 410                 415

Ala Val Asp Ala Val Ser Phe Thr Leu Leu Gln Asp Gln Leu Gln Asp
            420                 425                 430

Val Leu Glu Thr Leu Ser Glu Arg Glu Ala Gly Val Val Lys Leu Arg
        435                 440                 445

Phe Gly Leu Thr Asp Gly Met Pro Arg Thr Leu Asp Glu Ile Gly Gln
    450                 455                 460

Val Tyr Gly Val Thr Arg Glu Arg Ile Arg Gln Ile Glu Ser Lys Thr
465                 470                 475                 480

Met Ser Lys Leu Arg His Pro Ser Arg Ser Gln Val Leu Arg Asp Tyr
                485                 490                 495

Leu Asp

<210> SEQ ID NO 99
<211> LENGTH: 1234
<212> TYPE: DNA
<213> ORGANISM: Corynebacterium glutamicum
<220> FEATURE:
<221> NAME/KEY: CDS
<222> LOCATION: (101)..(1204)
<223> OTHER INFORMATION: RXA06048

<400> SEQUENCE: 99
agccgctgct gcagcgtgtc agacattttg ccgtcacct tatcaagttt gtggtgctat        60
cttagagcgc tatatccagc agggtgccca gtttgggtgg atg ttg ttg ctt act       115
                                              Met Leu Leu Leu Thr
                                              1               5 gaa ggc caa gcg ctt aac cct gat ggt cag gga tat cgt cag cgg ttt        163
Glu Gly Gln Ala Leu Asn Pro Asp Gly Gln Gly Tyr Arg Gln Arg Phe
            10                  15                  20 atg aat ggg ttt atc tat tgg cat cct tct act ggt gcg cac gcg gtt        211
Met Asn Gly Phe Ile Tyr Trp His Pro Ser Thr Gly Ala His Ala Val
                25                  30                  35 aat aat tac agt gca caa gtc tgg gag cgt aac ggt tgg gag tct ggg        259
Asn Asn Tyr Ser Ala Gln Val Trp Glu Arg Asn Gly Trp Glu Ser Gly
            40                  45                  50 tgg atg ggg tat ccc act ggt ggt gaa gtc cct gtg tct ggg tct aat        307
Trp Met Gly Tyr Pro Thr Gly Gly Glu Val Pro Val Ser Gly Ser Asn
    55                  60                  65 ccg att gat ggt gag ttg agt ggg tgg gtg caa acc ttc caa ggt ggg        355
```

-continued

```
Pro Ile Asp Gly Glu Leu Ser Gly Trp Val Gln Thr Phe Gln Gly Gly
 70                  75                  80                  85 cga gtg tat cgc agt ccg gta ttg gac ggt ttc cag gtg gcc agt att          403
Arg Val Tyr Arg Ser Pro Val Leu Asp Gly Phe Gln Val Ala Ser Ile
                 90                  95                 100 aat ggg ctg atc ttg gat aaa tgg ctt gaa ttg ggt ggt cct gat agt          451
Asn Gly Leu Ile Leu Asp Lys Trp Leu Glu Leu Gly Gly Pro Asp Ser
                105                 110                 115 gac ctt ggt ttt ccc att gcg gat gag gct gtg aca gct gac ggt gtg          499
Asp Leu Gly Phe Pro Ile Ala Asp Glu Ala Val Thr Ala Asp Gly Val
            120                 125                 130 ggc aga ttt tct gtt ttc cag aac gga gtt gtc tac tgg cat ccg caa          547
Gly Arg Phe Ser Val Phe Gln Asn Gly Val Val Tyr Trp His Pro Gln
        135                 140                 145 cac gga gct cac cct ata tta ggg aat ata tac agc atc tgg aga gaa          595
His Gly Ala His Pro Ile Leu Gly Asn Ile Tyr Ser Ile Trp Arg Glu
150                 155                 160                 165 gaa gga gct gag agt ggg gaa ttc ggt tac cct atc ggc gat cca gaa          643
Glu Gly Ala Glu Ser Gly Glu Phe Gly Tyr Pro Ile Gly Asp Pro Glu
                170                 175                 180 aag tat aca gaa aac atg gct aat cag gta ttc gaa aaa ggc gaa ctt          691
Lys Tyr Thr Glu Asn Met Ala Asn Gln Val Phe Glu Lys Gly Glu Leu
                185                 190                 195 gca gct aac cta tac ccc aat cct ctt gag gct ttt att gag ttt tta          739
Ala Ala Asn Leu Tyr Pro Asn Pro Leu Glu Ala Phe Ile Glu Phe Leu
            200                 205                 210 ccc ttt gct aat ctt gag gaa gca ata gag tat ttt gag aac gga ttg          787
Pro Phe Ala Asn Leu Glu Glu Ala Ile Glu Tyr Phe Glu Asn Gly Leu
        215                 220                 225 tca aat tct cgt gta gag gcg aat tca ctt aac gcc aag aaa gat tcg          835
Ser Asn Ser Arg Val Glu Ala Asn Ser Leu Asn Ala Lys Lys Asp Ser
230                 235                 240                 245 att caa tgt caa tcg caa tcc gct aac att cat gtg aga acg aag agt          883
Ile Gln Cys Gln Ser Gln Ser Ala Asn Ile His Val Arg Thr Lys Ser
                250                 255                 260 gac gga gtc ggg att agg gtt cca aag att ggg ttt aag gct agg atg          931
Asp Gly Val Gly Ile Arg Val Pro Lys Ile Gly Phe Lys Ala Arg Met
                265                 270                 275 gat tgc gac ctt cct gga act gtc tca gat gta gtg ggg tat gga tgg          979
Asp Cys Asp Leu Pro Gly Thr Val Ser Asp Val Val Gly Tyr Gly Trp
            280                 285                 290 att tac tac gac tat tgg gga cga tgg gct caa gca gca tat gca caa         1027
Ile Tyr Tyr Asp Tyr Trp Gly Arg Trp Ala Gln Ala Ala Tyr Ala Gln
        295                 300                 305 caa ttc ttc ggt aat agg aat tct gtt gtg caa acc aat tta gag gcg         1075
Gln Phe Phe Gly Asn Arg Asn Ser Val Val Gln Thr Asn Leu Glu Ala
310                 315                 320                 325 ggt tgc agc ggg gag aag aat aca tta ttt tgg ggt act tca tat ttt         1123
Gly Cys Ser Gly Glu Lys Asn Thr Leu Phe Trp Gly Thr Ser Tyr Phe
                330                 335                 340 cag gtg act tat gaa ggt cag ccg tat ttc ggt cag tca gca act aac         1171
Gln Val Thr Tyr Glu Gly Gln Pro Tyr Phe Gly Gln Ser Ala Thr Asn
                345                 350                 355 tac gct tat ctt ccg tgt acg ata gac cgt agt taacataagg aatggaatag       1224
Tyr Ala Tyr Leu Pro Cys Thr Ile Asp Arg Ser
            360                 365 gagaattgcg                                                               1234

<210> SEQ ID NO 100
```

-continued

```
<211> LENGTH: 368
<212> TYPE: PRT
<213> ORGANISM: Corynebacterium glutamicum

<400> SEQUENCE: 100

Met Leu Leu Thr Glu Gly Gln Ala Leu Asn Pro Asp Gly Gln Gly
 1               5                  10                  15

Tyr Arg Gln Arg Phe Met Asn Gly Phe Ile Tyr Trp His Pro Ser Thr
             20                  25                  30

Gly Ala His Ala Val Asn Asn Tyr Ser Ala Gln Val Trp Glu Arg Asn
         35                  40                  45

Gly Trp Glu Ser Gly Trp Met Gly Tyr Pro Thr Gly Glu Val Pro
     50                  55                  60

Val Ser Gly Ser Asn Pro Ile Asp Gly Glu Leu Ser Gly Trp Val Gln
 65                  70                  75                  80

Thr Phe Gln Gly Gly Arg Val Tyr Arg Ser Pro Val Leu Asp Gly Phe
                 85                  90                  95

Gln Val Ala Ser Ile Asn Gly Leu Ile Leu Asp Lys Trp Leu Glu Leu
            100                 105                 110

Gly Gly Pro Asp Ser Asp Leu Gly Phe Pro Ile Ala Asp Glu Ala Val
            115                 120                 125

Thr Ala Asp Gly Val Gly Arg Phe Ser Val Phe Gln Asn Gly Val Val
        130                 135                 140

Tyr Trp His Pro Gln His Gly Ala His Pro Ile Leu Gly Asn Ile Tyr
145                 150                 155                 160

Ser Ile Trp Arg Glu Glu Gly Ala Glu Ser Gly Glu Phe Gly Tyr Pro
                165                 170                 175

Ile Gly Asp Pro Glu Lys Tyr Thr Glu Asn Met Ala Asn Gln Val Phe
            180                 185                 190

Glu Lys Gly Glu Leu Ala Ala Asn Leu Tyr Pro Asn Pro Leu Glu Ala
        195                 200                 205

Phe Ile Glu Phe Leu Pro Phe Ala Asn Leu Glu Glu Ala Ile Glu Tyr
    210                 215                 220

Phe Glu Asn Gly Leu Ser Asn Ser Arg Val Glu Ala Asn Ser Leu Asn
225                 230                 235                 240

Ala Lys Lys Asp Ser Ile Gln Cys Gln Ser Gln Ser Ala Asn Ile His
                245                 250                 255

Val Arg Thr Lys Ser Asp Gly Val Gly Ile Arg Val Pro Lys Ile Gly
            260                 265                 270

Phe Lys Ala Arg Met Asp Cys Asp Leu Pro Gly Thr Val Ser Asp Val
        275                 280                 285

Val Gly Tyr Gly Trp Ile Tyr Tyr Asp Tyr Trp Gly Arg Trp Ala Gln
    290                 295                 300

Ala Ala Tyr Ala Gln Gln Phe Phe Gly Asn Arg Asn Ser Val Val Gln
305                 310                 315                 320

Thr Asn Leu Glu Ala Gly Cys Ser Gly Glu Lys Asn Thr Leu Phe Trp
                325                 330                 335

Gly Thr Ser Tyr Phe Gln Val Thr Tyr Glu Gly Gln Pro Tyr Phe Gly
            340                 345                 350

Gln Ser Ala Thr Asn Tyr Ala Tyr Leu Pro Cys Thr Ile Asp Arg Ser
        355                 360                 365

<210> SEQ ID NO 101
<211> LENGTH: 4560
<212> TYPE: DNA
```

-continued

```
<213> ORGANISM: Corynebacterium glutamicum
<220> FEATURE:
<221> NAME/KEY: CDS
<222> LOCATION: (1)..(4560)
<223> OTHER INFORMATION: RXA07005

<400> SEQUENCE: 101 atg gct aaa agc att ctt tcc cga ttc cga cct caa gta gcg gag tgg    48
Met Ala Lys Ser Ile Leu Ser Arg Phe Arg Pro Gln Val Ala Glu Trp
 1               5                  10                  15 ttc cgg gat gtc ttt gca tct ccg acc cct gtt cag gag gga acg tgg    96
Phe Arg Asp Val Phe Ala Ser Pro Thr Pro Val Gln Glu Gly Thr Trp
                20                  25                  30 gag gcg gta tct aag ggg aag aat gcc ctc gtg gtg gcg ccg acc ggt   144
Glu Ala Val Ser Lys Gly Lys Asn Ala Leu Val Val Ala Pro Thr Gly
            35                  40                  45 agt ggt aaa acc ttg gct gcg ttt ttg tgg gcg tta gat tcc ctc act   192
Ser Gly Lys Thr Leu Ala Ala Phe Leu Trp Ala Leu Asp Ser Leu Thr
        50                  55                  60 gaa caa aca ggt caa cag gtt tta gac acg gga aca ccg gtg cct gtt   240
Glu Gln Thr Gly Gln Gln Val Leu Asp Thr Gly Thr Pro Val Pro Val
 65                  70                  75                  80 cgt ggt ggg aaa gtg aaa gtg ctc tac att tcc cca ctc aaa gcg ctt   288
Arg Gly Gly Lys Val Lys Val Leu Tyr Ile Ser Pro Leu Lys Ala Leu
                85                  90                  95 ggc gtg gat gta gaa aat aat ctg cgt gca ccg ttg acc ggt att gcg   336
Gly Val Asp Val Glu Asn Asn Leu Arg Ala Pro Leu Thr Gly Ile Ala
               100                 105                 110 agg act gcc tct cgg atg ggt ttg gat gtg ccc aat atc act gtg gcg   384
Arg Thr Ala Ser Arg Met Gly Leu Asp Val Pro Asn Ile Thr Val Ala
            115                 120                 125 gtt cgt tcg ggt gat acg cca tcg gcg gag cgg gcc cgg cag gtg cgt   432
Val Arg Ser Gly Asp Thr Pro Ser Ala Glu Arg Ala Arg Gln Val Arg
        130                 135                 140 aag cct cca gac att ttg atc acc act ccg gag tcg gcg tat ttg atg   480
Lys Pro Pro Asp Ile Leu Ile Thr Thr Pro Glu Ser Ala Tyr Leu Met
145                 150                 155                 160 ttg acc tca aaa gcg ggg gcg acc ctt tcg gat gtt gat gtg gtg atc   528
Leu Thr Ser Lys Ala Gly Ala Thr Leu Ser Asp Val Asp Val Val Ile
                165                 170                 175 atc gat gaa atc cac gcc atg gcc gga acc aaa cgg gga gtg cat ctg   576
Ile Asp Glu Ile His Ala Met Ala Gly Thr Lys Arg Gly Val His Leu
               180                 185                 190 gcg ttg acg ctg gag cgt ttg gaa aag ctc gtg ggg cgg cct gtg cag   624
Ala Leu Thr Leu Glu Arg Leu Glu Lys Leu Val Gly Arg Pro Val Gln
            195                 200                 205 cga gtt ggt ttg tct gca acg gtg cgt cct ttg gaa acg gtg gcg ggt   672
Arg Val Gly Leu Ser Ala Thr Val Arg Pro Leu Glu Thr Val Ala Gly
        210                 215                 220 ttc ttg ggc ggt ggc aga ccc gtt gag att gtg gct cca cct gcg gag   720
Phe Leu Gly Gly Gly Arg Pro Val Glu Ile Val Ala Pro Pro Ala Glu
225                 230                 235                 240 aaa aag tgg gat ctc act gtc act gtg ccg gtg gaa gac atg tcg gat   768
Lys Lys Trp Asp Leu Thr Val Thr Val Pro Val Glu Asp Met Ser Asp
                245                 250                 255 ttg ccg gtt cag gag ccg gga tca act att ggt gaa cta gtc atg gat   816
Leu Pro Val Gln Glu Pro Gly Ser Thr Ile Gly Glu Leu Val Met Asp
               260                 265                 270 gat ccg ttg ggg att act ggc gaa tca gcg ctg cct act caa ggc tcg   864
Asp Pro Leu Gly Ile Thr Gly Glu Ser Ala Leu Pro Thr Gln Gly Ser
            275                 280                 285
```

-continued

| | |
|---|---|
| att tgg cca cac att gag cag cag gtg tac aac cag gtg atg tcg gcg<br>Ile Trp Pro His Ile Glu Gln Gln Val Tyr Asn Gln Val Met Ser Ala<br>290                      295                  300 | 912 |
| aaa tcg acc atc gtg ttt gta aat tcc agg cgt tcc gcg gag cgt tta<br>Lys Ser Thr Ile Val Phe Val Asn Ser Arg Arg Ser Ala Glu Arg Leu<br>305                      310                  315              320 | 960 |
| acc agt cgg ttg aat gaa atc tgg gcg atg gaa cac gat ccg gaa tcg<br>Thr Ser Arg Leu Asn Glu Ile Trp Ala Met Glu His Asp Pro Glu Ser<br>                  325                  330                  335 | 1008 |
| ctg tcg ccg cag ctg cga aga gat ccg gcg cag att atg tcg tca gcg<br>Leu Ser Pro Gln Leu Arg Arg Asp Pro Ala Gln Ile Met Ser Ser Ala<br>            340                  345                  350 | 1056 |
| gat gtg gca gga aaa gca cca cag gtg atc gca cgt gcg cac cac gga<br>Asp Val Ala Gly Lys Ala Pro Gln Val Ile Ala Arg Ala His His Gly<br>                  355                  360                  365 | 1104 |
| tcc gta tcc aaa gat gaa cgt gcc acc acc gaa acc atg ctg aag gaa<br>Ser Val Ser Lys Asp Glu Arg Ala Thr Thr Glu Thr Met Leu Lys Glu<br>370                      375                  380 | 1152 |
| ggt cgg ttg cgc gca gtt att tcc acc tcc tcg ctg gag ttg ggc att<br>Gly Arg Leu Arg Ala Val Ile Ser Thr Ser Ser Leu Glu Leu Gly Ile<br>385                      390                  395              400 | 1200 |
| gat atg ggt gcc gtg gac ctg gtg att cag gtg gaa tcg cca ccg tcc<br>Asp Met Gly Ala Val Asp Leu Val Ile Gln Val Glu Ser Pro Pro Ser<br>                  405                  410                  415 | 1248 |
| gtg gca agt ggc ctg cag cgc gtg ggg cgt gcg ggg cac acg gtg ggg<br>Val Ala Ser Gly Leu Gln Arg Val Gly Arg Ala Gly His Thr Val Gly<br>            420                  425                  430 | 1296 |
| gcg acg tcg ata ggc tcc ttt tat ccc aag cac cgc tcc gac ttg gtg<br>Ala Thr Ser Ile Gly Ser Phe Tyr Pro Lys His Arg Ser Asp Leu Val<br>                  435                  440                  445 | 1344 |
| caa acc gcg gtg acc gtg cag cgg atg aag gaa ggg ctg atc gaa gag<br>Gln Thr Ala Val Thr Val Gln Arg Met Lys Glu Gly Leu Ile Glu Glu<br>450                      455                  460 | 1392 |
| atc cac gtg ccc aaa aac gcg ctt gat gta ctg gca cag cag acg gtg<br>Ile His Val Pro Lys Asn Ala Leu Asp Val Leu Ala Gln Gln Thr Val<br>465                      470                  475              480 | 1440 |
| gcg gct gtc tcg att aaa gat gtg cag gtc gat gag tgg tac gag act<br>Ala Ala Val Ser Ile Lys Asp Val Gln Val Asp Glu Trp Tyr Glu Thr<br>                  485                  490                  495 | 1488 |
| att cgc aag gcg tat ccg tac cgg gat ttg gcg cgc gaa gtc ttc gat<br>Ile Arg Lys Ala Tyr Pro Tyr Arg Asp Leu Ala Arg Glu Val Phe Asp<br>            500                  505                  510 | 1536 |
| tcc gtc atc gac ctg gtc agc ggt gtg tat ccc tcc aca gat ttt gcc<br>Ser Val Ile Asp Leu Val Ser Gly Val Tyr Pro Ser Thr Asp Phe Ala<br>                  515                  520                  525 | 1584 |
| gag ctg aag cca cgt gtg gta tac gac cgg gtt tca ggc gtg ctg gag<br>Glu Leu Lys Pro Arg Val Val Tyr Asp Arg Val Ser Gly Val Leu Glu<br>530                      535                  540 | 1632 |
| ggc cgg cca gga tcc caa cgc gta gca gtg acc agt ggc gga aca att<br>Gly Arg Pro Gly Ser Gln Arg Val Ala Val Thr Ser Gly Gly Thr Ile<br>545                      550                  555              560 | 1680 |
| ccc gat cga gga atg ttc gga gtc ttc ctc gtc ggc gat ggt ccc cgg<br>Pro Asp Arg Gly Met Phe Gly Val Phe Leu Val Gly Asp Gly Pro Arg<br>                  565                  570                  575 | 1728 |
| cgc gtc ggc gag ctc gat gag gaa atg gtc tac gaa tcc cgc gtg ggc<br>Arg Val Gly Glu Leu Asp Glu Glu Met Val Tyr Glu Ser Arg Val Gly<br>            580                  585                  590 | 1776 |
| gat gtg ttt acg ctc ggg gcg tcg agt tgg cgg att gaa gag atc acc<br>Asp Val Phe Thr Leu Gly Ala Ser Ser Trp Arg Ile Glu Glu Ile Thr | 1824 |

-continued

```
                595                    600                    605
cgc gac cag gta ctg gtc act ccc gcg ccg ggt cac acg ggt cgg ctg        1872
Arg Asp Gln Val Leu Val Thr Pro Ala Pro Gly His Thr Gly Arg Leu
    610                 615                 620 cct ttt tgg acg ggc gat gcc gca ggc cgg ccc gct gag ctg ggt aaa        1920
Pro Phe Trp Thr Gly Asp Ala Ala Gly Arg Pro Ala Glu Leu Gly Lys
625                 630                 635                 640 gct tta ggc gct ttt cga cgc tcg acc ctc acc gat cca tcc agc tcc        1968
Ala Leu Gly Ala Phe Arg Arg Ser Thr Leu Thr Asp Pro Ser Ser Ser
                645                 650                 655 ggc ttg gaa ggc tgg gcg cac gac aac ctg atc gcc ttt tta cag gag        2016
Gly Leu Glu Gly Trp Ala His Asp Asn Leu Ile Ala Phe Leu Gln Glu
            660                 665                 670 cag gaa gaa tcc acc ggt gtg ttg ccg gat gag aag acg ttg gtg ttg        2064
Gln Glu Glu Ser Thr Gly Val Leu Pro Asp Glu Lys Thr Leu Val Leu
        675                 680                 685 gag cgt ttc aaa gat gaa cta ggc gac tgg cgc att gtc ctg cac act        2112
Glu Arg Phe Lys Asp Glu Leu Gly Asp Trp Arg Ile Val Leu His Thr
    690                 695                 700 cct tat gga cga gga gta aac gca gca tgg gct ttg gcc gtc ggg gcg        2160
Pro Tyr Gly Arg Gly Val Asn Ala Ala Trp Ala Leu Ala Val Gly Ala
705                 710                 715                 720 aaa atc gct gaa gag acc ggc atg gat gcg caa gcc gtg gca ggt gat        2208
Lys Ile Ala Glu Glu Thr Gly Met Asp Ala Gln Ala Val Ala Gly Asp
                725                 730                 735 gat ggc att gtg ctt cgg ttg ccg gaa ggg gat gaa gat ccc agc gca        2256
Asp Gly Ile Val Leu Arg Leu Pro Glu Gly Asp Glu Asp Pro Ser Ala
            740                 745                 750 gcg ttg ttt atg ttt gag gcg gaa gag atc gaa acg cta gtg aca gag        2304
Ala Leu Phe Met Phe Glu Ala Glu Glu Ile Glu Thr Leu Val Thr Glu
        755                 760                 765 cag gtg ggt aac tct gcg ctg ttt gcc agc agg ttc cgt gaa tgc gcc        2352
Gln Val Gly Asn Ser Ala Leu Phe Ala Ser Arg Phe Arg Glu Cys Ala
    770                 775                 780 gcg agg gcc cta ttg ctg ccg aga cga aac ccc ggc aag cgc gca ccg        2400
Ala Arg Ala Leu Leu Leu Pro Arg Arg Asn Pro Gly Lys Arg Ala Pro
785                 790                 795                 800 ctg tgg cag caa cga caa cga gca gca cag ctt ctt gat gtg gcc aga        2448
Leu Trp Gln Gln Arg Gln Arg Ala Ala Gln Leu Leu Asp Val Ala Arg
                805                 810                 815 aag tac ccg agt ttc ccg atc att ttg gaa aca gtg cgc gaa tgt ctt        2496
Lys Tyr Pro Ser Phe Pro Ile Ile Leu Glu Thr Val Arg Glu Cys Leu
            820                 825                 830 caa gat gtt tac gat ctg ccc gct ctg aag aat ctc att gag gat cta        2544
Gln Asp Val Tyr Asp Leu Pro Ala Leu Lys Asn Leu Ile Glu Asp Leu
        835                 840                 845 cag ctg cgg aag gta aga atc gcg gaa gtc acc acc cag cag ccc agt        2592
Gln Leu Arg Lys Val Arg Ile Ala Glu Val Thr Thr Gln Gln Pro Ser
    850                 855                 860 cct ttt gcc tcc gca ttg ctg ttc aat tac acc ggt gca ttc atg tac        2640
Pro Phe Ala Ser Ala Leu Leu Phe Asn Tyr Thr Gly Ala Phe Met Tyr
865                 870                 875                 880 gaa ggc gac agc ccg ctc gca gag aaa cgt gcc gca gcg ttg gcc ctg        2688
Glu Gly Asp Ser Pro Leu Ala Glu Lys Arg Ala Ala Ala Leu Ala Leu
                885                 890                 895 gat ccg gca ctg ttg gcg aaa ttg ctg ggt gag gtg gag ctt cga caa        2736
Asp Pro Ala Leu Leu Ala Lys Leu Leu Gly Glu Val Glu Leu Arg Gln
            900                 905                 910 tta ctg gat ccc gac atc atc gca gaa gtg cac caa caa ttg cgc agg        2784
```

-continued

| | | |
|---|---|---|
| Leu Leu Asp Pro Asp Ile Ile Ala Glu Val His Gln Gln Leu Arg Arg<br>     915                   920               925 | | |
| caa ggc gat cgt gcg gcg aga aac aat gaa gaa ctc gca gat tct ttg<br>Gln Gly Asp Arg Ala Ala Arg Asn Asn Glu Glu Leu Ala Asp Ser Leu<br>     930                   935               940 | | 2832 |
| agg att tta gga ccg att cct ttg gat gaa ttg ggc gaa cac atc acc<br>Arg Ile Leu Gly Pro Ile Pro Leu Asp Glu Leu Gly Glu His Ile Thr<br>945               950               955              960 | | 2880 |
| ttt gaa aac cca gac ctg gag gat cga gca atg act gtt cgg atc aac<br>Phe Glu Asn Pro Asp Leu Glu Asp Arg Ala Met Thr Val Arg Ile Asn<br>               965              970              975 | | 2928 |
| ggt cgg gaa cat tta gcg cag gtc ttg gat gca cct ttg ctt cga gat<br>Gly Arg Glu His Leu Ala Gln Val Leu Asp Ala Pro Leu Leu Arg Asp<br>             980               985              990 | | 2976 |
| gcc tta ggt gtt ccc gta ccg cct ggt gtg cct gcg cag gta gaa acc<br>Ala Leu Gly Val Pro Val Pro Pro Gly Val Pro Ala Gln Val Glu Thr<br>          995               1000             1005 | | 3024 |
| att acg gat gcg ttg gaa cag tta gtc aac agg tgg gtt cgt acc aga<br>Ile Thr Asp Ala Leu Glu Gln Leu Val Asn Arg Trp Val Arg Thr Arg<br>1010               1015             1020 | | 3072 |
| ggg cca ttt act gcg aat gat ttg gca gaa gcc ttt gga ctg ggc atc<br>Gly Pro Phe Thr Ala Asn Asp Leu Ala Glu Ala Phe Gly Leu Gly Ile<br>1025             1030             1035             1040 | | 3120 |
| gcc acg gcg atc acc gcc ctt caa agc gca cct gtg att gaa ggc cgc<br>Ala Thr Ala Ile Thr Ala Leu Gln Ser Ala Pro Val Ile Glu Gly Arg<br>               1045             1050             1055 | | 3168 |
| tac cga caa ggc gtg gac gtg cag gaa tac tgt gcg aca gaa gtg ttg<br>Tyr Arg Gln Gly Val Asp Val Gln Glu Tyr Cys Ala Thr Glu Val Leu<br>             1060             1065             1070 | | 3216 |
| tcg atc ata agg cga cgc agc ctc gca gca gcg agg aaa caa acc agg<br>Ser Ile Ile Arg Arg Arg Ser Leu Ala Ala Ala Arg Lys Gln Thr Arg<br>1075             1080             1085 | | 3264 |
| ccg gta tcg caa tca gcc ttt gcg cga ttc ctg ctt gat tgg caa cag<br>Pro Val Ser Gln Ser Ala Phe Ala Arg Phe Leu Leu Asp Trp Gln Gln<br>     1090                   1095              1100 | | 3312 |
| atc gca ccg gtg ggc gcc aca cct gaa ctc cga ggc gtt gat ggc acc<br>Ile Ala Pro Val Gly Ala Thr Pro Glu Leu Arg Gly Val Asp Gly Thr<br>1105             1110             1115             1120 | | 3360 |
| tac aca gtc att gaa caa ctc gcc ggt gta cgt ctt ccc gcc agt gcg<br>Tyr Thr Val Ile Glu Gln Leu Ala Gly Val Arg Leu Pro Ala Ser Ala<br>             1125             1130             1135 | | 3408 |
| tgg gaa gat ctc gtg ttg ccg cgc cgg gtt gcc gac tat tca ccg atc<br>Trp Glu Asp Leu Val Leu Pro Arg Arg Val Ala Asp Tyr Ser Pro Ile<br>             1140             1145             1150 | | 3456 |
| cat ctc gat gag ctg acc tcc aat ggg gaa gtc ctc atc gtg gga gcg<br>His Leu Asp Glu Leu Thr Ser Asn Gly Glu Val Leu Ile Val Gly Ala<br>             1155             1160             1165 | | 3504 |
| ggc caa gcc gga agc cgc gat ccg tgg att agc ttg ctg ccc gtg gat<br>Gly Gln Ala Gly Ser Arg Asp Pro Trp Ile Ser Leu Leu Pro Val Asp<br>     1170                   1175              1180 | | 3552 |
| tat gcg gcg cag ttg gtg ggg gag gcg tcg aca agc atg agc cca ttg<br>Tyr Ala Ala Gln Leu Val Gly Glu Ala Ser Thr Ser Met Ser Pro Leu<br>1185             1190             1195             1200 | | 3600 |
| cag gac gcc gtg ctt gac cag ctg cgt gcg gga ggc gcc ttc ctg ttt<br>Gln Asp Ala Val Leu Asp Gln Leu Arg Ala Gly Gly Ala Phe Leu Phe<br>             1205             1210             1215 | | 3648 |
| tct gac att ctc gaa gag aat ttc ggc tac acc aca gcc cag ctg caa<br>Ser Asp Ile Leu Glu Glu Asn Phe Gly Tyr Thr Thr Ala Gln Leu Gln<br>             1220             1225             1230 | | 3696 |

```
gaa gcg atg tgg ggg ctg gtg gaa gca ggc ctg gtc agc cct gat agc      3744
Glu Ala Met Trp Gly Leu Val Glu Ala Gly Leu Val Ser Pro Asp Ser
    1235                1240                1245 ttc gcg ccg atc cgc gcg cgc cta gcg tcg gga acc acg gcg cat cgg      3792
Phe Ala Pro Ile Arg Ala Arg Leu Ala Ser Gly Thr Thr Ala His Arg
1250                1255                1260 gcg aaa cgt cga cca gcg aga tcc cgg ctg cgc acc cgc acc agc ttc      3840
Ala Lys Arg Arg Pro Ala Arg Ser Arg Leu Arg Thr Arg Thr Ser Phe
1265                1270                1275                1280 gcg agc gac gtg ccc cca gac atg cgc gga cga tgg acg ctg tcc gtg      3888
Ala Ser Asp Val Pro Pro Asp Met Arg Gly Arg Trp Thr Leu Ser Val
        1285                1290                1295 caa ccc gcc gac gcc acc agc cgc tcc gtc gca cac ggc gaa ggc tgg      3936
Gln Pro Ala Asp Ala Thr Ser Arg Ser Val Ala His Gly Glu Gly Trp
    1300                1305                1310 ctc gac cgc tac ggc gtg ctc acc cgc ggg agc gtc gtc gcc gaa gac      3984
Leu Asp Arg Tyr Gly Val Leu Thr Arg Gly Ser Val Val Ala Glu Asp
1315                1320                1325 atc gtc gga ggc ttc gcc ctg gcc tac aaa gtg ctc tcc ggc ttc gaa      4032
Ile Val Gly Gly Phe Ala Leu Ala Tyr Lys Val Leu Ser Gly Phe Glu
1330                1335                1340 gaa agc ggc aaa gcg atg cgc ggc tac ttc atc gaa ggg ctc ggc gcc      4080
Glu Ser Gly Lys Ala Met Arg Gly Tyr Phe Ile Glu Gly Leu Gly Ala
1345                1350                1355                1360 gcg caa ttc tcc acg ccc gcc atc atc gac cgc ctc cgc ggc cac gac      4128
Ala Gln Phe Ser Thr Pro Ala Ile Ile Asp Arg Leu Arg Gly His Asp
        1365                1370                1375 gat tcc ccc gac gtc gaa ggc tgg ccc tcc ggc gcc acc gac cca gac      4176
Asp Ser Pro Asp Val Glu Gly Trp Pro Ser Gly Ala Thr Asp Pro Asp
    1380                1385                1390 gtc tac ctc ata gcc gcc gcc gac ccc gca aac ccc tac ggc gcc gca      4224
Val Tyr Leu Ile Ala Ala Ala Asp Pro Ala Asn Pro Tyr Gly Ala Ala
        1395                1400                1405 ctt ccc tgg cct gag cag ggg ccc agc cgc gcc gcc gga gct atg gtc      4272
Leu Pro Trp Pro Glu Gln Gly Pro Ser Arg Ala Ala Gly Ala Met Val
    1410                1415                1420 gtg ctt tgc gac gga ctc ctc ctc gcc cac ctc acc cgc ggc ggg cgc      4320
Val Leu Cys Asp Gly Leu Leu Leu Ala His Leu Thr Arg Gly Gly Arg
1425                1430                1435                1440 acc ctc acc gtg ttc tcc gac aat atc ccc aaa atc gcg aca gcc cta      4368
Thr Leu Thr Val Phe Ser Asp Asn Ile Pro Lys Ile Ala Thr Ala Leu
            1445                1450                1455 atc aca tac gaa agg ctc acg gta gaa aaa atc aac ggc gac aac gtc      4416
Ile Thr Tyr Glu Arg Leu Thr Val Glu Lys Ile Asn Gly Asp Asn Val
        1460                1465                1470 ttc gac tcc cca ctc ctg gaa caa ttc cgc aaa cac ggc gcc acc atc      4464
Phe Asp Ser Pro Leu Leu Glu Gln Phe Arg Lys His Gly Ala Thr Ile
    1475                1480                1485 acc ccg aag gga atg cga ttt cga cca cca gtg gca cgg gaa acc ccc      4512
Thr Pro Lys Gly Met Arg Phe Arg Pro Pro Val Ala Arg Glu Thr Pro
    1490                1495                1500 tca gat acg ctt ccc acc agg act ttt cgt gga ggc ttc gga cgg cgc      4560
Ser Asp Thr Leu Pro Thr Arg Thr Phe Arg Gly Gly Phe Gly Arg Arg
1505                1510                1515                1520
```

<210> SEQ ID NO 102
<211> LENGTH: 1520
<212> TYPE: PRT
<213> ORGANISM: Corynebacterium glutamicum

<400> SEQUENCE: 102

-continued

```
Met Ala Lys Ser Ile Leu Ser Arg Phe Arg Pro Gln Val Ala Glu Trp
 1               5                  10                  15

Phe Arg Asp Val Phe Ala Ser Pro Thr Pro Val Gln Glu Gly Thr Trp
                20                  25                  30

Glu Ala Val Ser Lys Gly Lys Asn Ala Leu Val Val Ala Pro Thr Gly
            35                  40                  45

Ser Gly Lys Thr Leu Ala Ala Phe Leu Trp Ala Leu Asp Ser Leu Thr
        50                  55                  60

Glu Gln Thr Gly Gln Gln Val Leu Asp Thr Gly Thr Pro Val Pro Val
 65                  70                  75                  80

Arg Gly Gly Lys Val Lys Val Leu Tyr Ile Ser Pro Leu Lys Ala Leu
                85                  90                  95

Gly Val Asp Val Glu Asn Asn Leu Arg Ala Pro Leu Thr Gly Ile Ala
                100                 105                 110

Arg Thr Ala Ser Arg Met Gly Leu Asp Val Pro Asn Ile Thr Val Ala
            115                 120                 125

Val Arg Ser Gly Asp Thr Pro Ser Ala Glu Arg Ala Arg Gln Val Arg
130                 135                 140

Lys Pro Pro Asp Ile Leu Ile Thr Thr Pro Glu Ser Ala Tyr Leu Met
145                 150                 155                 160

Leu Thr Ser Lys Ala Gly Ala Thr Leu Ser Asp Val Asp Val Val Ile
                165                 170                 175

Ile Asp Glu Ile His Ala Met Ala Gly Thr Lys Arg Gly Val His Leu
                180                 185                 190

Ala Leu Thr Leu Glu Arg Leu Glu Lys Leu Val Gly Arg Pro Val Gln
            195                 200                 205

Arg Val Gly Leu Ser Ala Thr Val Arg Pro Leu Glu Thr Val Ala Gly
    210                 215                 220

Phe Leu Gly Gly Gly Arg Pro Val Glu Ile Val Ala Pro Pro Ala Glu
225                 230                 235                 240

Lys Lys Trp Asp Leu Thr Val Thr Val Pro Val Glu Asp Met Ser Asp
                245                 250                 255

Leu Pro Val Gln Glu Pro Gly Ser Thr Ile Gly Glu Leu Val Met Asp
                260                 265                 270

Asp Pro Leu Gly Ile Thr Gly Glu Ser Ala Leu Pro Thr Gln Gly Ser
            275                 280                 285

Ile Trp Pro His Ile Glu Gln Gln Val Tyr Asn Gln Val Met Ser Ala
    290                 295                 300

Lys Ser Thr Ile Val Phe Val Asn Ser Arg Arg Ser Ala Glu Arg Leu
305                 310                 315                 320

Thr Ser Arg Leu Asn Glu Ile Trp Ala Met Glu His Asp Pro Glu Ser
                325                 330                 335

Leu Ser Pro Gln Leu Arg Arg Asp Pro Ala Gln Ile Met Ser Ser Ala
                340                 345                 350

Asp Val Ala Gly Lys Ala Pro Gln Val Ile Ala Arg Ala His His Gly
            355                 360                 365

Ser Val Ser Lys Asp Glu Arg Ala Thr Thr Glu Thr Met Leu Lys Glu
    370                 375                 380

Gly Arg Leu Arg Ala Val Ile Ser Thr Ser Ser Leu Glu Leu Gly Ile
385                 390                 395                 400

Asp Met Gly Ala Val Asp Leu Val Ile Gln Val Glu Ser Pro Pro Ser
                405                 410                 415
```

```
Val Ala Ser Gly Leu Gln Arg Val Gly Arg Ala Gly His Thr Val Gly
            420                 425                 430

Ala Thr Ser Ile Gly Ser Phe Tyr Pro Lys His Arg Ser Asp Leu Val
        435                 440                 445

Gln Thr Ala Val Thr Val Gln Arg Met Lys Glu Gly Leu Ile Glu Glu
    450                 455                 460

Ile His Val Pro Lys Asn Ala Leu Asp Val Leu Ala Gln Gln Thr Val
465                 470                 475                 480

Ala Ala Val Ser Ile Lys Asp Val Gln Val Asp Glu Trp Tyr Glu Thr
                485                 490                 495

Ile Arg Lys Ala Tyr Pro Tyr Arg Asp Leu Ala Arg Glu Val Phe Asp
            500                 505                 510

Ser Val Ile Asp Leu Val Ser Gly Val Tyr Pro Ser Thr Asp Phe Ala
        515                 520                 525

Glu Leu Lys Pro Arg Val Tyr Asp Arg Val Ser Gly Val Leu Glu
    530                 535                 540

Gly Arg Pro Gly Ser Gln Arg Val Ala Val Thr Ser Gly Thr Ile
545                 550                 555             560

Pro Asp Arg Gly Met Phe Gly Val Phe Leu Val Gly Asp Gly Pro Arg
                565                 570                 575

Arg Val Gly Glu Leu Asp Glu Glu Met Val Tyr Glu Ser Arg Val Gly
            580                 585                 590

Asp Val Phe Thr Leu Gly Ala Ser Ser Trp Arg Ile Glu Glu Ile Thr
        595                 600                 605

Arg Asp Gln Val Leu Val Thr Pro Ala Pro Gly His Thr Gly Arg Leu
    610                 615                 620

Pro Phe Trp Thr Gly Asp Ala Ala Gly Arg Pro Ala Glu Leu Gly Lys
625                 630                 635                 640

Ala Leu Gly Ala Phe Arg Arg Ser Thr Leu Thr Asp Pro Ser Ser Ser
                645                 650                 655

Gly Leu Glu Gly Trp Ala His Asp Asn Leu Ile Ala Phe Leu Gln Glu
            660                 665                 670

Gln Glu Glu Ser Thr Gly Val Leu Pro Asp Glu Lys Thr Leu Val Leu
        675                 680                 685

Glu Arg Phe Lys Asp Glu Leu Gly Asp Trp Arg Ile Val Leu His Thr
    690                 695                 700

Pro Tyr Gly Arg Gly Val Asn Ala Ala Trp Ala Leu Ala Val Gly Ala
705                 710                 715                 720

Lys Ile Ala Glu Glu Thr Gly Met Asp Ala Gln Ala Val Ala Gly Asp
                725                 730                 735

Asp Gly Ile Val Leu Arg Leu Pro Glu Gly Asp Glu Asp Pro Ser Ala
            740                 745                 750

Ala Leu Phe Met Phe Glu Ala Glu Glu Ile Glu Thr Leu Val Thr Glu
        755                 760                 765

Gln Val Gly Asn Ser Ala Leu Phe Ala Ser Arg Phe Arg Glu Cys Ala
    770                 775                 780

Ala Arg Ala Leu Leu Leu Pro Arg Arg Asn Pro Gly Lys Arg Ala Pro
785                 790                 795                 800

Leu Trp Gln Gln Arg Gln Arg Ala Ala Gln Leu Leu Asp Val Ala Arg
                805                 810                 815

Lys Tyr Pro Ser Phe Pro Ile Ile Leu Glu Thr Val Arg Glu Cys Leu
            820                 825                 830

Gln Asp Val Tyr Asp Leu Pro Ala Leu Lys Asn Leu Ile Glu Asp Leu
```

-continued

```
            835                 840                 845
Gln Leu Arg Lys Val Arg Ile Ala Glu Val Thr Thr Gln Gln Pro Ser
    850                 855                 860
Pro Phe Ala Ser Ala Leu Leu Phe Asn Tyr Thr Gly Ala Phe Met Tyr
865                 870                 875                 880
Glu Gly Asp Ser Pro Leu Ala Glu Lys Arg Ala Ala Leu Ala Leu
                885                 890                 895
Asp Pro Ala Leu Leu Ala Lys Leu Leu Gly Glu Val Glu Leu Arg Gln
                900                 905                 910
Leu Leu Asp Pro Asp Ile Ile Ala Glu Val His Gln Gln Leu Arg Arg
            915                 920                 925
Gln Gly Asp Arg Ala Ala Arg Asn Asn Glu Glu Leu Ala Asp Ser Leu
    930                 935                 940
Arg Ile Leu Gly Pro Ile Pro Leu Asp Glu Leu Gly Glu His Ile Thr
945                 950                 955                 960
Phe Glu Asn Pro Asp Leu Glu Asp Arg Ala Met Thr Val Arg Ile Asn
                965                 970                 975
Gly Arg Glu His Leu Ala Gln Val Leu Asp Ala Pro Leu Leu Arg Asp
            980                 985                 990
Ala Leu Gly Val Pro Val Pro Pro Gly Val Pro Ala Gln Val Glu Thr
            995                 1000                1005
Ile Thr Asp Ala Leu Glu Gln Leu Val Asn Arg Trp Val Arg Thr Arg
    1010                1015                1020
Gly Pro Phe Thr Ala Asn Asp Leu Ala Glu Ala Phe Gly Leu Gly Ile
1025                1030                1035                1040
Ala Thr Ala Ile Thr Ala Leu Gln Ser Ala Pro Val Ile Glu Gly Arg
                1045                1050                1055
Tyr Arg Gln Gly Val Asp Val Gln Glu Tyr Cys Ala Thr Glu Val Leu
            1060                1065                1070
Ser Ile Ile Arg Arg Arg Ser Leu Ala Ala Ala Arg Lys Gln Thr Arg
    1075                1080                1085
Pro Val Ser Gln Ser Ala Phe Ala Arg Phe Leu Leu Asp Trp Gln Gln
    1090                1095                1100
Ile Ala Pro Val Gly Ala Thr Pro Glu Leu Arg Gly Val Asp Gly Thr
1105                1110                1115                1120
Tyr Thr Val Ile Glu Gln Leu Ala Gly Val Arg Leu Pro Ala Ser Ala
                1125                1130                1135
Trp Glu Asp Leu Val Leu Pro Arg Arg Val Ala Asp Tyr Ser Pro Ile
            1140                1145                1150
His Leu Asp Glu Leu Thr Ser Asn Gly Glu Val Leu Ile Val Gly Ala
            1155                1160                1165
Gly Gln Ala Gly Ser Arg Asp Pro Trp Ile Ser Leu Leu Pro Val Asp
    1170                1175                1180
Tyr Ala Ala Gln Leu Val Gly Glu Ala Ser Thr Ser Met Ser Pro Leu
1185                1190                1195                1200
Gln Asp Ala Val Leu Asp Gln Leu Arg Ala Gly Gly Ala Phe Leu Phe
                1205                1210                1215
Ser Asp Ile Leu Glu Glu Asn Phe Gly Tyr Thr Thr Ala Gln Leu Gln
                1220                1225                1230
Glu Ala Met Trp Gly Leu Val Glu Ala Gly Leu Val Ser Pro Asp Ser
            1235                1240                1245
Phe Ala Pro Ile Arg Ala Arg Leu Ala Ser Gly Thr Thr Ala His Arg
    1250                1255                1260
```

-continued

```
Ala Lys Arg Arg Pro Ala Arg Ser Arg Leu Arg Thr Arg Thr Ser Phe
1265                1270                1275                1280

Ala Ser Asp Val Pro Pro Asp Met Arg Gly Arg Trp Thr Leu Ser Val
                1285                1290                1295

Gln Pro Ala Asp Ala Thr Ser Arg Ser Val Ala His Gly Glu Gly Trp
1300                1305                1310

Leu Asp Arg Tyr Gly Val Leu Thr Arg Gly Ser Val Val Ala Glu Asp
                1315                1320                1325

Ile Val Gly Gly Phe Ala Leu Ala Tyr Lys Val Leu Ser Gly Phe Glu
    1330                1335                1340

Glu Ser Gly Lys Ala Met Arg Gly Tyr Phe Ile Glu Gly Leu Gly Ala
1345                1350                1355                1360

Ala Gln Phe Ser Thr Pro Ala Ile Ile Asp Arg Leu Arg Gly His Asp
                1365                1370                1375

Asp Ser Pro Asp Val Glu Gly Trp Pro Ser Gly Ala Thr Asp Pro Asp
            1380                1385                1390

Val Tyr Leu Ile Ala Ala Ala Asp Pro Ala Asn Pro Tyr Gly Ala Ala
1395                1400                1405

Leu Pro Trp Pro Glu Gln Gly Pro Ser Arg Ala Ala Gly Ala Met Val
    1410                1415                1420

Val Leu Cys Asp Gly Leu Leu Leu Ala His Leu Thr Arg Gly Gly Arg
1425                1430                1435                1440

Thr Leu Thr Val Phe Ser Asp Asn Ile Pro Lys Ile Ala Thr Ala Leu
                1445                1450                1455

Ile Thr Tyr Glu Arg Leu Thr Val Glu Lys Ile Asn Gly Asp Asn Val
            1460                1465                1470

Phe Asp Ser Pro Leu Leu Glu Gln Phe Arg Lys His Gly Ala Thr Ile
        1475                1480                1485

Thr Pro Lys Gly Met Arg Phe Arg Pro Pro Val Ala Arg Glu Thr Pro
    1490                1495                1500

Ser Asp Thr Leu Pro Thr Arg Thr Phe Arg Gly Gly Phe Gly Arg Arg
1505                1510                1515                1520

<210> SEQ ID NO 103
<211> LENGTH: 1251
<212> TYPE: DNA
<213> ORGANISM: Corynebacterium glutamicum
<220> FEATURE:
<221> NAME/KEY: CDS
<222> LOCATION: (1)..(1251)
<223> OTHER INFORMATION: RXA07006

<400> SEQUENCE: 103 gtg tcg tct gag aaa gct tca tca aaa tca acc cct gag gca ccg tgg     48
Val Ser Ser Glu Lys Ala Ser Ser Lys Ser Thr Pro Glu Ala Pro Trp
  1               5                  10                  15 cca gtc cgg gaa gta aat act caa gtc aag cag tgg att gaa cgg ctt     96
Pro Val Arg Glu Val Asn Thr Gln Val Lys Gln Trp Ile Glu Arg Leu
             20                  25                  30 ggc cat ttg tgg gtg gag ggc cag ctc gct cag att aat gtg aag ccc    144
Gly His Leu Trp Val Glu Gly Gln Leu Ala Gln Ile Asn Val Lys Pro
         35                  40                  45 aat tgg aag ctg tcg tat ttg acg ctt cgt gat gtg gag caa gaa atg    192
Asn Trp Lys Leu Ser Tyr Leu Thr Leu Arg Asp Val Glu Gln Glu Met
     50                  55                  60 tct gtg cag ctg acc tgc ccg acg gac att atc cgc aat cgc ccc aca    240
Ser Val Gln Leu Thr Cys Pro Thr Asp Ile Ile Arg Asn Arg Pro Thr
 65                  70                  75                  80
```

-continued

```
                65                  70                  75                  80
ccg ctc aag gat ggc gac cgc gtg att gtg tac ggc aag ccc gcg ttt        288
Pro Leu Lys Asp Gly Asp Arg Val Ile Val Tyr Gly Lys Pro Ala Phe
                    85                  90                  95 tat gca ggc cgc ggc act ttt tcg ctg tgg gtg act gat atc cgt ccc        336
Tyr Ala Gly Arg Gly Thr Phe Ser Leu Trp Val Thr Asp Ile Arg Pro
            100                 105                 110 gtg ggt att ggt gag ttg ctg gcg cgc att gag gag ctg cgt aaa agg        384
Val Gly Ile Gly Glu Leu Leu Ala Arg Ile Glu Glu Leu Arg Lys Arg
        115                 120                 125 ctt gcc gcg gag ggt ctt ttt gat cca gct cgg aag aag cga ctg cca        432
Leu Ala Ala Glu Gly Leu Phe Asp Pro Ala Arg Lys Lys Arg Leu Pro
    130                 135                 140 ttt ctg ccc aac cgc gtt ggt ttg atc acg gga cgt ggt tca gcg gct        480
Phe Leu Pro Asn Arg Val Gly Leu Ile Thr Gly Arg Gly Ser Ala Ala
145                 150                 155                 160 gag cgc gat gtg ctg agc gtg gct aag gat cgc tgg ccg gaa gtg cag        528
Glu Arg Asp Val Leu Ser Val Ala Lys Asp Arg Trp Pro Glu Val Gln
                165                 170                 175 ttt gag gtg atc aac acg gca gtt cag ggc gct tca gct gtt cct gaa        576
Phe Glu Val Ile Asn Thr Ala Val Gln Gly Ala Ser Ala Val Pro Glu
            180                 185                 190 atc atc gaa gcg ttg cgg gtt tta gat cag gac cct cgc gtg gat gtc        624
Ile Ile Glu Ala Leu Arg Val Leu Asp Gln Asp Pro Arg Val Asp Val
        195                 200                 205 atc atc att gcc cgc ggc ggc ggt tct gtg gag gat ctg ctc ccc ttc        672
Ile Ile Ile Ala Arg Gly Gly Gly Ser Val Glu Asp Leu Leu Pro Phe
    210                 215                 220 tct gag gag gcc ttg cag cgc gca gtc gcg gca gcg cag acg ccc gtg        720
Ser Glu Glu Ala Leu Gln Arg Ala Val Ala Ala Ala Gln Thr Pro Val
225                 230                 235                 240 gtg tcc gcg att ggc cac gaa cca gat acg ccg gtg ttg gac aat gtc        768
Val Ser Ala Ile Gly His Glu Pro Asp Thr Pro Val Leu Asp Asn Val
                245                 250                 255 gcc gac ctt cgc gcg gcg acc ccg acc gat gca gca aag cgc gtg gtg        816
Ala Asp Leu Arg Ala Ala Thr Pro Thr Asp Ala Ala Lys Arg Val Val
            260                 265                 270 cct gat gtg gca gaa gaa cgc atg ttg atc aat cag ctt cgc agt cgt        864
Pro Asp Val Ala Glu Glu Arg Met Leu Ile Asn Gln Leu Arg Ser Arg
        275                 280                 285 agt gcc gcg gcg ttg cgc ggt tgg gtg cag cgc gag cag cag gcg ttg        912
Ser Ala Ala Ala Leu Arg Gly Trp Val Gln Arg Glu Gln Gln Ala Leu
    290                 295                 300 gca gcg att cgc acc agg ccg gtg ctg gct gat ccg atg acc ccg att        960
Ala Ala Ile Arg Thr Arg Pro Val Leu Ala Asp Pro Met Thr Pro Ile
305                 310                 315                 320 aac cgc cga cgt gat gag att gcc cag gct gtg ggc ttg att agg cgc       1008
Asn Arg Arg Arg Asp Glu Ile Ala Gln Ala Val Gly Leu Ile Arg Arg
                325                 330                 335 gat gtc acc cat ctc gtc cgc acc gag caa gca ctg gtg gcg tcg ttg       1056
Asp Val Thr His Leu Val Arg Thr Glu Gln Ala Leu Val Ala Ser Leu
            340                 345                 350 cgc gca cag gtt tcc gcg ctc ggc ccg tcc gca acc ttg gcg cgc ggt       1104
Arg Ala Gln Val Ser Ala Leu Gly Pro Ser Ala Thr Leu Ala Arg Gly
        355                 360                 365 tat tcc gtg gtg cag gtt att cct cgc gac ggc agc gcc ccg gaa gtg       1152
Tyr Ser Val Val Gln Val Ile Pro Arg Asp Gly Ser Ala Pro Glu Val
    370                 375                 380 gtc acc acc atc gag caa tca ccg ccc ggc agc cag ctg cgc atc cgc       1200
```

-continued

```
Val Thr Thr Ile Glu Gln Ser Pro Pro Gly Ser Gln Leu Arg Ile Arg
385                 390                 395                 400
gtt gcc gac ggc tcc atc act gcg gca tcc atg ggc acc cag caa gca    1248
Val Ala Asp Gly Ser Ile Thr Ala Ala Ser Met Gly Thr Gln Gln Ala
                405                 410                 415
aac                                                                 1251
Asn <210> SEQ ID NO 104
<211> LENGTH: 417
<212> TYPE: PRT
<213> ORGANISM: Corynebacterium glutamicum

<400> SEQUENCE: 104

Val Ser Ser Glu Lys Ala Ser Lys Ser Thr Pro Glu Ala Pro Trp
 1               5                  10                  15

Pro Val Arg Glu Val Asn Thr Gln Val Lys Gln Trp Ile Glu Arg Leu
                 20                  25                  30

Gly His Leu Trp Val Glu Gly Gln Leu Ala Gln Ile Asn Val Lys Pro
             35                  40                  45

Asn Trp Lys Leu Ser Tyr Leu Thr Leu Arg Asp Val Glu Gln Glu Met
 50                  55                  60

Ser Val Gln Leu Thr Cys Pro Thr Asp Ile Ile Arg Asn Arg Pro Thr
 65                  70                  75                  80

Pro Leu Lys Asp Gly Asp Arg Val Ile Val Tyr Gly Lys Pro Ala Phe
                 85                  90                  95

Tyr Ala Gly Arg Gly Thr Phe Ser Leu Trp Val Thr Asp Ile Arg Pro
             100                 105                 110

Val Gly Ile Gly Glu Leu Leu Ala Arg Ile Glu Glu Leu Arg Lys Arg
         115                 120                 125

Leu Ala Ala Glu Gly Leu Phe Asp Pro Ala Arg Lys Lys Arg Leu Pro
130                 135                 140

Phe Leu Pro Asn Arg Val Gly Leu Ile Thr Gly Arg Gly Ser Ala Ala
145                 150                 155                 160

Glu Arg Asp Val Leu Ser Val Ala Lys Asp Arg Trp Pro Glu Val Gln
                165                 170                 175

Phe Glu Val Ile Asn Thr Ala Val Gln Gly Ala Ser Ala Val Pro Glu
            180                 185                 190

Ile Ile Glu Ala Leu Arg Val Leu Asp Gln Asp Pro Arg Val Asp Val
        195                 200                 205

Ile Ile Ile Ala Arg Gly Gly Gly Ser Val Glu Asp Leu Leu Pro Phe
    210                 215                 220

Ser Glu Glu Ala Leu Gln Arg Ala Val Ala Ala Gln Thr Pro Val
225                 230                 235                 240

Val Ser Ala Ile Gly His Glu Pro Asp Thr Pro Val Leu Asp Asn Val
                245                 250                 255

Ala Asp Leu Arg Ala Ala Thr Pro Thr Asp Ala Ala Lys Arg Val Val
            260                 265                 270

Pro Asp Val Ala Glu Glu Arg Met Leu Ile Asn Gln Leu Arg Ser Arg
        275                 280                 285

Ser Ala Ala Ala Leu Arg Gly Trp Val Gln Arg Glu Gln Gln Ala Leu
    290                 295                 300

Ala Ala Ile Arg Thr Arg Pro Val Leu Ala Asp Pro Met Thr Pro Ile
305                 310                 315                 320

Asn Arg Arg Arg Asp Glu Ile Ala Gln Ala Val Gly Leu Ile Arg Arg
```

-continued

```
                    325                 330                 335
Asp Val Thr His Leu Val Arg Thr Glu Gln Ala Leu Val Ala Ser Leu
            340                 345                 350

Arg Ala Gln Val Ser Ala Leu Gly Pro Ser Ala Thr Leu Ala Arg Gly
            355                 360                 365

Tyr Ser Val Val Gln Val Ile Pro Arg Asp Gly Ser Ala Pro Glu Val
            370                 375                 380

Val Thr Thr Ile Glu Gln Ser Pro Pro Gly Ser Gln Leu Arg Ile Arg
385                 390                 395                 400

Val Ala Asp Gly Ser Ile Thr Ala Ala Ser Met Gly Thr Gln Gln Ala
            405                 410                 415

Asn
```